United States Patent
Wang et al.

(10) Patent No.: US 11,344,534 B2
(45) Date of Patent: May 31, 2022

(54) CHOLINERGIC AGONISM FOR THE TREATMENT OF PANCREATIC CANCER

(71) Applicant: The Trustees of Columbia University in the City of New York, New York, NY (US)

(72) Inventors: Timothy C. Wang, New York, NY (US); Bernhard Renz, Germering (DE)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 23 days.

(21) Appl. No.: 16/725,668

(22) Filed: Dec. 23, 2019

(65) Prior Publication Data

US 2020/0206194 A1    Jul. 2, 2020

Related U.S. Application Data

(63) Continuation-in-part of application No. PCT/US2018/039606, filed on Jun. 26, 2018.

(60) Provisional application No. 62/525,052, filed on Jun. 26, 2017.

(51) Int. Cl.
| | |
|---|---|
| *A61K 31/4178* | (2006.01) |
| *A61P 35/00* | (2006.01) |
| *A61K 31/27* | (2006.01) |
| *A61K 9/00* | (2006.01) |
| *A61K 31/337* | (2006.01) |

(Continued)

(52) U.S. Cl.
CPC .......... *A61K 31/4178* (2013.01); *A61K 31/27* (2013.01); *A61P 35/00* (2018.01); *A61K 9/0053* (2013.01); *A61K 31/337* (2013.01); *A61K 31/7068* (2013.01); *A61K 45/06* (2013.01)

(58) Field of Classification Search
CPC .. A61K 31/4178; A61K 31/27; A61K 9/0053; A61K 31/337; A61K 31/7068; A61K 45/06; A61K 31/16; A61K 31/34; A61K 31/435; A61P 35/00; A61P 35/04
USPC ......................................................... 514/397
See application file for complete search history.

(56) References Cited

U.S. PATENT DOCUMENTS

| | | | |
|---|---|---|---|
| 3,536,809 | A | 10/1970 | Applezweig |
| 3,598,123 | A | 8/1971 | Zaffaroni |
| 3,845,770 | A | 11/1974 | Theeuwes et al. |

(Continued)

FOREIGN PATENT DOCUMENTS

| | | |
|---|---|---|
| WO | WO-2014113893 | 7/2014 |
| WO | WO-2016028744 | 2/2016 |
| WO | WO-2019005874 | 1/2019 |

OTHER PUBLICATIONS

Pour et al ,Modification of Pancreatic Carcinogenesis in the Hamster Model. XI. Inhibitory Effect of Pilocarpine Hydrochloride, J Natl Cancer Inst. Jan. 1984;72(1):191-4.. (Year: 1984).*

(Continued)

*Primary Examiner* — Taylor V Oh
(74) *Attorney, Agent, or Firm* — Wilmer Cutler Pickering Hale and Dorr LLP

(57) ABSTRACT

The invention provides for methods for treating pancreatic cancer, reducing or inhibiting pancreatic tumor cells, inhibiting or treating pancreatic cancer metastases, and inhibiting pancreatic cancer stem cell growth in a subject by administering a cholinergic agonist.

29 Claims, 54 Drawing Sheets
(44 of 54 Drawing Sheet(s) Filed in Color)
Specification includes a Sequence Listing.

(51) Int. Cl.
A61K 31/7068 (2006.01)
A61K 45/06 (2006.01)

(56) References Cited

U.S. PATENT DOCUMENTS

| | | | |
|---|---|---|---|
| 3,916,899 A | 11/1975 | Theeuwes et al. |
| 4,008,719 A | 2/1977 | Theeuwes et al. |
| 4,710,384 A | 12/1987 | Rotman |
| 5,059,595 A | 10/1991 | Le Grazie |
| 5,073,543 A | 12/1991 | Marshall et al. |
| 5,120,548 A | 6/1992 | McClelland et al. |
| 5,354,556 A | 10/1994 | Sparks et al. |
| 5,591,767 A | 1/1997 | Mohr et al. |
| 5,639,476 A | 6/1997 | Oshiack et al. |
| 5,674,533 A | 10/1997 | Santus et al. |
| 5,733,566 A | 3/1998 | Lewis |
| 2006/0052368 A1 | 3/2006 | Ernst et al. |
| 2015/0182583 A1 | 7/2015 | Fidler |
| 2016/0074400 A1 | 3/2016 | Kahn et al. |

OTHER PUBLICATIONS

Pour et al., Modfication of Pancreatic Carcinogenesis in the Hamster Model, 7. Inhibitory Effect of Bethanechol Chloride Am J Pathol 1983, 112:178-184. (Year: 1983).*

SALAGEN Product Monograph, Product Monograph, Pfizer Canada Inc. Sep. 25, 2014, p. 1-33). (Year: 2014).*

Prescribing Information, Duvoid ,Paladin Labs Inc., May 21, 2009, p. 1-4. (Year: 2009).*

Abdul-Ridha, A. et al., "Mechanistic Insights into Allosteric Structure-Function Relationships at the $M_1$ Muscarinic Acetylcholine Receptor", Journal of Biological Chemistry, 289:33701-33711, Nov. 28, 2014 (11 pages).

Abrams, J. et al., "Barrett's Esophagus Translational Research Network (BETRNet): The pivotal role of multi-institutional collaboration in esophageal adenocarcinoma research", Author Manuscript published in final edited form as Gastroenterology, 146(7):1586-1590, Jun. 2014 (8 pages).

Addeo, P. et al., "Resection of Borderline Respectable and Locally Advanced Pancreatic Adenocarcinomas after Neoadjuvant Chemotherapy", Oncology, 89:37-46, published online Mar. 7, 2015 (10 pages).

Albo, D. et al., "Neurogenesis in Colorectal Cancer Is a Marker of Aggressive Tumor Behavior and Poor Outcomes", Cancer, 117:4834-4845, Nov. 1, 2011 (12 pages).

Alvarez, M.J. et al., "Network-based inference of protein activity helps functionalize the genetic landscape of cancer", Author manuscript published in final edited form as: Nat Genet., 48(8): 838-847. doi:10.1038/ng.3593, Aug. 2016 (27 pages).

Arslan, A. et al., "Anthropometric Measures, Body Mass Index and Pancreatic Cancer: a Pooled Analysis from the Pancreatic Cancer Cohort Consortium (PanScan)", Author Manuscript Published in final edited form as: Arch Intern Med., 170(9):791-802, doi:10.1001/archinternmed.2010.63, May 10, 2010 (28 pages).

Asfaha, S. et al., "Krt19(+)/Lgr5(−) cells are radioresistant cancer initiating stem cells in the colon and intestine", Author Manuscript published in final edited form as Cell: Stem Cell., 16(6): 627-638, doi:10.1016/j.stem.2015.04.013, Jun. 4, 2015 (24 pages).

Ayala, G. E. et al., "Cancer-Related Axonogenesis and Neurogenesis in Prostate Cancer", Clin Cancer Res, 14(23):7593-7603, Dec. 1, 2008 (11 pages).

Aytes, A. et al., "Cross-species analysis of genome-wide regulatory networks identifies a synergistic interaction between FOXM1 and CENPF that drives prostate cancer malignancy", Author Manuscript Published in final edited form as: Cancer Cell, 25(5):638-651, doi:10.1016/j.ccr.2014.03.017, May 12, 2014 (26 pages).

Bansal, M. et al., "A community computational challenge to predict the activity of pairs of compounds", Author manuscript Published in final edited form as: Nat Biotechnol., 32(12):1213-1222, doi:10.1038/nbt.3052, Dec. 2014 (28 pages).

Barrett, T. et al., "NCBI GEO: archive for functional genomics data sets—update", Nucleic Acids Research, 41, Database issue D991-D995, doi: 10.1093/nar/gks1193, 2013, published online Nov. 27, 2012 (5 pages).

Basso, K. et al., "Reverse engineering of regulatory networks in human B cells", Nature Genetics, 37(4):382-390, Apr. 2005 (9 pages).

Bellon, E. et al., "Pancreatic cancer and liver metastases: state of the art", Updates Surg, DOI 10.1007/s13304-016-0407-7, Italian Society of Surgery (SIC), published online Nov. 10, 2016 (5 pages).

Benjamin, Y., et al., "Controlling the False Discovery Rate: A Practical and Powerful Approach to Multiple Testing", J. Royal Statist. Soc. B (Methodological), 57(1): 289-300, (1995) (13 pages).

Berthoud, H.R., et al., "Functional and chemical anatomy of the afferent vagal system", Autonomic Neuroscience: Basic & Clinical 85:1-17, 2000 (17 pages).

Bisikirska, B. et al., "Elucidation and Pharmacological Targeting of Novel Molecular Drivers of Follicular Lymphoma Progression", Cancer Res, 76(3) 664-674 doi: 10.1158/0008-5472.CAN-15-0828, published online Nov. 10, 2015 (12 pages).

Blaukat, A. et al., "G Protein-Coupled Receptor-Mediated Mitogen-Activated Protein Kinase Activation through Cooperation o $G\alpha_q$ and $G\alpha_i$ Signals", Mol. Cell. Biol., 20(18):6837-6848, Sep. 2000 (12 pages).

Blazer, M. et al., "Neoadjuvant Modified (m) FOLFIRINOX for Locally Advanced Unresectable (LAPC) and Borderline Respectable (BRPC) Adenocarcinoma of the Pancreas", Ann Surg Oncol, 22:1153-1159, DOI 10.1245/s10434-014-4225-1, 2015 (7 pages).

Boj, S. et al., "Organoid Models of Human and Mouse Ductal Pancreatic Cancer", Cell, 160:324-338, Jan. 15, 2015 (15 pages).

Boilly, B. et al., "Nerve Dependence: From Regeneration to Cancer", Cancer Cell, 31:342-354, Mar. 13, 2017 (13 pages).

Bonaz, B., "The Cholinergic Anti-Inflammatory Pathway and the Gastrointestinal Tract", Gastroenterology, 133(4):1370-1373, Oct. 2007 (4 pages).

Borovikova, L. et al., "Vagus nerve stimulation attenuates the systemic inflammatory response to endotoxin", Nature, 405:458-462, May 2000 (5 pages).

Brittan, M., et al., "Stem Cell in Gastrointestinal Structure and Neoplastic Development", Gut, 53:899-910, doi: 10.1136/gut.2003.025478, 2004 (12 pages).

Califano, A., et al., "The recurrent architecture of tumor initiation, progression, and drug-sensitivity", Author Manuscript published in final edited form as: Nat Rev Cancer, 17(2): 116-130, doi:10.1038/nrc.2016.124, Feb. 2017 (35 pages).

Califano, A. et al., "Leveraging models of cell regulation and GWAS data in integrative network-based association studies", Nature Genetics, 44(8):841-847, Aug. 2012 (7 pages).

Calvani, M. et al., "Norepinephrine promotes tumor microenvironment reactivity through beta3-adrenoreceptors during melanoma progression", Oncotarget, 6:(7)4615-4632, Dec. 6, 2014 (18 pages).

Carro, M. S. et al., "The transcriptional network for mesenchymal transformation of brain tumours", Nature, 463:318-325, doi:10.1038/nature08712, Jan. 21, 2010 (10 pages).

Chandra, R., et al., "Modulation of Pancreatic Exocrine and Endocrine Secretion", Author Manuscript published in final edited form as: Curr Opin Gastroenterol., 29(5):517-522, doi:10.1097/MOG.0b013e3283639326, Sep. 2013 (10 pages).

Chang, A. et al., "Neural Regulation of Pancreatic Cancer: A Novel Target for Intervention", Cancers, 7:1292-1312, Jul. 17, 2015 (22 pages).

Chen, J. C. et al., "Identification of Causal Genetic Drivers of Human Disease through Systems-Level Analysis of Regulatory Networks", Cell, 159:402-414, Oct. 9, 2014 (27 pages).

Cheng, K. et al., "Transactivation of the Epidermal Growth Factor Receptor Mediates Cholinergic Agonist-Induced Proliferation of H508 Human Colon Cancer Cells", Cancer Research 63:6744-6750, Oct. 15, 2003 (8 pages).

Chio, I.I.C., et al., "NRF2 Promotes Tumor Maintenance by Modulating mRNA Translation in Pancreatic Cancer", Cell, 166:963-976, Aug. 11, 2016 (37 pages).

(56) References Cited

OTHER PUBLICATIONS

Chou, T.C., "Drug Combination Studies and Their Synergy Quantification Using the Chou-Talalay Method", Cancer Res; 70(2):440-446, Jan. 12, 2010 (8 pages).
Chowdhury, S. et al., "Hormonal Responses to Cholinergic Input Are Different in Humans with and without Type 2 Diabetes Mellitus", PLoS ONE, 11(6):e0156852, DOI:10.1371/journal.pone.0156852, Jun. 15, 2016 (22 pages).
Compagno, M. et al., "Mutations of multiple genes cause deregulation of NF-κB in diffuse large B-cell lymphoma", Author Manuscript published in final edited form as: Nature, 459(7247): 717-721, doi:10.1038/nature07968, Jun. 4, 2009 (13 pages).
Conroy, T. et al., "FOLFIRINOX or Gemcitabine as Adjuvant Therapy for Pancreatic Cancer", N Engl J Med., 379(25):2395-2406, Dec. 20, 2018 (12 pages).
Conroy, T. et al., "FOLFIRINOX versus Gemcitabine for Metastatic Pancreatic Cancer", N Engl J Med, 364(19):1817-1825, May 12, 2011 (9 pages).
De Couck, M. et al., "Vagal nerve activity predicts overall survival in metastatic pancreatic cancer, mediated by inflammation", Cancer Epidemiol, 40:47-51, 2016, published online Nov. 24, 2015 (5 pages).
De Couck, M. et al., "You may need the vagus nerve to understand pathophysiology and to treat diseases", Clinical Science, 122:323-328, 2012, published online Dec. 7, 2011 (6 pages).
De Jonge, W. J. et al., "Stimulation of the vagus nerve attenuates macrophage activation by activating the Jak2-STAT3 signaling pathway", Nature Immunology, 6(8):844-851, Aug. 2005, published online Jul. 17, 2005; Erratum, Nature Immunology, 6(9):954, Sep. 2005 (9 pages).
Demir, I. E. et al., "Neural plasticity in pancreatitis and pancreatic cancer", Nature Reviews: Gastroenterology & Hepatology, 12:649-659, Nov. 2015, published online Oct. 13, 2015 (11 pages).
Draghici, S. et al., "A systems biology approach for pathway level analysis", Genome Research, 17:1537-1545, Nov. 2007 (10 pages).
Du, L. et al., "CD44 is of Functional Importance for Colorectal Cancer Stem Cells", Clin Cancer Res, 14(21):6751-6760, Nov. 1, 2008; Correction, Clin Cancer Res, 14(23):7964-7967, Dec. 1, 2008 (15 pages).
Dubeykovskaya, Z. et al., "Neural innervation stimulates splenic TFF2 to arrest myeloid cell expansion and cancer", Nature Communications, 7:10517, DOI:10.1038/ncomms10517, Feb. 4, 2016 (11 pages).
Edwards, B. K. et al., "Annual Report to the Nation on the Status of Cancer, 1975-2002, Featuring Population-Based-Trends in Cancer Treatment", Journal of the National Cancer Institute, 97(19):1407-1427, Oct. 5, 2005 (21 pages).
Elbaz, M. et al., "Novel role of cannabinoid receptor 2 in inhibiting EGF/EGFR and IGF-I/IGF-IR pathways in breast cancer", Oncotarget, 8(18):29668-29678, 2017, published May 17, 2016 (11 pages).
Epstein, J. et al., "A clinical trial of bethanechol in patients with xerostomia after radiation therapy: A pilot study", Oral Surg Oral Med Oral Pathol, 77:610-614, Jun. 1994 (5 pages).
Erin, N. et al., "Vagotomy enhances experimental metastases of 4THMpc breast cancer cells and alters substance P level", Regul. Pept., 151:35-42, 2008 (8 pages).
Erin, N. et al., "Activation of vagus nerve by semapimod alters substance P levels and decreases breast cancer metastasis", Regulatory Peptides, 179:101-108, 2012 (9 pages).
Erin, N. et al., "Capsaicin-mediated Denervation of Sensory Neurons Promotes Mammary Tumor Metastasis to Lung and Heart", Anticancer Research, 24:1003-1009, Mar. 2004 (8 pages).
Fernandez, R. et al., "Neural reflex regulation of systemic inflammation: potential new targets for sepsis therapy", Frontiers in Physiology, vol. 5, Article 489, Dec. 15, 2014 (9 pages).
Franke, TF, "PI3K/Akt: getting it right matters", Oncogene, 27:6473-6488, 2008 (16 pages).
Fujii, T. et al., "Expression and Function of the Cholinergic System in Immune Cells", Frontiers in Immunology, vol. 8, Article 1085, Sep. 6, 2017 (19 pages).

Gentleman, R. C. et al., "Bioconductor: open software development for computational biology and bioinformatics", Genome Biology, vol. 5, Issue 10, Article R80, Sep. 15, 2004 (16 pages).
Gerber, D. J. et al., "Hyperactivity, elevated dopaminergic transmission, and response to amphetamine in M1 muscarinic acetylcholine receptor-deficient mice", PNAS, 98(26):15312-15317, Dec. 18, 2001 (6 pages).
Gidron, Y. et al., "Does the vagus nerve inform the brain about preclinical tumours and modulate them", Lancet Oncol, 6:245-248, Apr. 2005 (4 pages).
Gorsky, M. et al., "The efficacy of pilocarpine and bethanechol upon saliva production in cancer patients with hyposalivation following radiation therapy", Oral Surg Oral Med Oral Pathol Oral Radiol Endod, 97(2):190-195, Feb. 2004 (6 pages).
Gross, E. R. et al., "Neuronal Serotonin Regulates Growth of the Intestinal Mucosa in Mice", Gastroenterology, 143(2):408-417, Aug. 2012 (12 pages).
Hao, J. et al., "In Vitro and In Vivo Prostate Cancer Metastasis and Chemoresistance Can Be Modulated by Expression of either CD44 or CD147", PLoS One, 7(8):e40716, Aug. 3, 2012 (14 pages).
Hayakawa, Y. et al., "Nerves switch on angiogenic metabolism: Adrenergized blood vessels contribute to prostate cancer progression", Science, 358(6361):305-306, Oct. 20, 2017 (3 pages).
Hayakawa, Y. et al., "Mist1 Expressing Gastric Stem Cells Maintain the Normal and Neoplastic Gastric Epithelium and Are Supported by a Perivascular Stem Cell Niche", Cancer Cell, 28:800-814, Dec. 14, 2015 (40 pages).
Hayakawa, Y. et al., "Nerve Growth Factor Promotes Gastric Tumorigenesis through Aberrant Cholinergic Signaling", Cancer Cell, 31:21-34, Jan. 9, 2017 (35 pages).
Hidalgo, M. "Pancreatic Cancer", N Engl J Med, 362(17):1605-1617, Apr. 29, 2010 (13 pages).
Hingorani, S. R. et al., "$Trp53^{R172H}$ and $Kras^{G12D}$ cooperate to promote chromosomal instability and widely metastatic pancreatic ductal adenocarcinoma in mice", Cancer Cell, 7:469-483, DOI 10.1016/j.ccr.2005.04.023, May 2005 (15 pages).
Holmgren, S. et al., "Autonomic control of glands and secretion: A comparative view", Autonomic Neuroscience: Basic and Clinical, 165:102-112, 2011 (11 pages).
Li, H. et al., "Gastrointestinal stem cells in health and disease: from flies to humans", Disease Models & Mechanisms, 9:487-499, doi:10.1242/dmm.024232, 2016 (13 pages).
Horowitz, D. et al., "Use of adjuvant radiation therapy in the management of acinar cell carcinoma of the pancreas: results from the Survival, Epidemiology, and End Results database", Journal of Radiation Oncology, 3:299-306, Apr. 2014 (8 pages).
Hosein, P. et al., "A retrospective study of neoadjuvant FOLFIRINOX in unresectable or borderline-respectable locally advanced pancreatic adenocarcinoma", BMC Cancer, 12:199, <URL http://www.biomedcentral.com/1471-2407/12/199>, 2012 (7 pages).
Houghton, J. et al., "Gastric Cancer Originating from Bone Marrow-Derived Cells", Science, 306:1568-1571, Nov. 26, 2004 (5 pages).
Ielpo, B. et al., "A comparative study of neoadjuvant treatment with gemcitabine plus nab-paclitaxel versus surgery first for pancreatic adenocarcinoma", Surgical Oncology, 26:402-410, 2017 (9 pages).
Ihaka, R. et al., "R: A Language for Data Analysis and Graphics", Journal of Computational and Graphical Statistics, 5(3):299-314, 1996 (17 pages).
International Search Report and Written Opinion issued by U.S. Patent and Trademark Office as International Searching Authority in International Patent Application No. PCT/US18/39606, dated Dec. 12, 2018 (19 pages).
Jaguar, G. et al., "Double blind randomized prospective trial of bethanechol in the prevention of radiation-induced salivary gland dysfunction in head and neck cancer patients", Radiother Oncol., 115:253-256, available online Apr. 15, 2015 (4 pages).
Jensen, D. et al., "Neurokinin 1 receptor signaling in endosomes mediates sustained nociception and is a viable therapeutic target for prolonged pain relief", Science Translational Medicine, 9:eaal3447, May 31, 2017 (17 pages).
Jin, G. et al., "Progastrin Stimulates Colonic Cell Proliferation via CCK2R- and β-Arrestin—Dependent Suppression of BMP2", Gastroenterology, 145(4):820-830, Oct. 2013 (21 pages).

(56) References Cited

OTHER PUBLICATIONS

Jobling, P. et al., "Nerve-Cancer Cell Cross-Talk: A Novel Promoter of Tumor Progression", Cancer Res, 75(9), 1777-1781, May 1, 2015, published online Mar. 20, 2015 (6 pages).
Jung, S.-R. et al., "Muscarinic receptor regulates extracellular signal regulated kinase by two modes of arrestin binding", PNAS, 114:E5579-E5588, Jun. 26, 2017 (10 pages).
Kamiya, A. et al., "Genetic manipulation of autonomic nerve fiber innervation and activity and its effect on breast cancer progression", also including Supplemental Information of Nature Research Reporting Summary dated Oct. 2018, Nature Neuroscience, 22:1289-1305, Aug. 2019 (23 pages).
Kanai, M. et al., "A phase I/II study of gemcitabine-based chemotherapy plus curcumin for patients with gemcitabine-resistant pancreatic cancer", Cancer Chemother Pharmacol, 68:157-164, 2011 (8 pages).
Kanehisa, M. et al., "The KEGG resource for deciphering the genome", Nucleic Acids Research, 32(Database issue):D277-D280, DOI: 10.1093/nar/gkh063, 2004 (4 pages).
Katayama, Y. et al., "Signals from the Sympathetic Nervous System Regulate Hematopoietic Stem Cell Egress from Bone Marrow", Cell, 124:407-421, Jan. 27, 2006 (15 pages).
Katz, M. H. G. et al., "Borderline Respectable Pancreatic Cancer: Need for Standardization and Methods for Optimal Clinical Trial Design", Ann Surg Oncol, 20:2787-2795, Feb. 23, 2013 (9 pages).
Keshet, Y. et al., "Chapter 1: The MAP Kinase Signaling Cascades: A System of Hundreds of Components Regulates a Diverse Array of Physiological Functions", in Methods in Molecular Biology, vol. 661, Rony Seger, editor, Springer Science+Business Media, LLC, Berlin, Germany, pp. 3-38, 2010 (36 pages).
Kessler, W. et al., "The vagal nerve as a link between the nervous and immune system in the instance of polymicrobial sepsis", Langenbecks Arch Surg., 391:83-87, published online Mar. 28, 2006 (5 pages).
Kiba, T. et al., "Ventromedial Hypothalamic Lesion-Induced Vagal Hyperactivity Stimulates Rat Pancreatic Cell Proliferation", Gastroenterology, 110(3), 885-893, Mar. 1996 (9 pages).
Kim, D. et al., "TopHat2: accurate alignment of transcriptomes in the presence of insertions, deletions and gene fusions", Genome Biology, 14:R36, <URL http://genomebiology.com/2013/14/4/R36>, 2013 (13 pages).
Li, X.-P. et al., "Expression of CD44 in pancreatic cancer and its significance", Int J Clin Exp Pathol, 8(6):6724-6731, Jun. 15, 2015 (8 pages).
Knox, S.M. et al., "Parasympathetic innervation maintains epithelial progenitor cells during salivary organogenesis", Author Manuscript Published in final edited form as: Science, 329(5999):1645-1647, doi:10.1126/science.1192046, Sep. 24, 2010 (8 pages).
Koo, J. et al., "Wireless bioresorbable electronic system enables sustained nonpharmacological neuroregenerative therapy", including Reporting Summary dated Apr. 2018, Nature Medicine, 24:1830-1836, Dec. 2018 (12 pages).
Langmead, B. et al., "Fast gapped-read alignment with Bowtie 2", Author Manuscript Published in final edited form as: Nat Methods, 9(4): 357-359, doi:10.1038/nmeth.1923, Apr. 1, 2013 (8 pages).
Law, C. W. et al., "voom: precision weights unlock linear model analysis tools for RNA-seq read counts", Genome Biology, 15:R29, 2014 (17 pages).
Li, C. et al., "Identification of Pancreatic Cancer Stem Cells", Cancer Res, 67(3):1030-1037, Feb. 1, 2007 (9 pages).
Liu, R. et al., "Why weight? Modelling sample and observational level variability improves power in RNA-seq analyses", Nucleic Acids Research, 43(15):e97, doi: 10.1093/nar/gkv412, Apr. 29, 2015 (11 pages).
Lorusso, P. M. et al., "Phase 0 Clinical Trials: An Answer to Drug Development Stagnation?", Journal of Clinical Oncology, 27(16) 2586-2588, Jun. 1, 2009 (3 pages).
Loukopoulos, P. et al., "Orthotopic Transplantation Models of Pancreatic Adenocarcinoma Derived From Cell Lines and Primary Tumors and Displaying Varying Metastatic Activity", Pancreas, 29(3):193-203, Oct. 2004 (11 pages).
Lundgren, O. et al., "Intestinal Epithelial Stem/Progenitor Cells Are Controlled by Mucosal Afferent Nerves", PLoS ONE, 6(2):e16295, Feb. 9, 2011 (13 pages).
Lundin, J. et al., "Prognostic Value of Immunohistochemical Expression of p53 in Patients with Pancreatic Cancer", Oncology, 53:104-111, 1996 (8 pages).
Lundin, J. et al., "Prognostic Value of Ki-67 Expression, Ploidy and S-Phase Fraction in Patients with Pancreatic Cancer", Anticancer Res., 15:2659-2668, 1995 (10 pages).
Lutz, M. P. et al., "3rd St. Gallen EORTC Gastrointestinal Cancer Conference: Consensus recommendations on controversial issues in the primary treatment of pancreatic cancer", European Journal of Cancer, 79:41-49, 2017 (10 pages).
Magnon, C. et. al., "Autonomic Nerve Development Contributes to Prostate Cancer Progression", Science, 341(6142): 1236361-1-1236361-10, Jul. 12, 2013 (11 pages).
Marrache, F. et al., "Basic-Liver, Pancreas, and Biliary Tract: Overexpression of lnterleukin-1β in the Murine Pancreas Result in Chronic Pancreatitis", Gastroenterology, 135(4):1277-1287, Oct. 2008 (11 pages).
Mattingly, R. R. et al., "Muscarinic Receptors Transform NIH 3T3 Cells through a Ras-Dependent Signaling Pathway Inhibited by the Ras-GTPase-Activating Protein SH3 Domain", Mol. Cell. Biol., 14(12):7943-7952, 1994 (10 pages).
Mitra, D. et al., "An ultraviolet-radiation-independent pathway to melanoma carcinogenesis in the red hair/fair skin background", NATURE, 491:449-453, Nov. 15, 2012 (6 pages).
Mitrofanova, A. et al., "Predicting Drug Response in Human Prostate Cancer from Preclinical Analysis of In Vivo Mouse Models", Cell Reports, 12:2060-2071, Sep. 29, 2015 (33 pages).
Moreno, J.A. et al., "Fluorescent Orthotopic Mouse Model of Pancreatic Cancer", Journal of Visualized Experiments, 115:e54337, doi: 10.3791/54337, Sep. 2016 (5 pages).
Mosquera, C. et al., "Molecular targeted therapy for pancreatic adenocarcinoma: A review of completed and ongoing late phase clinical trials", Cancer Genetics., 209:567-581, 2016 (15 pages).
Muranaka, T. et al., "Comparison of efficacy and toxicity of FOLFIRINOX and gemcitabine with nab-paclitaxel in unresectable pancreatic cancer", J Gastrointest Oncol, 8(3):566-571, Jun. 2017 (6 pages).
Murphy, J. et al., "Total Neoadjuvant Therapy With FOLFIRINOX Followed by Individualized Chemoradiotherapy for Borderline Respectable Pancreatic Adenocarcinoma: A Phase 2 Clinical Trial", JAMA Oncol., 4(7):963-969, doi:10.1001/jamaoncol.2018.0329, published online May 3, 2018 (7 pages).
Nakagawa, H. et al., "The targeting of the cyclin D1 oncogene by an Epstein-Barr virus promoter in transgenic mice causes dysplasia in the tongue, esophagus and forestomach", Oncogene, 14:1185-1190, 1997 (6 pages).
Nakashima, A. et al., "Agonist-Independent GPCR Activity Regulates Anterior-Posterior Targeting of Olfactory Sensory Neurons", Cell, 154:1314-1325, S1-S7, Sep. 12, 2013 (19 pages).
Oberstein, P. E. et al., "Abstract 1637: Depletion of tumor stroma with Smoothened inhibition leads to altered epithelial differentiation and paradoxical acceleration of pancreatic tumorigenesis", Poster presentation at AACR 104th Annual Meeting, Washington, DC, Apr. 6-10, 2013 (2 pages).
Oberstein, P.E. et al., "Uptake and Patterns of Use of Gemcitabine for Metastatic Pancreatic Cancer: A Population-Based Study", Cancer Investigation, 31(5):316-322, published online Apr. 24, 2013 (8 pages).
Oberstein, P. E. et al., "Pancreatic cancer: why is it so hard to treat?", Therapeutic Advances in Gastroenterology, 6(4): 321-337, 2013 (17 pages).
Oberstein, P. E. et al., "Safety and Efficacy of Everolimus in Adult Patients with Neuroendocrine Tumors", Clinical Medicine Insights: Oncology 6:41-51 (2012) 11 pages.
Olive, K. P. et al. "Inhibition of Hedgehog Signaling Enhances Delivery of Chemotherapy in a Mouse Model of Pancreatic Cancer", Science, 324:1457-1461, Jun. 12, 2009 (6 pages).

(56) References Cited

OTHER PUBLICATIONS

Padro, C.J. et al., "Neuroendocrine regulation of inflammation", Author Manuscript Published in final edited form as: Semin Immunol., 26(5): 357-368. doi:10.1016/j.smim.2014.01.003., Oct. 2014 (30 pages).

Park, S.Y. et al., "Norepinephrine induces VEGF expression and angiogenesis by a hypoxia-inducible factor-1α protein-dependent mechanism", Int. J. Cancer, 128:2306-2316, 2011 11 pages)—Retracted.

Partecke, L. I. et al., "Subdiaphragmatic vagotomy promotes tumor growth and reduces survival via TNFα in murine pancreatic cancer model", Oncotarget, 8(14):22501-22512 Feb. 2, 2017 (12 pages).

Pavolv, V. A. et al., "The Cholinergic Anti-inflammatory Pathway: A Missing Link in Neuroimmunomodulation", Molecular Medicine, 9(5-8):125-134, May-Aug. 2003 (10 pages).

Peterson, S. C. et al., "Basal Cell Carcinoma Preferentially Arises from Stem Cells within Hair Follicle and Mechanosensory Niches", Cell Stem Cell, 16:400-412, Apr. 2, 2015 (26 pages).

Piovan, E. et al., "Direct reversal of glucocorticoid resistance by AKT inhibition in acute lymphoblastic leukemia", Author Manuscript Published in final edited form as: Cancer Cell., vol. 24, Issue 6, doi:10.1016/j.ccr.2013.10.022., Dec. 9, 2013 (24 pages).

Pocai, A. et al., "Hypothalamic $K_{ATP}$ channels control hepatic glucose production", Nature, 434:1026-1031, Apr. 21, 2005 (6 pages).

Ponti, D. et al., "Isolation and In vitro Propagation of Tumorigenic Breast Cancer Cells with Stem/Progenitor Cell Properties", Cancer Res, 65(13):5506-5511, Jul. 1, 2005 (7 pages).

Quante, M. et al., "Bile Acid and inflammation activate gastric cardia stem cells in a mouse model of Barrett-like metaplasia", Author Manuscript Published in final edited form as: Cancer Cell., 21(1):36-51, doi:10.1016/j.ccr.2011.12.0004, Jan. 17, 2012 (26 pages).

Quante, M. et al., "Bone Marrow-Derived Myofibroblasts Contribute to the Mesenchymal Stem Cell Niche and Promote Tumor Growth", Cancer Cell, 19:257-272, Feb. 15, 2011 (16 pages).

Quante, M. et al., "The Gastrointestinal Tumor Microenvironment", Gastroenterology, 145:63-78, 2013 (16 pages).

Quante, M. et al., "The Rapid Rise in Gastroesophageal Junction Tumors: Is Inflammation of the Gastric Cardia the Underwater Iceberg?", Gastroenterology, 145(4):708-711, doi: 10.1053/j.gastro. 2013.08.023, Oct. 2013 (6 pages).

Raufman, J.-P. et al., "Muscarinic receptor subtype-3 gene ablation and scopolamine butylbromide treatment attenuate small intestinal neoplasia in $Apc^{min}/+$ mice", Carcinogenesis, 32(9):1396-1402, Jun. 24, 2011 (7 pages).

Reichert, M. et al., "Isolation, culture and genetic manipulation of mouse pancreatic ductal cells", Author Manuscript Published in final edited form as: Nat. Protoc., 8(7):1354-1365, doi:10.1038/nprot.2013.079, 2013 (31 pages).

Renz, B.W. et al., "Cholinergic Signaling via Muscarinic Receptors Directly and Indirectly Suppresses Pancreatic Tumorigenesis and Cancer Stemness", Cancer Discovery, 8:1458-1473, doi:10.1158/2159-8290.CD-18-0046, published online Sep. 5, 2018 (17 pages).

Renz, B.W. et al., "β2 Adrenergic-Neurotrophin Feedforward Loop Promotes Pancreatic Cancer", Cancer Cell, 33:75-90, Jan. 8, 2018 (38 pages).

Rhim, A. D. et al., "Stromal Elements Act to Restrain, Rather Than Support, Pancreatic Ductal Adenocarcinoma", Cancer Cell, 25:735-747, Jun. 16, 2014 (29 pages).

Rodriguez-Barrueco, R. et al., "Inhibition of the autocrine IL-6-JAK2-STAT3-calprotectin axis as targeted therapy for HR$^-$/HER2$^+$ breast cancers", Genes & Development 29:1631-1648, Jul. 30, 2015 (19 pages).

Saloman, J. L. et al., "Ablation of sensory neurons in a genetic model of pancreatic ductal adenocarcinoma slows initiation and progression of cancer", PNAS, 113(11):3078-3083, Mar. 15, 2016 (6 pages).

Saloman, J. L. et al., "Can Stopping Nerves, Stop Cancer?", Author manuscript Published in final edited form as: Trends Neurosci. 39(12): 880-889, doi:10.1016/j.tins.2016.10.002, Dec. 2016 (19 pages).

Schepers, A. et al., "Wnt Signaling, Stem Cells, and Cancer of the Gastrointestinal Tract", Cold Spring Harbor Perspectives in Biology, 4:a007989, 2012 (14 pages).

Shah, N. et al., "Muscarinic receptors and ligands in cancer", Am J Physiol: Cell Physiology, 296(2):C221-C232, Feb. 2009, published online Nov. 16, 2008 (27 pages).

Shang, Y., "Hormones and cancer", Cell Research, 17:277-279, Apr. 10, 2007 (3 pages).

Sherman, W.H. et al., "Neoadjuvant Gemcitabine, Docetaxel, and Capecitabine Followed by Gemcitabine and Capecitabine/Radiation Therapy and Surgery in Locally Advanced, Unresectable Pancreatic Adenocarcinoma", Cancer, 121:673-680, Mar. 1, 2015, published online Dec. 9, 2014 (8 pages).

Shi, M. et al., "Central and peripheral nervous systems: master controllers in cancer metastasis", Cancer Metastasis Rev., 32:603-621, 2013 (19 pages).

Siegel, R.L. et al., "Cancer Statistics, 2018", CA Cancer J Clin, 68(1):7-30, Jan./Feb. 2018 (24 pages).

Siegel, R.L. et al., "Cancer Statistics, 2016", CA Cancer J Clin, 66(1):7-30, Jan./Feb. 2016 (24 pages).

Sinha, S. et al., PanIN Neuroendocrine Cells Promote Tumorigenesis via Neuronal Cross-talk, Cancer Res, 77(8): 1868-1879, Apr. 15, 2017 (13 pages).

Sloan, E. K. et al., "The Sympathetic Nervous System Induces a Metastatic Switch in Primary Breast Cancer", Cancer Res, 70(18), 7042-7052, Sep. 15, 2010 (12 pages).

Soares, K. et al., "TGF-β blockade depletes T regulatory cells from metastatic pancreatic tumors in a vaccine dependent manner", Oncotarget, 6(40):43005-43015, Oct. 15, 2015 (11 pages).

Soares, K.C. et al., "A Preclinical Murine Model of Hepatic Metastases", J. Vis. Exp. (91):e51677, Sep. 27, 2014 (10 pages).

Song, J.-W. et al., "New Morphological Features for Grading Pancreatic Ductal Adenocarcinomas", BioMed Research International, vol. 2013, Article ID 175271, 2013 (25 pages).

Spindel, E. R. et al., "Muscarinic Receptor Agonists and Antagonists: Effects on Cancer", Author Manuscript published in final edited form as Handb Exp Pharmacol, 208:451-468, 2012 (20 pages).

Stanton, K. et al., "Analysis of Ki-67 antigen expression, DNA proliferative fraction, and survival in resected cancer of the pancreas", Am J. Surg., 186:486-492, 2003 (7 pages).

Stein, W. D. et al., "Tumor Growth Rates Derived from Data for Patients in a Clinical Trial Correlate Strongly with Patient Survival: A Novel Strategy for Evaluation of Clinical Trial Data", Author Manuscript Published in final edited form as Oncologist., 13(10): 1046-1054, doi:10.1634/theoncologist.2008-0075, Oct. 2008 (16 pages).

Sumazin, P. et al., "An Extensive MicroRNA-Mediated Network of RNA-RNA Interactions Regulates Established Oncogenic Pathways in Glioblastoma", Cell, 147:370-381, Oct. 14, 2011 (21 pages).

Sun, X.-J. et al., "Role of the tumor microenvironment in pancreatic adenocarcinoma", Front Biosci (Landmark Ed.), 21:31-41, Jan. 1, 2016 (11 pages).

Takaishi, S. et al., "Identification of Gastric Cancer Stem Cells Using the Cell Surface Marker CD44", Stem Cells, 27:1006-1020, 2009 (15 pages).

Tarca, A.L. et al., "A novel signaling pathway impact analysis", Bioinformatics, Original Paper, 25(1):75-82, 2009, published online Nov. 5, 2008 (8 pages).

Tascilar, M. et al., "Pancreatic cancer after remote peptic ulcer surgery", J Clin Pathol, 55:340-345, 2002 (6 pages).

Tempero, M.A. et al., "NCCN: Pancreatic Adenocarcinoma, Version 2.2017: Clinical Practice Guidelines in Oncology", J Natl Compr Canc Netw, 15(8): 1028-1061, doi: 10.6004/jnccn.2017.0131, Aug. 2017 (34 pages).

Titchenell, P.M. et al., "Direct Hepatocyte Insulin Signaling Is Required for Lipogenesis but Is Dispensable for the Suppression of Glucose Production", Cell Metabolism, 23:1154-1166, Jun. 14, 2016 (22 pages).

(56) References Cited

OTHER PUBLICATIONS

Tracey, K.J., "Reflex control of immunity", Nature Reviews: Immunology, 9:418-428, Jun. 2009 (11 pages).

Tsutsumi, T. et al., "Modulation of the myocardial redox state by vagal nerve stimulation after experimental myocardial infarction", Cardiovascular Research, 77:713-721, doi:10.1093/cvr/cvm092, 2008, published online Dec. 7, 2007 (9 pages).

Tu, S. et al., "Overexpression of Interleukin-1β Induces Gastric Inflammation and Cancer and Mobilizes Myeloid-Derived Suppressor Cells in Mice", Cancer Cell, 14:408-419, Nov. 4, 2008 (12 pages).

Ukegawa, J.-I. et al., "Growth-promoting effect of muscarinic acetylcholine receptors in colon cancer cells", J Cancer Res Clin Oncol, 129:272-278, DOI 10.1007/s00432-003-0433-y, published online May 14, 2003 (7 pages).

Von Hoff, D.D. et al., "Increased Survival in Pancreatic Cancer with nab-Paclitaxel plus Gemcitabine", N Engl J Med, 369(18):1691-1703, Oct. 31, 2013 (13 pages).

Van Rees, B.P. et al., "Remote partial gastrectomy as a risk factor for pancreatic cancer: Potential for preventive strategies", Ann Oncol, 10(Suppl. 4):S204-S207, 1999 (4 pages).

Van Westerloo, D.J. et al., "The Vagus Nerve and Nicotinic Receptors Modulate Experimental Pancreatitis Severity in Mice", Gastroenterology, 130:1822-1830, May 2006 (9 pages).

Wang, Y. et al., "A Real-World Comparison of FOLFIRINOX, Gemcitabine Plus nab-Paclitaxel, and Gemcitabine in Advanced Pancreatic Cancers", *J Gastrointest Cancer*, 50:62-68, <URL https://doi.org/10.1007/s12029-017-0028-5>, published online Nov. 2017 (7 pages).

Wang, T.C. et al., "Mammary hyperplasia and carcinoma in MMTV-cyclin D1 transgenic mice", Nature, 369:669-671, Jun. 23, 1994 (3 pages).

Wang, K. et al., "Genome-wide identification of post-translational modulators of transcription factor activity in human B cells", Nat Biotechnol, 27(9):829-837, Sep. 2009 (11 pages).

Westcott, M.P. et al., "Pancreatic Ductal Morphogenesis and the Pdx1 Homeodomain Transcription Factor", Molecular Biology of the Cell, 20:4838-4844, Nov. 15, 2009 (7 pages).

Westphalen, C. B. et al., "Dclk1 Defines Quiescent Pancreatic Progenitors that Promote Injury-Induced Regeneration and Tumorigenesis", Cell Stem Cell, 18:441-455, Apr. 7, 2016 (45 pages).

Westphalen, C. B. et al., "Long-lived intestinal tuft cells serve as colon cancer-initiating cells", The Journal of Clinical Investigation, 124(3): 1283-1295, Mar. 2014 (13 pages).

Woo, J. H. et al., "Elucidating Compound Mechanism of Action by Network Perturbation Analysis", Cell, 162:441-451, Jul. 16, 2015 (30 pages).

Wood, N. "Pancreatic cancer: Pancreatic tumour formation and recurrence after radiotherapy are blocked by targeting CD44", Nat. Rev Gastroenterol Hepatol, 11:73, published online Jan. 21, 2014 (1 page).

Worthley, D. et al., "Gremlin1 Identifies a Skeletal Stem Cell with Bone, Cartilage, and Reticular Stromal Potential", Cell, 160:269-284, Jan. 15, 2015 (23 pages).

Xu, H. et al., "CD44 correlates with clinicopathological characteristics and is upregulated by EGFR in breast cancer", International Journal of Oncology, 49:1343-1350, 2016 (8 pages).

Xu, Q. et al., "EGF induces epithelial-mesenchymal transition and cancer stem-like cell properties in human oral cancer cells via promoting Warburg effect", Oncotarget, 8(6):9557-9571, 2017, published online Dec. 1, 2016 (15 pages).

Yang, X. D. et al., "Histamine deficiency promotes inflammation-associated carcinogenesis through reduced myeloid maturation and accumulation of $CD11b^+Ly6G^+$immature myeloid cells", Author manuscript Published in final edited form as: *Nat Med.*, 17(1):87-95, doi:10.1038/nm.2278, Jan. 2011 (29 pages).

Yarwood, R.E. et al., "Endosomal signaling of the receptor for calcitonin gene-related peptide mediates pain transmission", PNAS, 114(46):12309-12314, Nov. 14, 2017 (6 pages).

Yu, T. et al., "Krüppel-like Factor 4 Regulates Intestinal Epithelial Cell Morphology and Polarity", PLoS ONE, 7(2):e32492, published Feb. 24, 2012 (9 pages).

Zahalka, A. et al., "Adrenergic nerves activate an angio-metabolic switch in prostate cancer", Science, 358:321-326, Oct. 20, 2017 (7 pages).

Zhang, N. et al., "Synergistic combination of microtubule targeting anticancer fludelone with cytoprotective panaxytriol derived from panax ginseng against MX-1 cells in vitro: experimental design and data analysis using the combination index method", Am J Cancer Res, 6(1):97-104, 2016 (8 pages).

Zhang, Q.C. et al., "Structure-based prediction of protein-protein interactions on a genome-wide scale", Author manuscript published in final edited form as Nature, 490(7421):556-560, doi:10.1038/nature11503, Oct. 25, 2012 (16 pages).

Zhao, C.-M. et al., "Denervation suppresses gastric tumorigenesis", Author Manuscript published in final edited form as Sci Transl Med, 6(250):250ra115, doi:10.1126/scitranslmed.3009569, Aug. 20, 2014 (25 pages).

Zhong, S. et al., "Lung Tumor Suppressor GPRC5A Binds EGFR and Restrains Its Effector Signaling", Cancer Res, 75(9):1801-1814, published online Mar. 5, 2015 (15 pages).

\* cited by examiner

FIG. 1A
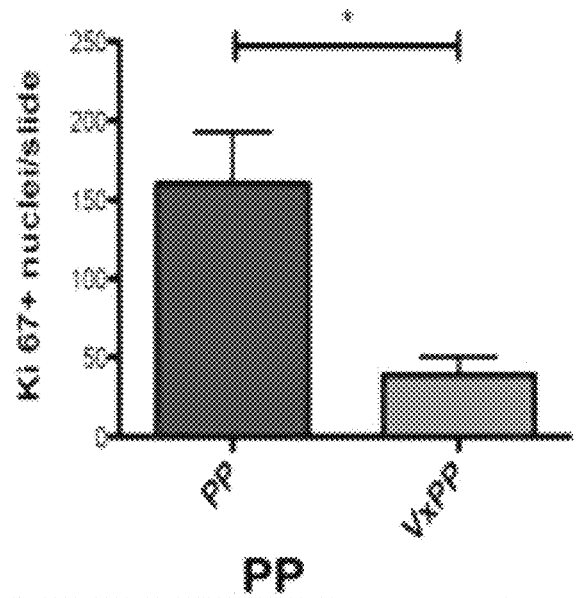
FIG. 1B
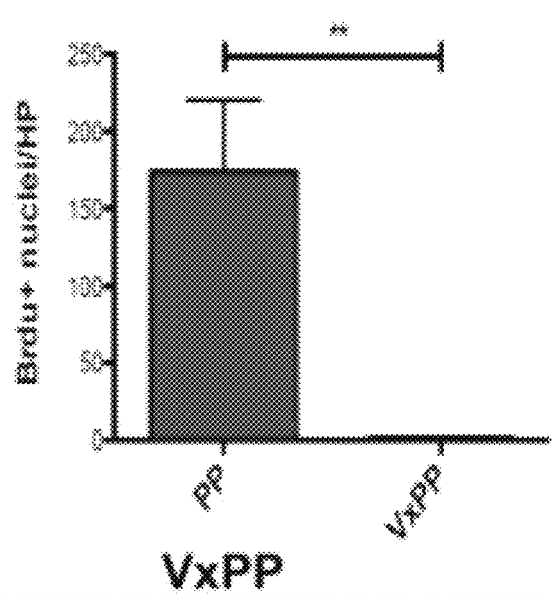
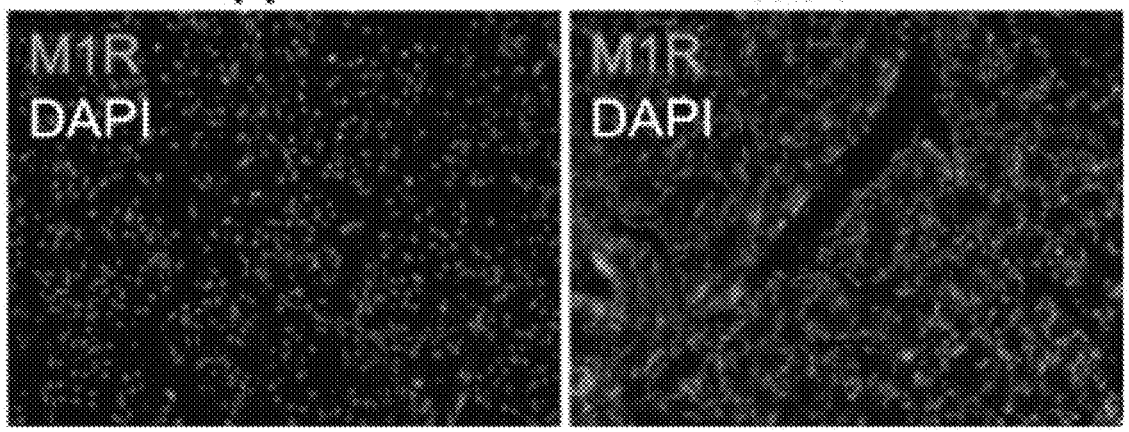
FIG. 1C

FIG. 2A
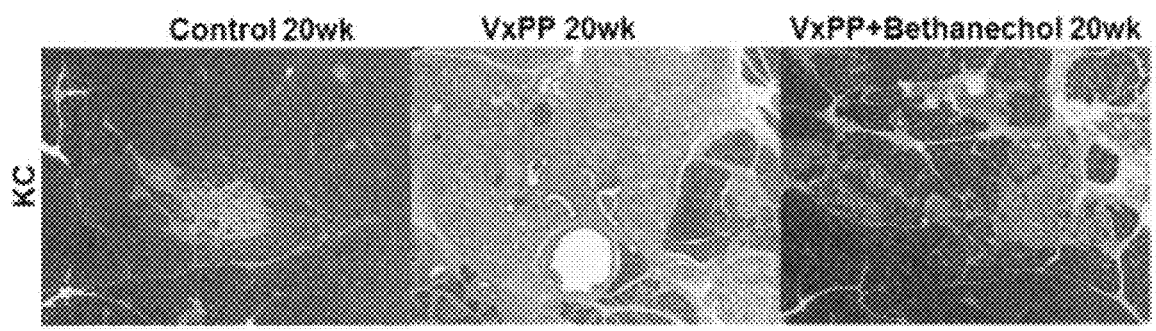
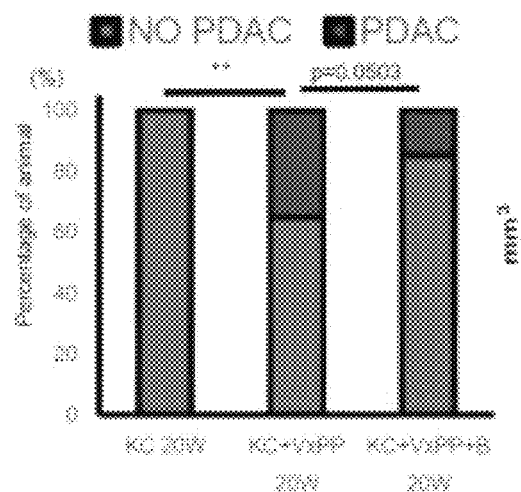
FIG. 2B
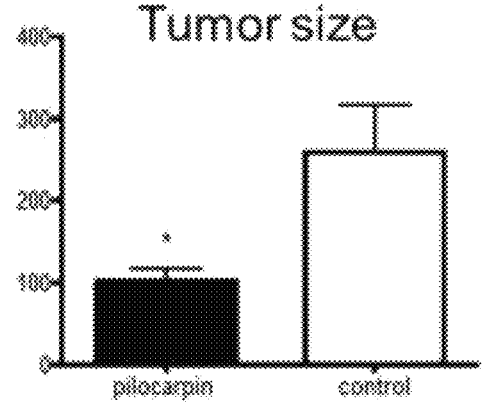
FIG. 2C

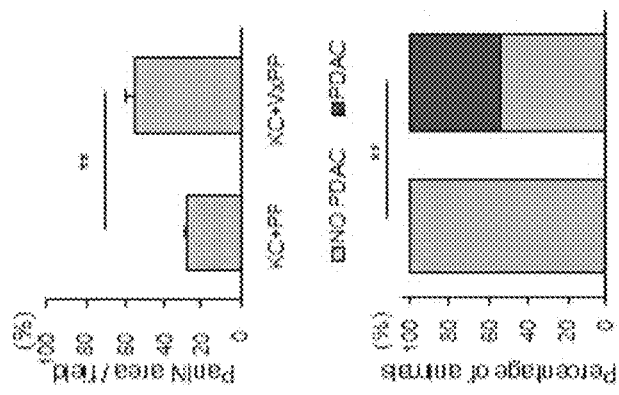
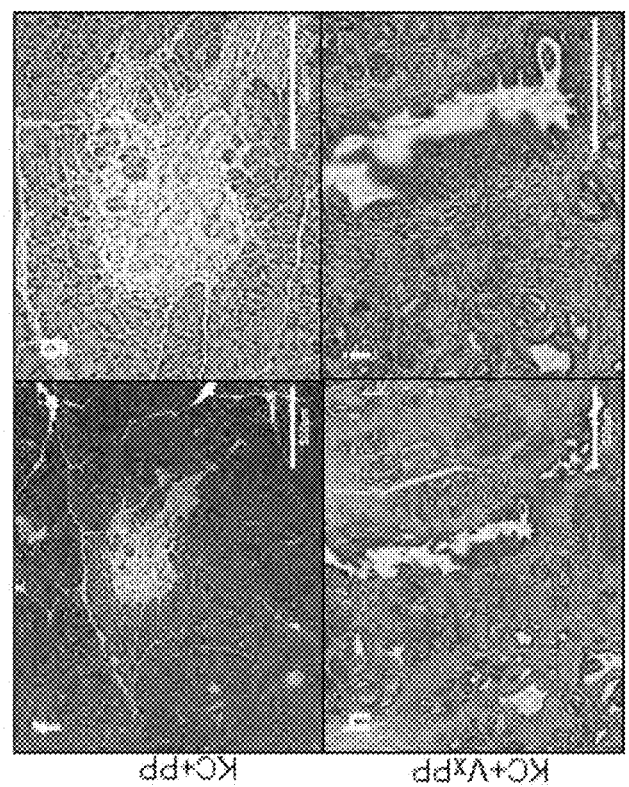
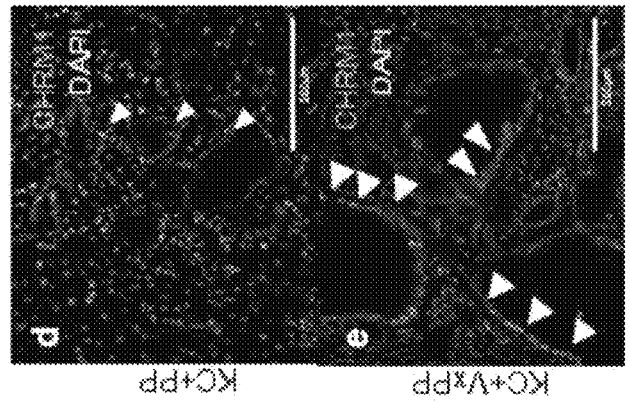

FIG. 8J
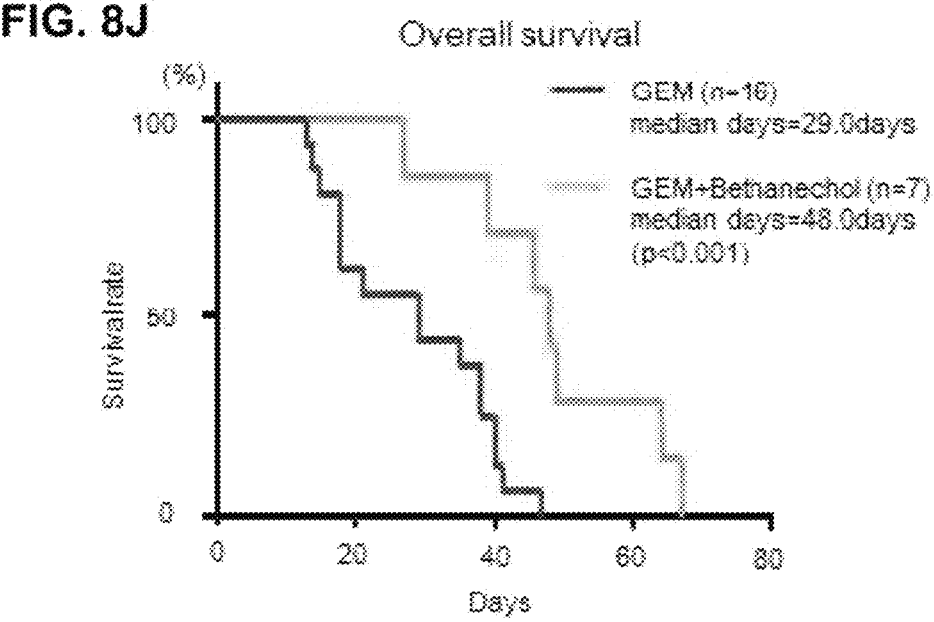
FIG. 8K KPC with GEM
FIG. 8L KPC with GEM+Bethanechol
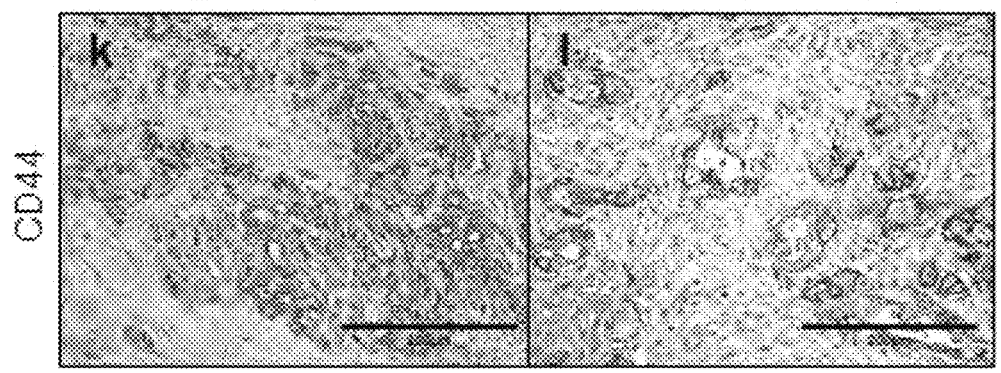
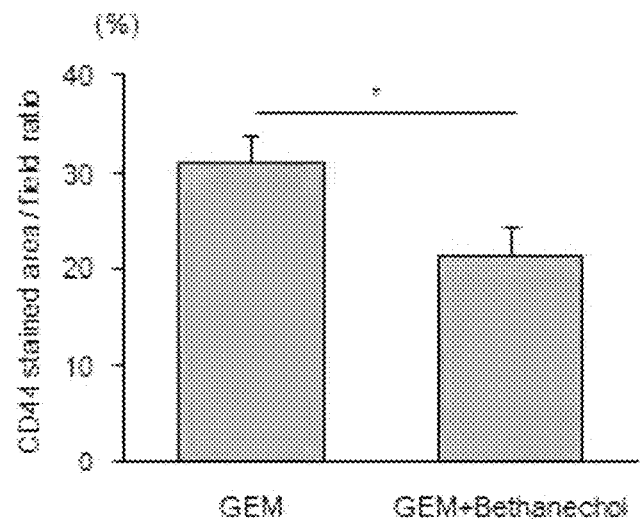
FIG. 8M

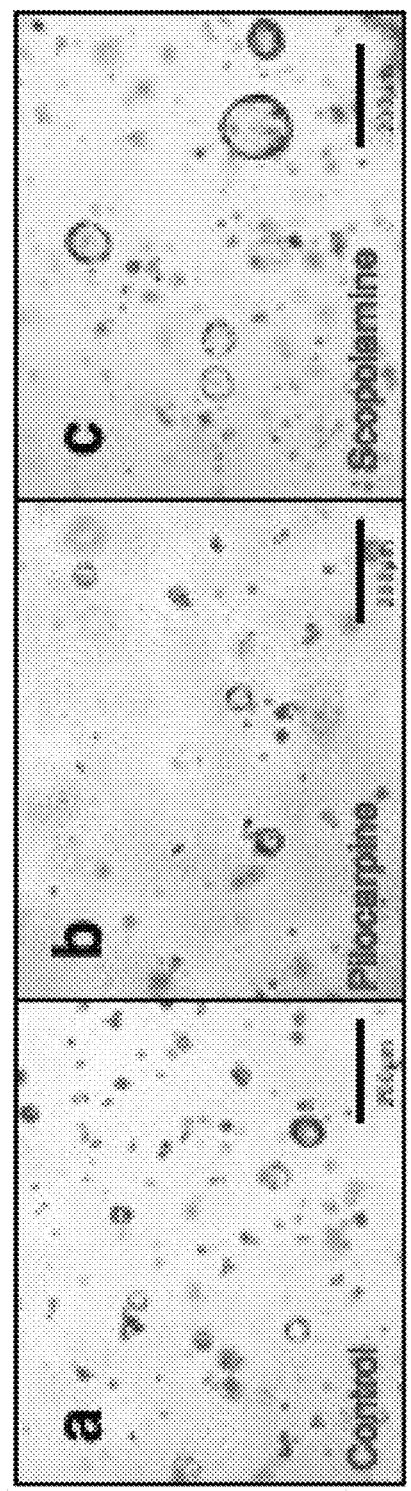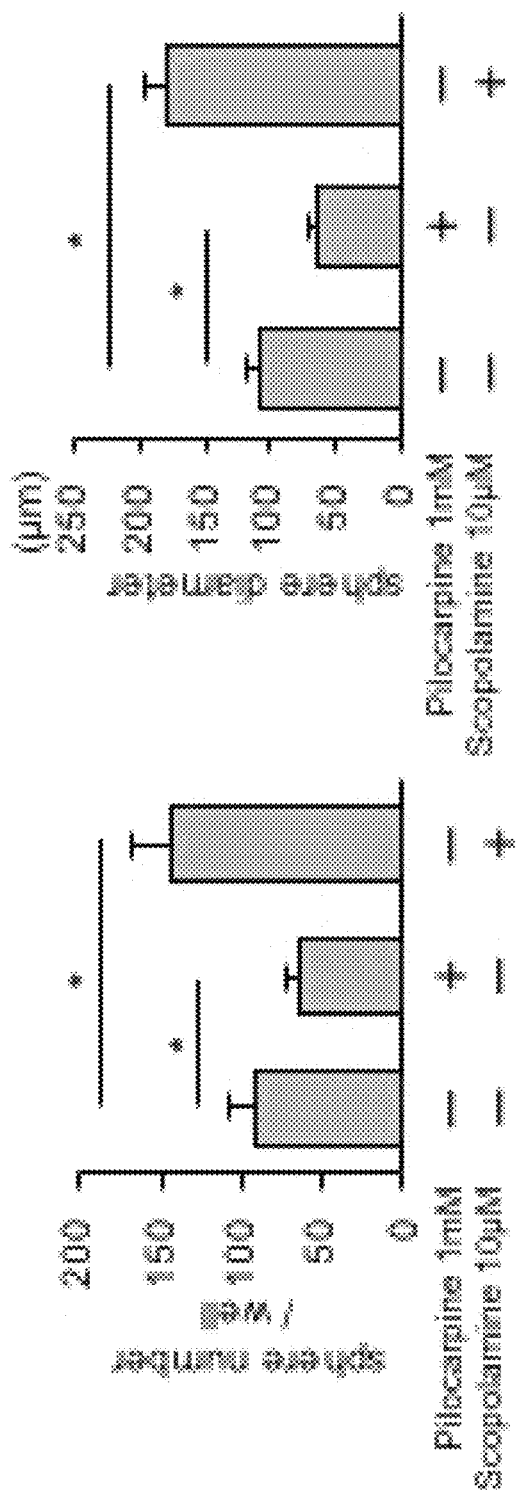

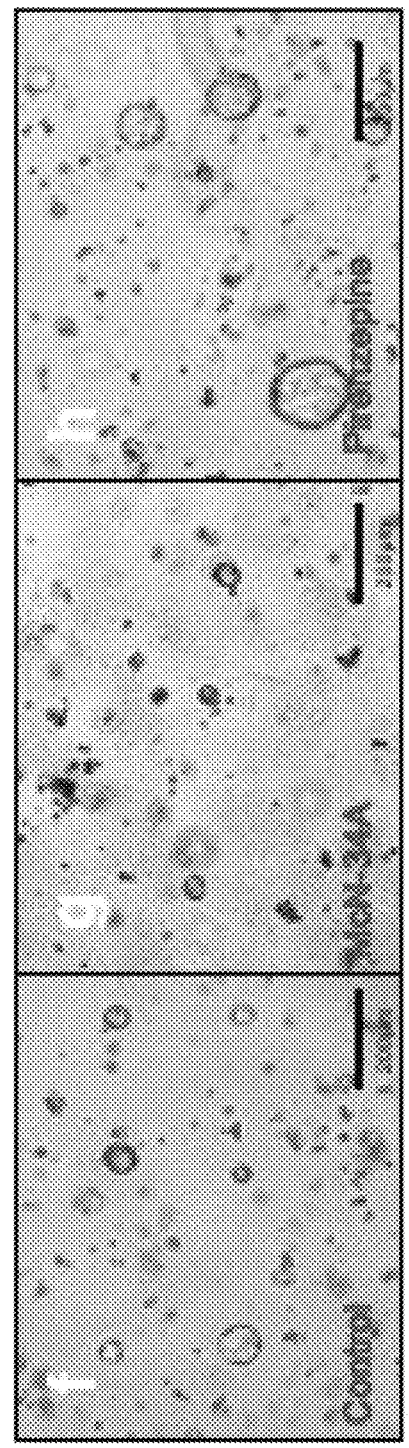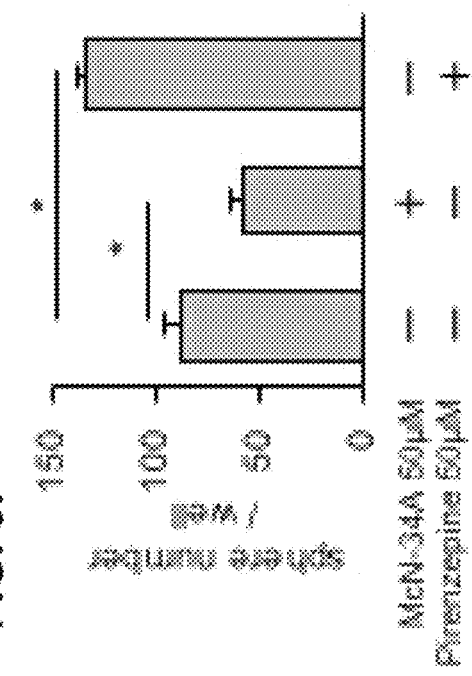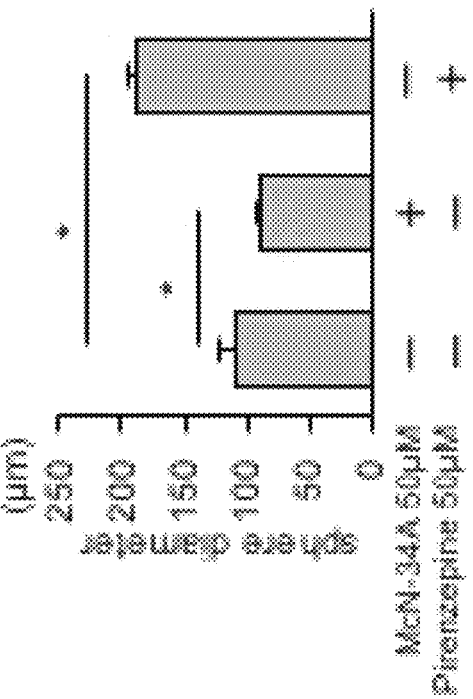

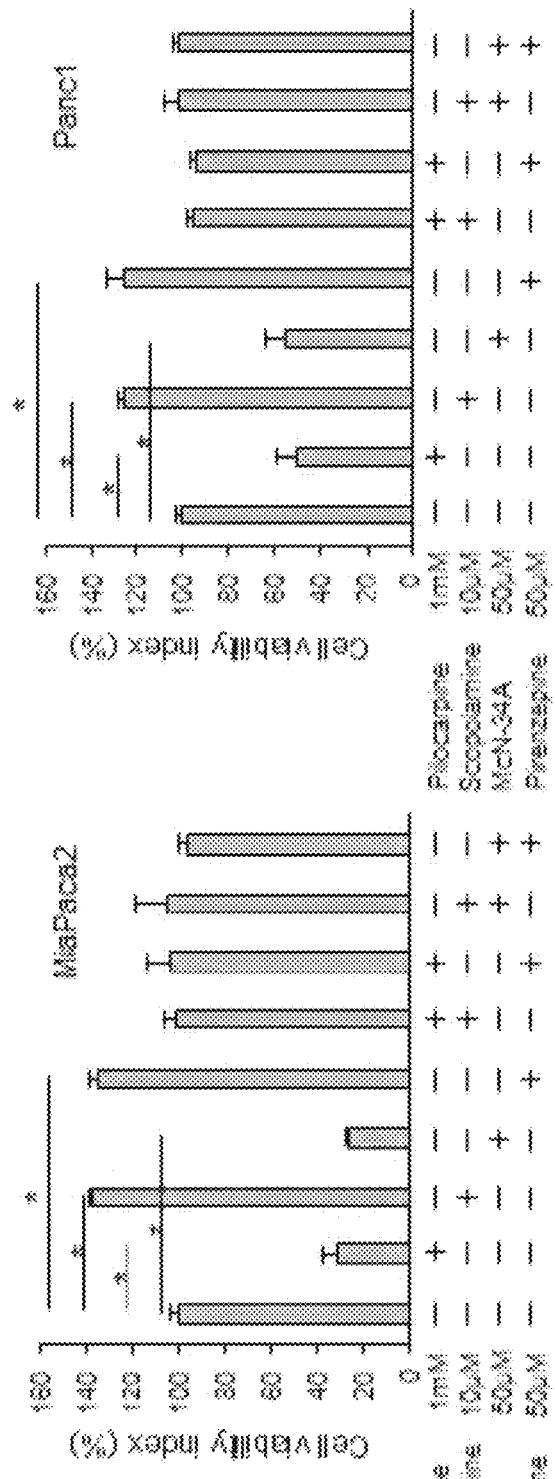
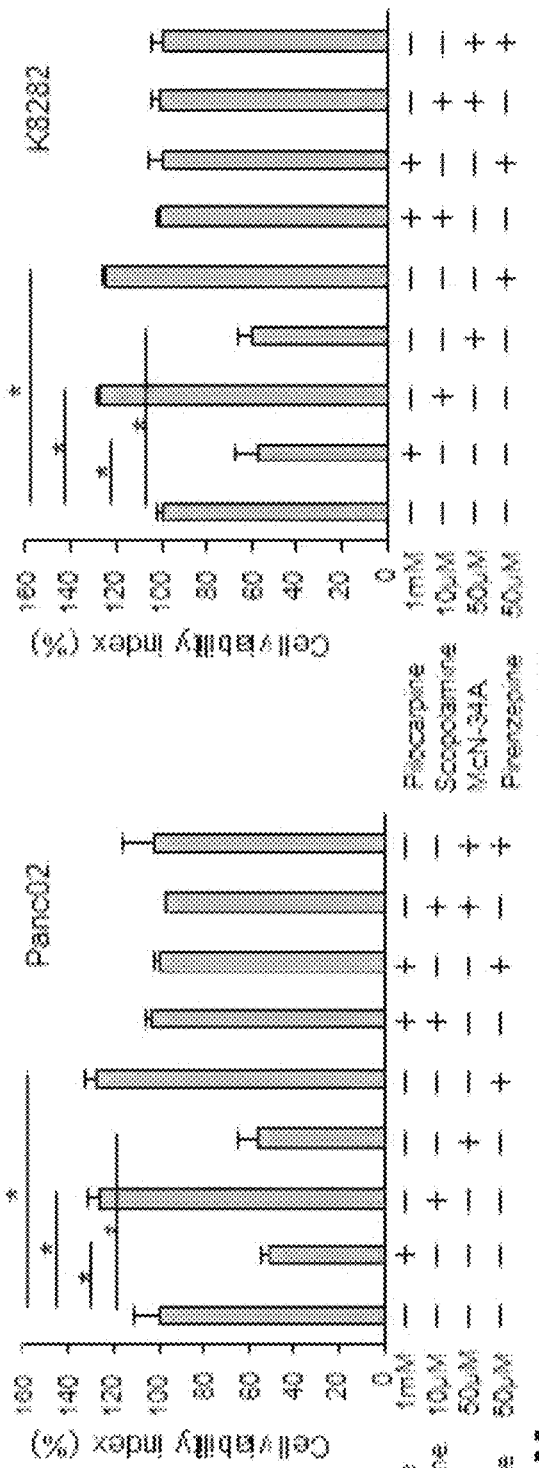
FIG. 9K  FIG. 9L  FIG. 9M  FIG. 9N

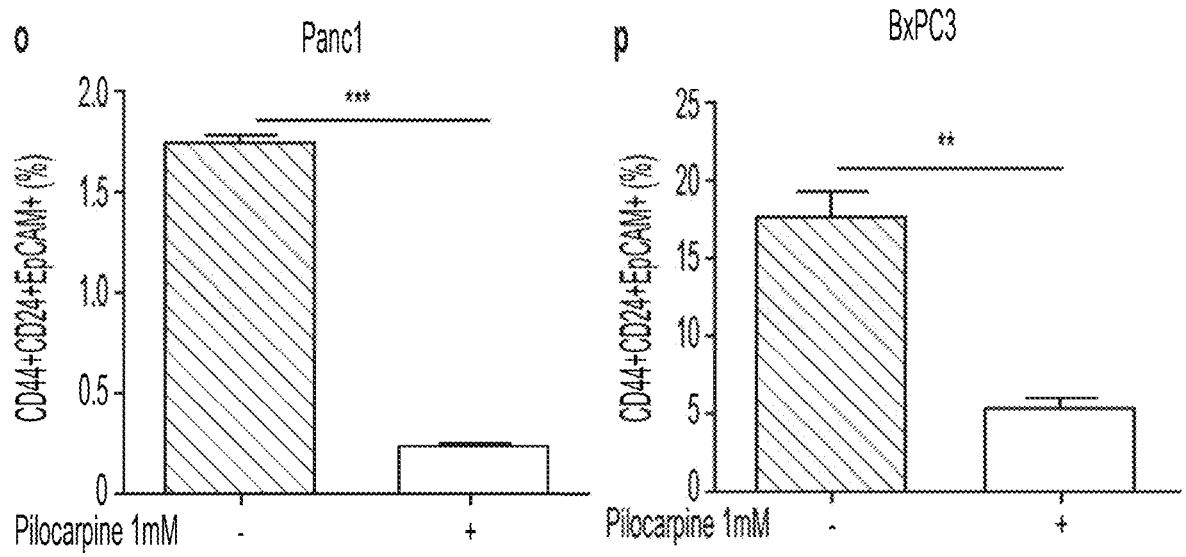
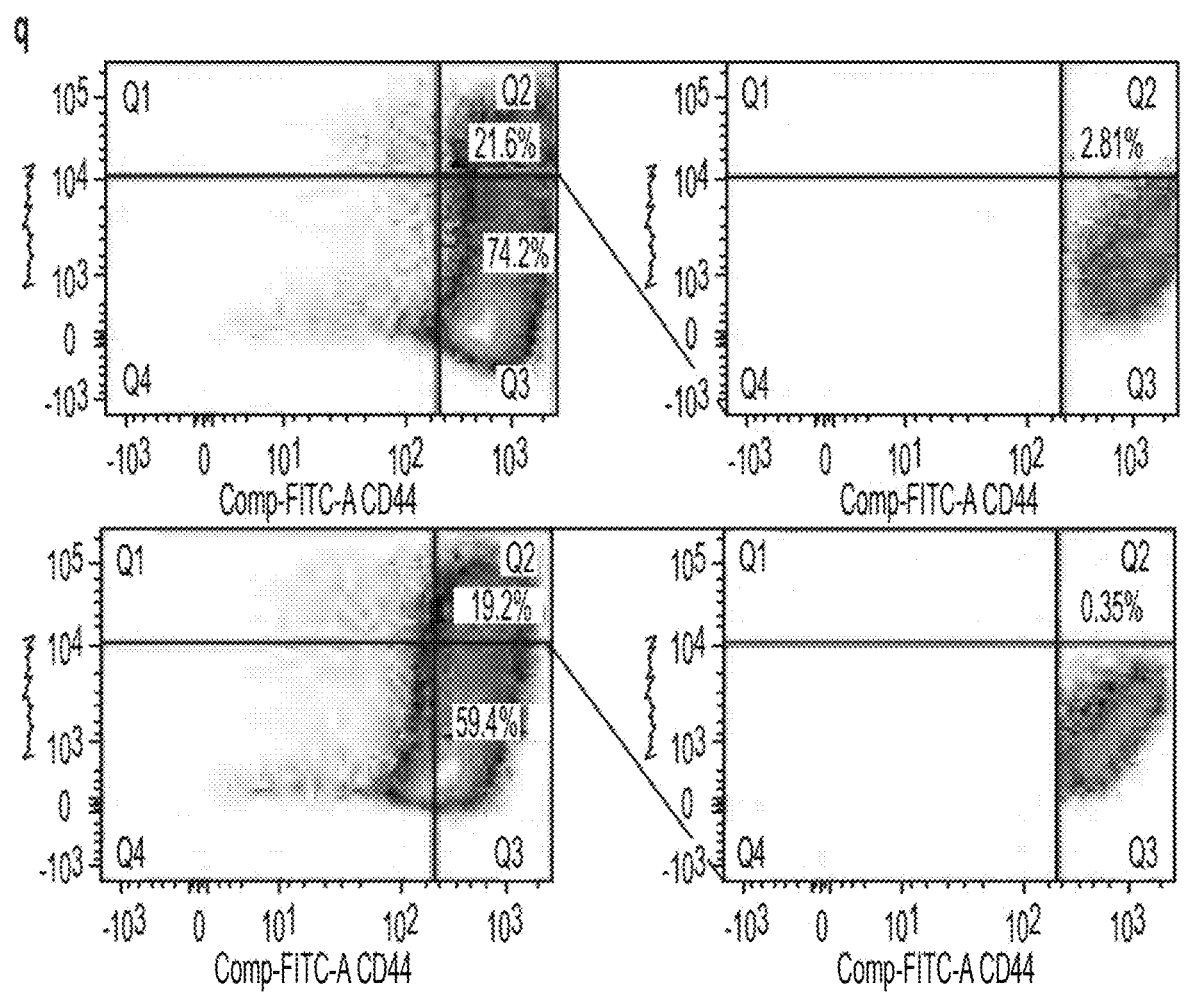
FIGS. 9O-9Q

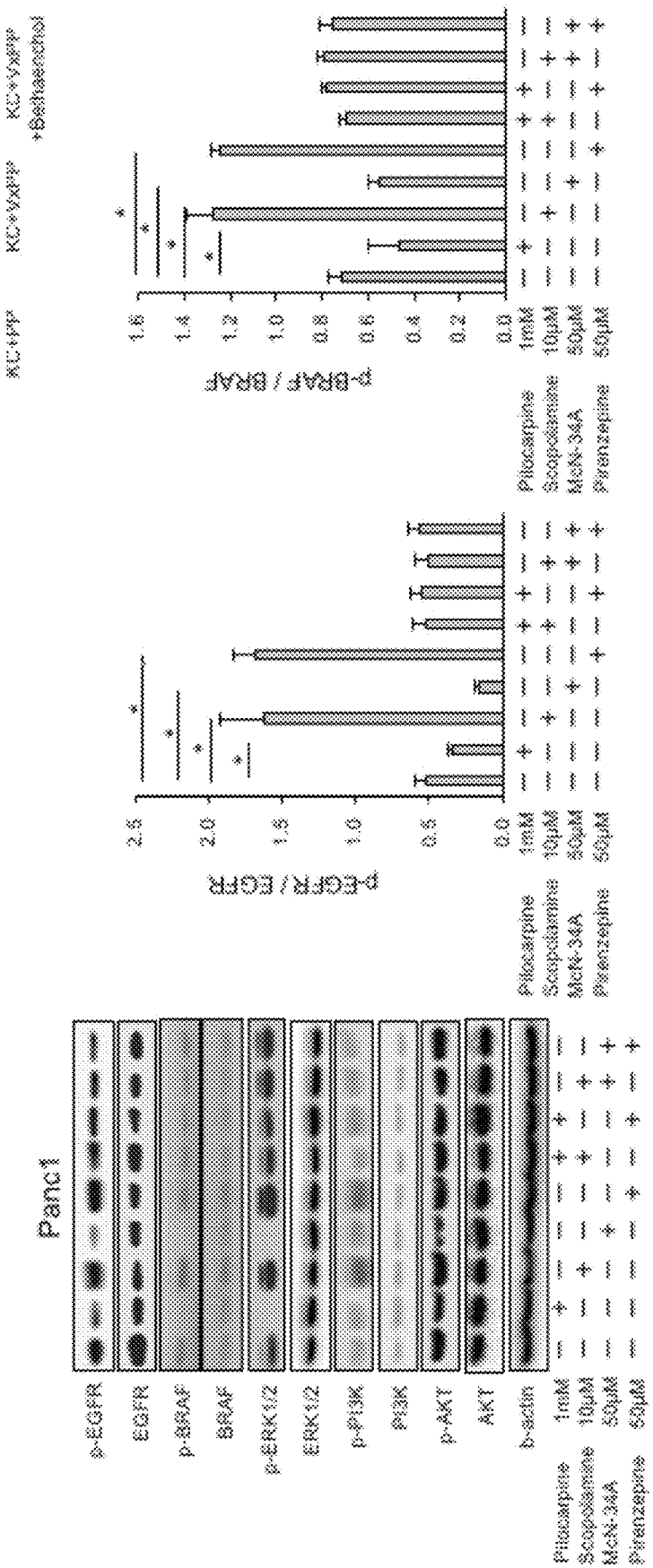

FIG. 11A
FIG. 11C
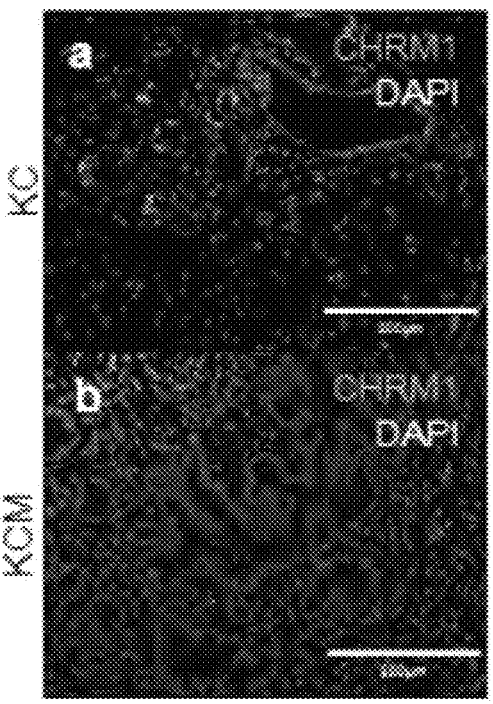
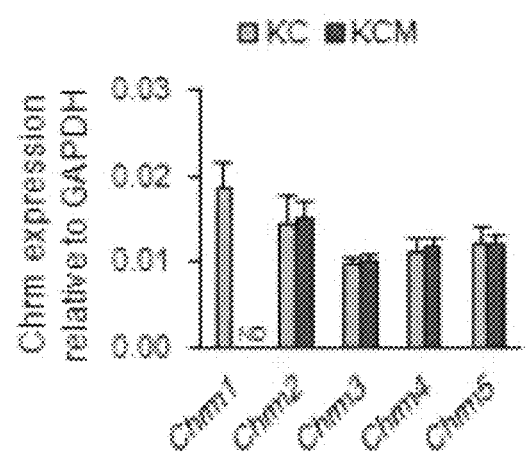
FIG. 11B
FIG. 11E
FIG. 11D
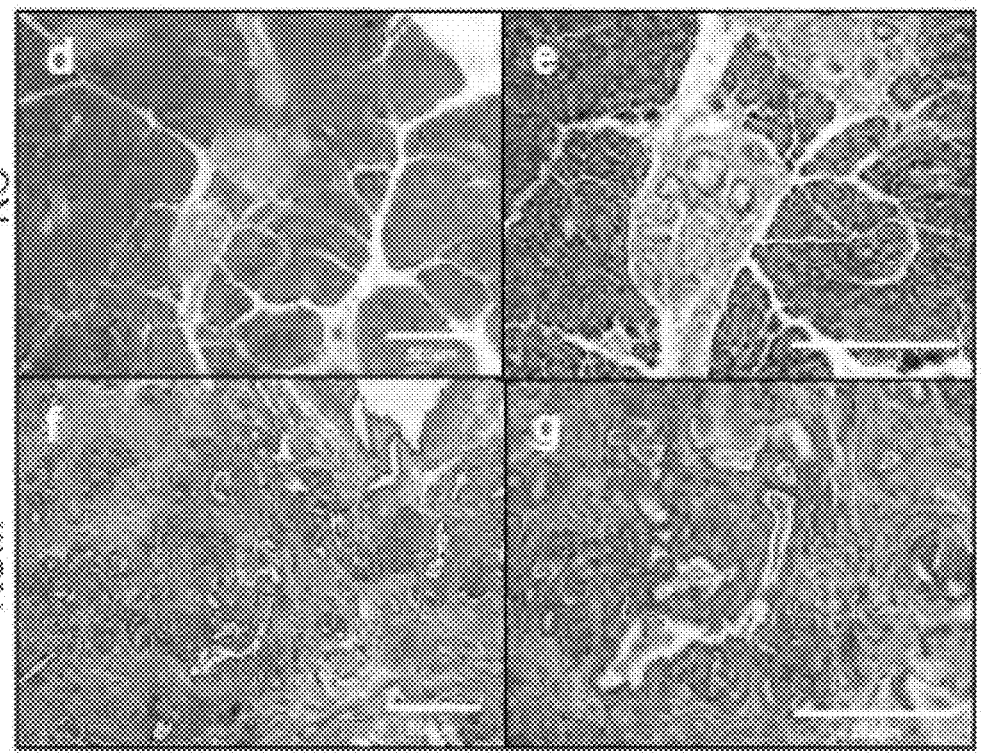
FIG. 11F  FIG. 11G

FIG. 13H
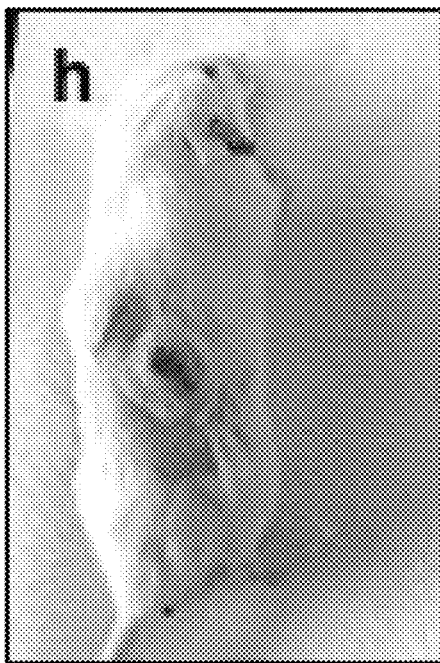
FIG. 13I
FIG. 13J
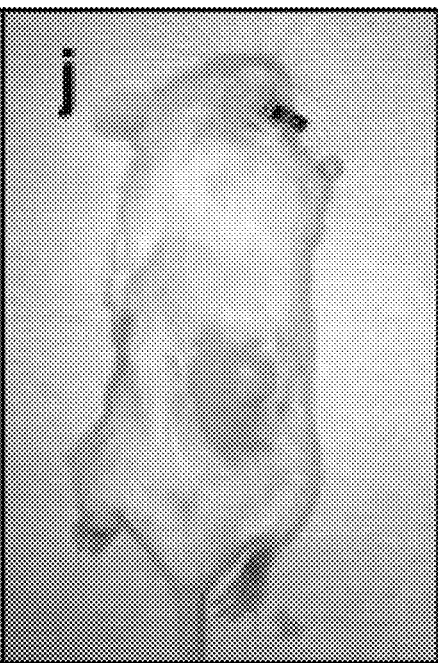
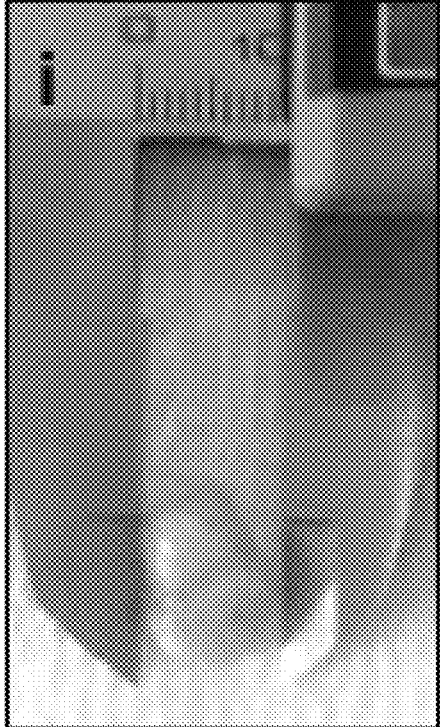
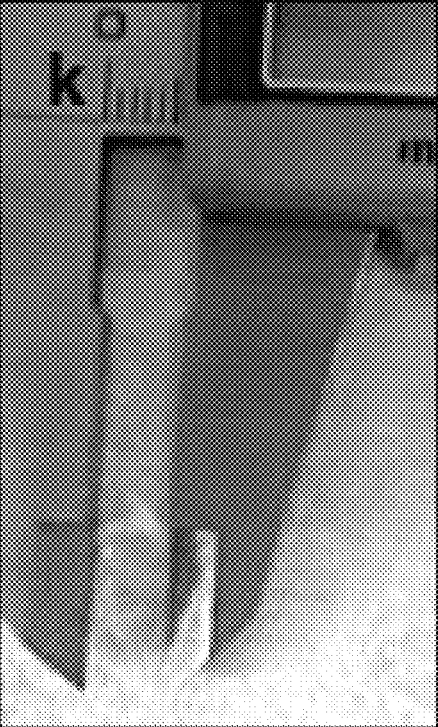
FIG. 13K

| | SYMBOL | ENTREZID | log₂FC | FC(Ratio) | P.Value | fdr |
|---|---|---|---|---|---|---|
| 1 | KDR(RTK) | 3791 | -1.31 | 0.40 | 1.0E-04 | 6.2E-04 |
| 2 | NTRK2(TRKB) | 4915 | -1.18 | 0.44 | 3.39E-05 | 3.32E-04 |
| 3 | EGFR | 1956 | -1.06 | 0.48 | 6.2E-06 | 4.1E-04 |
| 4 | ITGAV(ITGA) | 3685 | -0.73 | 0.60 | 4.2E-05 | 3.7E-04 |
| 5 | BRAF(RafB) | 673 | -0.65 | 0.64 | 6.6E-04 | 2.3E-03 |
| 6 | PIK3CA(PI3K) | 5290 | -0.63 | 0.64 | 8.4E-05 | 5.4E-04 |

FIG. 14A

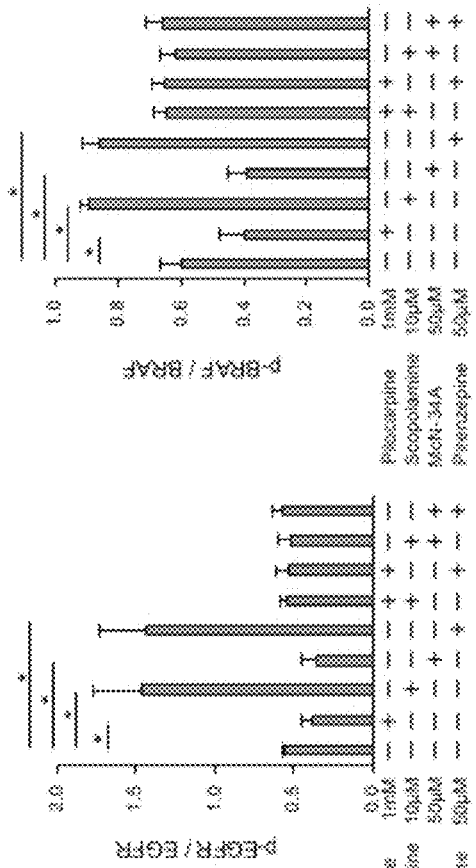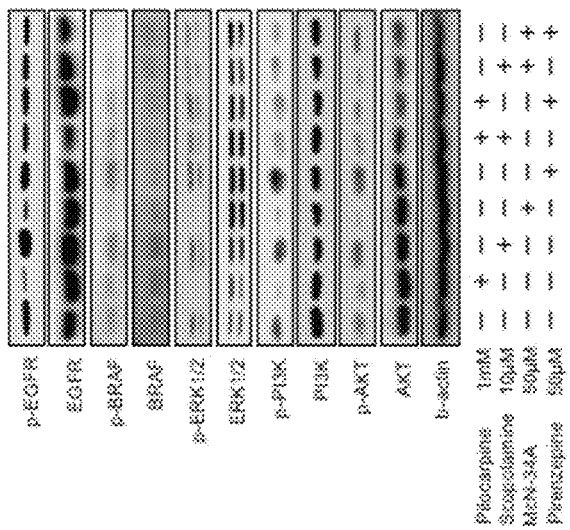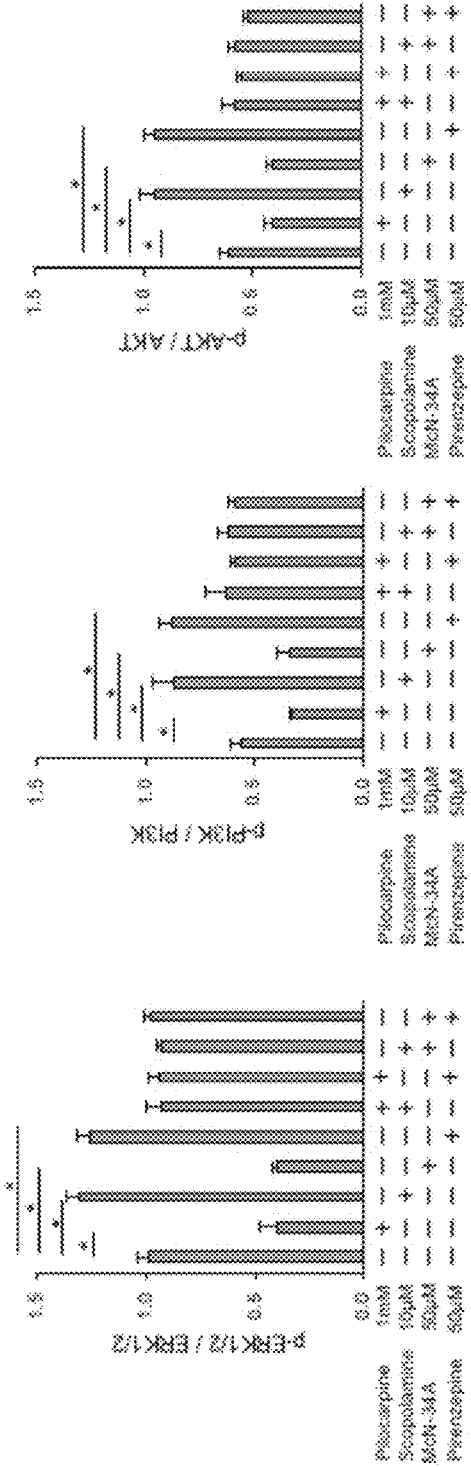
FIG. 15J  FIG. 15K  FIG. 15L  FIG. 15M  FIG. 15N  FIG. 15O

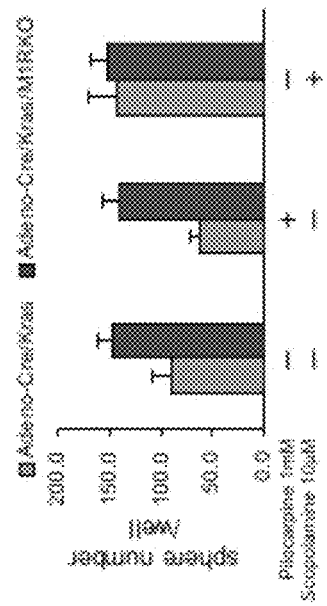
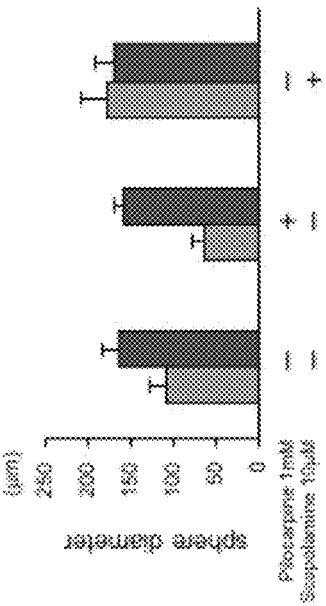
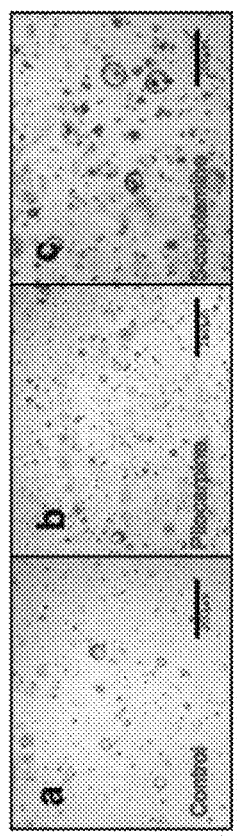
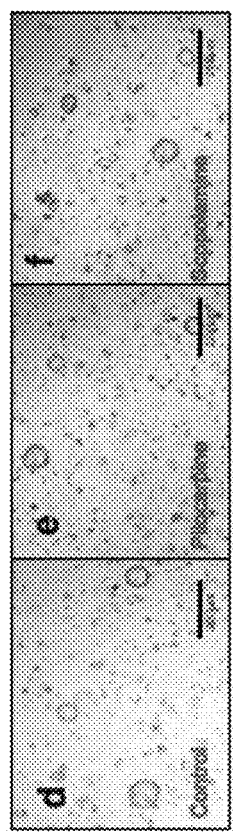

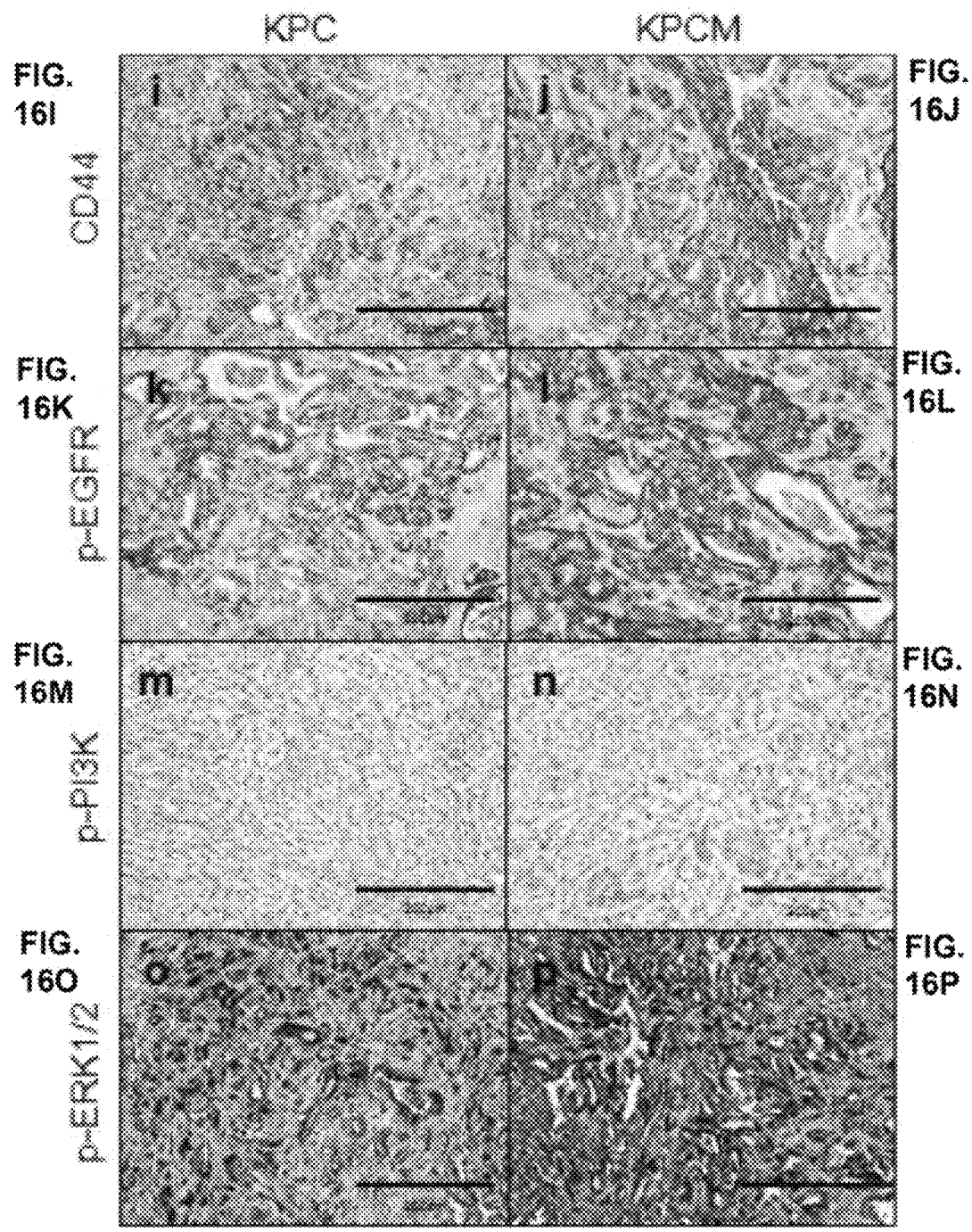

SEQUENCE LISTING

```
<160> NUMBER OF SEQ ID NOS: 24

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cagaagtggt gatcaagatg cctat                                           25

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tggagcacaa caagatccag aat                                             23

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 3
ccagttggtg tgttcttcct t                                              21

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gtgactgcca tcgagatcgt ac                                             22

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggcccagaga gaacggaac                                                 19

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tcattgtcat accaggaaat gag                                            23

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gagcttttgg gaggctgctt                                                20

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cccctgaacg cagttttca                                                 19

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 9
aggaagagct gatgttggga                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
caaactttcg ggccacattg                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ttcccgttgt tgaggtgctt                                              20

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
agaaacctgc caagtatgat gac                                          23

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ttcctcaggg gaaagtcatc                                              20

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tgcgttctct aatcagtagc ca                                           22

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
```
ggcctgtgcc gatctgatta t                                              21

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
agattgtgac gaagcagaca ggca                                           24

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gaccaacaat ggctgtcaca aggt                                           24

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ccccatggtg tctgagcg                                                  18

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gtgtttgggt ccctggaga                                                 19

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cttcaagcct ccaccacctc                                                20

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21

```
cggcctcgtg atggaaaag                                                    19

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tttaaaggtg gcgttgcaca gagc                                              24

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tctgttgcag agggcatagc agat                                              24

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cgacagtcag ccgcatctt                                                    19
```

CHOLINERGIC AGONISM FOR THE TREATMENT OF PANCREATIC CANCER

This application is a continuation-in-part of International Application No. PCT/US2018/039606, filed on Jun. 26, 2018, which claims the benefit of and priority to U.S. Provisional Patent Application No. 62/525,052, filed on Jun. 26, 2017, the content of each of which are hereby incorporated by reference in their entirety.

All patents, patent applications and publications cited herein are hereby incorporated by reference in their entirety. The disclosure of these publications in their entireties are hereby incorporated by reference into this application.

GOVERNMENT SUPPORT

This invention was made with government support under Grant No. DK097016 awarded by the National Institutes of Health. The Government has certain rights in the invention.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

SEQUENCE LISTING

The instant application contains a sequence listing which has been submitted electronically in ASCII format and is hereby incorporated by reference in its entirety. Said ASCII copy, created on Mar. 17, 2020, is named 0019240_01127US2_SL.txt and is 5,790 bytes in size.

BACKGROUND OF THE INVENTION

The treatment of patients with pancreatic cancer remains a formidable challenge, and therapies in the past have employed multiple cytotoxic drugs (standard chemotherapy) with significant toxicity. These drugs usually fail to achieve long-term survival, and recent studies have shown that this is due in part to contributions by the abundant surrounding cells, the stroma, that helps sustain the tumor. There is a continuing need for novel treatments for cancers, including pancreatic cancers.

SUMMARY OF THE INVENTION

In certain aspects, the invention provides a method for treating pancreatic cancer in a subject in need thereof, the method comprising administering to the subject a cholinergic agonist. In some embodiments, the method further comprises performing surgery and/or administering chemotherapy in combination with the cholinergic agonist.

In certain aspects, the invention provides a method for reducing proliferation of pancreatic tumor cells, the method comprising administering a cholinergic agonist. In some embodiments, the method further comprises performing surgery and/or administering chemotherapy in combination with the cholinergic agonist.

In certain aspects, the invention provides a method for inhibiting proliferation of pancreatic tumor cells, the method comprising administering a cholinergic agonist. In some embodiments, the method further comprises performing surgery and/or administering chemotherapy in combination with the cholinergic agonist.

In certain aspects, the invention provides a method of treating pancreatic cancer metastasis, the method comprising administering a cholinergic agonist. In some embodiments, the method further comprises performing surgery and/or administering chemotherapy in combination with the cholinergic agonist.

In certain aspects, the invention provides a method for inhibiting pancreatic cancer metastasis, the method comprising administering a cholinergic agonist. In some embodiments, the method further comprises performing surgery and/or administering chemotherapy in combination with the cholinergic agonist.

In certain aspects, the invention provides a method for treating pancreatic tumor reoccurrence in a subject in need thereof, the method comprising administering to the subject a cholinergic agonist. In some embodiments, the method further comprises performing surgery and/or administering chemotherapy in combination with the cholinergic agonist.

In certain aspects, the invention provides a method for inhibiting the growth of pancreatic cancer stem cells, the method comprising administering a cholinergic agonist. In some embodiments, the method further comprises performing surgery and/or administering chemotherapy in combination with the cholinergic agonist.

In some embodiments, the surgery is surgical removal or resection of the pancreatic tumor. In some embodiments, the surgery is a partial resection of the pancreatic tumor. In some embodiments, the surgery is a Whipple procedure. In some embodiments, the surgery is a distal pancreatectomy.

In some embodiments, the chemotherapy comprises administration of gemcitabine, fluorouracil (5-FU), erlotinib, FOLFIRINOX (a combination of folinic acid, 5-FU, irinotecan, and oxaliplatin), nab-paclitaxel, or a combination thereof. In some embodiments, the chemotherapy comprises administration of gemcitabine in combination with erlotinib, FOLFIRINOX, or nab-paclitaxel. In some embodiments, neoadjuvant chemotherapy or chemoradiotherapy is administered prior to surgery and/or treatment with the cholinergic agonist.

In some embodiments, the pancreatic cancer or tumor cells are pancreatic adenocarcinoma (PDAC). In some embodiments, the pancreatic cancer or tumor cells also includes but not limited to acinar cell carcinoma of the pancreas, cystadenocarcinoma, pancreatoblastoma, pancreatic mucinous cystic neoplasms, other pancreatic exocrine cancers (e.g. adenosquamous carcinomas, signet ring cell carcinomas, hepatoid carcinomas, colloid carcinomas, undifferentiated carcinomas, and undifferentiated carcinomas with osteoclast-like giant cells, solid pseudopapillary tumor), and pancreatic neuroendocrine tumors. In some embodiments, the pancreatic adenocarcinoma is a Stage 1 or Stage 2A PDAC. In some embodiments, the pancreatic cancer or tumor cells or metastases have a mutation in KRAS. In some embodiments, the pancreatic cancer metastasis can be to lymph nodes, liver, peritoneal cavity, large intestine, or lungs.

In some embodiments, the cholinergic agonist is a small molecule. In some embodiments, the cholinergic agonist is a muscarinic receptor agonist. In some embodiments, the cholinergic agonist is bethanechol. In some embodiments, the cholinergic agonist is a cholinergic muscarinic receptor 3 (CHRM3; referred to as "M3") agonist. In some embodiments, the cholinergic agonist is a cholinergic muscarinic receptor 1 (CHRM1; referred to as "M1") agonist. In some embodiments, the M1 agonist is McN-34A. In some embodiments, the cholinergic agonist is a non-selective muscarinic agonist. In some embodiments, the non-selective muscarinic agonist is pilocarpine. In some embodiments, the cholingeric agonist increases ACh signalling. In some embodiments, the cholinergic agonist is a cholinergic analog.

In some embodiments, the method further comprises administering a cytotoxic therapy. In some embodiments, the cholinergic agonist, is administered before, during, or after the administration of the cytotoxic therapy. In some embodiments, the cytotoxic therapy is radiotherapy or chemotherapy (e.g. gemcitabine).

In some embodiments, the method further comprises performing a resection surgery, Whipple or distal pancreatectomy. In some embodiments, the cholinergic agonist is administered before, during, or after the resection surgery, Whipple or distal pancreatectomy is performed.

In certain aspects, the invention provides a method for treating pancreatic cancer in a subject in need thereof, the method comprising administering to the subject a therapeutically effective amount of McN-34A to the subject in need thereof.

In certain aspects, the invention provides a method for treating pancreatic cancer in a subject in need thereof, the method comprising administering to the subject a therapeutically effective amount of pilocarpine to the subject in need thereof.

In certain aspects, the invention provides a method for treating pancreatic cancer in a subject in need thereof, the method comprising administering to the subject a therapeutically effective amount of bethanechol to the subject in need thereof.

BRIEF DESCRIPTION OF THE FIGURES

The patent or application file contains at least one drawing executed in color. Copies of this patent or patent application publication with color drawing(s) will be provided by the United States Patent and Trademark Office upon request and payment of the necessary fee.

FIGS. 1A-C: A-B. Quantification of Ki67 (A) and Brdu (B) of the pancreas in WT mice with Vagotomy+pylroplasty (VxPP) or pylroplasty (PP) alone. C. Immunostaining of M1R.

FIGS. 2A-F: A. Representative H&E images of the pancreas from KC mice subjected to VxPP, VxPP+Bethanechol treatment or not (control). B. Incidences of PDAC in KC mice with or without VxPP and/or Bethanechol. C. Tumor burden (sizes) of NOD SCID mice engrafted SQ with 25,000 Panc1 cells. D. Quantification of spheres from Panc1 cells treated with cholinergic receptor antagonist and/or agonist. E. Stem cell population from Panc-1 cells with or without Pilocarpine treatment analyzed by FACS. F. Survival analysis of KPC mice receiving Bethanechol+GEM or GEM alone. Enrolled mice harboring 3-4 cm tumors are confirmed by 3D Ultrasound.

FIG. 6A shows Ki67 staining of Panc02 liver mets with or without bethanechol treatment. FIG. 6B shows quantitation of Panc02 liver mets with or without bethanechol treatment.

FIG. 7A, Experimental set up for the studies depicted in FIGS. 7B-N: KC mice were randomized to receive vagotomy and pyloroplasty (KC+VxPP) (n=12) or only pyloroplasty (KC+PP) (n=10), which were performed at 8 weeks. Mice were sacrificed and analyzed at 20 weeks. FIG. 7D, Representative image of CHRM1 immunostaining of pancreata from KC+PP at 20 weeks. White arrowheads indicate positive cells in PanIN lesions. FIG. 7E, Representative image of CHRM1 slides from KC+VxPP at 20 weeks showing more positive cells compared to KC+PP. FIGS. 7F, G, Representative images of H&E stained pancreatic sections from KC+PP mice at 20 weeks showing low grade PanIN lesions in low and high magnification. FIGS. 7H, I, Representative images of H&E stained pancreatic sections from KC+VxPP mice at 20 weeks showing murine pancreatic cancer in low and high magnification. FIG. 7J. Percentage of PanIN area in higher power fields in KC+VxPP mice and KC+PP mice at 20 weeks (p<0.01). FIG. 7K, Percentage of KC+VxPP mice compared to KC+PP mice that developed pancreatic cancer at 20 weeks (p<0.05). FIG. 7N, Quantitative analysis of CD44+ stained area in KC+PP mice compared to KC+VxPP mice, which developed pancreatic cancer at 20 weeks (p<0.05). Scale bars, 500 μm (FIGS. 7F, H) and 200 μm (remaining images). Means±SEM. *p<0.05; **p<0.01.

FIGS. 8A-M show that parasympathetic stimulation suppresses pancreatic tumorigenesis and extends overall survival in KPC mice. FIG. 8A, Experimental set up for the studies depicted in FIGS. 8B-H: KC mice underwent vagotomy and pyloroplasty (KC+VxPP) at 8 weeks and were subsequently treated with bethanechol in the drinking water (400 μg/ml) (KC+VxPP+bethanechol) (n=13) or water without bethanechol (n=12). Mice were sacrificed and analyzed at 20 weeks. FIGS. 8B, C, Representative images of H&E stained pancreatic sections from KC+VxPP mice and KC+VxPP+bethanechol mice at 20 weeks. FIG. 8D, Quantification of PanIN area per high power field in KC+VxPP mice and KC+VxPP+bethanechol mice at 20 weeks (p<0.01). FIG. 8E, Percentage of KC+VxPP compared to KC+VxPP+bethanechol mice with pancreatic ductal adenocarcinoma (p<0.05). FIGS. 8F, G. Representative images of CD44+ immunostained pancreatic sections from KC+VxPP and KC+VxPP+bethanechol at 20 weeks. FIG. 8H, Quantitative analysis of CD44 stained area in KC+VxPP+bethanechol mice compared to KC+VxPP mice with pancreatic cancer at 20 weeks (p<0.05). FIG. 8I, Experimental set up for the studies depicted in FIGS. 8J-8M: LSL-Kras$^{G12D}$/LSL-Trp53$^{R172H}$/Pdx1-Cre (KPC) mice were enrolled with tumors of 5-6 mm, confirmed by high resolution ultrasound, and treated gemcitabine (GEM) (100 mg/kg) biweekly (n=15) or GEM and bethanechol in the drinking water (400 μg/ml) (n=10) until they became moribund and needed to be sacrificed. FIG. 8J, Kaplan-Meier curve comparing overall survival after enrollment of control (GEM only) and treatment group (GEM and bethanechol) (p<0.001). FIGS. 8K, L, Representative images of pancreatic sections from mice stained for CD44 in KPC+GEM and KPC+GEM+bethanechol groups at the time of necrospy.

FIG. 8M, Quantitative analysis of CD44$^+$ stained area in KPC+GEM compared to KPC+GEM+bethanechol (p<0.05). Scale bars, 200 μm. Means±SEM. *p<0.05; p<0.01; * p<0.001.

FIGS. 9A-Q show that parasympathetic signaling directly promotes cell proliferation in Kras mutant spheres via CHRM1 and regulates cancer stemness. Representative photographs of spheres isolated from LSL-Kras$^{+/G12D}$ mice and treated (FIG. 9A) only with Adeno-Cre virus or (FIG. 9B) Adeno-Cre virus and pilocarpine or (FIG. 9C) Adeno-Cre virus and scopolamine. All sphere cultures were analyzed at day 5-post plating. (FIGS. 9D, E) Number and size of spheres isolated from LSL-Kras$^{+/G12D}$ mice cultured in the presence of Adeno-Cre virus and then untreated, treated with pilocarpine, or treated with scopolamine (n=3). FIGS. 9F-G, Representative images of spheres isolated from LSL-Kras$^{+/G12D}$ mice and treated with (FIG. 9F) Adeno-Cre virus or (FIG. 9G) Adeno-Cre virus and McN-34A (CHRM1 selective agonist) or (FIG. 9H) Adeno-Cre virus and pirenzepine (CHRM1 selective antagonist). All sphere cultures were analyzed at day 5 post plating. FIGS. 9I, J, Number and size of spheres isolated from LSL-Kras$^{+/G12D}$ cultured in the presence of Adeno-Cre virus and then untreated, treated with McN-34A, or treated with pirenzepine (n=3). FIGS. 9K, L, MTT assay of MiaPaca2 (FIG. 9K) and Panc1 (FIG. 9L) human PDAC cell lines treated with or without pilocarpine, scopolamine, McN-34A and/or pirenzepine. FIGS. 9M, N, MTT assay of Panc02 (FIG. 9M) and K8282 (FIG. 9N) murine PDAC cell lines, the latter of which was obtained from a KPC tumor. Murine PDAC cell lines were also treated with or without pilocarpine, scopolamine, McN-34A and/or pirenzepine. FIG. 9O, Flow cytometric analysis of CD44$^+$CD24$^+$EpCAM$^+$ cells in human Panc1 cells before and 72 hours after pilocarpine treatment. FIG. 9P, Flow cytometric analysis of CD44$^+$CD24$^+$EpCAM$^+$ cells in murine K8282 cells before and 72 hours after pilocarpine treatment. FIG. 9Q, Representative results from flow cytometric analysis of Panc1 cells for CD44$^+$CD24$^+$EpCAM$^+$ before and 72 hours after pilocarpine treatment. Scale bars, 200 μm. Means±SEM. *p<0.05; **p<0.01.

FIGS. 10A-R show that parasympathetic signaling inhibits downstream EGFR/MAPK and PI3K/AKT signaling in PDAC cells. FIGS. 10A-C, Representative images of immunohistochemical staining of p-EGFR in pancreatic sections from (FIG. 10A) KC+PP mice, (FIG. 10B) KC+VxPP mice, and (FIG. 10C) KC+VxPP+bethanechol mice. FIG. 10D, Quantitative analysis of p-EGFR stained area in pancreatic sections from KC+PP, KC+VxPP, and KC+VxPP+bethanechol mice (p<0.05). FIG. 10M, Western Blot analysis of signaling pathways after no treatment (lane 1) and/or pilocarpine and/or scopolamine and/or McN-34A and/or pirenzepine treatment of Panc1 cells. FIGS. 10N-R, Quantification of densitometry of Western Blots depicted in FIG. 10M for (FIG. 10N) p-EGFR/EGFR, (FIG. 10O) p-BRAF/BRAF, (FIG. 10P) p-ERK1/2/ERK1/2, (FIG. 10Q) p-PI3K/PI3K, and (FIG. 10R) p-AKT/AKT (*p<0.05). Scale bars, 200 μm. Means±SEM. *p<0.05; **p<0.01.

FIGS. 11A-S show that knockout of CHRM1 results in greater PanIN area and tumor incidence in KC mice and shorter overall survival In KPC mice. FIG. 11A, Representative image of CHRM1 immunostaining of pancreatic sections from KC mice at 20 weeks, showing a few positive cells in PanIN lesions. FIG. 11B, Representative image of CHRM1 immunostaining of pancreatic sections from KCM mice at 20 weeks, showing no positive cells in PanINs lesions. FIG. 11C, Fold change (relative to GAPDH) in pancreas mRNA levels of cholinergic muscarinic receptors, Chrm1-Chrm5, in KCM mice compared to KC mice at 20 weeks. FIGS. 11D, E, Representative images of H&E stained pancreatic sections from KC mice at 20 weeks showing low-grade PanIN lesions. FIGS. 11F, G Representative images of H&E stained sections of pancreas sections from KCM mice at 20 weeks showing murine pancreatic cancer in low and high magnification. FIGS. 11J-Q, Representative images of immunohistochemical staining of pancreas sections from KC and KCM mice for (FIGS. 11J, K) CD44, L and M p-EGFR, (FIGS. 11N, O) p-PI3K, and (FIGS. 11P, Q) p-ERK1/2.

FIG. 12A, Experimental set up for the studies depicted in B-S: WT type C57BL/6 mice received splenic injections of 2×10$^6$ GFP-labeled Panc02 cells and were then divided into 3 groups: untreated controls (n=6), bethanechol treated (n=5), and selective liver denervation by transection of the hepatic branch of the vagus (n=8). Mice were observed until they became moribund and needed to be sacrificed. FIG. 12B, Mouse exhibiting massive bloody ascites. FIGS. 12C, D, Cancer cells replaced the normal liver tissue as large pale nodules. FIG. 12T, Schematic model for parasympathetic suppression of PDAC. Parasympathetic signaling via Chrm1 can directly suppress the growth of pancreatic tumor cells through MAPK and PI3K-AKT pathway at both primary and metastatic tumor sites. Scale bars, 200 m. Means±SEM. *p<0.05; **p<0.01.

FIGS. 13A-M show that parasympathetic signaling modulates only CHRM1, and directly regulates cell proliferation in PDAC cell lines and suppresses cancer stemness in NOD/SCID mice. FIGS. 13A-D, Fold change of mRNA levels of muscarinic cholinergic receptors CHRM1-CHRM5 in human MiaPaca2 and Panc1, and Chrm1-Chrm5 in murine Panc02, and K8282 cells treated with pilocarpine or scopolamine, compared with untreated control. FIG. 13E, Representative images of colonies in soft agar from Panc-1 and K8282 cells treated by direct parasympathetic agonists or antagonists at day 14. FIG. 13F, Number of resulting spheroid colonies of human Panc1 cells plated in soft agar at day 14 and treated by direct parasympathetic agonists or antagonists. FIG. 13G, Number of resulting spheroid colonies of murine pancreatic cancer cells (K8282) plated in soft agar at day 14 and treated by direct parasympathetic agonists or antagonists. FIGS. 13H, I, Representative gross images of subcutaneous tumors in NOD/SCID mice 6 weeks after implantation of 25,000 Panc1 cells. FIGS. 13J, K, Representative gross images of subcutaneous tumors in NOD/SCID mice 6 weeks after injection of 25,000 Panc1 cells pretreated for 72 hours with pilocarpine (n=10 each group). FIG. 13L, Percentage of NOD/SCID mice developing tumors 6 weeks after injection of 25,000 injected Panc1 cells with and without pretreatment of pilocarpine (*p<0.05). FIG. 13M, Volume of tumors in NOD/SCID mice 6 weeks after injection of 25,000 implanted Panc1 cells with and without pretreatment of pilocarpine (*p<0.05). Scale bars, 500 µm. Means±SEM. *p<0.05; **p<0.01.

FIGS. 14A-C show key KEGG pathways in RNAseq of Panc1 cells with and without treatment with pilocarpine. FIG. 14A, Table showing changes in expression of proliferation related genes from RNAseq of Panc1 cells after pilocarpine treatment. FIGS. 14B, C. Gene symbols in parenthesis indicate how the gene is represented. $\log_2$FC (Fold change) and fold change are for treated vs untreated. FIG. 14B, PI3-AKT pathway. The expression of PIK3CA (PI3K) is downregulated. PIK3CA(PI3K) is activated by both KDR(RTK) and ITGAV (ITGA), both of which are downregulated, which tends to inhibit PI3KCA on a signaling level as well. Inhibition of PI3KCA leads to reduction of activation of AKT. Since AKT inhibits p21 (CDKN1A) and p27 (CDKN1B), reduction of activation of AKT leads to an increase in activation of these anti-proliferative genes, thereby slowing the cell cycle. FIG. 14C, Classical MAPK signaling pathway. EGFR, NTRKB, and BRAF are all part of a proliferative pathway. Since these genes are downregulated, proliferation is slowed.

FIGS. 15A-O show that parasympathetic signaling inhibits downstream EGFR/MAPK and PI3K/AKT signaling in murine PDAC cells. FIGS. 15A, B, Representative images of immunohistochemical staining of p-EGFR in pancreatic sections from (FIG. 15A) KPC mice treated with GEM (KPC with GEM) and (FIG. 15B) KPC mice treated with GEM and bethanechol (KPC with GEM+bethanechol). FIG. 15C, Quantitative analysis of p-EGFR stained area in pancreatic sections from KPC+GEM and KPC+GEM+bethanechol mice (*p<0.05). FIGS. 15D, E, Representative images of immunohistochemical staining of p-PI3K in pancreatic sections from (FIG. 15D) GEM treated KPC mice and (FIG. 15E) GEM+bethanechol KPC mice. FIG. 15F, Quantitative analysis of p-PI3K stained area in pancreatic sections from GEM treated KPC mice and GEM+bethanechol KPC mice (*p<0.05). FIGS. 15G, H, Representative images of immunohistochemical staining of p-ERK1/2 in (FIG. 15G) GEM treated KPC mice and (FIG. 15H) GEM+bethanechol KPC mice. FIG. 15I, Quantitative analysis of p-ERK1/2 stained area in GEM treated KPC mice and GEM+bethanechol KPC mice (*p<0.05). FIG. 15J, Western Blot analysis of signaling pathways with or without pilocarpine, scopolamine, McN-34A, and/or pirenzepine treatment of K8282 cells. FIGS. 15K-O, Quantification of densitometry of Western Blot depicted in (FIG. 15J) for K p-EGFR/EGFR, (FIG. 15L) p-BRAF/BRAF, (FIG. 15M) p-ERK1/2/ERK1/2, (FIG. 15N) p-PI3K/PI3K, (FIG. 15O) p-AKT/AKT. (*p<0.05). Scale bars, 200 µm. Means±SEM. *p<0.05; **p<0.01.

FIGS. 16A-Q show that parasympathetic signaling directly promotes cell proliferation in Kras mutant spheres via CHRM1. FIGS. 16A-C, Representative images of 3D spheroid cultures, isolated from LSL-Kras$^{+/G12D}$ mice and treated with (FIG. 16A) Adeno-Cre virus alone, or (FIG. 16B) Adeno-Cre virus and pilocarpine, or (FIG. 16C) Adeno-Cre virus and scopolamine. Spheroid cultures were analyzed at day 5 post isolation. FIGS. 16D-F, Representative images of 3D spheroid cultures isolated from LSL-Kras$^{+/G12D}$/Chrm1-KO mice and treated with (FIG. 16D) Adeno-Cre virus alone, or (FIG. 16E) Adeno-Cre virus and pilocarpine, or (FIG. 16F) Adeno-Cre virus and scopolamine. Cultures were analyzed at day 5 post isolation. FIGS. 16G, H, Number and size of spheres isolated from LSL-Kras$^{+/G12D}$ (green) and LSL-Kras$^{+/G12D}$/Chrm1-KO mice (red). FIGS. 16I-P, Representative images of immunofluorescence staining of (FIGS. 16I, J) CD44, (FIGS. 16K, L), p-EGFR, (FIGS. 16M, N) p-PI3K, and (FIGS. 16O, P) p-ERK1/2 in pancreatic sections from KPC and KPCM mice. FIG. 16Q, Quantitative analysis of CD44, p-EGFR, p-PI3K, and p-ERK1/2 stained area in KPC (green) and KPCM (red) mice (*p<0.05, respectively). Scale bars, 200 µm. Means±SEM. *p<0.05; **p<0.01.

FIG. 17A, A left subcostal incision was performed, and the spleen was exposed through the incision. FIG. 17B, the spleen was divided into upper and lower halves by placing two Horizon medium sized clips in the center of the spleen. FIG. 17C, 150 µl of phosphate buffered saline was drawn up into a 27 G×5/8" syringe. 100 µl of Panc02 ($2\times10^6$) cells were also drawn up into the same syringe, and the cells were injected slowly into the exposed lower-hemispleen. FIG. 17D, Lower hemisplenectomy was performed by dividing the splenic vessels distal to the pancreas. FIG. 17E, Anatomical photograph of vagus nerve and hepatic branch (white arrow). FIGS. 17F, G. Representative photographs of (FIG. 17F) H&E labeled sections (scale bar: 500 µm) and (FIG. 17G) GFP-immunofluorescence showing labeled cancer cells in the liver metastases (scale bar: 50 μm). FIG. 17H, Gross image showing representative sizes of liver metastatic nodule in untreated mice.

FIG. 18A, Vagotomy increases and bethanechol inhibits PDA at 20 weeks in KC mice. FIG. 18B, Bethanechol prolongs survival in GEM-treated KPC mice (p=0.002).

FIG. 19A, Suppression of Panc1 cell growth through M1 receptor. FIG. 19B, Number of Kras mutant spheres after treatment with pilocarpine+scopolamine. FIG. 19C, Survival of KPC mice after M1R deletion.

FIG. 20A, Experimental protocol for treatment in Panc02 metastatic model. FIG. 20B, Gross image of Panc02 liver metastasis at 3 weeks. FIG. 20C, Survival curves showing effects of vagotomy and bethanechol (*p<0.05;***p<0.001). FIGS. 20D,E. Effect of vagotomy and bethanechol on tumor number (D) and maximum tumor volume (E).

(FIG. 21C) Dose dependent decrease in CD44+CD24+EpCAM+ cell population in the human Panc1 cell line. (FIG. 21D) Percentage of NOD/SCID mice developing tumors 6 weeks after injection of 25,000 Panc1 cells with and without pre-treatment with pilocarpine (n=10 in each group). *p<0.05; **p<0.01.

FIG. 22A, TNFα concentration in plasma from patients with non-malignant pancreatic disease (IPMN, N=5), patients with PDA (N=7) and patients treated with bethanechol for 1 week (N=2) measured by ELISA. Error bars represent standard error of the mean. FIG. 22B, Plasma TNFα concentration in a study patient, pre-treatment, and after 1 week of treatment with bethanechol (post-treatment). Error bars represent SEM between technical replicates. FIG. 22C, Human cytokine antibody array to identify putative inflammatory biomarkers in paired plasma samples from a study patient, pre-treatment and after 1 week of treatment with bethanechol (post-treatment). FIG. 22D, Quantification of mean pixel density of expressed cytokines from the human cytokine antibody array pre- and post-treatment. Letters a-f correlate with array dots in FIG. 22C. Error bars represent standard deviation.

FIG. 24A, CA19-9 data were used. FIG. 24B, tumor measurement data were used to estimate the growth rate. In both cases growth rates are lower in the GTX cohort. (GTX=gemcitabine, paclitaxel, capectabine)

DETAILED DESCRIPTION OF THE INVENTION

Figure 2D:
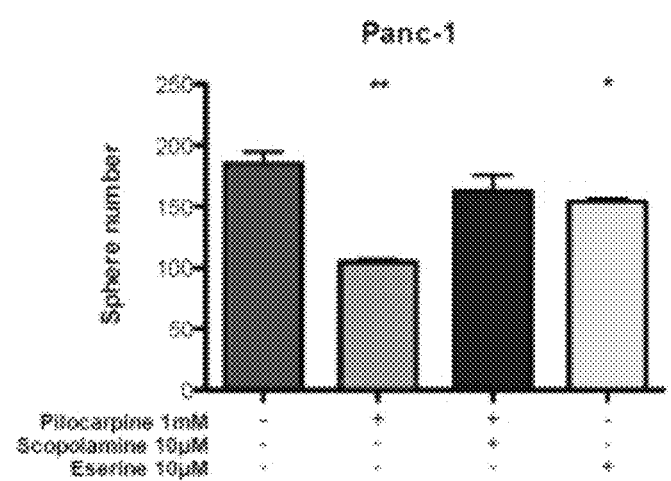

The patent and scientific literature referred to herein establishes knowledge that is available to those skilled in the art. The issued patents, applications, and other publications that are cited herein are hereby incorporated by reference to the same extent as if each was specifically and individually indicated to be incorporated by reference.

The singular forms "a", "an" and "the" include plural reference unless the context clearly dictates otherwise. The use of the word "a" or "an" when used in conjunction with the term "comprising" in the claims and/or the specification may mean "one," but it is also consistent with the meaning of "one or more," "at least one," and "one or more than one."

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

As would be apparent to one of ordinary skill in the art, any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

An "effective amount", "sufficient amount" or "therapeutically effective amount" as used herein is an amount of a compound that is sufficient to effect beneficial or desired results, including clinical results. As such, the effective amount may be sufficient, for example, to reduce or ameliorate the severity and/or duration of an affliction or condition, or one or more symptoms thereof, prevent the advancement of conditions related to an affliction or condition, prevent the recurrence, development, or onset of one or more symptoms associated with an affliction or condition, or enhance or otherwise improve the prophylactic or therapeutic effect(s) of another therapy. An effective amount also includes the amount of the compound that avoids or substantially attenuates undesirable side effects.

The term "carrier" refers to a diluent, adjuvant, excipient, or vehicle with which a compound is administered. Non-limiting examples of such pharmaceutical carriers include liquids, such as water and oils, including those of petroleum, animal, vegetable or synthetic origin, such as peanut oil, soybean oil, mineral oil, sesame oil and the like. The pharmaceutical carriers may also be saline, gum acacia, gelatin, starch paste, talc, keratin, colloidal silica, urea, and the like. In addition, auxiliary, stabilizing, thickening, lubricating and coloring agents may be used. Other examples of suitable pharmaceutical carriers are described in Remington: The Science and Practice of Pharmacy, 21$^{st}$ Edition (University of the Sciences in Philadelphia, ed., Lippincott Williams & Wilkins 2005); and Handbook of Pharmaceutical Excipients, 7$^{th}$ Edition (Raymond Rowe et al., ed., Pharmaceutical Press 2012); each hereby incorporated by reference in its entirety.

The terms "animal," "subject" and "patient" as used herein includes all members of the animal kingdom including, but not limited to, mammals, animals (e.g., cats, dogs, horses, swine, etc.) and humans.

Methods of Treatment Using Cholinergic Agonists

Described herein is the role of cholinergic nerves in the suppression of pancreatic cancer growth. Cholinergic innervation is part of the normal gut stem cell niche and is needed for cancer initiation and progression in the stomach. Thus, given accumulating data that nerves are involved in PDAC, it was expected that a similar cholinergic dependence would be observed for the pancreas and pancreatic cancer. However, as described herein it is shown that surgical cholinergic denervation (i.e. vagotomy) accelerates pancreatic cancer in PanIN/KC mice and is ameliorated by muscarinic agonists such as bethanechol. Moreover, while cholinergic stimulation induces proliferation of the normal pancreas and in WT pancreatic spheroids, mutation (G12D) of the KRAS gene in pancreatic spheroids results in an altered cholinergic response, such that cholinergic stimulation now suppresses their growth.

Muscarinic stimulation suppresses the growth of human pancreatic cancer cell lines, to a large extent by suppressing the number of pancreatic cancer stem cells. Cholinergic stimulation also reduces tumor infiltration by tumor-associated macrophages. Analysis of muscarinic receptors indicates that the M1R is highly expressed in the murine pancreas, upregulated following denervation, and is moderately suppressed during pancreatic tumor suppression. Muscarinic-1 receptor agonists and antagonists effectively modulate the proliferation of pancreatic spheres. In contrast, human pancreatic cancer cells predominantly express the M3 receptor, which mediates a similar inhibitory response to pilocarpine; this inhibitory response has been investigated using RNAseq. Finally, treatment of KPC mice with Bethanechol and Gemcitabine leads to significantly increased survival compared to Gemcitabine alone.

Accordingly, described herein is the use of bethanechol as an effective medication with limited toxicity in patients with advanced PDAC. In particular, only 20% of patients who under Whipple operation are cured, treatment with bethanechol post-surgery can increase the cure rate by at least 2-fold. The stimulation of normal pancreatic growth by bethanechol is also advantageous. Thus, bethanechol and related cholinergic agonists can be used for treating patients with pancreatic cancer.

In certain aspects, bethanechol or other cholinergic agonists can be used as a neoadjuvant treatment for patients with Stage I or Stage 2A PDAC, replacing the loss vagal signal after surgery. In other aspects, bethanechol or other cholinergic agonists can be used to treat patients with metastatic PDAC to the liver and elsewhere. Described herein is the effective treatment of liver metastases with bethanechol.

In some embodiments, the invention is directed to cholinergic agonism, including specific agonism of the M1 or M3 receptor, but covering all muscarinic receptors. In some embodiments, cholinergic agonism is used as an adjunct to traditional forms of cytotoxic therapy, including chemotherapy and radiation therapy. In some embodiments, cholinergic agonism is achieved using bethanechol. Other cholinergic agonists, including all known pharmaceutical drugs and molecules that are known to have cholinergic effects can also be used. In some embodiments, cholinergic agonism is used as a pancreatic cancer treatment. In some embodiments, cholinergic agonism is used as a cancer treatment in combination with chemotherapy, for example, patients can be treated with bethanechol and gemcitabine. Drugs such as bethanechol have an established safety profile and are widely used for a number of clinical indications.

In certain aspects, the invention provides a method for treating pancreatic cancer (e.g. PDAC) in a subject in need thereof, the method comprising administering to the subject a cholinergic agonist. In some embodiments, the method further comprises performing surgical resection, a Whipple surgery, or a distal pancreatectomy. In some embodiments the method further comprises administering to the subject a cytotoxic therapy. In some embodiments, the cholinergic agonist is bethanechol, pilocarpine, or McN-34. In some embodiments, a therapeutically effective amount of the cholinergic agonist is administered to the subject in need thereof.

In certain aspects, the invention provides a method for treating pancreatic cancer (e.g. PDAC) in a subject in need thereof, the method comprising administering to the subject bethanechol. In some embodiments, a therapeutically effective amount of the bethanechol is administered to the subject in need thereof.

In certain aspects, the invention provides a method for treating pancreatic cancer (e.g. PDAC) in a subject in need thereof, the method comprising administering to the subject bethanechol and gemcitabine. In some embodiments, a therapeutically effective amount of the bethanechol and gemcitabine is administered to the subject in need thereof.

In certain aspects, the invention provides a method for treating pancreatic cancer (e.g. PDAC) in a subject in need thereof, the method comprising administering to the subject pilocarpine. In some embodiments, a therapeutically effective amount of the pilocarpine is administered to the subject in need thereof.

In certain aspects, the invention provides a method for treating pancreatic cancer (e.g. PDAC) in a subject in need thereof, the method comprising administering to the subject McN-34. In some embodiments, a therapeutically effective amount of the McN-34 is administered to the subject in need thereof.

In some embodiments, the invention provides a method of treating pancreatic cancer (e.g. PDAC) in a subject in need thereof, the method comprising administering a cholinergic agonist in combination with a cytotoxic therapy. In some embodiments, the cholinergic agonist is administered before, during, or after the administration of the cytotoxic therapy. In some embodiments, the cytotoxic therapy is radiotherapy or chemotherapy (e.g. gemcitabine). In some embodiments, the cholinergic agonist is bethanechol, pilocarpine, or McN34. In some embodiments, a therapeutically effective amount of the cholinergic agonist is administered to the subject in need thereof.

In some embodiments, the invention provides a method of treating pancreatic cancer (e.g. PDAC) in a subject in need thereof, the method comprising administering a cholinergic agonist in combination with surgery. In some embodiments, the cholinergic agonist is administered before, during, or after the surgery. In some embodiments, the surgery is surgical resection, a Whipple surgery, or a distal pancreatectomy. In some embodiments, the cholinergic agonist is bethanechol, pilocarpine, or McN34. In some embodiments, a therapeutically effective amount of the cholinergic agonist is administered to the subject in need thereof.

In some embodiments, the invention provides a method of treating pancreatic cancer (e.g. PDAC) in a subject in need thereof, the method comprising administering a cholinergic agonist and a cytotoxic therapy in combination with surgery. In some embodiments, the cholinergic agonist and/or the cytotoxic therapy is administered before, during, or after the surgery. In some embodiments, the surgery is surgical resection, a Whipple surgery, or a distal pancreatectomy. In some embodiments, the cholinergic agonist is bethanechol, pilocarpine, or McN-34A. In some embodiments, the cytotoxic therapy is radiotherapy or chemotherapy (e.g. gemcitabine). In some embodiments, a therapeutically effective amount of the cholinergic agonist is administered to the subject in need thereof.

In some embodiments, the cholinergic agonist is a small molecule. In some embodiments, the cholinergic agonist is bethanechol. In some embodiments, the cholinergic agonist is pilocarpine. In some embodiments, the cholinergic agonist is McN-34A. In some embodiments, the cholinergic agonist activates the M3 muscarinic receptor. In some embodiments, the cholinergic agonist activates the M1 muscarinic receptor. Examples of cholinergic agonists include, but are not limited to pilocarpine, aceclidine, arecoline, cevimeline, bethanechol, muscarine, oxotremorine, carbachol or methacholine.

In certain aspects, the invention provides a method for reducing proliferation of pancreatic tumor cells, the method comprising administering a cholinergic agonist. In some embodiments, the method further comprises performing surgery and/or administering chemotherapy in combination with the cholinergic agonist.

In certain aspects, the invention provides a method for inhibiting proliferation of pancreatic tumor cells, the method comprising administering a cholinergic agonist. In some embodiments, the method further comprises performing surgery and/or administering chemotherapy in combination with the cholinergic agonist.

In certain aspects, the invention provides a method of treating pancreatic cancer metastasis, the method comprising administering a cholinergic agonist. In some embodiments, the method further comprises performing surgery and/or administering chemotherapy in combination with the cholinergic agonist. In some embodiments, a therapeutically effective amount of the cholinergic agonist is administered to the subject in need thereof.

In certain aspects, the invention provides a method for inhibiting pancreatic cancer metastasis, the method comprising administering a cholinergic agonist. In some embodiments, the method further comprises performing surgery and/or administering chemotherapy in combination with the cholinergic agonist.

In certain aspects, the invention provides a method for treating pancreatic tumor reoccurrence in a subject in need thereof, the method comprising administering to the subject a cholinergic agonist. In some embodiments, the method further comprises performing surgery and/or administering chemotherapy in combination with the cholinergic agonist. In some embodiments, a therapeutically effective amount of the cholinergic agonist is administered to the subject in need thereof.

In certain aspects, the invention provides a method for inhibiting the growth of pancreatic cancer stem cells, the method comprising administering a cholinergic agonist. In some embodiments, the method further comprises performing surgery and/or administering chemotherapy in combination with the cholinergic agonist.

In some embodiments, the invention provides a method for reducing proliferation of pancreatic tumor cells, a method for inhibiting proliferation of pancreatic tumor cells, a method for inhibiting pancreatic cancer metastasis, a method for inhibiting the growth of pancreatic cancer stem cells, or a method for treating pancreatic tumor reoccurrence the method comprising administering a cholinergic agonist.

In some embodiments, the invention provides a method for reducing proliferation of pancreatic tumor cells, a method for inhibiting proliferation of pancreatic tumor cells, a method for inhibiting pancreatic cancer metastasis, a method for inhibiting the growth of pancreatic cancer stem cells, or a method for treating pancreatic tumor reoccurrence the method comprising administering a cholinergic agonist in combination with a cytotoxic therapy. In some embodiments the cholinergic agonist, is administered before, during, or after the administration of the cytotoxic therapy. In some embodiments, the cytotoxic therapy is radiotherapy or chemotherapy (e.g. gemcitabine). In some embodiments, the cholinergic agonist is bethanechol, pilocarpine, or McN-34A. In some embodiments, a therapeutically effective amount of the cholinergic agonist is administered to the subject in need thereof.

In some embodiments, the invention provides a method for reducing proliferation of pancreatic tumor cells, a method for inhibiting proliferation of pancreatic tumor cells, a method for inhibiting pancreatic cancer metastasis, a method for inhibiting the growth of pancreatic cancer stem cells, or a method for treating pancreatic tumor reoccurrence the method comprising administering a cholinergic agonist in combination with surgery. In some embodiments, the cholinergic agonist is administered before, during, or after the surgery. In some embodiments, the surgery is surgical resection, a Whipple surgery, or a distal pancreatectomy. In some embodiments, the cholinergic agonist is bethanechol, pilocarpine, or McN-34A. In some embodiments, a therapeutically effective amount of the cholinergic agonist is administered to the subject in need thereof.

In some embodiments, the invention provides a method for reducing proliferation of pancreatic tumor cells, a method for inhibiting proliferation of pancreatic tumor cells, a method for inhibiting pancreatic cancer metastasis, a method for inhibiting the growth of pancreatic cancer stem cells, or a method for treating pancreatic tumor reoccurrence the method comprising administering a cholinergic agonist and a cytotoxic therapy in combination with surgery. In some embodiments, the cholinergic agonist is administered before, during, or after the surgery. In some embodiments, the surgery is surgical resection, a Whipple surgery, or a distal pancreatectomy. In some embodiments, the cholinergic agonist is bethanechol, pilocarpine, or McN-34A. In some embodiments, the cytotoxic therapy is radiotherapy or chemotherapy (e.g. gemcitabine). In some embodiments, a therapeutically effective amount of the cholinergic agonist is administered to the subject in need thereof.

In some embodiments, the invention provides a method for reducing proliferation of pancreatic tumor cells, a method for inhibiting proliferation of pancreatic tumor cells, a method for inhibiting pancreatic cancer metastasis, a method for inhibiting the growth of pancreatic cancer stem cells, or a method for treating pancreatic tumor reoccurrence in a subject in need thereof. In some embodiments, the subject has pancreatic cancer. In some embodiments, the subject is at high risk of developing pancreatic cancer. In some embodiments, the subject has pancreatic ductal adenocarcinoma (PDAC).

In some embodiments the cholinergic agonist is a small molecule. In some embodiments, the cholinergic agonist is bethanechol. In some embodiments, the cholinergic agonist is pilocarpine. In some embodiments, the cholinergic agonist is carbachol. In some embodiments, the cholinergic agonist is aceclidine. In some embodiments, the cholinergic agonist is arecoline. In some embodiments, the cholinergic agonist is cevimeline. In some embodiments, the cholinergic agonist is muscarine. In some embodiments, the cholinergic agonist is oxotremorine. In some embodiments, the cholinergic agonist is methacholine. In some embodiments, the cholinergic agonist activates the M3 muscarinic receptor. In some embodiments, the cholinergic agonist is a cholinergic muscarinic receptor 1 (CHRM1; referred to as "M1") agonist. In some embodiments, the M1 agonist is McN-34A.

In one embodiment, the invention provides a cholinergic agonist for use in the manufacture of a medicament for the treatment of pancreatic cancer in a subject who has pancreatic cancer for the treatment of said disease. In one embodiment, the invention provides bethanechol, pilocarpine, or McN-34A for use in the manufacture of a medicament for the treatment of pancreatic cancer in a subject who has pancreatic cancer for the treatment of said disease. In some embodiments, the subject has PDAC. In some embodiments, the subject has Grade 1 or Grade 2A PDAC.

In one embodiment, the invention provides a cholinergic agonist for use in the manufacture of a medicament for the treatment of pancreatic cancer in a subject who has pancreatic cancer metastasis for the treatment of said disease. In one embodiment, the invention provides bethanechol, pilocarpine, or McN-34A for use in the manufacture of a medicament for the treatment of pancreatic cancer in a subject who has pancreatic cancer metastasis for the treatment of said disease. In some embodiments, the subject has PDAC. In some embodiments, the subject has Grade 1 or Grade 2A PDAC.

In one embodiment, the invention provides a cholinergic agonist for use in the manufacture of a medicament for the treatment of pancreatic cancer in a subject who has pancreatic cancer and has had a resection surgery, a Whipple surgery, or a distal pancreatectomy for the treatment of said disease. In one embodiment, the invention provides bethanechol, pilocarpine, or McN-34A for use in the manufacture of a medicament for the treatment of pancreatic cancer in a subject who has had a resection surgery, a Whipple surgery, or a distal pancreatectomy pancreatic cancer for the treatment of said disease. In some embodiments, the subject has PDAC. In some embodiments, the subject has Grade 1 or Grade 2A PDAC.

Pancreatic Cancer

The present invention provides methods for treating pancreatic cancer, the method comprising administering a cholinergic agonist. In one embodiment, the pancreatic cancer is pancreatic adenocarcinoma (PDAC). In some embodiments, the pancreatic cancer or tumor cells also includes but not limited to acinar cell carcinoma of the pancreas, cystadenocarcinoma, pancreatoblastoma, pancreatic mucinous cystic neoplasms, other pancreatic exocrine cancers (e.g. adenosquamous carcinomas, signet ring cell carcinomas, hepatoid carcinomas, colloid carcinomas, undifferentiated carcinomas, and undifferentiated carcinomas with osteoclast-like giant cells, solid pseudopapillary tumor), and pancreatic neuroendocrine tumors. In some embodiments, the methods described herein are used to treat a subject with Stage 1 or Stage 2A PDAC. In some embodiments, the pancreatic cancer or tumor cells or metastases have a mutation in KRAS.

In some embodiments, the subject is already suspected to have a pancreatic cancer (e.g. PDAC). In other embodiments, the subject is being treated for a pancreatic cancer (e.g. PDAC), before being treated according to the methods of the invention. In other embodiments, the subject is not being treated for a pancreatic cancer, before being treated according to the methods of the invention.

The present invention also provides methods for decreasing pancreatic tumor growth in a subject, the method comprising administering a cholinergic agonist. Tumor growth can be measured in a variety of ways, known to one of skill in the art. For example, tumor growth can be measured by measuring the tumor volume over time. Tumor volume can be measured in a variety of ways, known to one of skill in the art including, but not limited to, positron emission tomography and computed tomography (PET-CT), single-photon emission computed tomography (SPECT-CT), magnetic resonance spectroscopy (MR), X-ray computed tomography (CT), and molecular imaging.

The present invention provides methods for decreasing cell proliferation in a subject, the method comprising administering a cholinergic agonist. In one embodiment, the cells are pancreatic cancer stem cells. In another embodiment the pancreatic cancer stem cells are tumor associated. In another embodiment, the gastric cancer stem cell is a gastric cancer stem cell associated with a tumor. For example, the tumor can be any solid tumor associated with pancreatic cancer stem cells. A tumor is a growth of tissue forming an abnormal mass, and can be benign, pre-malignant, or malignant. In one embodiment, the tumor is a pancreatic tumor (e.g. PDAC).

The invention also provides methods for protecting and promoting normal pancreatic cell growth and restoring physiological structure and function to the pancreas after removal of pancreatic cancer or tumors. In some embodiments, administering a cholinergic agonist can be used to activate or induce normal growth in the pancreas.

The present invention also provides a kit for treating a pancreatic cancer (e.g. PDAC) in a subject. In one embodiment, the kit for treating a pancreatic cancer (e.g. PDAC) comprises a cholinergic agonist to administer to a subject and instructions of use.

The present invention also provides a kit for reducing or inhibiting proliferation of pancreatic tumor cells in a subject. In one embodiment, the kit for reducing or inhibiting proliferation of pancreatic tumor cells comprises a cholinergic agonist to administer to a subject and instructions of use.

The present invention also provides a kit for inhibiting or treating pancreatic cancer metastases in a subject. In one embodiment, the kit for inhibiting or treating pancreatic cancer metastases comprises a cholinergic agonist to administer to a subject and instructions of use.

The present invention also provides a kit for reducing or inhibiting growth of pancreatic cancer stem cells in a subject. In one embodiment, the kit for reducing or inhibiting growth of pancreatic cancer stem cells comprises a cholinergic agonist to administer to a subject and instructions of use.

In one embodiment, the subject is an animal. In another embodiment, the subject is an animal that has or is diagnosed with a pancreatic cancer (e.g. PDAC). In one embodiment, the subject is a human. In other embodiments, the subject is a mammal. In one embodiment, the subject is a dog. In another embodiment, the subject is a cat. In some embodiments, the subject is a rodent, such as a mouse or a rat. In some embodiments, the subject is a cow, pig, sheep, goat, cat, horse, dog, and/or any other species of animal used as livestock or kept as pets.

Cholinergic Agonists

Cholinergic agonists can be useful in the methods of the present invention. In some embodiments the cholinergic agonists can activate one or more characteristic responses of a muscarinic receptor. Examples of cholinergic agonists include, but are not limited to pilocarpine ((3S,4R)-3-ethyl-4-[(3-methylimidazol-4-yl)methyl]oxolan-2-one) with structure:

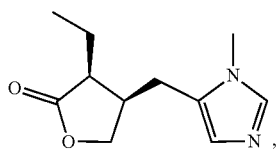

or analogs or pharmaceutically acceptable salts thereof, Aceclidine (1-azabicyclo[2.2.2]octan-3-yl acetate) with structure:

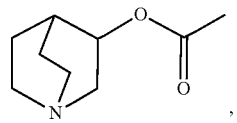

or analogs or pharmaceutically acceptable salts thereof arecoline (methyl 1-methyl-3,6-dihydro-2H-pyridine-5-carboxylate) with structure:

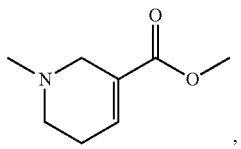

or analogs or pharmaceutically acceptable salts thereof, cevimeline ((2R,5R)-2-methylspiro[1,3-oxathiolane-5,3'-1-azabicyclo[2.2.2]octane]) with structure:

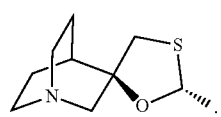

or analogs or pharmaceutically acceptable salts thereof, bethanechol, or analogs or pharmaceutically acceptable salts thereof, muscarine ([(2S,4R,5S)-4-hydroxy-5-methyloxolan-2-yl]methyl-trimethylazanium) with structure:

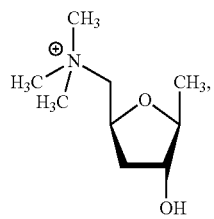

or analogs or pharmaceutically acceptable salts thereof, oxotremorine (1-(4-pyrrolidin-1-ylbut-2-ynyl)pyrrolidin-2-one) with structure:

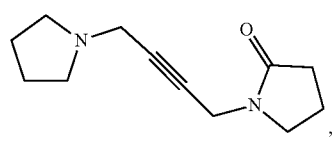 [SMILES: O=C1CCCN1CC#CCN1CCCC1]

or analogs or pharmaceutically acceptable salts thereof, carbachol (2-carbamoyloxyethyl(trimethyl)azanium) with structure:

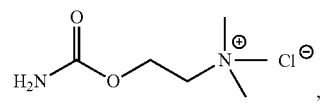

or analogs or pharmaceutically acceptable salts thereof, methacholine (2-acetyloxypropyl(trimethyl)azanium) with structure:

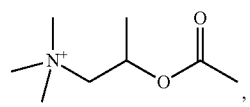

or analogs or pharmaceutically acceptable salts thereof, or McN-34A, or analogs or pharmaceutically acceptable salts thereof.

In some embodiments, the invention relates to methods of inhibiting or reducing the growth of pancreatic tumors and/or pancreatic cancer stem cells and/or pancreatic cancer metastases by activating muscarinic M3 receptors. M3 receptors can be activated by a variety of agents, including but not limited to, cholinergic agonists (e.g. pilocarpine, aceclidine, arecoline, cevimeline, bethanechol, muscarine, oxotremorine, carbachol, methacholine), M3 receptor agonists, or by overexpression of M3 receptor nucleic acid sequences.

The polynucleotide and polypeptide sequences of the muscarinic M3 receptor are publically available and accessible through sequence databases (e.g. CHRM3 located on chromosome 1q43 (Gene ID 1131); GenBank U29589.1 (DNA); NM_000740 (mRNA); NP_000731.1 (Protein); UniProt P20309 (Protein)). The publically available polynucleotide and polypeptide sequences of the muscarinic M3 receptor are hereby incorporated by reference in their entireties.

Bethanechol (2-[(aminocarbonyl)oxy]-N,N,N-trimethyl-1-propanaminium) is a parasympathomimetic choline carbamate with the following structure:

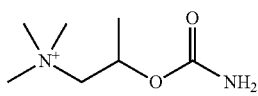

Bethanechol is a selective stimulator of muscarinic receptors but does not affect nicotinic receptors. Generally, cholinergic agonists are compounds that mimic the action of acetylcholine and can also be referred to as muscarinic receptor agonists because they activate the activity of the muscarinic acetyl choline receptor.

Pharmaceutical Compositions, Methods of Administration and Combination Treatments In some embodiments, a cholinergic agonist can be supplied in the form of a pharmaceutical composition, comprising an isotonic excipient prepared under sufficiently sterile conditions for human administration. Choice of the excipient and any accompanying elements of the composition comprising a cholinergic agonist will be adapted in accordance with the route and device used for administration. In some embodiments, a composition comprising a cholinergic agonist can also comprise, or be accompanied with, one or more other ingredients that facilitate the delivery or functional mobilization of the cholinergic agonist.

These methods described herein are by no means all-inclusive, and further methods to suit the specific application is understood by the ordinary skilled artisan. Moreover, the effective amount of the compositions can be further approximated through analogy to compounds known to exert the desired effect.

According to the invention, a pharmaceutically acceptable carrier can comprise any and all solvents, dispersion media, coatings, antibacterial and antifungal agents, isotonic and absorption delaying agents, and the like, compatible with pharmaceutical administration. The use of such media and agents for pharmaceutically active substances is well known in the art. Any conventional media or agent that is compatible with the active compound can be used. Supplementary active compounds can also be incorporated into the compositions.

A cholinergic agonist (such as, e.g. pilocarpine, aceclidine, arecoline, cevimeline, bethanechol, muscarine, oxotremorine, carbachol, methacholine, McN-34A), can be administered to the subject one time (e.g., as a single injection or deposition). Alternatively, a cholinergic agonist can be administered once or twice daily to a subject in need thereof for a period of from about 2 to about 28 days, or from about 7 to about 10 days, or from about 7 to about 15 days. It can also be administered once or twice daily to a subject for a period of 1, 2, 3, 4, 5, 6, 7, 8, 9, 10, 11, 12 times per year, or a combination thereof. Furthermore, a cholinergic agonist can be co-administered with another therapeutic. In some embodiments, 200 mg of bethanechol is administered per day. In some embodiments, 100 mg of bethanechol is administered once per day to a subject in need thereof. In some embodiments, 100 mg of bethanechol is administered twice daily to a subject in need thereof. In some embodiments, between about 50 mg and about 500 mg of bethanechol is administered per day. In some embodiments, 10 mg, 20 mg, 30 mg, 40 mg, 50 mg, 60 mg, 70 mg, 80 mg, 90 mg, 100 mg, 150 mg, 200 mg, 250 mg, 300 mg, 350 mg, 400 mg, 450 mg, or 500 mg of bethanechol is administered per day to a subject in need thereof. In some embodiments, 10 mg, 20 mg, 30 mg, 40 mg, 50 mg, 60 mg, 70 mg, 80 mg, 90 mg, 100 mg, 150 mg, 200 mg, or 250 mg of bethanechol is administered twice daily to a subject in need thereof. In some embodiments, 10 mg, 20 mg, 30 mg, 40 mg, 50 mg, 60 mg, 70 mg, 80 mg, 90 mg, 100 mg, or 150 mg, of bethanechol is administered three times per day to a subject in need thereof. In some embodiments, 110 mg, 120 mg, 130 mg, 140 mg, 150 mg, 160 mg, 170 mg, 180 mg, or 190 mg of bethanechol is administered daily to a subject in need thereof. In some embodiments, 210 mg, 220 mg, 230 mg, 240 mg, 250 mg, 260 mg, 270 mg, 280 mg, or 290 mg of bethanechol is administered daily to a subject in need thereof. In some embodiments 200 mg of bethanechol is administered per day for a period of 14, 15, 16, 17, 18, 19, 20, or 21 days. In some embodiments, bethanechol is administered orally. In some embodiments, 10 mg of pilocarpine is administered three times per day to a subject in need thereof. In some embodiments, 5 mg of pilocarpine is administered three to four times per day to a subject in need thereof. In some embodiments 30 mg of pilocarpine is administered per day to a subject in need thereof. In some embodiments, 5 mg, 10 mg, 15 mg, 20 mg, or 25 mg of pilocarpine is administered to a subject in need thereof. In some embodiments, 35 mg, 40 mg, 45 mg, 50 mg, 55 mg, or 60 mg of pilocarpine is administered to a subject in need thereof. In some embodiments, 30 mg of pilocarpine per day is administered to a subject in need thereof prior to the resection surgery, Whipple surgery, or distal pancreatectomy. In some embodiments, 50 mg of McN-34A per day is administered to a subject in need thereof. In some embodiments, 10 mg, 20 mg, 30 mg, or 40 mg of McN-34A per day is administered to a subject in need thereof. In some embodiments, 60 mg, 70 mg, 80 mg, or 90 mg of McN-34A per day is administered to a subject in need thereof. In some embodiments, 100 mg of McN-34A per day is administered to a subject in need thereof. In some embodiments, 110 mg, 120 mg, 130 mg, 140 mg, 150 mg, 160 mg, 170 mg, 180 mg, or 190 mg of McN-34A per day is administered to a subject in need thereof. In some embodiments, 200 mg of McN-34A per day is administered to a subject in need thereof. In some embodiments, 210 mg, 220 mg, 230 mg, 240 mg, 250 mg, 260 mg, 270 mg, 280 mg, or 290 mg of McN-34A per day is administered to a subject in need thereof. In some embodiments, 200 mg of McN-34A per day is administered to a subject in need thereof prior to the resection surgery, Whipple surgery, or distal pancreatectomy.

In one embodiment, a cholinergic agonist can be co-administrated with a cytotoxic therapy. In one embodiment, a cholinergic agonist can be co-administrated with a chemotherapy drug. In one embodiment, a cholinergic agonist can be co-administrated with gemcitabine. In one embodiment, a cholinergic agonist can be co-administrated with 5-FU. In one embodiment, a cholinergic agonist can be co-administrated with gemcitabine and erlotinib. In one embodiment, a cholinergic agonist can be co-administrated with gemcitabine and FOLFIRINOX. In one embodiment, a cholinergic agonist can be co-administrated with gemcitabine and nab-paclitaxel.

In one embodiment, a cholinergic agonist can be co-administrated with radiation therapy. Some non-limiting examples of conventional radiation therapy include: external beam radiation therapy, sealed source radiation therapy, unsealed source radiation therapy, particle therapy, and radioisotope therapy.

In one embodiment, a cholinergic agonist can be co-administrated with a cancer immunotherapy. Cancer immunotherapy comprises using the immune system of the subject to treat a cancer. For example, the immune system of a subject can be stimulated to recognize and eliminate cancer cells. Some non-limiting examples of cancer immunotherapy include: cancer vaccines, therapeutic antibodies, such as monoclonal antibody therapy, cell-based immunotherapy, and adoptive cell-based immunotherapy.

A cholinergic agonist may also be used in combination with surgical or other interventional treatment regimens used for the treatment of pancreatic cancer (e.g. PDAC). In one embodiment, the surgical treatment is a resection surgery. In one embodiment, the surgical treatment is a Whipple surgery. In one embodiment, the surgical treatment is a distal pancreatectomy. In one embodiment, a cholinergic agonist is administered or performed before, during, or after the surgery is performed. Other surgical treatments for pancreatic cancer can be used and will be apparent to one of skill in the art.

In some embodiments, the cholinergic agonist can be administered during a neoadjuvant pre-operative period. In some embodiments, the pre-operative period begins about 2 to 3 weeks before admission to a healthcare facility (e.g., a hospital) for a surgical procedure (e.g., pancreatic cancer surgery). In some embodiments 200 mg of bethanechol is administered per day for a period of 14, 15, 16, 17, 18, 19, 20, or 21 days prior to a surgical procedure, Whipple surgery, or distal pancreatectomy. In some embodiments, the administration of the cholinergic agonist is stopped about 48 hours prior to the surgical procedure. In some embodiments, the cholinergic agonist can be administered after the surgical procedure.

In some embodiments, the subject matter disclosed herein relates to a method of treatment for treating pancreatic cancer in a subject in need thereof, the method including administering to the subject a combination therapy of cholinergic agonist with "GA", gemcitabine plus nab-paclitaxel (Abraxane®). In some embodiments, bethanechol can be administered in combination with "GA", gemcitabine plus nab-paclitaxel (Abraxane®) as neoadjuvant chemotherapy to subjects in need thereof. Chemotherapy can be administered on a day 1, 8 and 15 schedule with gemcitabine at a dose of 1000 mg/m$^2$ and Abraxane at 125 mg/m$^2$. 4-6 cycles of gemcitabine/Abraxane can be administered to about 33 patients with borderline resectable pancreatic cancer. A small fraction of patients do not tolerate gemcitabine/Abraxane, and present with fever, edema, or early onset neuropathy. To avoid any confusion from the effects of the bethanechol, and to provide baseline tumor measurements and serum CA19-9 levels for pre-bethanechol kinetics, gemcitabine/Abraxane can be administered alone in the first 2 cycles. Beginning with cycle 3, oral bethanechol can be administered at a dose of 100 mg twice daily for the remaining cycles. Biomarker assays can be assessed in biopsy cores obtained at diagnosis, and in the surgical resection specimen.

The compositions of this invention can be formulated and administered to reduce the symptoms associated with pancreatic cancer by any means that produce contact of the active ingredient with the agent's site of action in the body of a human or non-human subject. For example, the compositions of this invention can be formulated and administered to reduce the symptoms associated with pancreatic cancer, or cause a decrease in cell proliferation, or a decrease in tumor growth. They can be administered by any conventional means available for use in conjunction with pharmaceuticals, either as individual therapeutic active ingredients or in a combination of therapeutic active ingredients. They can be administered alone but are generally administered with a pharmaceutical carrier selected on the basis of the chosen route of administration and standard pharmaceutical practice.

Pharmaceutical compositions for use in accordance with the invention can be formulated in conventional manner using one or more physiologically acceptable carriers or excipients. The therapeutic compositions of the invention can be formulated for a variety of routes of administration, including systemic and topical or localized administration. Techniques and formulations generally can be found in *Remington's Pharmaceutical Sciences*, Meade Publishing Co., Easton, Pa. (20$^{th}$ ed., 2000), the entire disclosure of which is herein incorporated by reference. For systemic administration, an injection is useful, including intramuscular, intravenous, intraperitoneal, and subcutaneous. For injection, the therapeutic compositions of the invention can be formulated in liquid solutions, for example in physiologically compatible buffers, such as PBS, Hank's solution, or Ringer's solution. In addition, the therapeutic compositions can be formulated in solid form and redissolved or suspended immediately prior to use. Lyophilized forms are also included. Pharmaceutical compositions of the present invention are characterized as being at least sterile and pyrogen-free. These pharmaceutical formulations include formulations for human and veterinary use.

Any of the therapeutic applications described herein can be applied to any subject in need of such therapy, including, for example, a mammal such as a dog, a cat, a cow, a horse, a rabbit, a monkey, a pig, a sheep, a goat, or a human.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EM™ (BASF, Parsippany, N.J.) or phosphate buffered saline (PBS). The composition must be sterile and fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyetheylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, and thimerosal. In many cases, it can be useful to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the cholinergic agonist in the required amount in an appropriate solvent with one or a combination of ingredients enumerated herein, as required, followed by filtered sterilization. Dispersions are prepared by incorporating the active compound into a sterile vehicle which contains a basic dispersion medium and the required other ingredients from those enumerated herein. In the case of sterile powders for the preparation of sterile injectable solutions, examples of useful preparation methods are vacuum drying and freeze-drying which yields a powder of the active ingredient plus any additional desired ingredient from a previously sterile-filtered solution thereof.

Oral compositions include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as known in the art.

A composition of the invention can be administered to a subject in need thereof. Subjects in need thereof can include but are not limited to, for example, a mammal such as a dog, a cat, a cow, a horse, a rabbit, a monkey, a pig, a sheep, a goat, or a human.

A composition of the invention can also be formulated as a sustained and/or timed-release formulation. Such sustained and/or timed release formulations can be made by sustained release means or delivery devices that are well known to those of ordinary skill in the art, such as those described in U.S. Pat. Nos. 3,845,770; 3,916,899; 3,536,809; 3,598,123; 4,008,719; 4,710,384; 5,674,533; 5,059,595; 5,591,767; 5,120,548; 5,073,543; 5,639,476; 5,354,556; and 5,733,566, the disclosures of which are each incorporated herein by reference. The pharmaceutical compositions of the invention (e.g., that have a therapeutic effect) can be used to provide slow or sustained release of one or more of the active ingredients using, for example, hydropropylmethyl cellulose, other polymer matrices, gels, permeable membranes, osmotic systems, multilayer coatings, microparticles, liposomes, microspheres, or the like, or a combination thereof to provide the desired release profile in varying proportions. Suitable sustained release formulations known to those of ordinary skill in the art, including those described herein, can be readily selected for use with the pharmaceutical compositions of the invention. Single unit dosage forms suitable for oral administration, such as, but not limited to, tablets, capsules, gel-caps, caplets, or powders, that are adapted for sustained release are encompassed by the invention.

The dosage administered can be a therapeutically effective amount of the composition sufficient to result in treatment of pancreatic cancer (e.g. PDAC), a decrease in cell proliferation, or a decrease in tumor growth, and can vary depending upon known factors such as the pharmacodynamic characteristics of the active ingredient and its mode and route of administration; time of administration of active ingredient; age, sex, health and weight of the recipient; nature and extent of symptoms; kind of concurrent treatment, frequency of treatment and the effect desired; and rate of excretion.

In one embodiment, a cholinergic agonist is administered at least once daily. In another embodiment, a cholinergic agonist is administered at least twice daily. In some embodiments, a cholinergic agonist is administered for at least 1 week, for at least 2 weeks, for at least 3 weeks, for at least 4 weeks, for at least 5 weeks, for at least 6 weeks, for at least 8 weeks, for at least 10 weeks, for at least 12 weeks, for at least 18 weeks, for at least 24 weeks, for at least 36 weeks, for at least 48 weeks, or for at least 60 weeks. In further embodiments, a cholinergic agonist is administered in combination with a second therapeutic agent or with a surgical procedure.

Toxicity and therapeutic efficacy of therapeutic compositions of the present invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Therapeutic agents that exhibit large therapeutic indices are useful. Therapeutic compositions that exhibit some toxic side effects can be used.

Experimental animals can be used as models for human disease. For example, mice can be used as a mammalian model system. The physiological systems that mammals possess can be found in mice, and in humans, for example. Certain diseases can be induced in mice by manipulating their environment, genome, or a combination of both.

Administration of a cholinergic agonist is not restricted to a single route but may encompass administration by multiple routes. Multiple administrations may be sequential or concurrent. Other modes of application by multiple routes will be apparent to one of skill in the art.

EXAMPLES

The following examples illustrate the present invention and are set forth to aid in the understanding of the invention and should not be construed to limit in any way the scope of the invention as defined in the statements of the invention which follow thereafter.

The Examples described below are provided to illustrate aspects of the present invention and are not included for the purpose of limiting the invention.

Example 1—Targeting Cholinergic Receptors to Suppress Pancreatic Cancer

To date, only a limited number of drugs targeting the tumor microenvironment (TME) have made it to late stage clinical trials. Further, the role of nerves in the TME has only recently been appreciated, and their contribution to disease progression and therapeutic resistance has not been well studied in pancreatic adenocarcinoma (PDAC). Described herein is the discovery that, in contrast to its effects on the normal pancreas, cholinergic signaling via the vagus nerve suppresses the growth of PDAC, with vagotomy leading to marked acceleration of PDAC growth in the KC mouse and in metastatic models. Using five distinct model systems, it has now been firmly established that cholinergic signaling inhibits PDAC growth and metastases through muscarinic receptors. Described herein are results in the KPC mouse model and in a Panc02 liver metastatic model that muscarinic agonist treatment leads to a significant increase in survival. Work with muscarinic agonists will also be extended, additional biomarkers and mechanisms of action defined, and pilot clinical study in patients can be performed.

First, whether muscarinic signaling play a role in restraining metastatic pancreatic cancer and is muscarinic agonism effective in suppressing the growth of liver metastases can be investigated. A metastatic model can be used to understand dose-response relationship of muscarinic agonists, their utility in combination with gemcitabine, and their effect on potential biomarkers. Second, the mechanism by which mutant KRAS signaling leads to an inhibition of proliferation by muscarinic signaling, in contrast to effects on non-mutated pancreatic acinar cells can be investigated. Multiplex kinase assays and RNAseq can be performed following muscarinic stimulation, and several bioinformatics algorithms (VIPER and DEMAND) can be used to interrogate the RNAseq dataset to identify and validate candidate mechanism of action (MoA). Third, the safety of muscarinic agonism as a therapy for patients with potentially resectable pancreatic cancer can be investigated, along with studying whether the therapy leads to detectable changes in tissue. A pilot clinical trial of 15 patients in a neoadjuvant setting can be performed. Patients identified as surgical candidates will be enrolled and treated for at least 2 weeks with an oral muscarinic drug (bethanechol), in order to assess tolerability and effects on biomarkers. It is expected that the preclinical studies will demonstrate synergy with chemotherapy, identify additional biomarkers and provide insights into the mechanism of action. This clinical trial is predicted to show safety and suppression of tissue biomarkers, and provide a foundation for future clinical trials, contributing to the goal of doubling PDAC survival by 2020.

Described herein is the discovery that key cell types that regulate pancreatic cancer growth are "nerves". In particular, a certain type of nerve that secretes the neurotransmitter called "acetylcholine" which stimulates normal pancreatic growth, instead inhibits or suppresses growth of pancreatic cancer cells. This switch to an inhibitory signal is probably related to mutations (e.g. KRAS) in pancreatic cancer cells and represents an "Achilles heel" for the tumor. Unfortunately, these nerves are usually cut during surgery for pancreatic cancer, thus releasing the inhibitory signal, and the nerves are also less abundant when the tumor spreads for example to the liver. Described herein is the suppression of pancreatic growth in cultured cells and multiple mouse models by acetylcholine signaling. Treatment with a widely available synthetic (cholinergic) analogue leads to increased survival in mice with tumors. These drugs have much less toxicity than currently available cytotoxic drugs and are well tolerated in patients but have not been studied in pancreatic cancer.

The cholinergic drug will be studied in combination with chemotherapy in mouse model of metastatic pancreatic cancer, and better define biomarkers that predict a good response. A range of different doses will also be examined. A gene expression dataset and computer algorithms will also be used to understand better why acetylcholine is able to inhibit pancreatic tumor cells. A computer program has been created that can take gene expression data from sequenced RNA to identify the mechanism of action of drugs. A pilot clinical trial of 15 patients undergoing surgery will also be completed, these patients will be treated for 2 weeks before surgery with the cholinergic drug, to examine safety and biomarker responses. Given the data described herein from cells and mice, and easy availability and low toxicity of these cholinergic drugs, the completion of this study will allow a relatively quick pathway to additional trials and potential patient benefit. Further, a better understanding of how these drugs work may lead to additional therapeutic strategies. Overall, this project should make a significant contribution to the 2020 goal of doubling survival in pancreatic cancer.

Scientific Validation

A convergence of multiple stromal cell types is required to develop a tumorigenic niche that nurtures the initial development of cancer and its dissemination. Although the immune system and vascular systems have strong influences on cancer, a growing body of evidence points to a role of the nervous system in adapting and modulating cancer development (1, 2). In particular, cholinergic innervation is an essential player in the gut stem cell niche (3-5) and is needed for cancer initiation and progression in the stomach (3, 6). In the pancreas, however, an opposite effect of the cholinergic system for the normal pancreas and pancreatic cancer (PDAC) has been observed, which may lead to a different strategy for cancer intervention.

Cholinergic Nerves Promote Normal Proliferation but Suppresses PDAC Development.

Vagotomy in wild-type mice results in a significant decrease of proliferative cells in the normal pancreas (Ki67 by 3-fold, and BrdU uptake by >100-fold, FIG. 1A-B). This response is accompanied by a remarkable upregulation of muscarinic acetylcholine receptor M1 (M1R) expression (FIG. 1C). In contrast, vagotomy in Pdx1-Cre; LSL-K-Ras$^{G12D}$ (KC) mice, leads to accelerated PanIN progression and PDAC formation. Importantly, treatment with Bethanechol, a broad MR agonist, can abrogate the accelerated tumorigenesis and rescue the normal KC phenotype (FIG. 2 A-B). Vagal denervation increases tumor-associated macrophages (TAM), an effect which is abolished after Bethanechol treatment.

Organoid cultures derived from LSL-K-Ras$^{G12D}$ pancreata (7) when not treated by an Adeno-Cre virus, have an increased sphere forming capacity when treated with non-selective (Bethanechol) or M1R-selective agonist (McN-A-343) while treatment with non-selective (Scopolamine) or M1R-selective antagonist (Pirenzepine) significantly prevents sphere formation. These data suggest that cholinergic signaling modulates murine pancreatic proliferation, primarily through M1R. Intriguingly, after activating the oncogenic K-Ras allele by an adeno-Cre virus an opposite effect is observed, where non-selective or M1R-selective agonists significantly suppresses sphere formation and growth and non-selective or M1R-selective antagonists enhance sphere forming capacity in these organoids cultures.

Figure 2E:
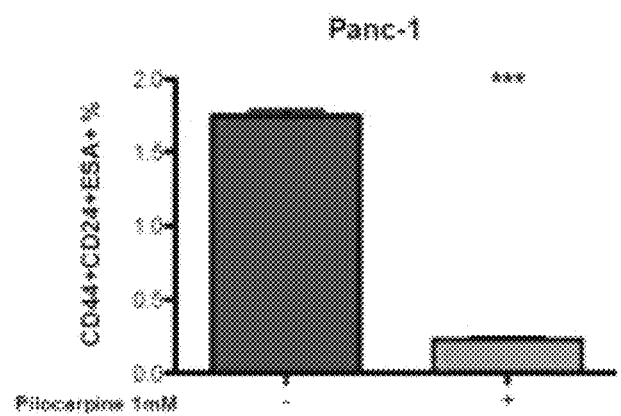
Figure 2F:
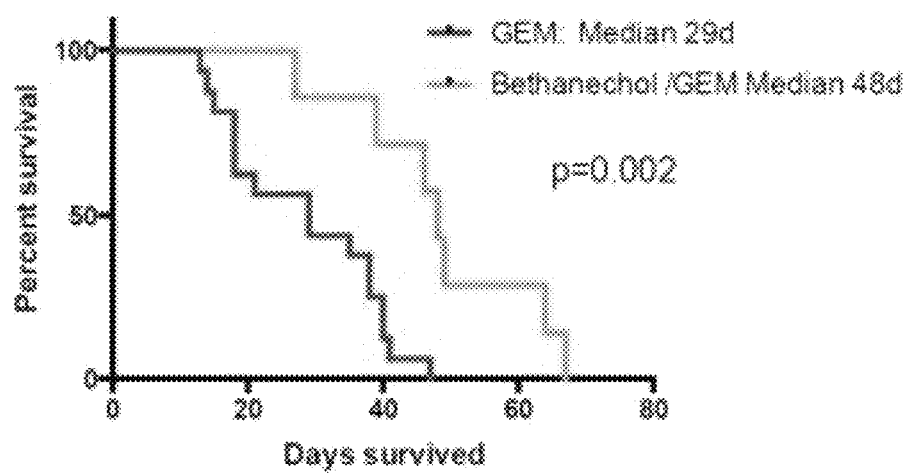

Similar results were observed with human pancreatic cancer cells. Implantation in NOD/SCID mice of 25.000 human Panc-1 cells after treatment with treatment with Pilocarpine, also a nonselective muscarinic agonist, this resulted in fewer and smaller tumors (FIG. 2C). This inhibition of human PDAC growth by Pilocarpine appeared to be linked to a remarkable suppression of the putative cancer stem cell population $CD44^+CD24^+EpCAM^+$ by FACS analysis. This finding was supported by results from anchorage independent tumor sphere assays (soft agar) showing significantly fewer colonies after Pilocarpine treatment. (FIG. 2D-E). Moreover, gene expression analysis by RNAseq, RT-qPCR and immunoblotting elucidates that cholinergic stimulation modulates multiple signaling pathways including mTOR, PI3K-AKT and MAPK signaling in KRas-mutant human cancer cells.

Cholinergic Stimulation Suppresses Tumorigenesis and Prolongs Survival in a GEMM of PDAC.

Importantly, it was found in studies of the KPC model that treatment of Bethanechol in combination with Gemcitabine (GEM) significantly extended overall survival (48 vs. 29 d) compared to GEM alone (FIG. 2F) when mice were treated after 4-5 mm tumors were detected by palpation and high-resolution ultrasound.

Taken together, cholinergic signaling plays a suppressive role in K-Ras-driven PDAC initiation and progression and offers therapeutic promise. Retrospective register studies are supportive as studies by van Rees et al (8) and Tascilar et al (9) showed a strong correlation between vagotomy and risk for PDAC. Finally, De Couck et al (10) showed that higher vagal nerve activity was associated with better overall survival in metastatic PDAC. The role of cholinergic signaling in metastatic pancreatic cancer can be investigated, the clinical treatment of cholinergic stimulation as a treatment modality can be tested, and some of the mechanisms of action (MoA) can be determined. The pre- and early phase clinical findings described herein can be a promising new therapeutic strategy in a cancer for which patients have long needed new approaches to manage their devastating disease in order to contribute to the goal of doubling PDAC survival by 2020.

Clinical Need

While growing data suggest a role for neural modulation of pancreatic cancer, it has been difficult to identify specific pathways that can be modulated safely. In addition, even patients that undergo resection for cure have a high rate (e.g. 80%) of relapse following surgery. Given the findings described herein that pancreatic denervation via vagotomy leads to increased growth of pancreatic cancer, cholinergic agonism may be an effective drug in patients undergoing resection. Furthermore, in late stage patients with metastatic disease, there is a need for additional therapies and ideally these therapies would not be cytotoxic drugs that could enhance the toxicity of other therapies. While there has been much interest in immune therapies in other cancers, to date these have not shown much efficacy in PDAC. Thus, other approaches are clearly needed.

Methodology Feasibility

Described herein is the feasibility and efficacy of muscarinic agonism in several different models—in vitro spheres, in vitro cancer cell lines, xenograft models, KC mice and KPC mice. A metastatic model of pancreatic cancer that has been established in the laboratory can also be used. In addition, the regulatory network leading to inhibitory responses to bethanechol can be dissected.

Specific Aims

Cholinergic innervation is part of the normal gut stem cell niche and is needed for cancer initiation and progression in the stomach (1, 2). Thus, given accumulating data that nerves are involved in PDAC3, it was expected that a similar cholinergic dependence would be observed for the pancreas and pancreatic cancer. However, the results described herein have shown that surgical cholinergic denervation (i.e. vagotomy) accelerates pancreatic cancer in PanIN/KC mice, which is ameliorated by muscarinic agonists such as bethanechol. Moreover, while cholinergic stimulation induces proliferation of the normal pancreas and in WT pancreatic spheroids, mutation (G12D) of the KRAS gene in pancreatic spheroids results in an altered cholinergic response, such that cholinergic stimulation now suppresses their growth. Muscarinic stimulation suppresses the growth of human pancreatic cancer cell lines, to a large extent by suppressing the number of pancreatic cancer stem cells (CSC). Cholinergic stimulation also reduces tumor infiltration by tumor-associated macrophages. Analysis of muscarinic receptors indicates that the M1R is highly expressed in the murine pancreas, upregulated following denervation, and is moderately suppressed during pancreatic tumor suppression. Muscarinic-1 receptor agonists and antagonists effectively modulate the proliferation of pancreatic spheres. In contrast, human pancreatic cancer cells predominantly express the M3 receptor, which mediates a similar inhibitory response to pilocarpine; this inhibitory response has been investigated using RNAseq. Finally, treatment of KPC mice with Bethanechol+Gemcitabine leads to significantly increased survival compared to Gemcitabine alone. Given this data, bethanechol may be an effective medication with limited toxicity in patients with advanced PDAC. Additional preclinical studies can be carried out to understand the efficacy and mechanism of action of muscarinic signaling, and at the same time begin a pilot neoadjuvant clinical study in patients.

In order to study the role of muscarinic signaling in restraining metastatic pancreatic cancer and the effectiveness of muscarinic agonism in suppressing the growth of liver metastases: (1) The dose-response profile of pharmacologic modulation of muscarinic signaling on metastatic pancreatic cancer can be examined; (2) The utility of bethanechol in combination with gemcitabine on metastatic PDAC can be determined; (3) clinical responses can be correlated with candidate biomarkers of response, including markers of proliferation, cancer stem cells and macrophages, and gene expression.

In order to study the mechanism by which mutant KRAS signaling leads to an inhibition of proliferation by muscarinic signaling, in contrast to effects on non-mutated pancreatic acinar cells: (1) Changes in signaling in WT versus Kras pancreatic tissues in response to cholinergic stimulation can be analyzed using a multiplex kinase assay platform; (2) Changes in gene expression using RNAseq in WT versus Kras pancreatic spheres in response to cholinergic stimulation can be investigated; (3) C. A candidate mechanism of action (MoA) for the inhibitory effect of cholinergic agonism can be identified and validated through development and interrogation of a pancreas-specific gene regulatory network with cholinergic agonist RNASeq signatures, using the DEMAND and VIPER algorithms.

In order to study whether muscarinic agonism a safe therapy for patients with potentially resectable pancreatic cancer and whether the therapy lead to detectable changes in tissue: (1) A pilot clinical trial of 15 patients in a neoadjuvant setting will be initiated. Patients that are identified as surgical candidates will be enrolled and treated preoperatively with bethanechol 100 mg bid. Tolerability of the treatment will be assessed, and effects on tissue biomarkers and gene networks will be analyzed.

Research Design and Methods

Role of muscarinic signaling in restraining metastatic pancreatic cancer and the effectiveness of muscarinic agonism in suppressing the growth of liver metastases In the data described herein, it has been established that cholinergic agonism suppresses the early development and primary growth of PDAC using both in vitro and in vivo models. Thus, described herein is the inhibitory effects of muscarinic agonists (pilocarpine or bethanechol) in the sphere forming capacity of Kras-mutant murine organoids, PanIN progression in KC mice, survival of KPC mice treated with gemcitabine, the growth of murine (K-822) and human (Panc-1, Mia PaCa2) cancer cell lines in vitro, and the subcutaneous growth of Panc-1 cells in xenograft models. Most patients diagnosed with PDAC have invasive disease that is unresectable, and the vast majority of patients needing therapy have metastatic disease, often involving the liver. Thus, whether cholinergic agonism could suppress the growth of PDAC will be studied in a metastatic model.

Figure 3C:
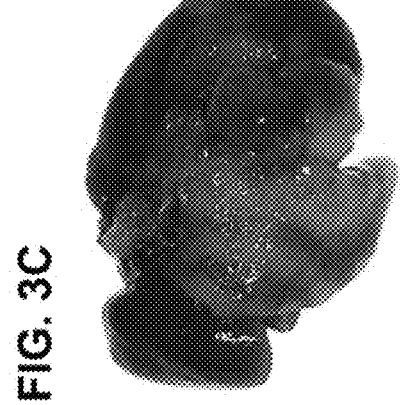
FIGS. 3A-F shows metastatic PDAC model and hepatic denervation. (A, B). Cartoon and image of splenectomy & injection. (C, D). Gross image and histopathology of Panc02 mets to the liver at 4 wks. (E). Diagram of vagal innervation of the liver—hepatic branch comes off of the anterior vagal branch. (F). Gross image of surgery for hepatic denervation.
Figure 3F:
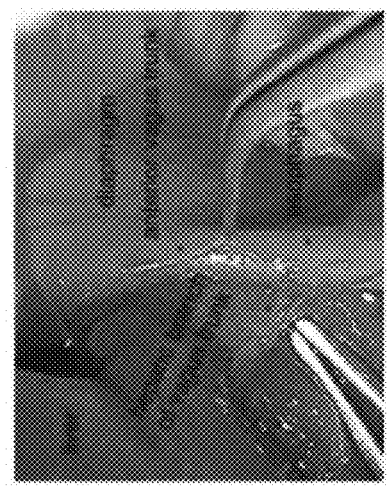
Figure 3B:
Figure 3E:
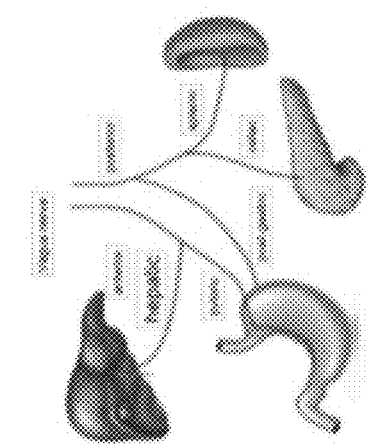
Figure 3A:
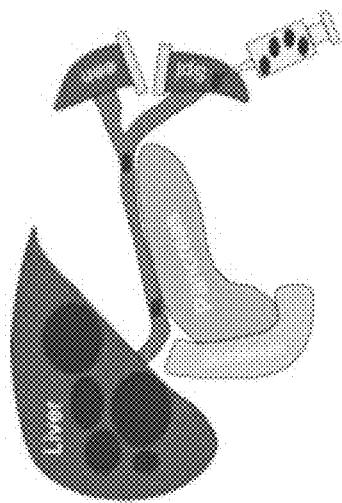
Figure 3D:

A metastatic mouse model of pancreatic cancer has been developed. The procedure reported by Lei Zheng has been modified and involves resecting half the spleen followed by injection $2 \times 10^6$ Panc02 (or other PDAC cell lines) into the spleen (4, 5). (FIG. 3A, B). Mice are then sacrificed 30-60 days later. This model leads to multiple hepatic metastases (FIG. 3C, D), which can be confirmed by immunostaining or by labeling of cells with GFP or RFP tags. The model is quite reproducible with a predictable survival curve. In combination with this metastatic model of pancreatic cancer, a surgical approach to achieve selective cholinergic denervation of the liver has been developed. This involves identifying and isolating the hepatic branch of the vagal nerve, followed by resection of the hepatic branch (FIG. 3E, F).

Figure 4:
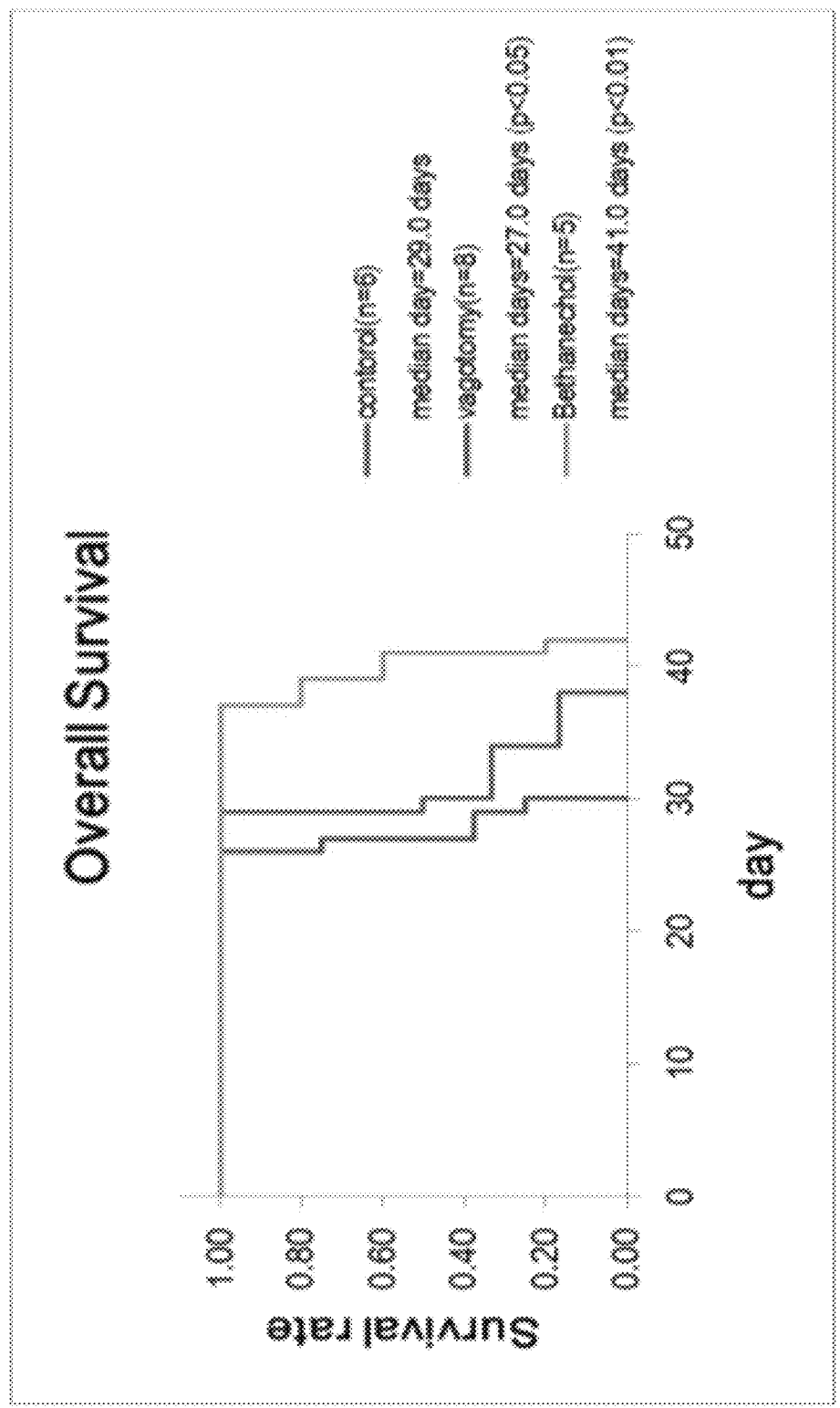
FIG. 4. Survival in Panc02 liver metastatic model with selective vagotomy or bethanechol treatment.

In additional preliminary studies, the effects of bethanechol on the progression of liver metastases and in survival were examined. Control (untreated) mice were compared to mice with selective vagotomy to mice treated with bethanechol in their drinking water. There were 5-8 mice in each group. Surprisingly, selective liver vagotomy resulted in accelerated tumor growth ($p<0.05$) and decreased survival (27 days) compared to controls (29 days), while bethanechol treatment extended survival to 41 days ($p<0.01$) (FIG. 4). These findings will be confirmed and extended, and it will be determined if there are biomarkers that can predict responses and if combination treatment shows additional advantages.

Figure 5:
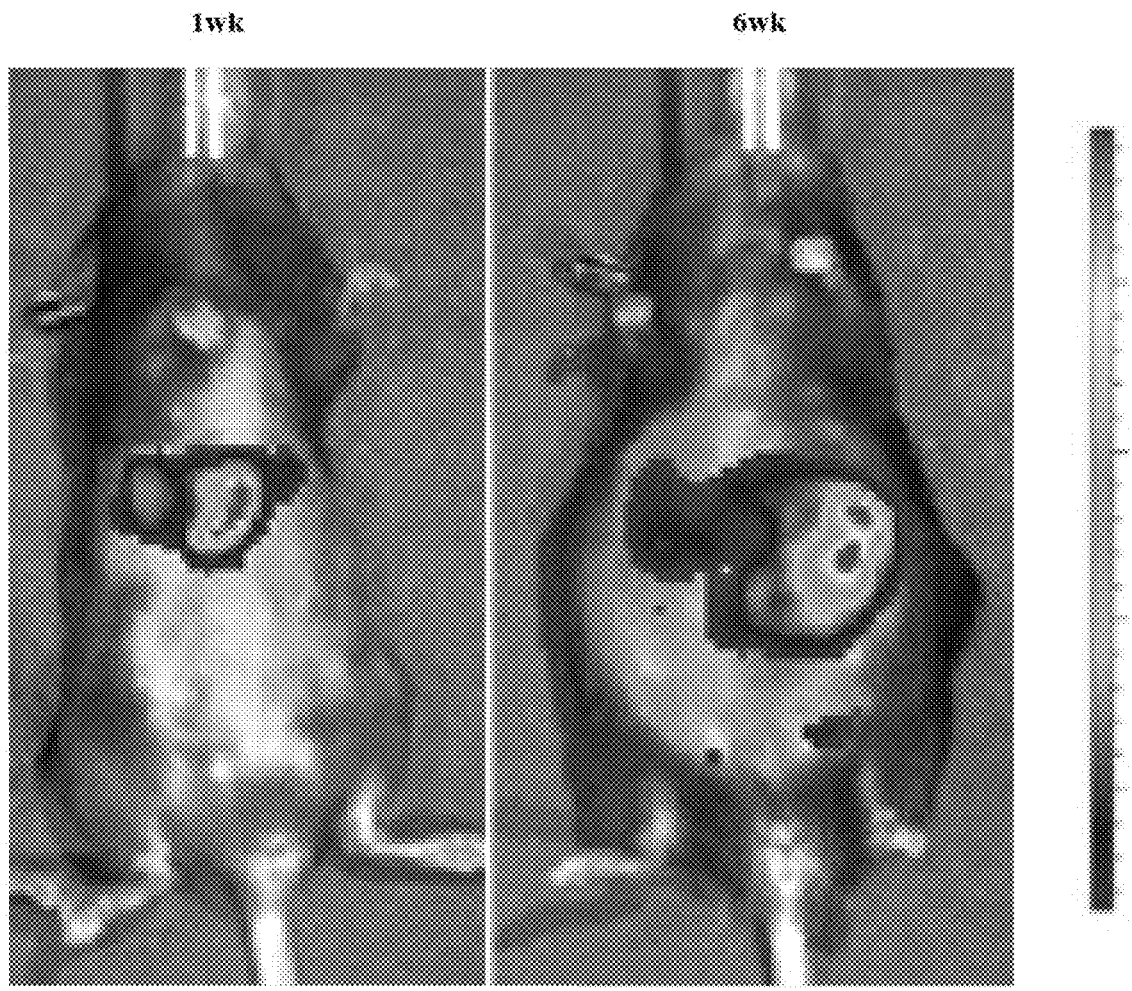
FIG. 5. Bioluminescence imaging of B6 mice with 1.5× $10^6$ GFP-Luciferase Panc02 cells metastatic to the liver at 1 & 6 wks.

Proposed experiments include:

(A) Dose response studies. In the initial studies, previously reported doses of bethanechol (800 mg/L) were used, which calculates to 80 mg/kg/day/mouse. Given that this dose is reasonably effective, the therapeutic range and potential toxic level can be determined. This study will be repeated using a large range (400, 800, 1200, and 1600 mg/L) in the Panc02 liver metastatic model, with Panc02 cells transfected with GFPLuciferase constructs. In addition to an untreated control group, mice that are treated with a broad muscarinic antagonist, scopolamine (given via an osmotic micropump 0.5 mg/kg/day; Sigma-Aldrich), or saline as previously described (6) will also be tested. Osmotic pumps will be implanted at the time of surgery, and bethanechol will be started in the drinking water several days after surgery. There will be a minimum of 8 mice in each group and mice will be weighed weekly and sacrificed when they meet typical endpoint criteria for euthanasia. Tumor growth will also be followed using a bioluminescence imaging system (FIG. 5).

(B) Combination with chemotherapy. The data shows a strong inhibitory effect of bethanechol alone on inhibiting PDAC growth, it is expected that cholinergic agonists—if used in the clinic—would be used in combination with chemotherapy. It has been shown that this Gemcitabine/ Bethanechol combination is effective in KPC mice. Thus, both the efficacy and toxicity of bethanechol in combination with gemcitabine in the metastatic model of PDAC can be determined. The Panc02 cell line will be used with at least 8 mice in each group; the groups will include (1) untreated control; (2) bethanechol 800 mg/L in the drinking water; (3) gemcitabine given by i.p. injection at a dose of 100 mg/kg twice a week, given as 5 mg/ml saline solution by i.p. injections as described7; (4) bethanechol+gemcitabine. The primary endpoint for this study will again be survival, and mice will be euthanized when they meet endpoint criteria.

(C) Immunohistochemical biomarkers. The changes in potential biomarkers after bethanechol treatment will be studied to help better predict future responses in patients. Immunohistochemical staining will be performed for markers of proliferation (Ki67), cancer stem cell markers (C44), macrophage (F4/80) markers, nerves (peripherin or neurofilament), signaling markers (phospho-EGFR and phosphor-PI3K) which are all decreased with bethanechol. Immune (T, B and MDSC) cells and chemokines (e.g. CCL2/CCL5) will be measured more broadly.

(D) Gene expression biomarkers. Changes in mRNA from the previous RNAseq data in Panc-1 cells treated with pilocarpine will be confirmed. The top 7 genes modulated with pilocarpine included downregulation of BRAF, EGFR, PIK3CA, ITGAV, KDR, and FOXO3, and upregulation of STK11 and FOX06. Additional genetic targets identified may be assayed at later times. RT-PCR of tumor RNA from dissected, fresh frozen metastatic lesions can be used to assess expression of genes from the different treatment groups, to confirm a correlation between smaller tumor growth with downregulation of muscarinic signaling target genes compared to controls.

The Mechanism by which Mutant KRAS Signaling Results in Inhibition of Proliferation by Muscarinic Signaling, in Contrast to Effects on Non-Mutated Pancreatic Epithelial Cells.

The inhibitory effects of bethanechol on growth of KRAS-mutant PDAC cells is in many ways remarkable, given the stimulatory effect of bethanechol on WT acinar cells. This was confirmed in the in vivo studies with KC and KPC mice, and the in vitro studies with KC and WT pancreatic spheres. Without being bound by theory, mutant KRAS signaling will somehow converts M1R or M3R signaling from a proliferative pathway to an inhibitory pathway. This suggests that Kras mutation leads to special vulnerability to muscarinic signaling, a form of oncogene dependence or synthetic lethality. However, given the importance of KRAS target, the alteration in signaling associated with the mutant Kras and muscarinic signaling combination can be studied further. The means by which KRAS oncogenic leads to inhibitory effects can be investigated through following series of studies:

(A) Multiplex kinase assays to assess changes in signaling. Specifically, the ProteomeProfiler™ phosphorylation assay kit will be used, which is a membrane-based multiplex antibody array, to simultaneously detect relative levels of phosphorylation of 39 mouse kinase phosphorylation sites. The human version of this multiplex array has been a successful tool in identifying adrenergic signaling candidates. To attain optimal sensitivity with minimal background from mouse tissues, the input sample amount will be initially determined for this array by testing the starting range from 200 to 800 μg of protein lysates. In addition, same-sample lysates will be used for further validation by Western blotting. Tissue from WT animals treated for 2 weeks with and without bethanechol, and vagotomized KC mice treated with and without bethanechol will be isolated and analyzed. Like most GCPRs, muscarinic receptors primarily signal through the protein phosphorylation cascades, so it is expected that the key MR-driven signaling elements that are specific to normal pancreas or cancer will be identified. These studies can be confirmed with studies of WT and KRAS pancreatospheres, along the lines of the RNA studies outlined below.

(B) Gene expression profile using RNAseq analysis of WT and KRAS mutant pancreatic spheres with and without pilocarpine treatment. KRAS G12D mutant pancreatic spheres will be grown from either KC (PDX1-Cre: KRAS G12D LSL) or KRAS G12D LSL mice followed by adenoviral—Cre transduction. In this RNAseq study, 2 types of spheres (WT and KRAS G12D), 2 different doses of pilocarpine (1 mM and 5-25 mM), and 3 different time points for each dose will be used. This particular number of samples (6 for each group+6 controls) has proved to be optimal for the analysis (e.g. DEMAND) to be carried out below. Pancreatospheres will be grown as previously described (8). The lower dose used (pilocarpine 1 mM) is one that has been shown to result in a significant inhibitory effect, and the higher dose (5-25 mM) used will be determine by further dose-response studies designed to find the highest sublethal dose tolerated by the cells in vitro. Following treatment, pancreatospheres will be isolated and pooled, and RNA prepared and cDNAs generated by random priming for sequencing. Initial analysis of this data will involve sorting the genes with the biggest differences and performing preliminary pathway analysis, but the data will primarily be used for the analysis described below.

(C) Bioinformatics approach. RNASeq based signatures of Kras-mediated changes in response to muscarinic agonists will be analyzed to prioritize proteins representing their mechanism of action (MoA) for experimental validation. In order to approach the possible mechanism for cholinergic inhibition of KRAS mutated pancreatic cell growth in unbiased fashion, experimentally validated regulatory network-based methodologies will be used for the de novo, genome-wide elucidation of compound-specific MoA proteins, using a pancreatic cancer regulatory model generated using the ARACNe algorithm (Alvarez et al Nat Genet 2016). This network will be interrogated with RNASeq-based gene expression profiles (GEP) from WT and KRAS mutant pancreatic spheres treated or not with pilocarpine using recently validated algorithms designed to find the downstream mechanistic targets. This will be accomplished using two algorithms that provide complementary insight into drug MoA, including VIPER (9), which identifies specific changes in regulatory protein activity, and DEMAND (10), which identifies changes in protein interactions resulting from small molecule perturbations.

VIPER is a newly introduced algorithm based on Virtual Interference of Protein activity by Enriched Regulatory analysis (VIPER). It allows an accurate assessment of protein activity based on the differential expression of their regulator targets, thus allowing effective transformation of gene expression profiles into protein activity profiles9. VIPER's probabilistic framework, which accounts for both positively regulated (activated) and repressed targets, can identify changes in protein activity using a single gene expression profile representing the aberrant state of the cell resulting from tumorigenic mutations or from pharmacological perturbations. Critically, it has been used to correctly predict the effect of short-term pharmacologic perturbations (e.g. 166 compounds) on the activity of downstream regulatory proteins (9). Specifically, RNAseq data will be analyzed using VIPER to identify proteins whose activity mediates the effect of muscarinic agonists.

Next, the same data will be analyzed using DEMAND, an algorithm for detecting mechanism of action by network dysregulation through compound perturbations (10). DEMAND works by pinpointing proteins whose network connectivity changes significantly as a result of a pharmacological perturbation. Recent studies suggest that DEMAND is able to use systemic gene expression profiles (GEP) analysis of cells following pharmacologic perturbation to elucidate established MoA proteins for 70% of tested compounds and also to elucidate novel proteins that were experimentally confirmed. To infer compound MoA, DEMAND also requires relatively small GEP datasets (N≥6 samples) representing in vitro or in vivo compound perturbations, at multiple time points and compound concentrations. GEP data cells treated with pilocarpine will thus be generated at 3 distinct times points and at two concentrations, using both KRAS mutant and WT control samples. While DEMAND can accurately predict MoA proteins, it cannot predict whether their activity will increase or decrease following perturbation. VIPER specifically compensates for this limitation (10). In any case, potential candidates will be pursued in followup experiments (e.g. in vitro knockdown studies) and also confirmed in vivo as biomarkers and predictors of response.

Safety of Muscarinic Agonism for Patients with Potentially Resectable Pancreatic Cancer and Detectable Changes in Tissue and Gene Expression from Short-Term Pre-Surgical Treatment.

Background Data:

Pancreatic ductal adenocarcinoma is the 3rd most common cause of cancer-associated death in the US and effective treatment options are limited (11). With currently available therapy, most patients will have disease progression after 3-6 months of treatment and median overall survival of <1 year (12, 13). New treatment paradigms and targets are urgently needed. The pancreas is richly innervated by the sympathetic and parasympathetic nervous systems, and as noted above, in pre-clinical models of pancreatic cancer it has been demonstrated that muscarinic stimulation results in diminished tumor growth. Here, a Phase 1, window of opportunity study of the commonly used parasympathetic agonist, bethanechol, is proposed to evaluate biomarkers of drug activity and nerve changes in subjects with pancreatic cancer who are proceeding to surgical resection.

Study Design:

This is a window of opportunity (Phase0/Phase 1) study evaluating short-term parasympathetic activation with fixed dose bethanechol in subjects with limited stage pancreatic cancer who are planning to proceed with definitive surgery. Subjects who present to the Pancreas Center for evaluation of PDAC will be enrolled. The overall study population will be subjects who are planning to undergo resection for this PDAC who have not received prior chemotherapy or radiation therapy. To minimize risk of toxicity that may delay surgery or lead to unacceptable complications, subjects will be carefully selected, excluding those with prior medical conditions as detailed below. In addition, only subjects who have or plan to obtain adequate baseline tumor sampling in order to compare pre- and post-treatment specimens will be selected. Subjects will be treated for a minimum of 2 weeks with bethanechol at 100 mg by mouth twice daily and will cease therapy 48 hours prior to scheduled surgery.

Objectives:

The primary objective of this study is to assess the impact of bethanechol therapy on tumor activity by looking at biomarkers of proliferation (Ki67), macrophage activation (F4/80), cancer stem cell (CD44) markers, and signaling (phosphor-EGFR, phospho-PI3K) markers in posttreatment specimens compared to pre-treatment specimens. Without being bound by theory, treatment with bethanechol will stimulate muscarinic pathways and reduce tumor proliferation, reduce macrophage activation, decrease CD44+ cancer stem cells, and other markers identified in the preclinical models. In addition, gene expression profiles from resected tumors will be analyzed following bethanechol treatment compared to untreated historical controls and compare these to changes in mouse models that respond to muscarinic inhibition.

Figure 6B:
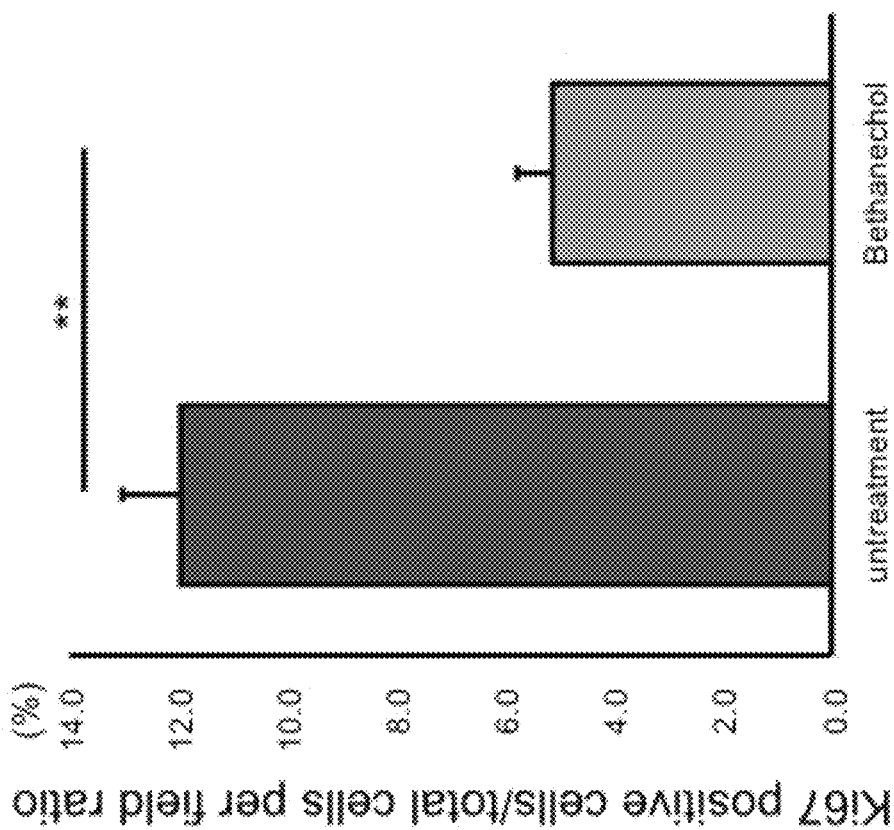
FIG. 6A-B.
Figure 6A:
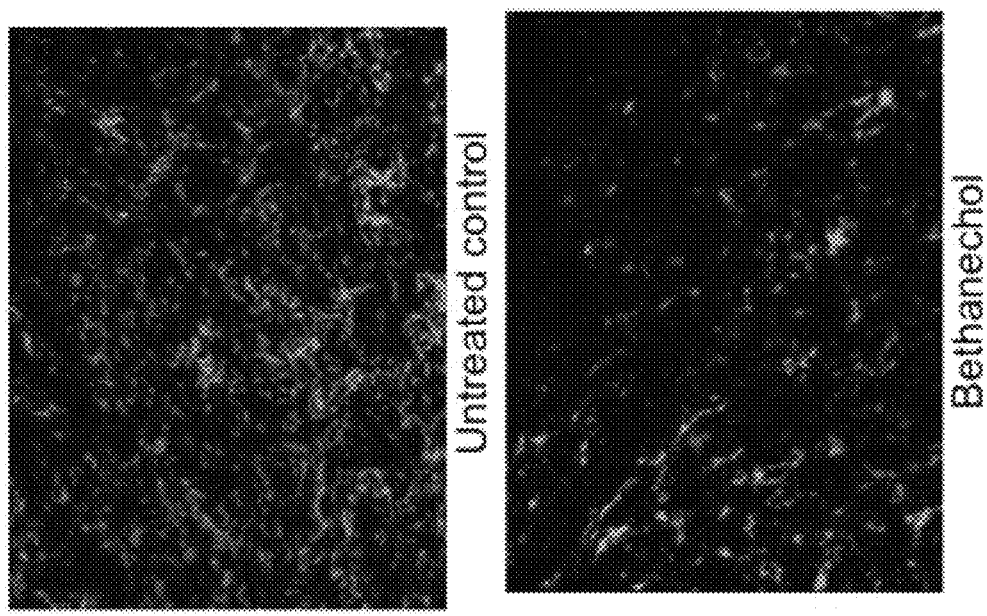

Statistics:

The primary endpoint is a change in Ki-67 cell proliferation. Previous studies utilized MIB-1 monoclonal Ab on paraffin sections from resected PDAC specimens, reporting a mean MIB-1 labeling index of 28% (14), while another study reported median Ki-67 staining in 26% of PDAC nuclei (15). Without being bound by theory, short-term treatment with bethanechol will result in decreased cell proliferation/Ki-67 staining. In mice, bethanechol results in a 50% reduction in Ki-67 staining of Panc02 liver mets (FIGS. 6A and B). With 15 analyzable pairs and assuming baseline Ki-67 expression of 28%, there will be 80% power to detect a change in Ki-67 of 12% (0.8 standard deviation) to 16% in the matched post-treatment specimens. The Type I error probability associated with this test of the null hypothesis that this response difference is zero is 0.05. Exploratory statistical analysis of gene profiles in treated tumors compared to historical data of untreated pancreatic cancer resection specimens will be explored. The secondary objective will be assessment of the tolerability of short course bethanechol and impact on surgical complications and outcomes.

Methods:

The overall goal is to assess the impact of short course bethanechol treatment in PDAC by analyzing tumor tissue obtained from patients treated on the clinical trial for biomarker response and for gene expression analysis. Fifteen (15) patients will undergo pre- and post-treatment tumor samples to provide tissue for analysis. Blood samples will be collected from all patients at baseline and at the time of surgery to provide matched normal DNA and to permit the future conduct of correlative studies. For the primary objective, IHC on paraffin fixed tumor samples obtained at diagnosis and surgical resection will be used, and tumor proliferation will be quantified by measuring Ki-67+ nuclei in >5 high-powered fields for each tumor time point. Macrophage activation will be assessed by quantifying F4/80 stained area in tumor specimens. Frozen samples will be collected from all subjects at the time of surgery per ongoing protocol. RNA will be isolated from these samples and RNASeq analysis conducted. As above, gene expression profiles and regulatory networks will be compared between treated samples and matched historical controls in the larger dataset of RNASeq profiles from resected pancreatic cancers (n>200). The findings will also be compared to findings from the murine regulatory networks derived from DEMAND and VIPER. To evaluate tolerability and safety all treatment related toxicities will be assessed with an emphasis on GI side effects and the impact of therapy on surgical delays or post-op complications. All subjects will be contacted 1 week after beginning therapy to assess toxicity including GI specific toxicity. Subjects will also be followed for safety for 30 days following completion of study medication. It is expected that short-duration treatment will be tolerable in this selected patient population and will not interfere with progression to surgery or increase surgical complications.

Rationale for Bethanechol Dosing:

Bethanechol, a synthetic ester related to acetylcholine, is approved by the FDA for use in treatment of urinary symptoms related to urinary retention and neurogenic bladder. The primary side effects relate to parasympathetic nervous system stimulation and are well characterized based on clinical experience. To minimize toxicity in this short-term study, a limited number of subjects will be selected who will be most likely to tolerate this therapy without excessive toxicity based on preexisting medical conditions. Bethanechol is currently used in the treatment of bladder spasm with recommended doses up to 50 mg 4 times daily though this primarily relates to the functional role of this agent. In other studies, single doses have been estimated up to 200 mg dose with only mild cholinergic toxicity (16). In cancer patients, bethanechol has been evaluated in the treatment of xerostomia at doses of 25 mg twice daily for several months without any severe (Grade 3) toxicity or need to stop the study for adverse effects (17). A previous study in cancer patients evaluated bethanechol up to doses of 50 mg three times daily to evaluate treatment of xerostomia. This study (18) as well as another earlier report (19) of bethanechol using lower dose (25 mg 3 times a day) did not identify any clinically significant side effects. Given the expected healthy population and exclusion of subjects with potential toxicity (see detailed exclusion criteria), a fixed dose of 100 mg twice daily with meals is planned (equivalent to 50 mg 4 times daily). Toxicity will be monitored with specific attention to GI toxicity and will monitor progression to surgery as detailed.

Implementation Solutions and Alternative Strategies

The abundant preclinical data described herein, demonstrates the effects of muscarinic agonism in 5 different model systems, including all stages of PDAC and in both human/murine cancer cells. The ideal dosage can be determined and can be tested in the metastatic model, as well as the tolerability of combination with gemcitabine therapy (although gemcitabine+nab-paclitaxel can also be used). An advantage of bethanechol is that it is well tolerated and has been utilized extensively in the clinic, and thus fewer interactions or toxicity in combination with standard chemotherapy is expected. Bethanechol is a broad muscarinic agonist (and thus does not target nicotinic receptors). An alternative approach might be direct vagal electrical stimulation, which has been utilized in preclinical models (20) but despite the recent SPARC initiative, implantable technology for long-term vagal stimulation is not yet available. RNAseq and gene expression studies will be used to develop better biomarkers that predict response. The mechanisms by which muscarinic agonism inhibits proliferation specifically in pancreatic cancer cells is unknown, but we the bioinformatics approach will provide further insight into the MoA, potentially identifying further targets. Neoadjuvant studies of an unproven agent may be unacceptable to some patients who are eager to undergo surgery for their PDAC, but there are many patients who are eager to participate in novel clinical studies given the overall poor prognosis. With assurance from the primary surgeon that this treatment is unlikely to delay surgery and will include a commonly used, FDA approved medication, a minimum of 1 subject each month of the study is expected. A preliminary analysis of toxicity and surgical outcomes will be performed after the first 3 subjects to evaluate any need for dose modification.

Contribution to 2020 Goal

The 2020 Goal is to double survival from pancreatic cancer, and it is unlikely that this can be accomplished with a single drug or therapy. Described herein is a currently available drug—bethanechol—FDA approved for patients with urinary retention—with significant suppressive activity in PDAC. Given its limited toxicity and potential unique mechanism of action, it is believed that it is ideally position for rapid introduction into the clinic. Given that PDAC patients that undergo surgical resection typical undergo simultaneous vagotomy, this therapy can have huge implications for adjuvant treatment and potentially contribute in the advanced setting. These studies can lead to direct improvement in patient survival and contribute to the goal of doubling pancreatic cancer survival by 2020.

This trial closely models the FDA recommended exploratory investigational new drug model (Phase 0 studies) (21) and will enable rapid testing of a novel pathway in pancreatic cancer. Additional trials, both in the adjuvant setting (e.g. post-Whipple) and in the treatment of stage IV metastatic pancreatic cancer, in combination with chemotherapy or other novel therapies can be performed.

Cell Lines Used and Authentications:

The cell lines to be used in the study herein have all been authenticated by the ATCC.

REFERENCES

1. Zhao C M, Hayakawa Y, Kodama Y, et al. Denervation suppresses gastric tumorigenesis. Sci Transl Med 2014; 6:250ra115.
2. Hayakawa Y, Sakitani K, Konishi M, et al. Nerve growth factor promotes gastric tumorigenesis through aberrant cholinergic signaling. Cancer Cell 2017; (in press).
3. Demir I E, Friess H, Ceyhan G O. Neural plasticity in pancreatitis and pancreatic cancer. Nat Rev Gastroenterol Hepatol 2015; 11:649-59.
4. Soares D C, Foley K, Olino K, et al. A preclinical murine model of hepatic metastases. J Vis Exp 2014; 91:51677. doi: 10.3791/51677.
5. 5. Soares D C, Rucki A A, Kim V, et al. TGF-b blockade depletes T regulatory cells from metastatic pancreatic tumors in a vaccine dependent manner. Oncotarget 2015; 6:43005-15.
6. Gross E R, Gershon M D, Margolis K G, et al. Neuronal serotonin regulates growth of the intestinal mucosa in mice. Gastroenterology 2012; 143:408-417.
7. Olive K P, Jacobetz M A, Davidson C J, et al. Inhibition of hedgehog signaling enhances delivery of chemotherapy in a mouse model of pancreatic cancer. Science 2009; 324:1457-61.
8. Westphalen C B, Takemoto Y, Tanaka T, et al. Dclk1 Defines Quiescent Pancreatic
9. Progenitors that Promote Injury-Induced Regeneration and Tumorigenesis. Cell Stem Cell 2016; 18:441-55. Alvarez M J, Shen Y, Giorgi F M, et al. Functional characterization of somatic mutations in cancer using network-based inference of protein activity. Nature Genetics 2016; 48:838-847.
10. Woo H H, Shimoni Y, Yang W S, et al. Elucidating compound mechanism of action by network perturbation analysis. Cell 2015; 162:441-451.
11. Siegel R L, Miller K D, Jemal A. Cancer statistics, 2016. C A Cancer J Clin 2016; 66:7-30.
12. Conroy T, Desseigne F, Ychou M, et al. FOLFIRINOX versus gemcitabine for metastatic pancreatic cancer. N Engl J Med 2011; 364:1817-25.
13. Van Hoff D D, Ervin T, Arena F P, et al. Increased survival in pancreatic cancer with nab-paclitaxel plus gemcitabine. N Engl J Med 2013; 369:1817-25.
14. Stanton K J, Sidner R A, Miller G A, et al. Analysis of Ki-67 antigen expression, DNA proliferative fraction, and survival in resected cancer of the pancreas. Am J Surg 2003; 186:486-92.
15. Lundin J, Nordling S, von Boguslawsky K, et al. Prognostic value of immunohistochemical expression of p53 in patients with pancreatic cancer. Oncology 1996; 53:104-111.
16. Chowdhury S, Wang S, Dunai J, et al. Hormonal Responses to Cholinergic Input Are Different in Humans with and without Type 2 Diabetes Mellitus. PLoS One 2016; 11:e0156852.
17. Jaguar G C, Lima E N, Kowalski L P, et al. Double blind randomized prospective trial of bethanechol in the prevention of radiation-induced salivary gland dysfunction in head and neck cancer patients. Radiother Oncol 2015; 115:253-6.
18. Gorsky M, Epstein J B, Parry J, et al. The efficacy of pilocarpine and bethanechol upon saliva production in cancer patients with hyposalivation following radiation therapy. Oral Surg Oral Med Oral Pathol Oral Radiol Endod 2004; 97:190-5.
19. Epstein J B, Burchell J L, Emerton S, et al. A clinical trial of bethanechol in patients with xerostomia after radiation therapy. A pilot study. Oral Surg Oral Med Oral Pathol 1994; 77:610-4.
20. Dubeykovskaya Z, Si Y, Chen X, et al. Neural innervation stimulates splenic TFF2 to arrest myeloid cell expansion and cancer. Nat Commun 2016; 7:10517. doi: 10.1038/ncomms10517.
21. LoRusso P M. Phase 0 clinical trials: an answer to drug development stagnation? J Clin Oncol 2009; 27:2586-8.

Example 2: Phase 1, Window of Opportunity Study of Parasympathetic Stimulation with Bethanechol in Localized Pancreatic Adenocarcinoma Prior to Surgery Study Design and Methodology:

This is a Phase 1 study evaluating short term parasympathetic activation with fixed dose bethanechol in subjects with pancreatic cancer who are planning to proceed with definitive surgery. It is anticipated to enroll 15 subjects with pancreatic ductal adenocarcinoma who are proceeding to surgical resection and have available baseline tumor specimens. Subjects will be treated for a minimum of 2 weeks with bethanechol at 100 mg by mouth twice daily and will cease therapy 48 hours prior to scheduled surgery.

Study Duration:

It is estimated that this study will accrue 1 subject month for 15 months with an additional 3 months for analysis and will be completed 18 months from first subject accrual.

Primary Objective:

The primary objective of this study is to assess the impact of bethanechol therapy on tumor activity by looking at biomarkers of proliferation, macrophage activation, and stem cell markers in post treatment specimens compared to pre-treatment specimens. Treatment with bethanechol may alter nerve conduction within tumors by stimulating the parasympathetic nervous system and reduce tumor proliferation, reduce macrophage activation and decrease CD44+ cancer stem cells.

Secondary Objectives:

The secondary objectives will be assessment of the safety and tolerability of short course bethanechol prior to surgery and the impact of this treatment on immediate surgical outcomes. All treatment related toxicities will be assessed with an emphasis on GI side effects and evaluate the impact of therapy on surgical delays or immediate post-op complications. All subjects will be contacted 1 week after beginning therapy to assess toxicity including GI specific toxicity. Subjects will also be followed for safety for 30 days following completion of study medication. Treatment for a minimum of 2 weeks should be tolerable in this selected patient population and will not interfere with progression to surgery or increase surgical complications. Secondary biomarker objective: Per standard practice fresh frozen tumor samples will be obtained at the time of surgical resection for RNA analysis (RNAseq) and gene expression and gene regulatory pathways compared in bethanechol treated samples compared to age and stage matched controls on the existing RNAseq database of resected pancreatic cancer specimens.

Diagnosis and Main Inclusion Criteria:

The overall study population will be subjects who are planned to undergo resection for their pancreatic adenocarcinoma and did not receive prior chemotherapy or radiation therapy.

Major Inclusion Criteria:—

Pancreatic Ductal Adenocarcinoma; —Plan to proceed to surgical resection without intervening therapy; —Available diagnostic tissue adequate for biomarker analysis; —Ability to tolerate PO meds and comply with study procedures.

Major Exclusion Criteria:—

Previous neoadjuvant chemotherapy or radiation; —Evidence of GI obstruction; —Baseline bradycardia (HR<55) or hypotension (systolic blood pressure<90); —Use of beta blocker or acetylcholinesterase inhibitors; —Medical conditions including: hyperthyroidism, coronary artery disease, seizure disorder, peptic ulcer disease.

Rationale for Study Population:

One current standard of care is for subjects with localized pancreatic cancer to undergo immediate surgical resection followed by adjuvant chemotherapy. The average time from initial surgical consultation to surgery in the Pancreas Center is 13.5 days (in 2015) and per the surgical team, it is appropriate in some patients to wait up to 3 weeks prior to surgery without compromising surgical outcomes or risk cancellation of surgery. This study will be conducted in subjects who are deemed by the surgical team to have localized tumors such that a 2-3-week period prior to surgery is unlikely to change the surgical approach. As bethanechol treatment is not expected to significantly change tumor outcomes the focus will be on patients with the lowest likelihood of treatment related toxicity. In the Pancreas Center, over 50 potentially eligible subjects are operated on a year and every patient is reviewed in multi-disciplinary conference which will enable us to identify at least 1 appropriate subject during each month of the active study and accrue 15 subjects within 2 years.

Study Product, Dose, Route, Regimen:

Study Drug: Bethanechol (generic), supplied as 50 mg oral tablets. Subjects will take 2 tablets (100 mg) twice daily from day 1 for a minimum of 2 weeks. Medication should be taken 1 hour before meals in AM and PM.

Duration of Administration:

Medication will begin on day 1 and continue until 2 days prior to scheduled surgery but for a minimum of 2 weeks and a maximum of 4 weeks.

Rationale for Study Product Dosing:

Due to the short duration of therapy a limited number of subjects will be selected who will be most likely to tolerate this therapy without excessive toxicity. Bethanechol is currently used in the treatment of bladder spasm with recommended doses up to 50 mg 4 times daily though this primarily relates to the functional role of this agent. In other studies, single doses have been estimated up to 200 mg dose with only mild cholinergic toxicity (2). In cancer patients, bethanechol has been evaluated in the treatment of xerostomia at doses of 25 mg twice daily for several months without any severe (Grade 3) toxicity or need to stop the study for adverse effects (3). A previous study in cancer patients evaluated bethanechol up to doses of 50 mg three times daily to evaluate treatment of xerostomia. This study (4) as well as another earlier report (5) of bethanechol using lower dose (25 mg 3 times a day) did not identify any clinically significant side effects.

Given the expected healthy population and exclusion of subjects with potential toxicity (see detailed exclusion criteria) a fixed dose of 100 mg twice daily with meals is planned. Toxicity will be monitored with specific attention to GI toxicity. Progression to surgery will also be monitored as detailed.

Statistical Methodology:

Each individual tumor will be analyzed, comparing pre- and post bethanechol samples. The primary endpoint will be change in cell proliferation by Ki-67 expression in tumor cells. Previous studies have reported utilizing the MIB-1 monoclonal antibody on paraffin embedded tissue of resected pancreatic cancer specimens reported a mean MIB-1 labeling index of 28.1 with a standard deviation of 14.7 and staining in 94% of specimens (6) while another study reported median Ki-67 staining in 26% of pancreatic cancer nuclei (7). Short term treatment with bethanechol may result in decreased cell proliferation and reduced Ki-67 staining. With 15 analyzable pairs and assuming baseline Ki-67 expression of 28%, there will be 80% power to detect a change in Ki-67 of 12% (0.8 standard deviations) to 16% in the matched post-treatment specimens. The Type I error probability associated with this test of the null hypothesis that this response difference is zero is 0.05.

Study Procedures:

All subjects will be assessed by their primary surgeon and through inclusion criteria to be suitable for this therapy and able to complete a minimum of 2 weeks of bethanechol prior to surgery. Slides from FFPE biopsy specimens will be obtained for all subjects. Subjects will undergo fixed dose bethanechol therapy for a minimum of 2 weeks and stop treatment 48 hours prior to their planned surgery. At the time of surgical resection both fresh frozen and FFPE tumor specimens will be obtained for analysis.

Initial Visit:

After potentially eligible subjects are identified by the surgical team they will be approached by the study personnel. For the majority of subjects, it is anticipated that potential subjects will be identified prior to their first visit and will be approached at the initial visit. Some subjects will be identified after the initial visit and will be contacted and offered a study specific visit. At this initial visit, the subject eligibility will be reviewed, and the subject will sign the ICF. Prior to initiating study medication, all eligibility criteria will be reviewed. If a subject is eligible they will begin Bethanechol 100 mg PO BID as described on the day following study enrollment.

Safety Follow Up #1:

7 days (+/−2 days) from beginning study medication. Subjects will be contacted, and toxicity will be reviewed and tabulated.

Safety Follow Up #2:

30 days (+/−7 days) post surgery. Subjects will be contacted (or seen if coming in for a clinic visit) and toxicity will be reviewed, and standardized surgical outcome data collected. These will include length of stay; estimated blood loss; unexpected surgical complications; post-op pancreatic leak; readmission within 30 days; and evaluation of time to feeding and time to resumption of urinary function post operatively.

Study Timeline:

Day 0: Sign informed consent, review eligibility, and receive study medication. Day 1: Begin study medication, fixed dose 100 mg bethanechol twice daily. Day 7 (+/−2 days): Contact (phone or in person) by study team to review GI and other study specific toxicity. Day 14+: 48 hours prior to scheduled surgery, subjects will be instructed to stop study medication. Day Post-op 30+/−7 days: Subject will be contacted to assess safety and toxicity and immediate surgical complication information (blood loss, ICU stay, hospital stay, unexpected events) will be collected from the medical chart and surgical team.

Specimen Collection:

Pre-treatment sample: Subjects will only be enrolled if they have a minimum of 5 available paraffin embedded slides (FFPE) from a tumor biopsy via core needle biopsy or fine needle aspirate. Subjects who have not had a biopsy will be eligible for consent prior to this procedure but will only be enrolled once biopsy has been obtained and sample adequacy verified. Surgical Specimen: Fresh frozen tumor specimen will be collected per standard protocol. In addition, a minimum of 20 blank FFPE slides from tumor samples will be obtained from each subject for correlative analysis.

REFERENCES

1. LoRusso P M. Phase 0 clinical trials: an answer to drug development stagnation? J Clin Oncol 2009; 27:2586-8.
2. Chowdhury S, Wang S, Dunai J, et al. Hormonal Responses to Cholinergic Input Are Different in Humans with and without Type 2 Diabetes Mellitus. PLoS One 2016; 11:e0156852.
3. Jaguar G C, Lima E N, Kowalski L P, et al. Double blind randomized prospective trial of bethanechol in the prevention of radiation-induced salivary gland dysfunction in head and neck cancer patients. Radiother Oncol 2015; 115:253-6.
4. Gorsky M, Epstein J B, Parry J, et al. The efficacy of pilocarpine and bethanechol upon saliva production in cancer patients with hyposalivation following radiation therapy. Oral Surg Oral Med Oral Pathol Oral Radiol Endod 2004; 97:190-5.
5. Epstein J B, Burchell J L, Emerton S, et al. A clinical trial of bethanechol in patients with xerostomia after radiation therapy. A pilot study. Oral Surg Oral Med Oral Pathol 1994; 77:610-4.
6. Stanton K J, Sidner R A, Miller G A, et al. Analysis of Ki-67 antigen expression, DNA proliferative fraction, and survival in resected cancer of the pancreas. Am J Surg 2003; 186:486-92.
7. Lundin J, Nordling S, von Boguslawsky K, et al. Prognostic value of Ki-67 expression, ploidy and S-phase fraction in patients with pancreatic cancer. Anticancer Res 1995; 15:2659-68.

Example 3—Parasympathetic Signaling Via Chrm1 Directly Regulates Pancreatic Carcinogenesis and Cancer Stemness Through MAPK and PI3K/Akt Pathway Abstract The autonomic nervous system, composed of sympathetic and parasympathetic signals, is one of the common feature of the microenvironment. In many sold tumors, parasympathetic input is provided by the vagus nerve, which has been shown to modulate growth through effects on the tumor and the stroma. However, whether parasympathetic signaling directly regulates the progression of pancreatic cancer (PDAC) has not been defined. Herein, it is determined that vagotomy (Vx) accelerated significantly pancreatic tumor development, while treatment with the muscarinic agonist Bethanechol suppressed tumorigenesis in Pdx1-Cre/KRas$^{G12D}$ (KC) mice. Furthermore, in Pdx1-Cre/KRas$^{G12D}$/Trp53$^{R172H}$ (KPC) mice with established PDAC, Bethanechol significantly extended overall survival. Parasympathetic signaling suppressed the growth of PDAC cells in both in vivo and vitro studies, and its effects appeared to be mediated through the cholinergic muscarinic receptor 1 (Chrm1) and its downstream MAPK and PI3K/Akt pathways. Reduced cholinergic signaling led to an increase in the abundance of pancreatic cancer stem cells, and also accelerated metastatic growth in the liver. Taken together, these data suggested that parasympathetic signaling directly suppresses the growth of pancreatic cancer cells and therapies directed at stimulating muscarinic receptors may be useful in inhibiting the growth and progression of PDAC.

Described here is: (1) Vagal denervation accelerated pancreatic carcinogenesis in K-Ras$^{+/LSL-G12D}$; Pdx-1-Cre (KC) mice; (2) Vagal stimulation suppresses pancreatic carcinogenesis and extended overall survival in K-Ras$^{+/LSL-G12D}$; p53$^{+/R172H}$; Pdx-1-Cre (KPC) mice (3) The effect of parasympathetic signaling is mediated via cholinergic muscarinic receptor 1 (Chrm1), which acts through downstream MAPK/PI3K pathways to promote cancer stemness; and (4) Parasympathetic signaling suppresses pancreatic tumorigenesis at both primary and liver metastatic sites.

Introduction

Pancreatic ductal adenocarcinoma (PDAC) is one of the most lethal malignant diseases with a poor response to most therapies (Hidalgo M et al. 2012, Olive K P et al. 2009). With few specific symptoms and no means for early detection, PDAC is usually diagnosed at an advanced, incurable stage (Edwards B K et al. 2005, Arslan A A et al. 2010). Even for patients with surgically resectable tumors, cures are uncommon. Thus, the median overall survival is only 5-6 months after conventional therapies for locally advanced and metastatic disease, and the 5-year overall survival rate is less than 8% (Siegel et al. 2016).

The resistance of PDAC to treatment has recently been attributed in part to the tumor microenvironment and the complex desmoplastic stroma, which includes an expansion of numerous cell types, including nerves.

Accumulating evidence has revealed a key role for the autonomic nervous system in the development of cancer. Multiple studies have reported a marked increase in neural density and nerve size in solid tumors. In addition, experimental model systems have shown a direct contribution of nerves to the development of prostate cancer, ovarian cancer, basal cell carcinoma, and gastric cancer. In addition, studies have shown that there is the crosstalk between tumor cells and nerves, with tumors able to induce active axonogenesis (Mattingly R R et al. 1994, Ayala G E et al. 2008). The stomach in particular is regulated predominantly by the parasympathetic nervous system, through the vagus nerve that promotes epithelial proliferation and stem cell activity. Thus, in the case of gastric cancer, abrogation of cholinergic stimulation by vagotomy or chemical denervation inhibits the growth of gastric cancer.

Similar to many other solid organs, the pancreas is innervated by both sympathetic and parasympathetic nerves (Bonaz 2007, Fernandez et al. 2014). The nervous system regulates pancreatic exocrine and endocrine function, and also contributes to the epithelial homeostasis and growth, through modulation of stem and progenitor cells (Kitayama M et al. 2006, Lundgren O et al. 2011). In addition, the vagus nerve has been shown to stimulate normal proliferation by the exocrine pancreas, such that ventromedial hypothalamic (VMH) lesions that induce vagal hyperactivity stimulate pancreatic proliferation and lead to pancreatic hypertrophy, while vagotomy leads to decreased pancreatic acinar growth (Kiba et al. 1996). On the other hand, other studies have suggested that the vagus nerve may have the potential to slow tumor progression (Gidron Y et al. 2005). Indeed, several papers have reported a higher incidence of PDAC in patients who underwent gastric ulcer surgery with vagotomy (De Couck M et al. 2012) epidemiologically and as the research paper, the orthotopic and syngeneic PDAC models treated with vagotomy promoted tumor growth and shortened the overall survival (Partecke et al., 2017). In addition, tumor-bearing animals that underwent chemical or surgical vagotomy showed enhanced metastasis (Erin N et al. 2004, 2008, 2012).

Understanding better cholinergic effects on pancreatic cancer growth is important, since transection of parts of the vagus nerve or its local fibers is unavoidable in many surgical procedures in the upper gastrointestinal tract. Consequently, the direct contribution of the vagus nerve, cholinergic signaling and muscarinic receptors to pancreatic cancer was investigated in depth. It is found that, in contrast to its role in gastric cancer, the vagus nerve strongly suppresses the growth of pancreatic cancer.

Results

Parasympathetic Denervation Promotes Pancreatic Carcinogenesis and Expands Cancer Stem Cells Via the Cholinergic Muscarinic Receptor 1 (Chrm1).

The previous paper showed that vagotomy led to reduce the proliferation of acinar cells in normal pancreas (Kiba et al. 1996). On the other hand, another previous paper revealed that vagotomy or vagal denervation suppressed the growth of gastric cancer (Zao et al. 2014). Then, to investigate the effects of parasympathetic denervation on pancreatic carcinogenesis, the genetically engineered KC (K-Ras$^{+/LSL-G12D}$;Pdx-1-Cre) mouse model was utilized. KC mice were divided into two groups: mice that received Vagotomy (Vx) plus Pyloroplasty (PP), while control animals received pyloroplasty (PP) alone. The KC mice received surgery at 8 weeks of age, and then were sacrificed at 20 weeks. Vagotomy had no affect the ratio of pancreas weight to body weight, but significantly increased expression of Chrm1 (p<0.05) but not the other muscarinic receptors. Indeed, Chrm1 was much more highly expressed in acinar and tumor epithelial cells in in KC+VxPP mice compared with KC+PP mice. While the initial expectation was that Vx would show suppressed pancreatic carcinogenesis similar to its effects in the stomach (Zao et al. 2015), the completely opposite result was observed, as Vx clearly accelerated pancreatic carcinogenesis. Next, the inflammation area was defined as the area excluding the normal pancreatic parenchyma and the tumor part and measured by image J. The inflammation area in KC+VxPP mice was significantly higher than in KC+PP mice (p<0.01). Importantly, the tumor incidence in KC+VxPP mice was also significantly higher compared with that in KC+PP mice (p<0.05). Indeed, while no PDAC was seen in the KC mice, cancer was found in over 40% of the vagotomized KC mice. Furthermore, the finding of accelerated pancreatic carcinogenesis following vagal denervation was supported by the finding of significantly increased CD44 immunohistochemical expression in in KC+VxPP mice compared to KC+PP mice (p<0.05). CD44 is a useful early marker of malignant potential but is also a generally accepted marker of pancreatic cancer stem cells (Du et al 2008, Ponti et al 2005, Li et al 2007). Thus, the data suggest the possibility that parasympathetic denervation might promote both pancreatic carcinogenesis and the development of cancer stem cells.

Parasympathetic Stimulation Directly Suppresses Pancreatic Carcinogenesis and Extends Overall Survival in KPC Mice.

Given that parasympathetic denervation appeared to accelerate the development of pancreatic cancer, whether parasympathetic stimulation would have the opposite effect on pancreatic carcinogenesis, and possibly suppress it was determined. Thus, KC mice that underwent vagotomy treated with or without Bethanechol, a broad muscarinic agonist, were compared. Bethanechol treatment (400 µg/ml) started immediately after receiving surgery and continued till 20 weeks. Bethanechol treatment of vagotomized KC mice led to a significant reduction in the area of inflammation and the overall tumor incidence (p<0.01 and p<0.05, respectively) compared to the KC+VxPP control group. In addition, bethanechol treatment led to a significant decrease in expression of CD44, a marker of advanced PanINs, in vagotomized KC mice compared to controls. Taken together, these data suggest that parasympathetic stimulation appeared to suppress early stages of pancreatic carcinogenesis.

Next, the role of cholinergic signaling in advanced pancreatic cancer was investigated using the genetically engineered KPC (K-Ras$^{+/LSL-G12D}$;p53$^{+/R172H}$;Pdx-1-Cre) mouse model, which develops ductal adenocarcinoma by 17-19 weeks (Olive et al., 2009, Hingorani et al., 2005). KPC mice with pancreatic tumors that were between 3-5 mm were randomized to treatment with gemcitabine (GEM, given by i.p. injection biweekly or gemcitabine plus bethanechol given daily. Treatment with bethanechol+GEM extended the overall survival of KPC mice to 48 days (p=0.002), compared to 29 days in the control mice treated with GEM only. In addition, treatment of KPC mice with GEM and bethanechol led to a significant reduction in CD44 expression compared to KPC mice treated with GEM only (p<0.05). Then, parasympathetic stimulation might have potential to suppress pancreatic carcinogenesis and cancer stem cells in the opposite of the denervation.

Parasympathetic Signaling Directly Influences Cell Proliferation in K-Ras Mutant Sphere Formation Via Chrm1 and Regulates Cancer Stemness.

Cholinergic stimulation could in theory promote cancer indirectly through effects on stromal cells, or directly through effects on pancreatic epithelial cells. To determine whether cholinergic stimulation promoted tumor development in part through muscarinic receptors on cancer cells, the sphere forming capacity of K-Ras$^{+/LSL-G12D}$ mutant pancreatic acinar cells was assessed in a 3D Matrigel culture system, with or without muscarinic stimulation. K-Ras$^{+/LSL-G12D}$ mutant spheres were generated from K-Ras$^{+/LSL-G12D}$ pancreatic acinar cells by treatment with adenoviral delivered Cre (Ad-Cre). K-Ras$^{+/LSL-G12D}$ mutant spheres were treated with the non-selective muscarinic agonist pilocarpine (1 mM), the non-selective muscarinic antagonist scopolamine (10 µM), the Chrm1 selective agonist McN-34A (50 µM), or the Chrm1 selective antagonist pirenzepine (50 µM). Intriguingly, the spheres treated with pilocarpine formed significantly fewer spheres with a smaller size, while the spheres treated with scopolamine formed significantly more spheres with a larger size compared to the controls. In addition, the spheres treated with McN-34A formed significantly fewer spheres with a smaller size, while the spheres treated with pirenzepine formed significantly more spheres with a larger size compared with controls.

Analysis of muscarinic receptors expression in human and murine pancreatic cancer cells revealed increased Chrm1 expression with scopolamine treatment, and decreased Chrm1 expression with pilocarpine treatment, suggesting that Chrm1 was most likely mediating muscarinic responses. Moreover, MTT and soft agar assays demonstrated that muscarinic agonists decreased the proliferation of human and murine cancer cell lines, while muscarinic antagonists (scopolamine and pirenzepine) increased their proliferation. This increase in proliferation due to muscarinic antagonists could be blocked by not only pilocarpine but also by McN-34A, the Chrm1-specific agonist, supporting the conclusion that Chrm1 was largely response for modulating the anti-proliferative effects of muscarinic agonists. To address the possible parasympathetic effects on sternness, human pancreatic cancer cells (Panc1 and BxPC3) were treated with pilocarpine. Interestingly, FACS analysis after treatment with this muscarinic agonist showed a marked suppression of a well-defined CD44+CD24+EpCAM+pancreatic cancer stem cell population (Li et al. 2007). To further confirm the suppressive effect of muscarinic agonists on cancer stem cells, Panc1 cells were treated or not with pilocarpine, after which 25,000 cells were implanted subcutaneously into NOD/SCID mice. Treatment with pilocarpine resulted in a significant reduction in tumors incidence and tumor volume (p<0.05), consistent with an overall reduction in pancreatic cancer stem cells.

Parasympathetic Signaling Regulates the Downstream of MAPK and PIK-AKT Signal.

To determine the possible mechanisms by which muscarinic agonists were able to reduce pancreatic cancer cell growth and stemness, Panc-1 cells following pilocarpine treatment were analyzed using RNAseq. Growth related genes that were suppressed by pilocarpine included EGFR and PI3K. EGFR expresses on the surface of tumor cells in many solid tumor including pancreatic cancer and Erlotinib is well known as EGFR tyrosine kinase inhibition. Also, PI3K exists in upstream of PI3K/Akt pathway and plays an important role on oncogene of pancreatic cancer. (Mosquera C et al. 2016) Then, the expression of activated forms of EGFR and PI-3K (p-EGFR and p-PI3K) was examined by immunohistochemical staining under conditions of cholinergic stimulation and denervation. Interestingly, expression of p-EGFR and p-PI3K in vagotomized KC mice (KC+ VxPP) was significantly higher than in control KC mice (KC+PP mice) (p<0.05). In addition, expression of p-EGFR and p-PI3K was significantly suppressed in vagotomized KC mice following bethanechol treatment (p<0.05). Furthermore, expression of p-EGFR and p-PI3K was also significantly upregulated in KPC mice, and again suppressed following bethanechol treatment.

In order to further characterize downstream signaling pathways regulated in response to parasympathetic signaling, key signaling proteins in human Panc-1 cells and murine K8282 cells treated with pilocarpine, scopolamine, McN-34A, or pirenzepine were analyzed by western blot. While a number of kinases were activated following muscarinic inhibition, EGFR, BRAF, ERK1/2, PI3K, and Akt kinases were significantly more phosphorylated in response to Scopolamine or Pirenzepine, and significantly less phosphorylated in response to Pilocarpine or McN-34A. However, when treated with a muscarinic antagonist, the addition of an agonist completely abrogated the increases in phosphorylated that were otherwise observed. The ratios of pEGFR/EGFR, pBRAF/BRAF, pERK/ERK, pPI3K/PI3K and pAkt/Akt were significantly decreased after pilocarpine and McN-34A alone and increased after scopolamine and pirenzepine alone, and the effect of non-selective agonist and antagonist was blocked by pretreatment of these cells with Chrm1 selective agonist and antagonist. Therefore, the muscarinic 1 receptor (Chrm1) appears to represent the primary cholinergic receptor that suppresses signaling through EGFR and other downstream (ERK1/2, PI3K, Akt) pathways that likely contribute to pancreatic carcinogenesis.

Specific Chrm1 KO in KC Progresses Inflammation and Tumor Incidence and in KPC Shortens Overall Survival.

6 KCM and 12 KPCM are available.

Parasympathetic Signaling Influences the Survival in Liver Metastatic Model.

Considering these data, pancreatic cancer cells itself might directly receive the parasympathetic stimulation via Chrm1 and be suppressed. To the contrary, the inhibition of parasympathetic signaling could promote pancreatic carcinogenesis. Then, it was examined whether the direct parasympathetic signal influences the metastatic lesions. The liver is a major site of metastatic spread for pancreatic cancer as well as many other solid tumors, and many patients with advanced PDAC eventually die with liver metastases. In order to investigate the role of parasympathetic signaling on the growth of liver metastasis, a well established syngeneic model of metastatic pancreatic cancer (Soares et al. 2014) was utilized. At 30 days after injection of PDAC cells into the spleen, cancer cells appear as large pale nodules that macroscopically replace the normal liver. To increase the detection of small metastases, the pancreatic cancer cell line (Panc02) was stably transfected with a GFP-expressing construct, which were readily detected following splenic injection. Wild type C57BL/6 mice received splenic injections of 2×10$^6$ GFP-labeled Panc02 cells and were then divided into 3 groups (untreated controls, bethanechol treated, and selective liver denervation by transection of the hepatic branch of the vagus). The mice treated with bethanechol showed significantly longer survival (p<0.01), while the group treated with selective vagotomy showed significantly shorter survival, compared with the control group (p<0.05). Moreover, to confirm that the parasympathetic pathway directly regulated tumor cells at the liver metastatic site, expression of Ki67, CD44 and pEGFR was analyzed. As expected, the expression of these genes was significantly decreased in the bethanechol group (p<0.05), and significantly increased in the selective vagotomy group (p<0.05). Therefore, these data suggest that parasympathetic signaling suppresses the growth not only of the primary tumor, tumor at metastatic sites, such as the liver.

Discussion

Accumulating evidence has shown that the tumor growth is subject to neural regulation, particularly by the sympathetic and parasympathetic systems. Herein, it has been demonstrated that parasympathetic signaling, primarily acting via Chrm1 receptors present on tumor cells, strongly suppresses the growth of pancreatic cancer. Thus, parasympathetic denervation through surgical vagotomy led to accelerated progression in KC mice, with the development of pancreatic adenocarcinoma by 20 weeks post-vagotomy. Importantly, treatment with the broad muscarinic agonist bethanechol suppressed the development of tumor in vagotomized KC mice, and bethanechol treatment also extended significantly the survival of KC mice with established pancreatic cancer. In vivo, bethanechol treatment reduced the expression of CD44, a potential marker of dysplasia and cancer stem cells. In vitro studies have confirmed that muscarinic agonists suppressed the K-ras mutant pancreas spheres, and in cell lines reduced the growth of the CD44CD24+EpCAM+pancreatic cancer stem cells. In the absence of cholinergic stimulation, the muscarinic-1 receptor (Chrm1) was selectively upregulated consistent with denervation, and through the use of specific agonists and antagonists, it was established that the suppressive effect of cholinergic stimulation was mediated primarily through Chrm1. Analysis of downstream signaling pathways through RNAseq, western blotting and immunohistochemical staining indicated that Chrm1 signaling was able to suppress a number of growth factor pathways, such as the EGFR/MAPK/PI3K/Akt pathway. Finally, it is shown herein that the therapeutic benefits of bethanechol treatment extended beyond primary tumor models, and in fact was able to extend the survival of mice with mets to the liver. Taken together, these data revealed that parasympathetic signaling can directly suppress the growth of pancreatic tumor cells via Chrm1 at both primary and metastatic tumor sites.

The nervous system might have been reported to influence the progression of cancer by the immune functions, the metabolic reprogramming for tumor cells, angiogenesis, or the interactions between the tumor cells and the tumor microenvironment (Shang 2007; Sloan et al. 2010; Park et al. 2011; Shi et al. 2013; Calvani et al. 2015; Chang et al. 2015). In addition, autonomic neurotransmitters may stimulate the cancer cell growth through the activation of the cancer-related signaling pathways (Jobling et al. 2015). Recently, two significant neurobiological studies have been reported. One of them is prostate cancer. It has revealed that the sympathetic and parasympathetic nerves are significantly involved in all phases of the prostate cancer development in the mouse (Magnon et al. 2013). Another one is gastric cancer. This study has revealed that surgical or pharmacologic denervation of the mouse stomach strongly reduces tumor incidence and progression of the gastric cancer (Zhao et al. 2014). In particular, this paper showed that gastric denervation suppressed tumorigenesis via Chrm3 through Wnt signaling. The study herein revealed that vagal denervation promotes pancreatic tumorigenesis via Chrm1 through MAPK and PI3K pathway.

The study herein demonstrates that vagotomy can promote pancreatic carcinogenesis in a KC mouse, and thus cancer development could be inhibited by cholinergic muscarinic agonist. Previous studies in orthotopic and syngeneic PDAC models (Partecke et al., 2017) also showed that vagotomy promoted tumor growth and shortened the overall survival and the survival didn't change in TNFα knockdown mice treated with vagotomy. Although vagus nerve played an important role in immunomodulatory pathway (Borovikova et al., 2000, de Jonge et al, 2005, Kesseler et al, 2006, van Westerloo et al. 2006), this current study showed that the effects of parasympathetic signal directly affects pancreatic epithelial growth in 2D and 3D culture.

Furthermore, CD44 expression is correlated with tumor progression and metastatic phenotype in many cancers, including pancreatic cancer (Wood 2014, Takaishi et al, 2009) and EGFR contributes to the acquisition of cancer stem-like properties, including the enrichment of CD44+/CD24− population of cancer cells in oral cancer (Xu et al, 2017). CD44 also plays an important role in tumorigenesis and tumor progression mediated by promoting cell proliferation and migration via several signaling pathways/networks, including p-AKT or p-ERK (Hao et al, 2012, Xiaoping et al, 2015). In the previous paper, cholinergic ligand interaction with Chrms results in transactivation of EGFR, thereby stimulating cellular proliferation in colon cancer (Chang et al, 2003, Ukegawa et al, 2003). Considering these evidence, the study herein revealed that parasympathetic signal via Chrm1 interacted with EGFR and promoted pancreatic carcinogenesis and tumor growth in liver metastatic models through MAPK and PI3K pathway, and EGFR affected cancer stemness like CD44.

In summary, it was demonstrated that the parasympathetic signal via Chrm1 might directly contribute to pancreatic carcinogenesis through MAPK and PI3K/Akt signaling pathway. Although the crosstalk between tumor cells and microenvironment, including neuron, immune cells, and stroma, needs to be further investigated, these data might have the potential to be able to alter the surgical approach to pancreatic cancer (i.e. vagal-sparing Whipple) and suggest that novel devices or pharmacological drug that provide chronic vagal stimulation might be useful as adjunctive therapies in the treatment of pancreatic cancer in early phase and late phase.

Methods

Animals

K-Ras$^{+/LSL-G12D}$, p53$^{+/R172H}$, and Pdx-1-Cre mice were provided by Dr. Kenneth Olive (Columbia University). M1RKO mice were purchased from the Jackson Laboratory. KC mice and KPC mice were crossed with M1RKO mice. For several experiments, KC mice received pyloroplasty with or without vagotomy at 8 weeks and KC+VxPP mice were treated with or without bethanechol (400 µg/ml) after surgery immediately. They were sacrificed at 20 weeks. In addition, KPC mice were treated with gemcitabine biweekly and with or without bethanechol when the tumor size of 3-5 mm detected using ultrasound. They were sacrificed when the mice were moribund. For liver metastatic experiments, WT type C57/B6 mice received spleen injection and hemisplenectomy. One of three groups was untreated, one of them received the selective vagotomy of hepatic vagal branch simultaneously and another one was treated with bethanechol after surgery. They were sacrificed when the mice were moribund.

All animal studies and procedures were approved by the ethics committees at Columbia University. All mice were bred under specific pathogen free conditions. Comparisons were made with age- and sex-matched control animals.

Animal Surgery

Vagotomy, Plyroloplasty, and Selective Hepatic Branch Vagotomy

All surgical procedures were performed under isoflurane inhalation anesthesia (2-3%), with buprenorphine (0.1 mg/kg subcutaneously) given as postoperative analgesia. The vagotomy and pyloroplasty procedure were previously described (Zao. et al. 2014). In the present study, selective vagotomy of hepatic branch was performed according to the previous paper (Pocai et al., 2005). Briefly, the hepatic branch of this vagal trunk was isolated and then transected by microcautery, severing the hepatic vagus. Anatomical nerve transaction was verified at sacrifice by microscopic observation of the absence of vagal nerve fibers.

Liver Metastatic Procedure and Hemi-Splenectomy

Liver metastatic model procedure was performed previously described. (Soares K C et al. 2014) Briefly, a left subcostal incision was performed along the line with the left ear and the spleen was exposed through the incision. The spleen was divided into upper and lower spleen by placing two Horizon medium size ligating clips in the center of the spleen. 150 µl of phosphate buffered saline was drawn up into a 27 G×⅝" syringe and 100 µl of Panc02 ($2\times10^6$) cells was also drawn up into the same syringe and the cells were injected slowly into the exposed lower-hemispleen. Lower hemisplenectomy was performed by ligating pancreas spleen vessel and cutting above.

Histology, Immunohistochemistry, Immunofluorescence and Microscopy

5 µm paraffin embedded or PFA-fixed frozen sections were prepared for immunohistochemistry and immunofluorescence, respectively. For immunofluorescence, slides were washed with 1% Triton X-100 in PBS, rinsed and blocked for 30 min with 2% bovine serum albumin (BSA—Sigma-Aldrich). Primary antibodies and fluorophore-conjugated secondary antibodies were diluted in 2% BSA and incubated over night at 4° C. The following primary antibodies were used; Chrm1 (1:200 Santa Cruz), Ki67 (1:200 Abcam), pEGFR (1:100 Abcam), and CD44 (1:200 BIO-RAD). For immunohistochemical staining, slides were deparaffinized in xylene and endogenous peroxidase was blocked by incubation with 3% hydrogen peroxide in methanol for visualization using the peroxidase reaction. Alternatively, for visualization with the alkaline phosphatase reaction, slides were incubated with 20% acetic acid in methanol for 2 min. Antigen retrieval was performed by boiling the slides in citrate buffer (10 mM pH 6.0) in a water bath for 20 min. Slides were rinsed in PBS Tween 0.05% and blocked for 30 min. with 2% BSA. Primary antibodies and biotinylated secondary antibodies (Jackson Immunoresearch) were diluted in 2% BSA and incubated overnight at 4° C. The following primary antibodies were used; pEGFR (1:100 Abcam), CD44 (1:200 BIO-RAD), and pPI3K (1:100 Sigma-Aldrich). Subsequently, slides were incubated with alkaline phosphatase or peroxidase conjugated streptavidin (Dako) and either VectorRed substrate (Vector Laboratories) or 3,3'-diaminobenzidine (Sigma-Aldrich) as chromogens, respectively. Slides were counterstained with hematoxylin and mounted for viewing. Bright field and fluorescence images were acquired using an Eclipse TU2000-U microscope (Nikon) connected to a cooled color CCD camera (RTKE Diagnostic Instruments) using SPOT software (Spotimaging).

Cell Lines and Cell Culture

Three human PDAC cell lines (MiaPaca2, BxPC3 and Panc-1) and two murine PDAC cell lines (Panc02 and K8282) were used for experiments. RPMI1640 (Sigma Aldrich Inc.) supplemented with 10% fetal bovine serum (FBS) and Penicillin/Streptomycin (Invitrogen Inc.) and was used for cell culture, and the medium was replaced with fresh medium every 48-72 hours. All cultures were maintained in a 5% CO2 air-humidified atmosphere at 37° C.

Western Blot

To analyze EGFR and the MAPK and PI3K-Akt pathway in human and murine pancreatic cancer cell lines, cells were grown in 12-well plate to around ~70% confluent, changed the 0.5% FBS medium, added the drugs respectively and incubated them for further 72 hrs incubation in a typical CO2 incubator (~20% $O_2$). After removing the medium, cells were washed twice with PBS, and protein extraction was performed on ice using RIPA buffer with protease inhibitor (Complete) (Roche) cocktail and phosphatase inhibitor (phosSTOP) (Roche). Protein samples were subsequently separated in 10% Bis-Tris Gel NuPAGE® electrophoresis using MES SDS Running Buffer (Invitrogen, CA, USA). After transfer to nitrocellulose, membranes were blocked with 5% BSA, and samples were probed with the following primary antibodies: p-EGFR (Cell Signaling), EGFR (Cell Signaling), p-BRAF (Cell Signaling), BRAF (Cell Signaling), p-ERK1/2 (phosphorylated p44/42 MAPK) (Thr202/Tyr204) (Cell Signaling), ERK1/2 (p44/42 MAPK) (Thr202/Tyr204) (Cell Signaling), p-PI3K (Cell Signaling), PI3K (Cell Signaling), p-Akt (Cell Signaling), Akt (Cell Signaling), and β-actin (Cell Signaling) followed by horseradish peroxidase-coupled secondary antibody. Immunoreactive bands were visualized using 5-bromo-4-chloro-3-indolyl phosphate/nitro blue tetrazolium and bands were quantified with ImageJ.

MTT Assay and Soft Agar Assay

Cell proliferation in each cell line was assessed with a 3-(4,5-dimethylthiazol-2yl)-2,5-diphenyltetrazolium bromide (MTT) assay kit (Sigma) in accordance with the manufacturer's instructions. $3\times10^3$ cells were grown in 96-well plate to around ~70% confluent, changed the 0.5% FBS medium, added the drugs respectively and incubated them for further 72 hrs incubation in a typical CO2 incubator (~20% $O_2$). Treated cells were rinsed twice with PBS, incubated in 10 ll MTT solution for 4 hr at 37° C., and 100 uL DMSO was added to each well. The absorbance of each well was measured at 570 nm using Tilter-Tech 96-well multiscanner (Becton Dickinson, Heidelberg, Germany). The relative number of viable cells compared with the number of cells without drug treatment was expressed as percent cell viability using the following formula:

cell viability (%)=$A_{570}$ of treated cells/$A_{570}$ of untreated cells. Soft agar assay was employed to identify the ability of the A549-shTGIF cells and A549-shcon cells to grow as anchorage-independent colonies. Briefly, 2 ml of 0.6% of low-melting point agarose in RPMI-1640 medium containing 10% of FBS were poured into a 6-well plate and allowed to solidify at room temperature. After solidification, 500 cells were suspended in 1 ml of 0.35% low-melting point agarose in the same medium and then plated on top of the base layer (three wells per group). The cells were cultured for 18 days. Colonies with at least 50 cells were counted using a microscope at 100 times magnification, and the number of colonies in soft agar (five fields per well) was quantified.

Flow Cytometry

Panc-1 cells were grown in 6-well plate to around ~70% confluent, changed the 0.5% FBS medium, added the drugs respectively and incubated them for further 72 hrs incubation in a typical CO2 incubator (~20% $O_2$). Afterwards, cells were kept on ice in blocking solution (PBS pH 7.2 containing 3% bovine serum albumin, 2 mM EDTA) for 20 minutes. Cells were then stained with a PE-conjugated antibody against CD24, a FITC-conjugated antibody against CD44, and an APC-conjugated antibody against CD326 (1:100—in blocking solution) on ice for 30 minutes. The cells were then washed, reconstituted in sorting buffer (PBS pH 7.2 containing 0.5% bovine serum albumin, 2 mM EDTA)+DAPI and analyzed using a BD FACSAria II.

Generation of Panc02 cells stably expressing GFP protein

Panc02 cells stably expressing GFP proteins (Panc02-GFP) was generated as follows. Parental Panc02 cells was transduced with 5×10$^6$ IFU Lentivirus particles containing GFP vectors under the control of suCMV promoter (GenTarget Inc.). Transduced cells were incubated with puromycin (2 µg/mL) for 1 week to select GFP-positive cells. Strong GFP-expressing cells were further sorted by FACS and cultured in the complete medium containing puromycin. Stable Panc02-GFP cells were maintained by puromycin at 0.5 ug/mL prior to intra-splenic injection.

Sphere Cultures 3D cultures were performed as described previously (Wescott et al., 2009). Organoids were cultured for 5 days before analysis. Adenoviral delivered Cre (Ad-Cre) was added to the cultures and medium was changed after 12 hours. Pilocarpine, scopolamine, McN-34A and pirenzepine containing medium was changed every day. Sphere size and in vitro were analyzed using ImageJ software.

Statistical Analysis

The difference between the means was compared by either Student's t-test or the Mann-Whitney U test. p values <0.05 were considered to indicate statistical significance.

REFERENCES

Arslan A A, Helzlsouer K J, Kooperberg C et al. Anthropometric measures, body mass index, and pancreatic cancer: a pooled analysis from the Pancreatic Cancer Cohort Consortium (PanScan) *Arch Intern Med.* 2010; 170: 791-802.

Ayala G E, Dai H, Powell M, Li R, Ding Y, Wheeler™, Shine D, Kadmon D,

Thompson T, Miles B J, Ittmann M M, Rowley D., Cancer-related axonogenesis and neurogenesis in prostate cancer. Clin Cancer Res. 2008; 14, 7593-7603.

Bonaz B. The cholinergic anti-inflammatory pathway and the gastrointestinal tract. Gastroenterology. 2007; 133: 1370-3.

Borovikova L V, Ivanova S, Zhang M, Yang H, Botchkina G I, Watkins L R, Wang H, Abumrad N, Eaton J W, Tracey K J., Vagus nerve stimulation attenuates the systemic inflammatory response to endotoxin, Nature 2000; 405: 458-462.

Calvani M, Pelon F, Comito G, Taddei M L, Moretti S, Innocenti S, Nassini R, Gerlini G, Borgognoni L, Bambi F, Giannoni E, Filippi L, Chiarugi P. Norepinephrine promotes tumor microenvironment reactivity through beta3-adrenoreceptors during melanoma progression. Oncotarget 2015; 6: 4615-4632.

Chang A, Kim-Fuchs C, Le C P, Hollande F, Sloan E K. Neural Regulation of Pancreatic Cancer: A Novel Target for Intervention. Cancers (Basel) 2015; 7: 1292-1312.

Cheng K, Zimniak P, Raufman J P. Transactivation of the epidermal growth factor receptor mediates cholinergic agonist-induced proliferation of H508 human colon cancer cells. Cancer Res. 2003; 63:6744-6750.

De Couck M, Mravec B, Gidron Y., You may need the vagus nerve to understand pathophysiology and to treat diseases, Clin. Sci. (Lond.) 2012; 122: 323-328.

de Jonge W J, van der Zanden E P, The F O, Bijlsma M F, van Westerloo D J, Bennink R J, Berthoud H R, Uematsu S, Akira S, van den Wijngaard R M, Boeckxstaens G E. Stimulation of the vagus nerve attenuates macrophage activation by activating the Jak2-STAT3 signaling pathway. Nat Immunol. 2005; 6:844-51. doi: 10.1038/ni1229.

Du L, Wang H, He L, Zhang J, Ni B, Wang X, Jin H, Cahuzac N, Mehrpour M, Lu Y, Chen Q. CD44 is of functional importance for colorectal cancer stem cells. Clin Cancer Res 2008; 14:6751-6760

Edwards B K, Brown M L, Wingo P A et al. Annual report to the nation on the status of cancer, 1975-2002, featuring population-based-trends in cancer treatment. J Natl Cancer Inst. 2005; 97: 1407-1427.

Erin N, Boyer P J, Bonneau R H, Clawson G A, Welch D R. Clawson, D. R. Welch, Capsaicin-mediated denervation of sensory neurons promotes mammary tumor metastasis to lung and heart, Anticancer Res. 2004; 24: 1003-1009.

Erin N, Akdas Barkan G, Harms J F, Clawson G A. Clawson, Vagotomy enhances experimental metastases of 4THMpc breast cancer cells and alters substance P level, Regul. Pept. 2008; 151: 35-42.

Erin N, Duymuş O, Oztürk S, Demir N., Activation of vagus nerve by semapimod alters substance P levels and decreases breast cancer metastasis, Regul. Pept. 2012; 10: 101-108.

Fernandez R, Nardocci G, Navarro C, Reyes E P, Acuna-Castillo C, Cortes P P. Neural reflex regulation of systemic inflammation: potential new targets for sepsis therapy. Frontiers in physiology. 2014; 5:489.

Gidron Y, Perry H, Glennie M., Does the vagus nerve inform the brain about preclinical tumours and modulate them? Lancet Oncol. 6 (2005) 245-248.

Hao J, Madigan M C, Khatri A, Power C A, Hung T T, Beretov J, Chang L, Xiao W, Cozzi P J, Graham P H, Kearsley J H, Li Y. In vitro and in vivo prostate cancer metastasis and chemoresistance can be modulated by expression of either CD44 or CD147. PLoS One 2012; 7: e40716.

Hidalgo M. Pancreatic cancer. *N Engl J Med* 2010; 362: 1605-1617.

Hingorani, S. R., Wang, L., Multani, A. S., Combs, C., Deramaudt, T. B., Hruban, R. H., Rustgi, A. K., Chang, S., Tuveson, D. A., Trp53R172H and KrasG12D cooperate to promote chromosomal instability and widely metastatic pancreatic ductal adenocarcinoma in mice. Cancer Cell 2005; 7: 469-483.

Jobling P, Pundavela J, Oliveira S M, Roselli S, Walker M M, Hondermarck H. Nerve-Cancer Cell Cross-talk: A Novel Promoter of Tumor Progression. Cancer Res 2015; 75: 1777-1781.

Katayama Y, Battista M, Kao W M, Hidalgo A, Peired A J, Thomas S A, Frenette P S., Signals from the sympathetic nervous system regulate hematopoietic stem cell egress from bone marrow. Cell 2006; 24, 407-421.

Kessler W, Traeger T, Westerholt A, Neher F, Mikulcak M, Muller A, Maier S, Heidecke C D. The vagal nerve as a link between the nervous and immune system in the instance of polymicrobial sepsis. Langenbecks Arch Surg. 2006; 391:83-7. doi: 10.1007/s00423-006-0031-y.

Kiba T, Takana K, Numata K, Hoashino M, Misugi K, Inoue S., Ventromedial hypothalamic lesion-induced vagal hyperactivity stimulates rat pancreatic cell proliferation. Gastroenterology 1996; 110:885-893.

Li C, Heidt D G, Dalerba P, Burant C F, Zhang L, Adsay V, Wicha M, Clarke M F, Simeone D M. Identification of pancreatic cancer stem cells. Cancer Res 2007; 67:1030-7

Lundgren O, Jodal M, Jansson M, Ryberg A T, Svensson L. Intestinal epithelial stem/progenitor cells are controlled by mucosal afferent nerves. PLOS One 2011; 6, e16295.

Magnon C, Hall S J, Lin J, Xue X, Gerber L, Freedland S J, Frenette P S. Autonomic nerve development contributes to prostate cancer progression. Science 2013; 341: 1236361.

Mattingly R R, Sorisky A, Brann M R, Macara I G. Macara, Muscarinic receptors transform NIH 3T3 cells through a Ras-dependent signalling pathway inhibited by the Ras-GTPase-activating protein SH3 domain. Mol. Cell. Biol. 1994; 14, 7943-7952.

Mosquera C, Maglic D, Zervos E E. Molecular targeted therapy for pancreatic adenocarcinoma: A review of completed and ongoing late phase clinical trials. Cancer Genet. 2016; 209: 567-581.

Olive K P, Jacobetz M A, Davidson C J, Gopinathan A, McIntyre D, Honess D, Madhu B, Goldgraben M A, Inhibition of Hedgehog signaling enhances delivery of chemotherapy in a mouse model of pancreatic cancer. *Science*. 2009; 324:1457-1461.

Park S Y, Kang J H, Jeong K J, Lee J, Han J W, Choi W S, Kim Y K, Kang J, Park C G, Lee H Y. Norepinephrine induces VEGF expression and angiogenesis by a hypoxia-inducible factor-1alpha protein-dependent mechanism. Int J Cancer 2011; 128: 2306-2316.

Partecke L I, Käding A, Trung D N, Diedrich S, Sendler M, Weiss F, Kühn J P, Mayerle J, Beyer K, von Bernstorff W, Heidecke C D, Keßler W. Subdiaphragmatic vagotomy promotes tumor growth and reduces survival via TNFα in a murine pancreatic cancer model. Oncotarget. 2017 Feb. 2. doi: 10.18632/oncotarget.15019. [Epub ahead of print]

Pocai, A., Lam, T. K., Gutierrez-Juarez, R., Obici, S., Schwartz, G. J., Bryan, J. Aguilar-Bryan, L., and Rossetti, L. (2005a). Hypothalamic K(ATP) channels control hepatic glucose production. Nature 2005; 434: 1026-1031.

Ponti D, Costa A, Zaffaroni N, Pratesi G, Petrangolini G, Coradini D, Pilotti S, Pierotti M A, Daidone M G. Isolation and in vitro propagation of tumorigenic breast cancer cells with stem/progenitor cell properties. Cancer Res 2005; 65:5506-11

Raufman J P, Shant J, Xie G, Cheng K, Gao X M, Shiu B, Shah N, Drachenberg C B, Heath J, Wess J, Khurana S., Muscarinic receptor subtype-3 gene ablation and scopolamine butylbromide treatment attenuate small intestinal neoplasia in Apcmin/+mice. Carcinogenesis 2011; 32, 1396-1402.

Shah N, Khurana S, Cheng K, Raufman J P., Muscarinic receptors and ligands in cancer. Am. J. Physiol. Cell Physiol. 2009; 296, C221-C232.

Shang Y. Hormones and cancer. Cell Res 2007; 17: 277-279.

Shi M, Liu D, Yang Z, Guo N. Central and peripheral nervous systems: master controllers in cancer metastasis. Cancer Metastasis Rev 2013; 32:603-621.

Siegel, R. L., Miller, K. D., Jemal, A., 2016. Cancer statistics, 2016. C A: A Cancer Journal for Clinicians 66, 7-30.

Sloan E K, Priceman S J, Cox B F, Yu S, Pimentel M A, Tangkanangnukul V, Arevalo J M, Morizono K, Karanikolas B D, Wu L, Sood A K, Cole S W. The sympathetic nervous system induces a metastatic switch in primary breast cancer. Cancer Res 2010; 70:7042-7052.

Soares K C, Foley K, Olino K, Leubner A, Mayo S C, Jain A, Jaffee E, Schulick R D, Yoshimura K, Edil B, Zheng L. A preclinical murine model of hepatic metastases. J Vis Exp. 2014 Sep. 27; (91):51677. doi: 10.3791/51677.

Takaishi S, Okumura T, Tu S, Shibata W, Vigneshwaran R, Gordon S A, Shimada Y, Wang T C. Identification of gastric cancer stem cells using the cell surface marker CD44. Stem Cells 2009; 27: 1006-1020.

Tracey K J, Reflex control of immunity, Nat. Rev. Immunol. 2009; 9:418-428.

Tsutsumi T, Ide T, Yamato M, Kudou W, Andou M, Hirooka Y, Utsumi H, Tsutsui H, Sunagawa K., Modulation of the myocardial redox state by vagal nerve stimulation after experimental myocardial infarction, Cardiovasc. Res. 2008; 77:713-721.

Ukegawa J I, Takeuchi Y, Kusayanagi S, Mitamura K. Growth-promoting effect of muscarinic acetylcholine receptors in colon cancer cells. J Cancer Res Clin Oncol. 2003; 129:272-8.

van Westerloo D J, Giebelen I A, Florquin S, Bruno M J, Larosa G J, Ulloa L, Tracey K J, van der Poll T. The vagus nerve and nicotinic receptors modulate experimental pancreatitis severity in mice. Gastroenterology. 2006; 130: 1822-30. doi: 10.1053/j.gastro.2006.02.022.

Wescott, M. P., Rovira, M., Reichert, M., von Burstin, J., Means, A., Leach, S. D., and Rustgi, A. K. (2009). Pancreatic ductal morphogenesis and the Pdx1 homeodomain transcription factor. Molecular biology of the cell 2009; 20:4838-4844.

Wood N J. Pancreatic cancer: pancreatic tumour formation and recurrence after radiotherapy are blocked by targeting CD44. Nat Rev Gastroenterol Hepatol 2014; 11:73.

Xiaoping L, Xiaowei Z, Leizhen Z, Weijian G. Expression of CD44 in pancreatic cancer and its significance. Int J Clin Exp Pathol 2015; 8:6724-6731

Xu Q, Zhang Q, Ishida Y, Hajjar S, Tang X, Shi H, Dang C V, Le A D. EGF induces epithelial-mesenchymal transition and cancer stem-like cell properties in human oral cancer cells via promoting Warburg effect. Oncotarget. 2017; 8:9557-9571

Zhao C M, Hayakawa Y, Kodama Y, Muthupalani S, Westphalen C B, Andersen G T, Flatberg A, Johannessen H, Friedman R A, Renz B W, Sandvik A K, Beisvag V, Tomita H, Hara A, Quante M, Li Z, Gershon M D, Kaneko K, Fox J G, Wang T C, Chen D. Denervation suppresses gastric tumorigenesis. Sci Transl Med. 2014; 20; 6:250ra115

Example 4—Parasympathetic Signaling Via Chrm1 Directly Suppresses Pancreatic Tumorigenesis and Cancer Stemness Through Inhibition of EGFR/MAPK and PI3K/AKT Pathway Abstract In many solid tumors, parasympathetic input is provided by the vagus nerve, which has been shown to modulate tumor growth. However, whether parasympathetic signaling directly regulates progression of pancreatic cancer (PDAC) has not been defined. Here, it is reported that parasympathetic denervation through surgical vagotomy in LSL-$Kras^{+/LSL-G12D}$;Pdx1-Cre (KC) mice significantly accelerated pancreatic cancer development, whereas treatment with the muscarinic agonist bethanechol restored the normal KC phenotype, thereby suppressing the accelerated tumorigenesis caused by parasympathetic denervation. Furthermore, in LSL-Kras$^{+/G12D}$;LSL-Trp53$^{+/R172}$H; Pdx1-Cre mice with established PDAC, bethanechol significantly extended survival. These effects were mediated through the cholinergic muscarinic receptor 1 (CHRM1), which inhibited downstream MAPK/EGFR and PI3K/AKT pathways. Enhanced cholinergic signaling led to a suppression of the cancer stem cell compartment and inhibited metastatic growth in the liver. Therefore, these data suggest that parasympathetic signaling directly suppresses growth of PDAC cells, and therapies that stimulate muscarinic receptors may be useful in the treatment of PDAC.

Statement of Significance

Parasympathetic denervation (vagotomy) or Chrm1 knockout accelerates pancreatic tumorigenesis, in part through an expansion of the cancer stem cell compartment. Muscarinic stimulation (muscarinic agonist, bethanechol) suppresses tumorgenesis through MAPK and PI3K/AKT signaling, in early stages of tumor growth as well as in more advanced, metastatic disease. Therefore, CHRM1 may represent an attractive therapeutic target.

Introduction

Pancreatic ductal adenocarcinoma (PDAC) is one of the most lethal malignant diseases, with a poor response to most therapies[1, 2]. With few specific symptoms and no reliable test for early detection, PDAC is usually diagnosed at a locally advanced or metastatic and thereby incurable stage[3, 4]. After careful staging, only 15-20% of patients diagnosed with PDAC are eligible for upfront radical surgery. Even for those patients, cures are uncommon. Thus, the median overall survival is only 5-6 months after conventional therapies for locally advanced or metastatic disease, and the 5-year overall survival rate is about 8%[5].

The resistance of PDAC to treatment has recently been attributed in part to the tumor microenvironment and the complex desmoplastic stroma, which includes immune cells, endothelial cells, stellate cells, matrix proteins and nerves[6, 7]. Accumulating evidence has revealed a key role for the autonomic nervous system in the development of cancer. Multiple studies have reported a marked increase in neural density and nerve size in solid tumors[8, 9]. In addition, experimental model systems have shown a direct contribution of nerves to the development of prostate cancer[10, 11], basal cell carcinoma[12], and to gastric cancer[13, 14] and PDAC[15]. Furthermore, growing evidence suggests that there is increased crosstalk between tumor cells and nerves, with tumors able to induce active axonogenesis[8, 9, 15, 16] In many cases, nerves appear to promote strongly the growth of tumors, but the result of neural input is likely site-specific, influenced largely by distinct nerve-tumor interactions. The stomach in particular is regulated predominantly by the parasympathetic nervous system, with the vagus nerve strongly promoting epithelial proliferation, stem cell activity, and tumorigenesis. Thus, in the case of gastric cancer, abrogation of cholinergic input by vagotomy or chemical denervation inhibits the growth of gastric cancer[13, 14]. In addition to directly regulating the epithelium, nerves have been shown to act indirectly through effects on the tumor stroma or microenvironment[10, 11]. In prostate cancer, for example, cholinergic signals transduced in the tumor stroma by the muscarinic type 1 receptor (CHRM1) promote tumor invasion in mouse models[10].

Similar to many other solid organs, the pancreas is innervated by both sympathetic and parasympathetic nerves[17, 18]. In the pancreas, the autonomic nervous system regulates both exocrine and endocrine function, and influences normal pancreatic development[19, 20]. In addition, the vagus nerve has been shown to stimulate proliferation of the normal exocrine pancreas, such that ventromedial hypothalamic lesions that induce vagal hyperactivity stimulate pancreatic proliferation and lead to pancreatic hypertrophy, whereas vagotomy leads to decreased pancreatic acinar growth[21]. On the other hand, a few studies have suggested that vagus nerve signaling may actually slow pancreatic tumor progression[22].

Indeed, one report noted a higher incidence of PDAC in patients who underwent vagotomy for gastric ulcer disease in the past[23]. Similarly, a study in orthotopic and syngeneic PDAC mouse models demonstrated that vagotomy promoted tumor growth and shortened overall survival, although this was largely attributed to indirect effects on tumor-associated macrophages and elevated TNFα levels[24]. In addition, tumor-bearing animals that underwent chemical or surgical vagotomy showed enhanced metastasis of breast cancer cells[25, 26]. Nevertheless, although these earlier studies suggested that vagal signaling could be suppressive in some cancer models, a direct role for cholinergic signaling in genetically engineered mouse models (GEMM) and metastatic models of PDAC has not been demonstrated, nor has the mechanism been elucidated. Consequently, the direct contribution of the vagus nerve, cholinergic signaling and muscarinic receptors to PDAC development and progression in LSL-Kras$^{+/LSL-G12D}$;Pdx1-Cre (KC), LSL-Kras$^{+/LSL-G12D}$;LSL-Trp53$^{+/R172H}$;Pdx1-Cre (KPC), and metastatic models was investigated herein.

Results

Parasympathetic Denervation Promotes Pancreatic Tumorigenesis Via the Cholinergic Muscarinic Receptor 1 (CHRM1).

Figure 7C:
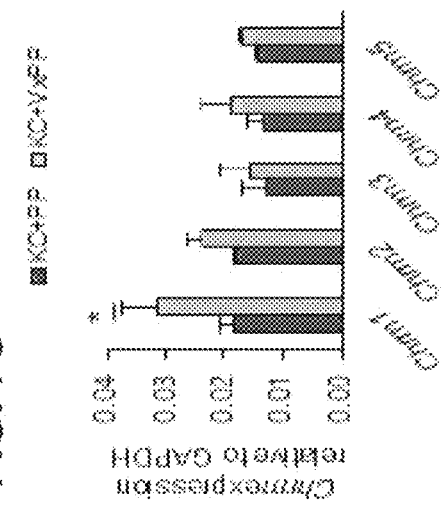
FIG. 7C. Fold change in pancretic mRNA levels, as measured by qRT-PCR, of muscarinic cholinergic receptors (Chrm1 to Chrm5) in KC+PP mice compared to KC+VxPP mice at 20 weeks.
Figure 7B:
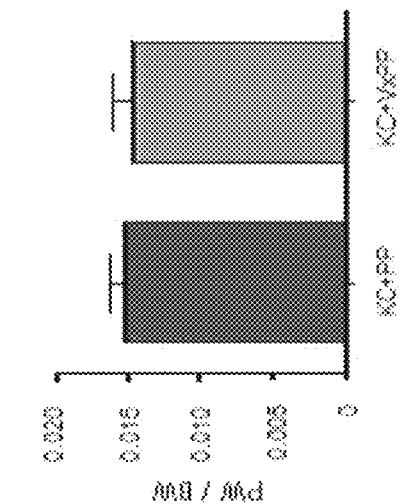
FIG. 7B, Pancreatic weight/body weight ratio in KC+PP mice compared to KC+VxPP mice.
Figure 7A:
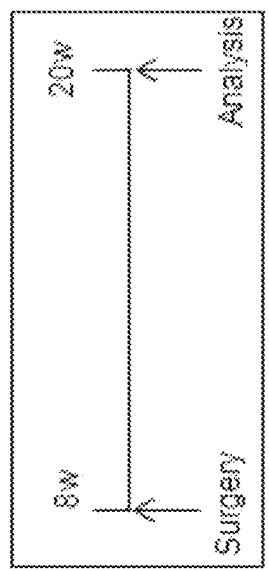
FIGS. 7A-N show that parasympathetic denervation promotes pancreatic tumorigenesis via the Cholinergic Muscarinic Receptor 1 (CHRM1).

To investigate the specific effects of parasympathetic denervation on PDAC development, the genetically engineered KC mouse model was utilized. KC mice were subdiaphragmatically vagotomized with a subsequent pyloroplasty (KC+VxPP) at 8 weeks of age, and then sacrificed at 20 weeks (FIG. 7A). Vagotomy had no effect on the ratio of pancreas weight to body weight (FIG. 7B), but significantly increased pancreatic expression of the muscarinic type 1 receptor (Chrm1) ($p < 0.05$), but not the other muscarinic receptors, compared with the control group that received only a pyloroplasty (KC+PP) at 8 weeks (FIG. 7C). This finding was confirmed by immunohistochemistry, where CHRM1 was more highly expressed in pancreatic acinar and tumor epithelial cells in KC+VxPP mice (n=13) compared with KC+PP mice (n=10) (FIGS. 7D, E).

Surprisingly, in pancreata of vagotomized (KC+VxPP) mice, the PanINs appeared to be more advanced than in the control (KC+PP) mice, with evidence for actual PDAC (FIGS. 7F-I). Therefore, PanIN lesions were quantified morphometrically in pancreata of KC+VxPP and KC+PP mice. The PanIN area in KC+VxPP mice was significantly larger than in KC+PP mice ($p < 0.01$) (FIG. 7J). Importantly, full blown cancer was found in more than 40% of KC+VxPP mice, while no PDAC was seen in KC+PP mice ($p < 0.05$) (FIG. 7K).

Figures 7L, 7M:
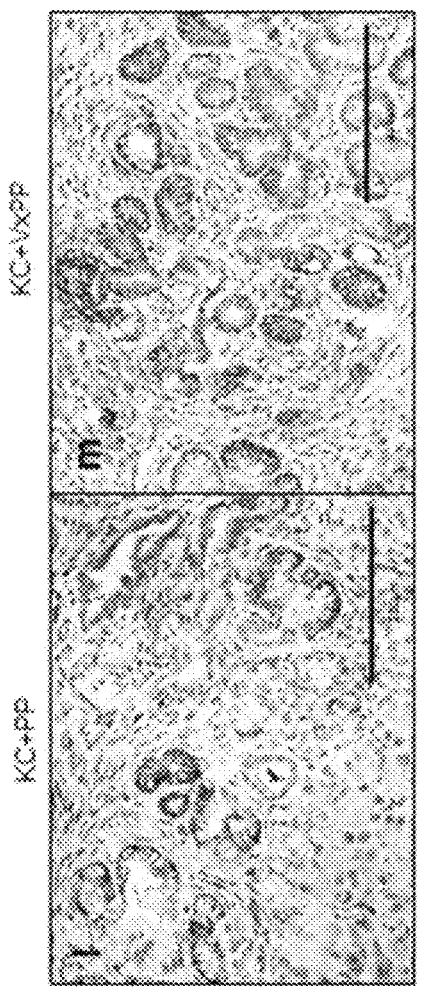
FIGS. 7L, M, Representative images of pancreatic sections immunostained for CD44 in KC+PP mice and KC+VxPP mice at 20 weeks.
Figure 7N:
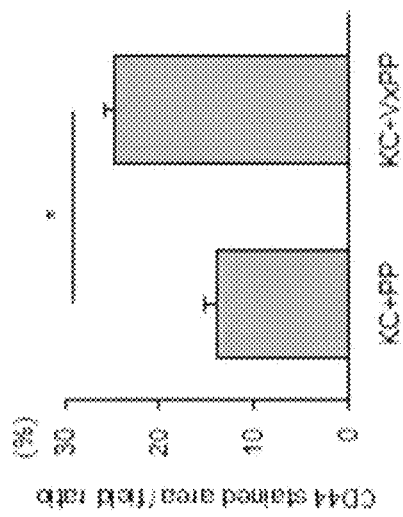

Furthermore, increased CD44 expression was found in pancreata of KC+VxPP mice compared to KC+PP mice ($p < 0.05$) (FIGS. 7L-N). CD44 has been associated with stem cell-like properties, and its expression often correlates with progression of dysplasia in PanINs[27, 28]. Thus, these data suggest that parasympathetic denervation promotes pancreatic tumorigenesis in the setting of an oncogenic Kras mutation, possibly by modulating the cancer stem cell compartment.

Parasympathetic Stimulation Suppresses Pancreatic Tumorigenesis and Extends Overall Survival in KPC Mice.

Figure 8A:
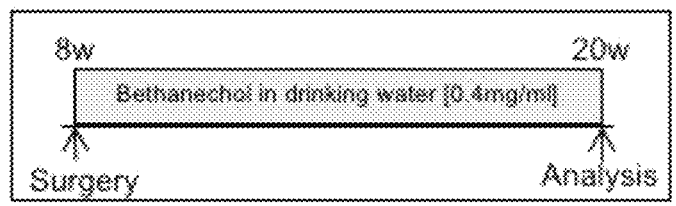
Figure 8A:
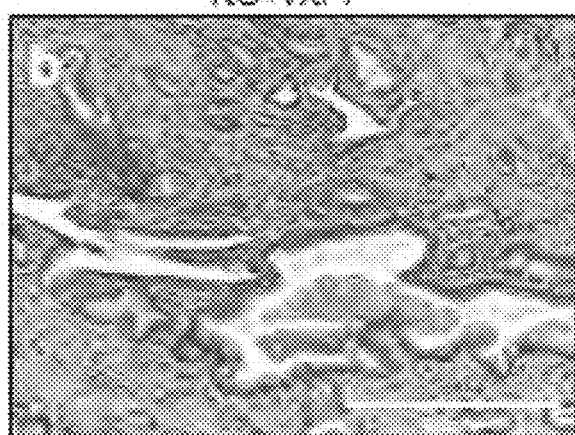
Figure 8A:
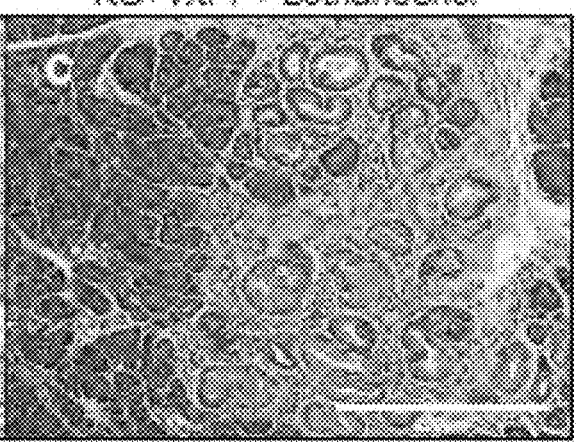
Figure 8A:
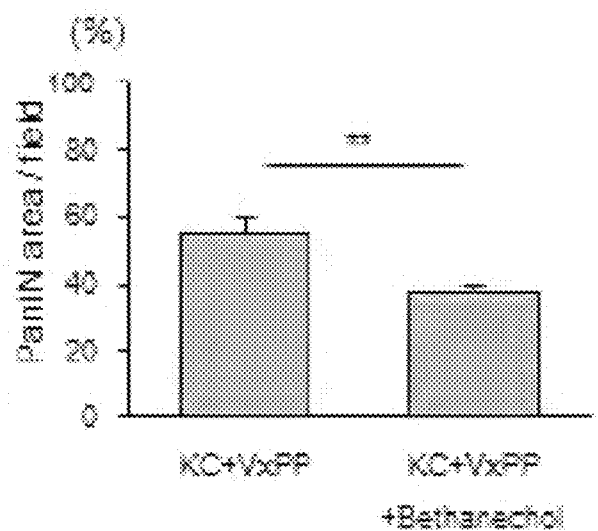
Figure 8A:
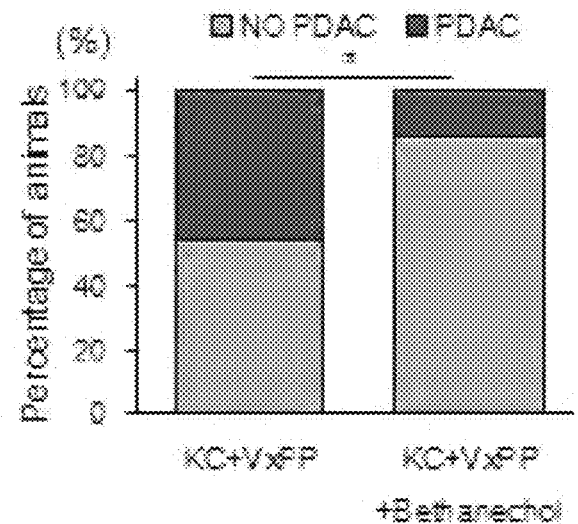
Figure 8H:
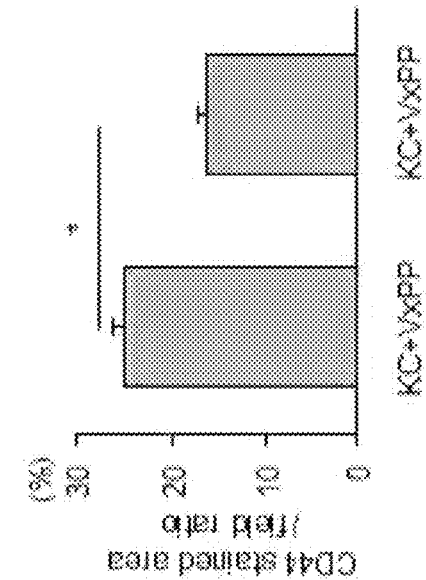
Figures 8F, 8G:
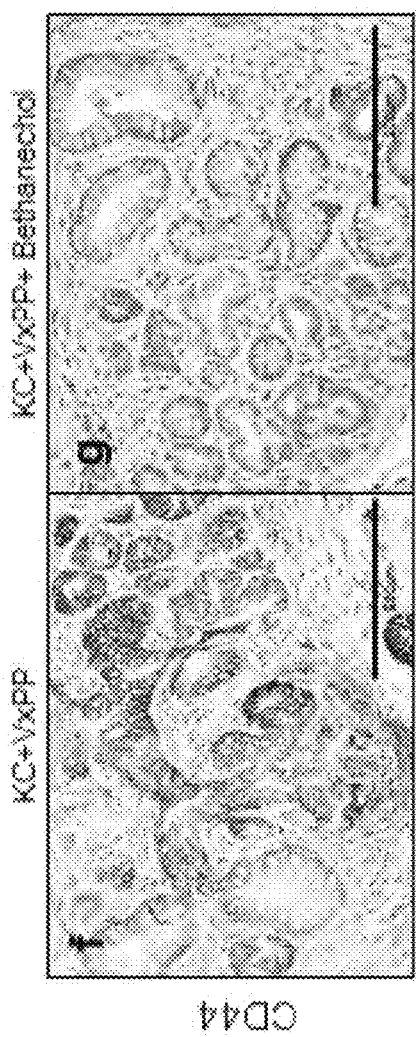

Given that parasympathetic denervation appeared to accelerate the development of PDAC, to was determine whether parasympathetic stimulation would have the opposite effect on pancreatic tumorigenesis. Thus, the effect of treatment with bethanechol, a broad muscarinic agonist, was examined on KC mice that had undergone vagotomy (FIG. 8A). Bethanechol treatment (400 µg/ml in drinking water) was started in KC mice at 8 weeks, immediately after the mice received surgery, and continued until 20 weeks of age. Bethanechol treatment in KC+VxPP mice (n=14) led to a significant reduction in PanIN area and pancreatic tumor incidence ($p<0.01$ and $p<0.05$, respectively) compared to untreated KC+VxPP mice (n=13) (FIGS. 8B-E). In addition, bethanechol treatment in KC+VxPP mice led to a significant decrease in pancreatic CD44 expression compared to KC+VxPP control mice (FIGS. 8F-H).

Figure 8I:
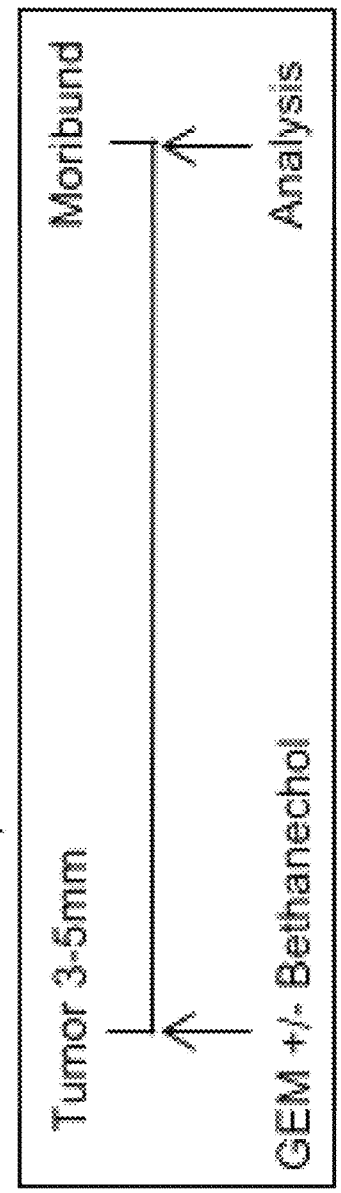
Figures 10A, 10B, 10C, 10D:
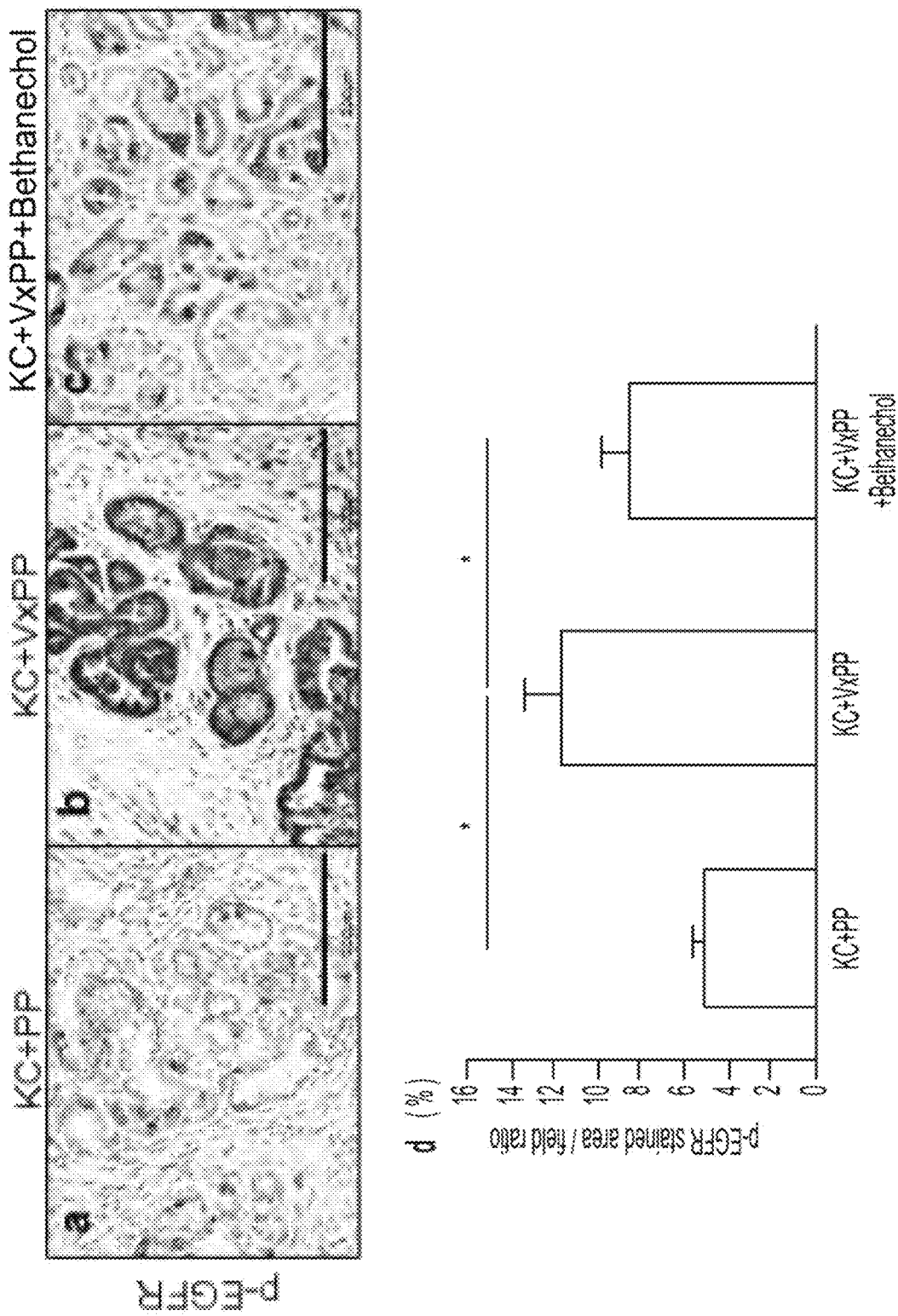
Figures 10E, 10F, 10G, 10H:
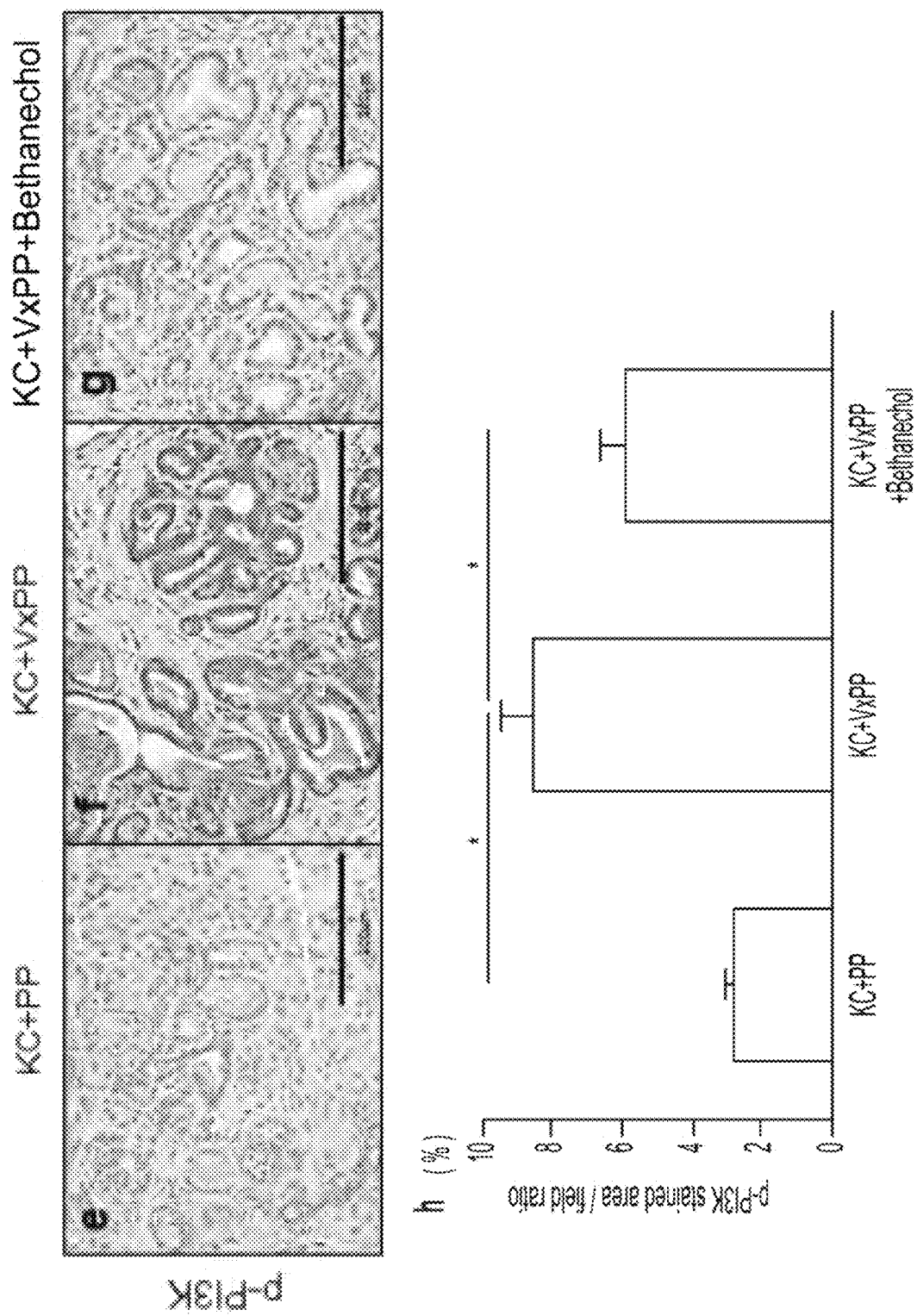
FIGS. 10E-G, Representative images of immunohistochemical staining of p-PI3K in (FIG. 10E) KC+PP mice, F KC+VxPP mice, and G KC+VxPP+bethanechol mice.
FIG. 10H, Quantitative analysis of p-PI3K stained area in KC+PP, KC+VxPP, and KC+VxPP+bethanechol mice (p<0.05).
Figures 10I, 10J, 10K, 10L:
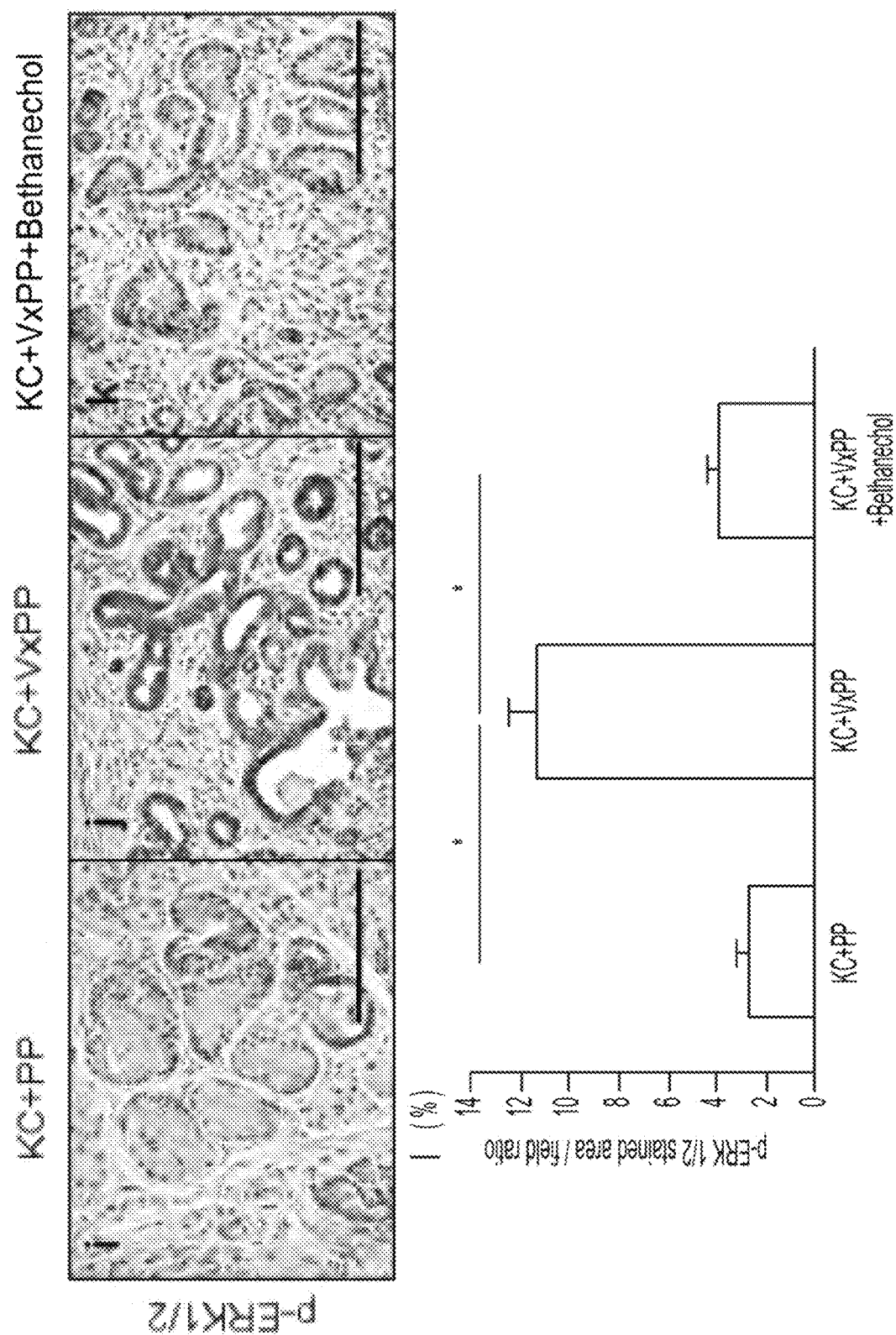
FIGS. 10I-K, Representative images of immunohistochemical staining of p-ERK1/2 in (FIG. 10I) KC+PP, mice (FIG. 10J) KC+VxPP mice, and (FIG. 10K) KC+VxPP+bethanechol mice.
FIG. 10L, Quantitative analysis of p-ERK stained area in KC+PP, KC+VxPP, and KC+VxPP+bethanechol mice (p<0.05).
Figure 10R:
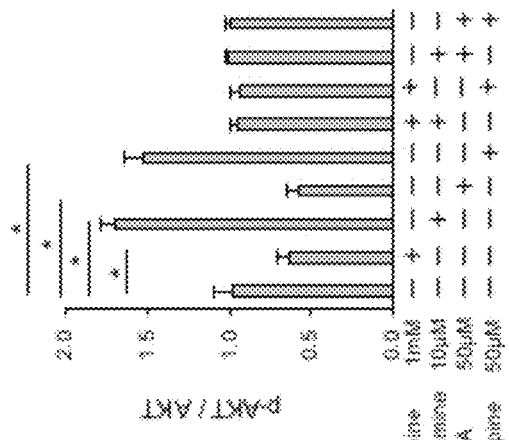
Figure 10Q:
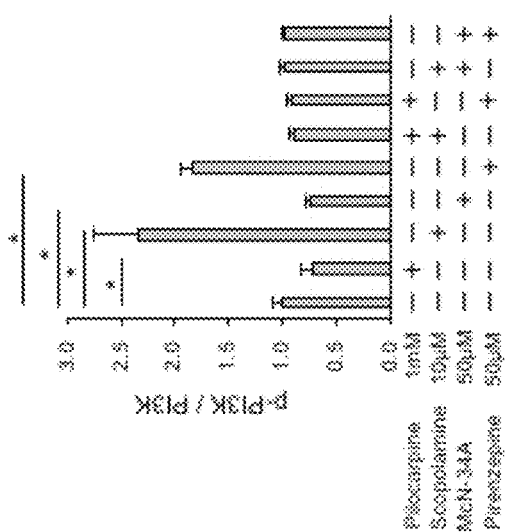
Figure 10P:
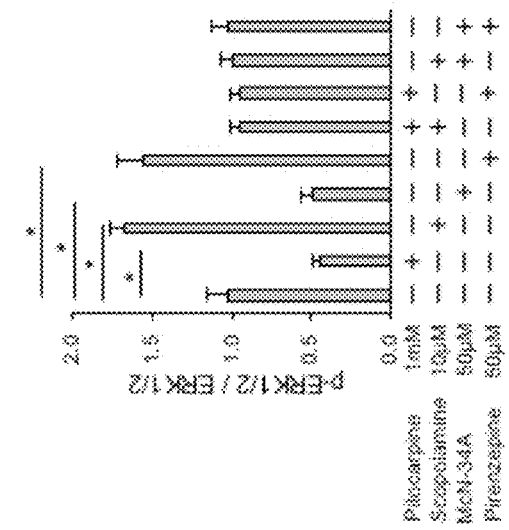

Next, the role of cholinergic signaling in established PDAC was investigated using the KPC mouse model, which develops PDAC at a median age of 17-19 weeks[2, 29]. KPC mice with pancreatic tumors that measured 3-5 mm in diameter on ultrasound were randomized to treatment with gemcitabine (GEM) alone, or GEM+bethanechol (FIG. 8I). Treatment with GEM+bethanechol extended the overall survival of control KPC mice treated with GEM alone from 29 to 48 days ($p=0.002$) (FIG. 8J). In addition, treatment with GEM+bethanechol led to a significant reduction in pancreatic CD44 expression compared to GEM alone ($p<0.05$) (FIGS. 8K-M). This suggests that parasympathetic stimulation with bethanechol can suppress pancreatic tumorigenesis and possibly reduce the expansion of the $CD44^+$ cancer stem cell compartment.

Parasympathetic Signaling Directly Promotes Cell Proliferation in Kras Mutant Spheres Via CHRM1 and Regulates Cancer Stemness.

To determine whether cholinergic stimulation suppresses tumor development in part through specific muscarinic receptors on cancer cells, the sphere forming capacity of $Kras^{+/LSL-G12D}$ pancreatic acinar cells in a 3D Matrigel culture system in the absence and presence of muscarinic agonists and antagonists was assessed. $Kras^{+/LSL-G12D}$ mutant spheres were generated from $Kras^{+/LSL-G12D}$ mice by delivery of an adenoviral Cre (Ad-Cre). $Kras^{+/LSL-G12D}$ mutant spheres were treated with the non-selective muscarinic agonist pilocarpine (1 mM), the non-selective muscarinic antagonist scopolamine (10 µM), the CHRM1-selective agonist McN-34A (50 µM), or the CHRM1-selective antagonist pirenzepine (50 µM). Intriguingly, the Kras mutant acinar cell cultures treated with pilocarpine formed significantly fewer and smaller spheres, while the acinar cultures treated with scopolamine formed significantly more and larger spheres compared to the controls (FIGS. 9A-E). In addition, the acinar cultures treated with McN-34A formed significantly fewer and smaller spheres, while the acinar cultures treated with pirenzepine formed significantly more and larger spheres compared with controls (FIGS. 9F-J).

Analysis of muscarinic receptor expression in human (MiaPaca2 and Panc1) and murine (Panc02 and K8282) PDAC cell lines revealed higher CHRM1 and Chrm1 expression after scopolamine treatment, respectively and lower CHRM1 and Chrm1 expression with pilocarpine treatment, respectively (FIGS. 13A-D) compared to control. Moreover, MTT assays demonstrated that muscarinic agonists decreased proliferation of human and murine cancer cell lines, while muscarinic antagonists (scopolamine and pirenzepine) increased their proliferation (FIGS. 9K-N). The increased proliferation could be inhibited to some extent not only by pilocarpine but also by McN-34A, showing that CHRM1 was largely responsible for modulating the antiproliferative effects of muscarinic agonists (FIGS. 9K-N).

Figures 13A, 13B, 13C, 13D:
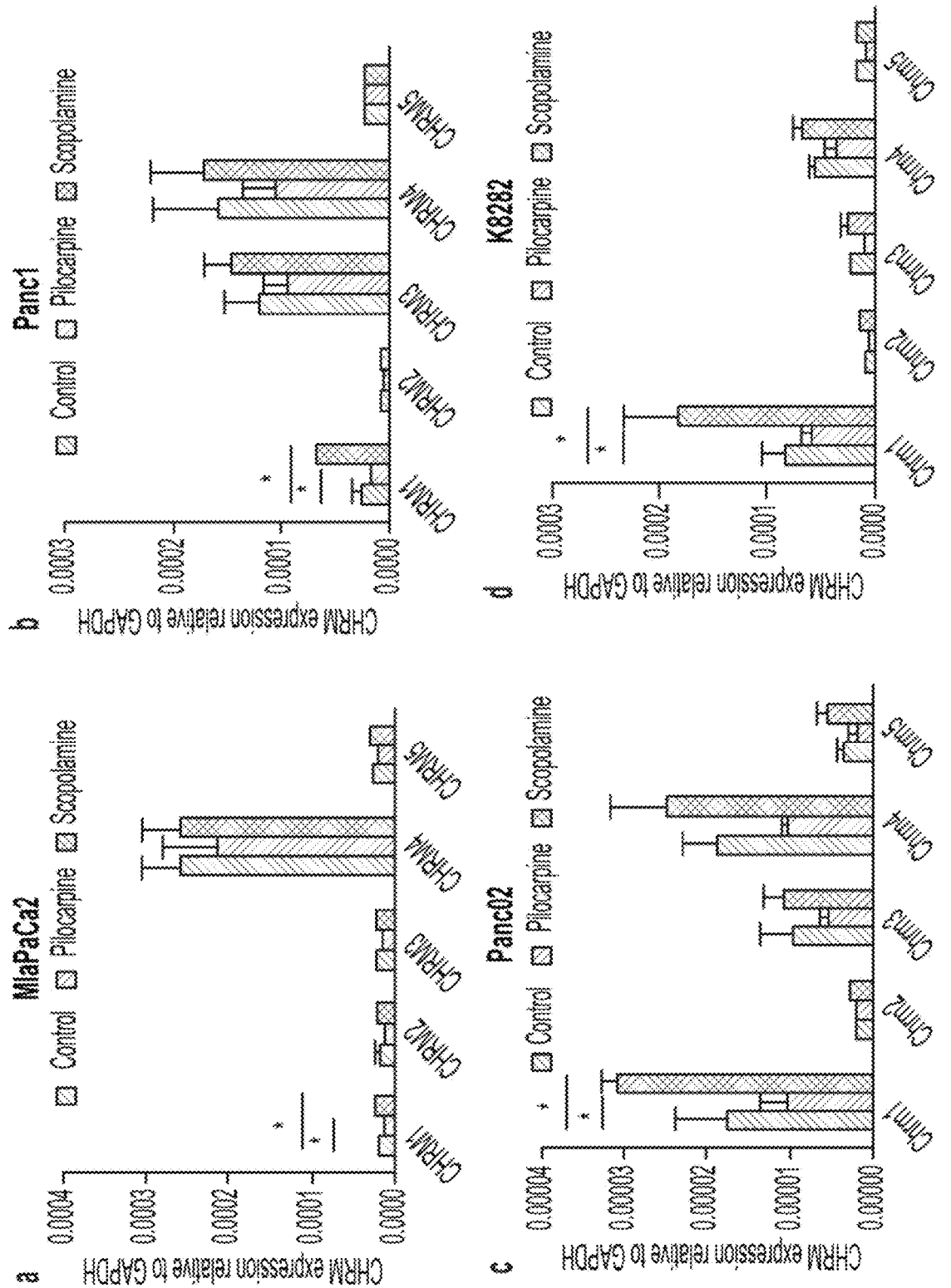
Figure 13E:
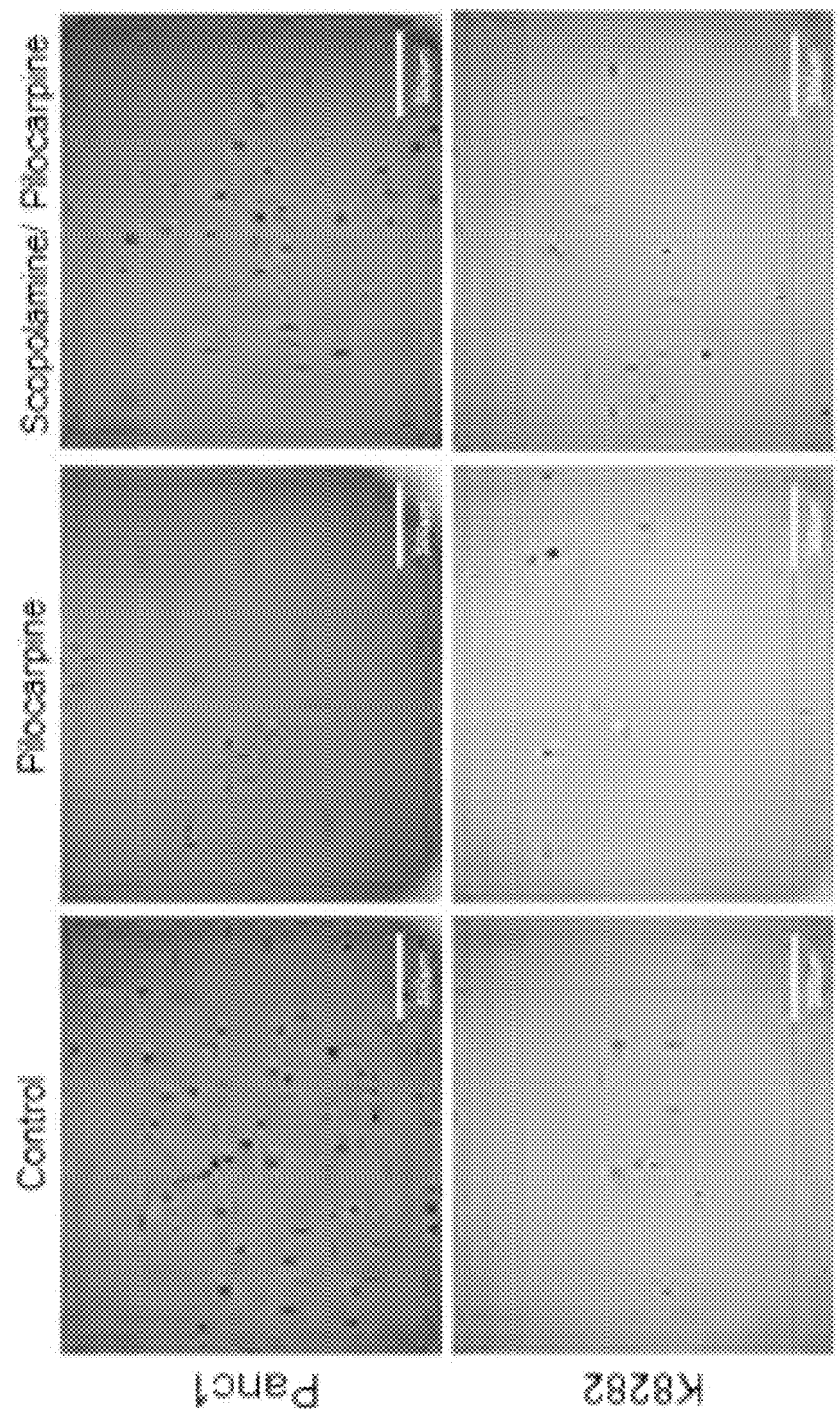
Figure 13F:
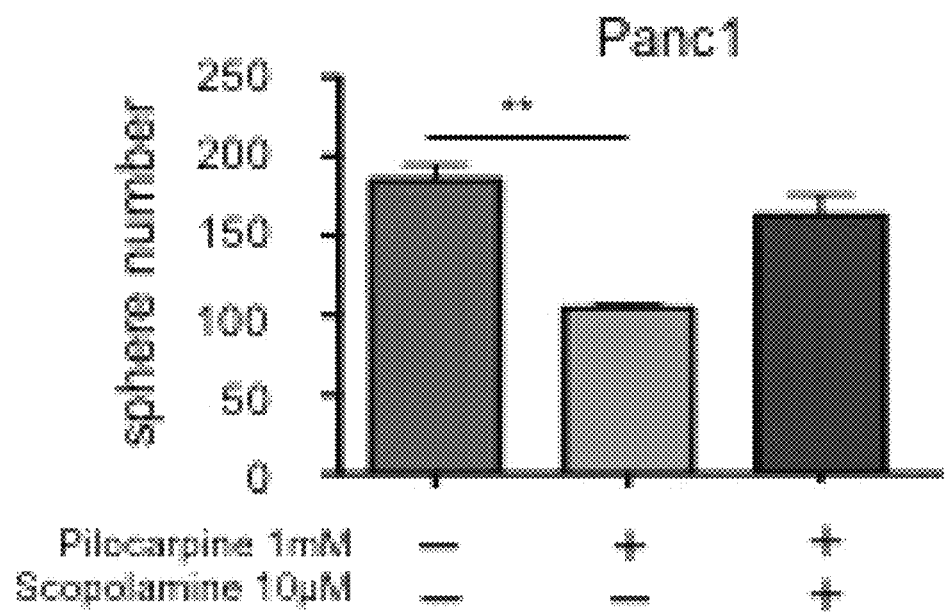
Figure 13G:
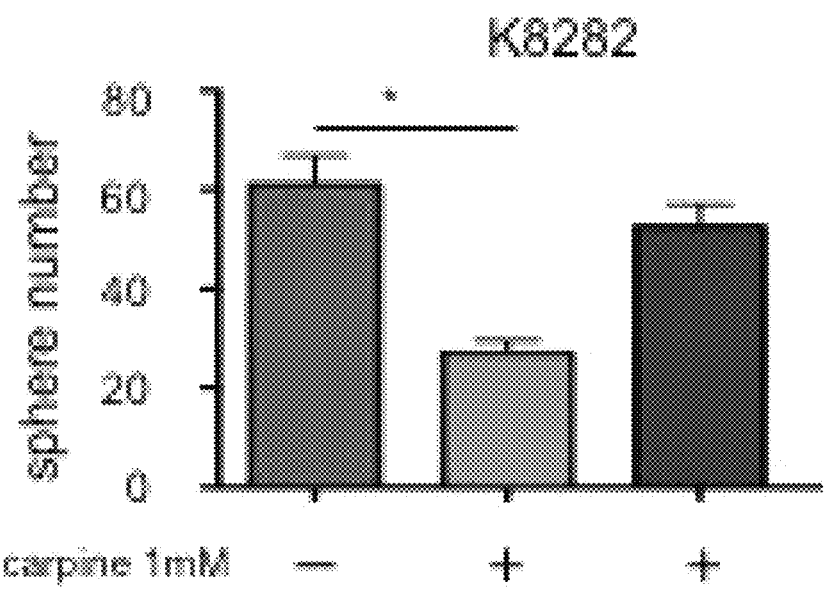
Figures 13L, 13M:
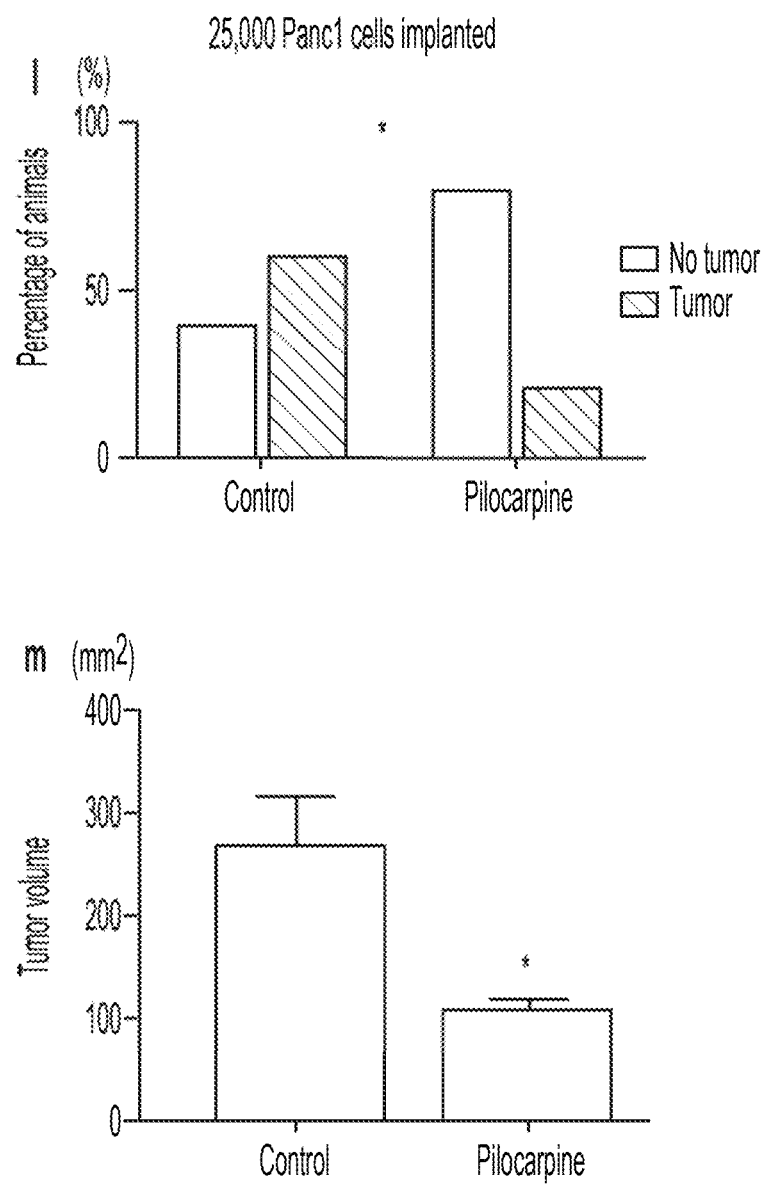

To address the possible parasympathetic effects on stemness, human pancreatic cancer cells (Panc1 and BxPC3) were treated with pilocarpine. Interestingly, FACS analysis after pilocarpine treatment showed a marked suppression of a well-defined ($CD44^+CD24^+EpCAM^+$) PDAC stem cell population (FIGS. 9O-Q, $p<0.001$)[27]. Moreover, soft agar assays also demonstrated that muscarinic agonists decreased sphere formation, thereby suggesting that muscarinic agonists suppress the stem cell compartment in human and murine cancer cell lines (FIGS. 13E-G). To further confirm the suppressive effect of muscarinic agonists on this triple positive population, Panc1 cells were treated with pilocarpine for 72 hours, after which 25,000 cells were implanted subcutaneously into NOD/SCID mice. Pre-treatment with pilocarpine resulted in a significant reduction in tumors incidence and tumor volume compared to untreated Panc1 cells ($p<0.05$) (FIGS. 13H-M), consistent with an overall reduction in pancreatic cancer stem cells.

Parasympathetic Signaling Inhibits Downstream EGFR/MAPK and PI3K/AKT Signaling in PDAC Cells.

Figure 14B:
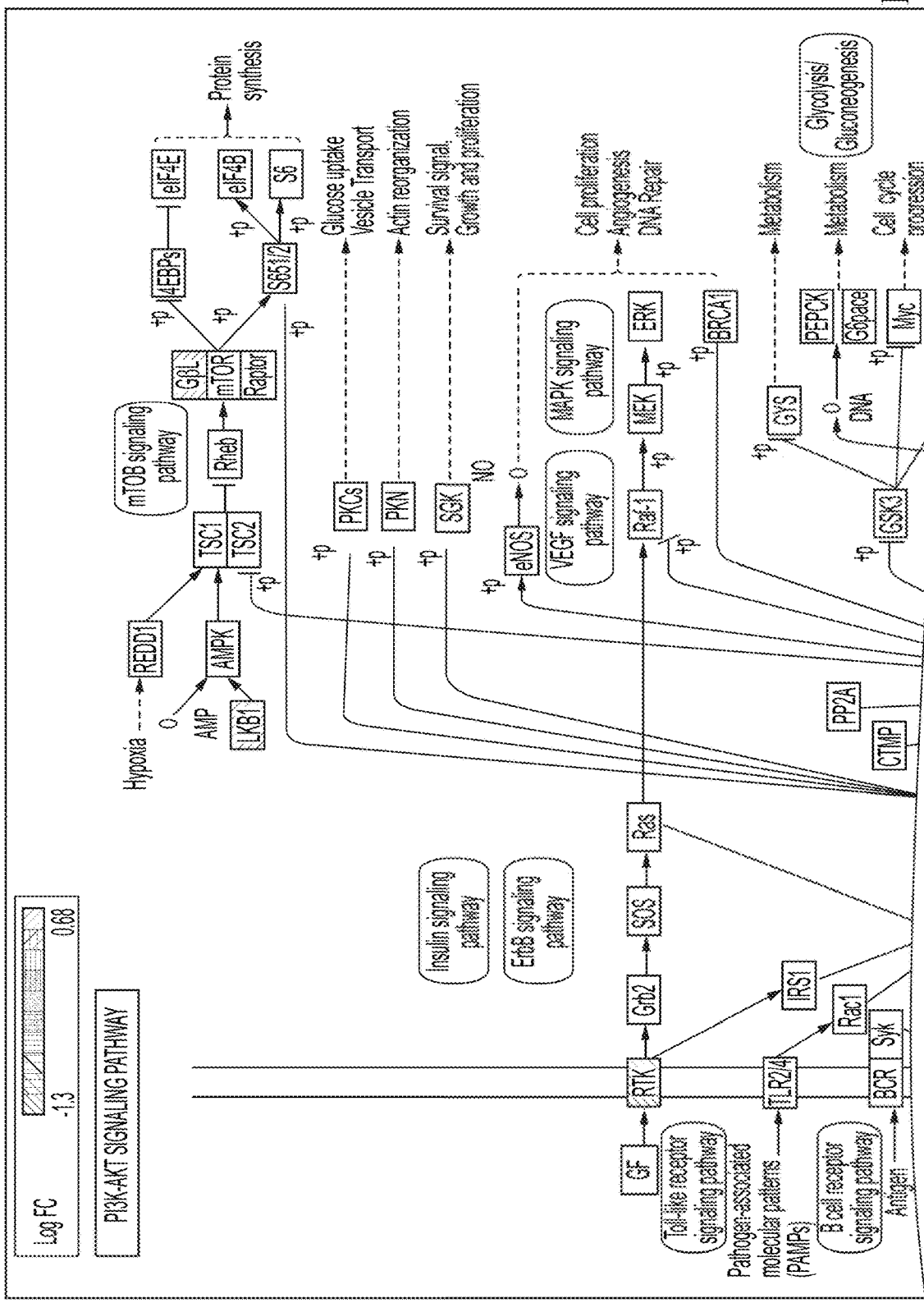
Figure 14B:
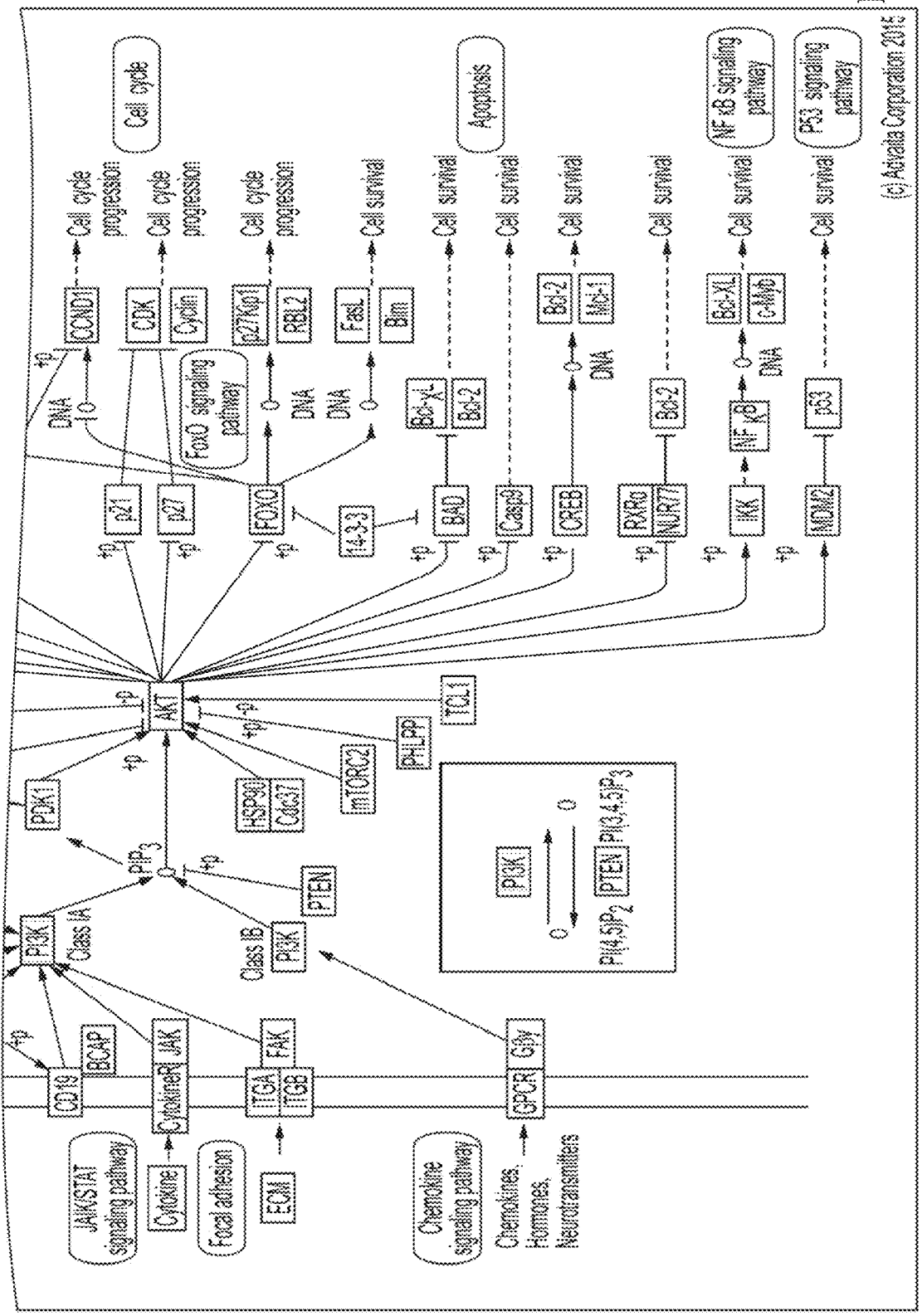
Figure 14C:
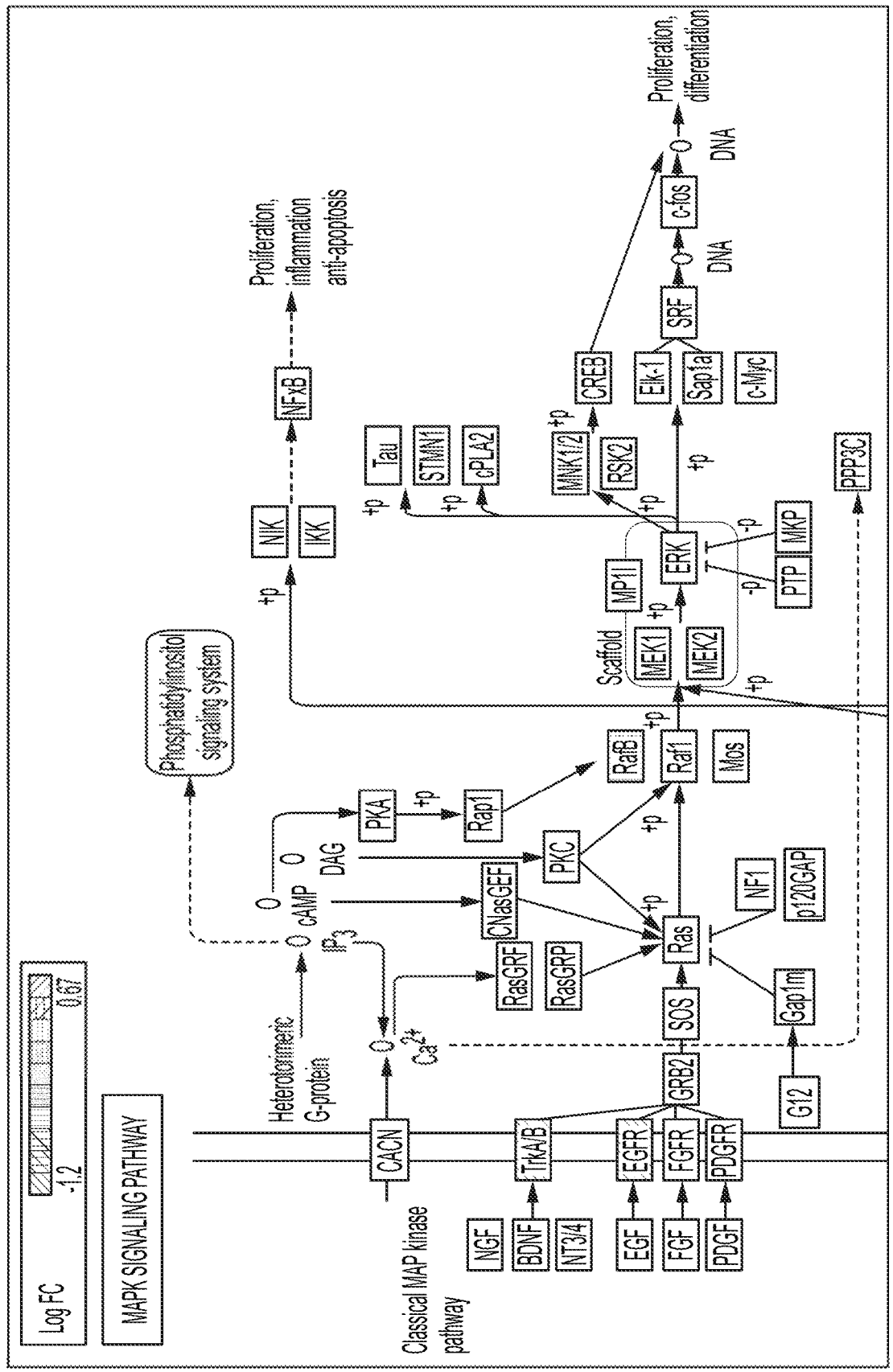
Figures 15A, 15B, 15C, 15D, 15E, 15F, 15G, 15H, 15I:
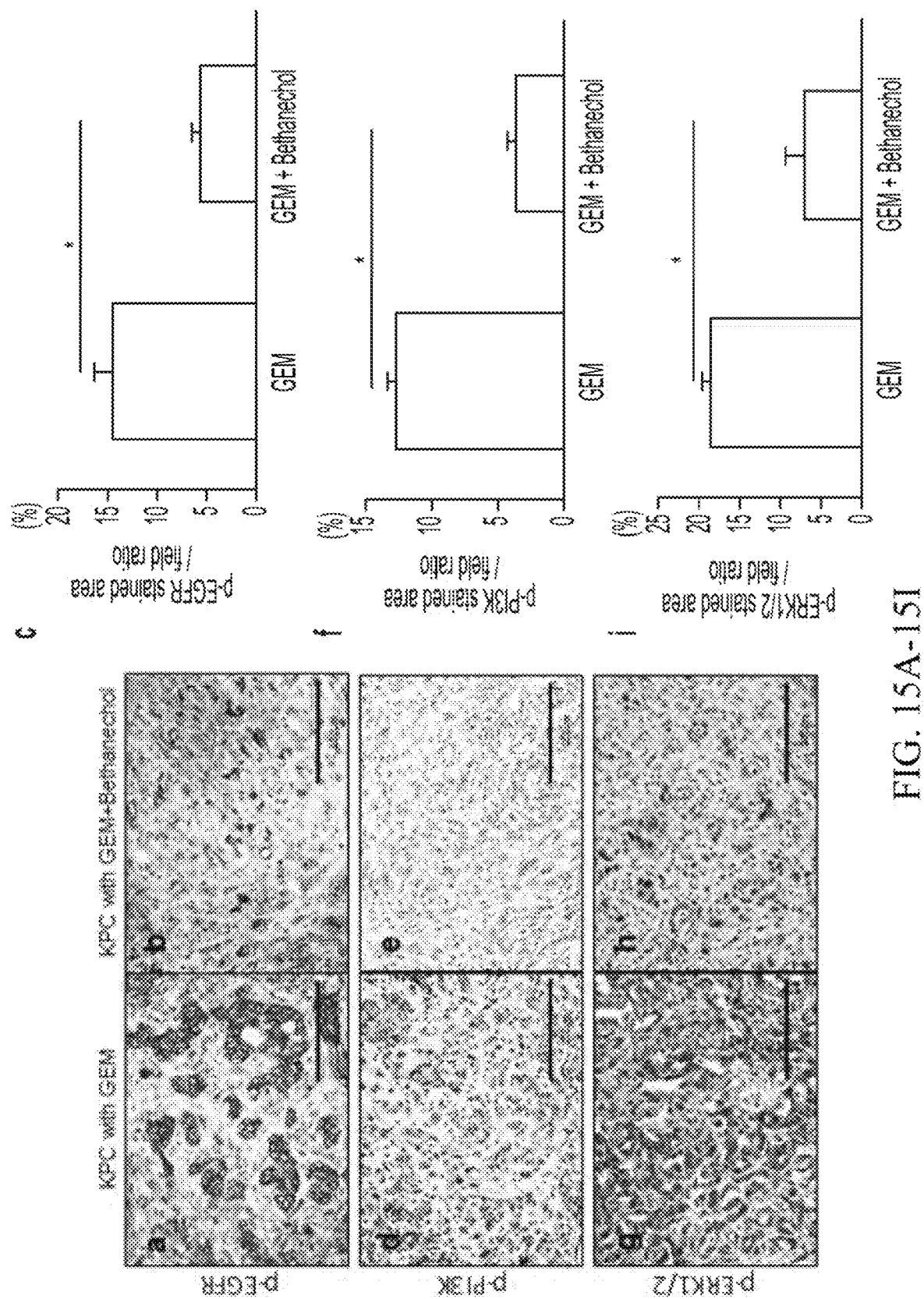
Figure 16Q:
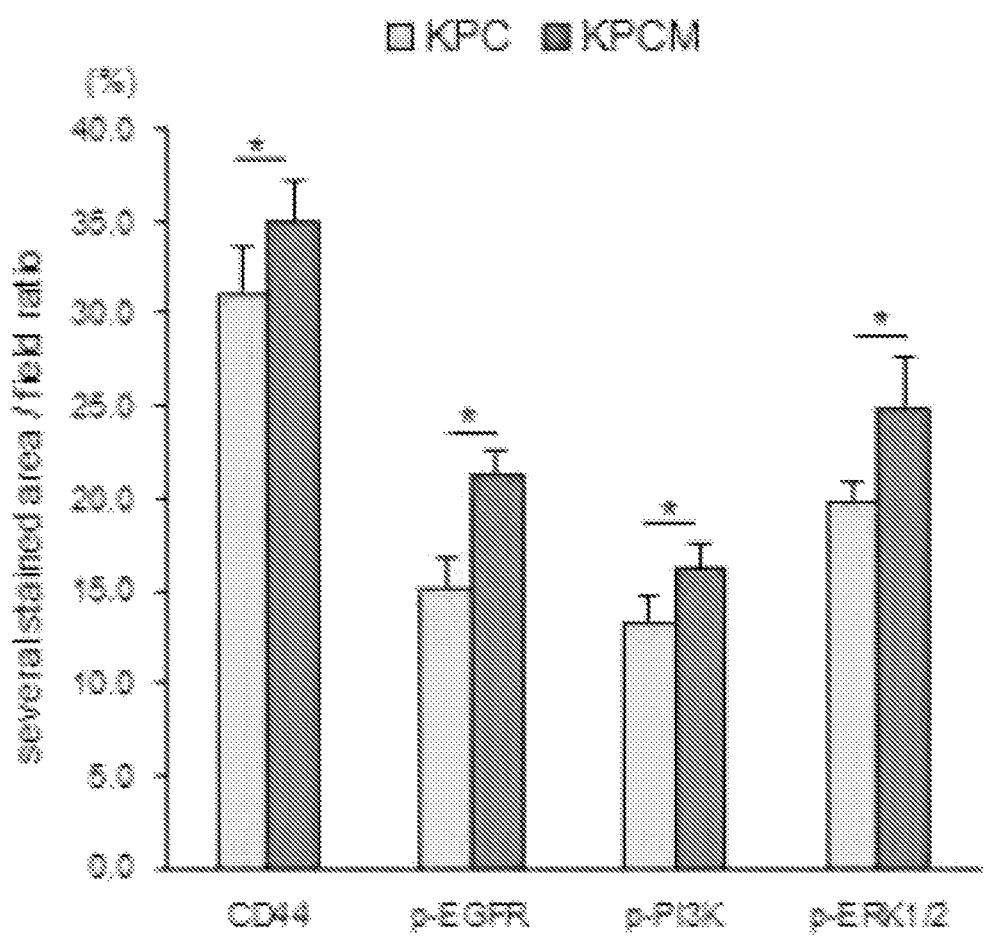

To determine the possible mechanisms by which muscarinic agonists were able to modulate the stem cell compartment in PDAC, Panc1 cells were analyzed following pilocarpine treatment using RNAseq (FIG. 14). Growth related genes that were suppressed by pilocarpine included EGFR and PI3K (FIG. 14A). A more detailed analysis of differentially expressed genes in terms of KEGG pathways using iPathwayGuide suggested a possible mechanism of tumor suppression through the PI3K-AKT and MAPK pathways (FIGS. 14B, C). These RNAseq data are consistent with inhibition by pilocarpine of the PI3K-AKT pathway (FIG. 14B)[30]. PIK3CA(PI3K) is activated by EGFR, KDR(RTK) and ITGAV(ITGA), all of which were downregulated, so that PIK3CA(PI3K) is inhibited at the signaling level as well. PIK3CA(PI3K) is an activator of AKT, so that inhibition of PIK3CA(PI3K) leads to inhibition of AKT, thus reducing proliferation. In the classical MAPK signaling pathway (FIG. 14C), NTRKB(TRKB) and BRAF(RafB), which are also pro-proliferative[31], were also downregulated by RNAseq.

To test key aspects of the above model, the expression of activated forms of EGFR, PI3K, and ERK (p-EGFR, p-PI3K, and p-ERK) was examined by immunohistochemical staining under conditions of cholinergic stimulation and denervation. Interestingly, expression of p-EGFR, p-PI3K, and p-ERK1/2 was significantly higher in pancreata of vagotomized KC mice (KC+VxPP) than in control KC mice (KC+PP mice) ($p<0.05$) (FIGS. 10A-L). In addition, their expression was significantly suppressed in vagotomized KC mice by bethanechol treatment ($p<0.05$) (FIGS. 10A-L). Furthermore, in pancreata of KPC mice treated with bethanechol, their expression was significantly downregulated compared with untreated KPC mice (FIGS. 15A-I).

To further characterize downstream signaling pathways modulated in PDAC cells in response to parasympathetic signaling, western blots were performed for key signaling proteins in human Panc1 cells and murine K8282 cells treated with pilocarpine, scopolamine, McN-34A, or pirenzepine (FIG. 10M and FIG. 15J). EGFR, BRAF, ERK1/2, PI3K, and AKT kinases were significantly more phosphorylated in response to the antagonists, scopolamine or pirenzepine, and significantly less phosphorylated in response to the agonists, pilocarpine or McN-34A. However, following treatment with a muscarinic antagonist, the addition of an agonist completely abrogated the increases in these phosphorylated kinases (FIG. 10M). The ratios of p-EGFR/EGFR, p-BRAF/BRAF, p-ERK/ERK, p-PI3K/PI3K and p-AKT/AKT were significantly decreased after pilocarpine or McN-34A treatment alone, and increased after scopolamine or pirenzepine treatment alone, and the effects of the non-selective agonist and antagonist, respectively were blocked by pretreatment of these cells with the CHRM1 selective agonist and antagonist (FIGS. 10N-R and FIGS. 15K-O). Therefore, CHRM1 appears to represent the primary cholinergic receptor that suppresses signaling through EGFR and other downstream (ERK1/2, PI3K, AKT) pathways that likely contribute to pancreatic tumorigenesis.

Knockout of CHRM1 Results in Larger PanIN Area and Tumor Incidence in KC Mice and Shorter Overall Survival in KPC Mice.

Figure 11H:
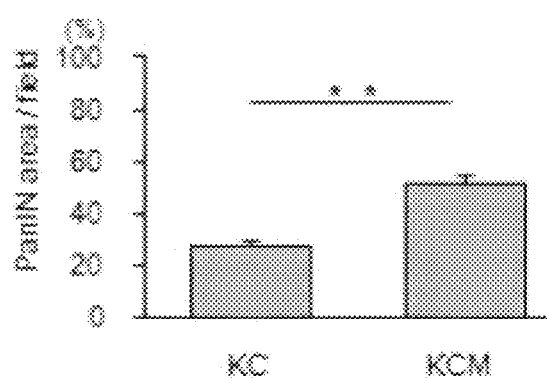
FIG. 11H, Quantification of PanIN area in pancreatic sections from KC and KCM mice at 20 weeks (p<0.01).
Figure 11I:
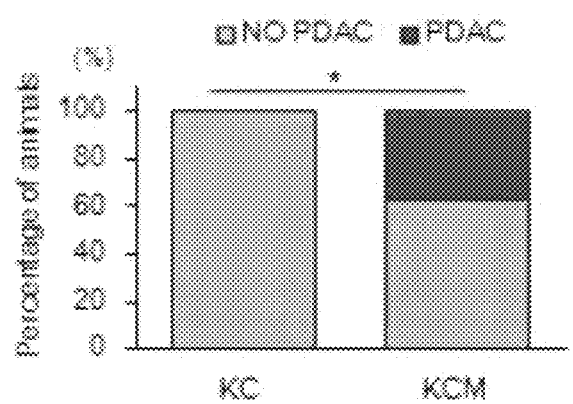
FIG. 11I. Percentage of KC and KCM mice with pancreatic cancer development at 20 weeks. (p<0.05).
Figure 11I:
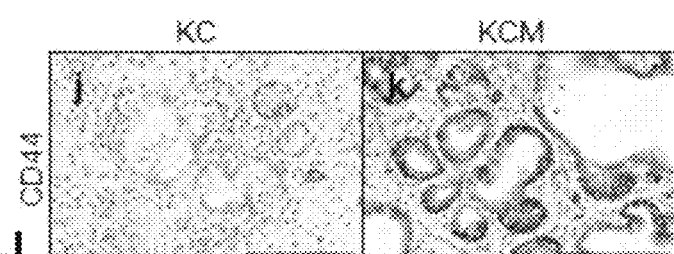
Figure 11I:
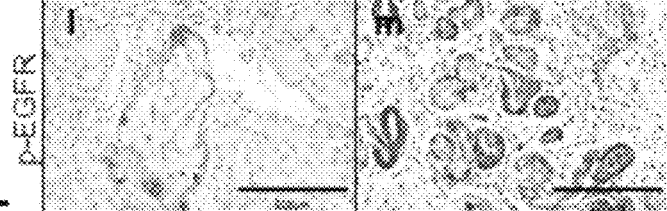
Figure 11I:
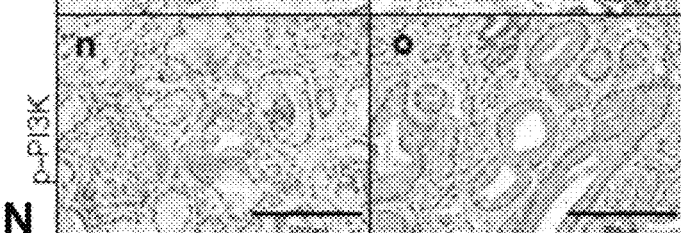
Figure 11I:
Figure 11R:
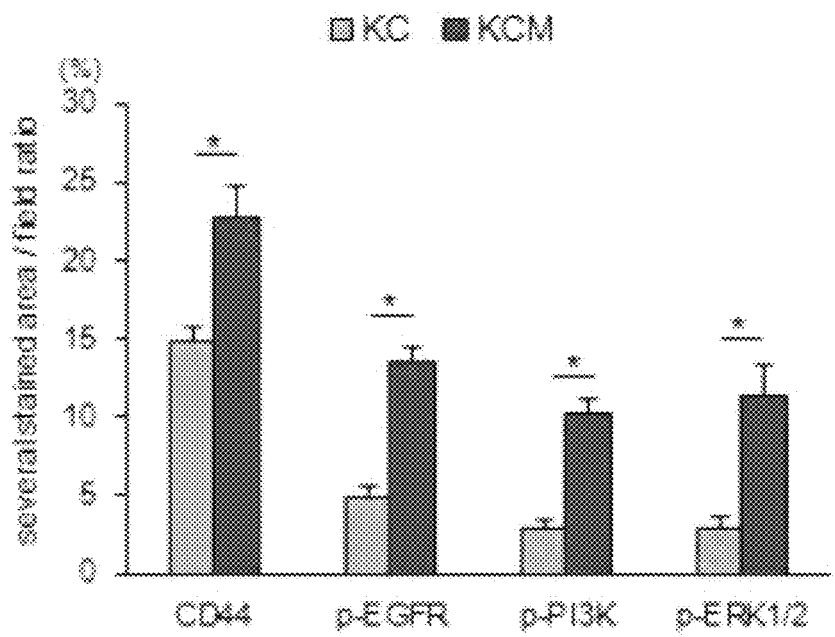
FIG. 11R, Quantitative analysis of CD44, p-EGFR, p-PI3K, and p-ERK1/2 stained areas in KC and KCM mice (p<0.05, respectively) FIG. 11S, Kaplan-Meier curve comparing overall survival in KPC and KPCM mice) (p<0.001). Scale bars, 500 μm (FIGS. 11D, F) and 200 μm (remaining images). Means±SEM. *p<0.05; **p<0.01.

Given that CHRM1 specific agonists and antagonists strongly modulated pancreatic tumorigenesis via MAPK and PI3K-Akt signaling, similar to nonspecific agonists and antagonists, the role of CHRM1 in pancreatic tumor development was confirmed. Consequently, KC mice were crossed to Chrm1-KO mice, and generated KC/Chrm1-KO (KCM) mice (n=1). The absence of Chrm1 expression in KCM mice was confirmed by qRT-PCR, and protein expression was confirmed by immunostaining (FIGS. 11A-C). In addition, similar to vagotomized KC, KCM mice appeared to have more advanced PanINs, including PDAC, which was absent in KC mice (FIGS. 11D-G). Morphometric analysis of the PanIN area revealed a significantly larger area in KCM mice compared to KC mice (n=10) ($p<0.01$) (FIG. 11H). Moreover, the PDAC incidence in KCM mice was significantly higher compared with control KC mice ($p<0.05$, 36.7% vs. 0%) (FIG. 11I). Furthermore, immunohistochemical staining revealed significantly increased expression of CD44 (FIGS. 11J, K), p-EGFR (FIGS. 11L, M), p-PI3K (FIGS. 11N, O), and p-ERK1/2 (FIGS. 11P, Q) in KCM mice compared to KC mice ($p<0.05$, respectively) (FIG. 11R).

Next, the sphere forming capacity of $Kras^{+/LSL-G12D}$ mutant spheres versus $Chrm1-KO;Kras^{+/LSL-G12D}$ mutant spheres was assessed in a 3D Matrigel culture system. The Kras mutation was activated in spheres by infection with Adenoviral-Cre. As expected, the $Chrm1-KO;Kras^{+/LL-G12D}$ sphere cultures formed more spheres compared with $Kras^{+/LSL-G12D}$ control spheres. Consistent with an absence of cholinergic signaling, after pilocarpine or scopolamine treatment, $Chrm1-KO;Kras^{+/LSL-G12D}$ spheres showed a similar size and number compared to the untreated controls, whereas $Kras^{+/LSL-G12D}$ spheres showed a decrease or increase, respectively (FIGS. 16A-H).

Figure 11S:
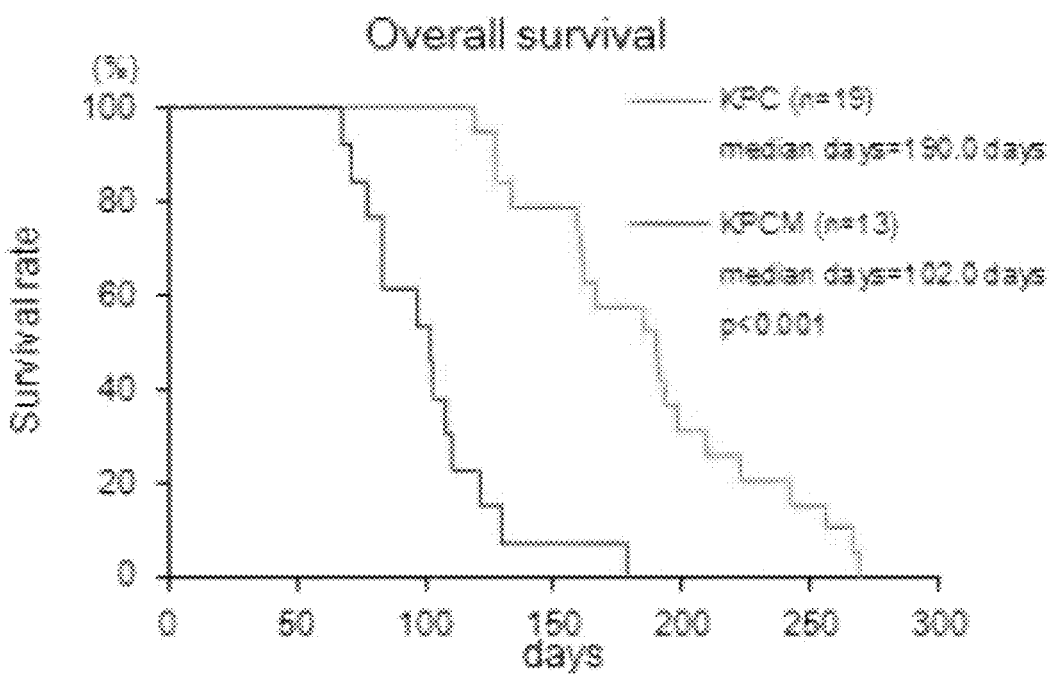

Finally, KPC mice were crossed to Chrm1-KO mice, generating KPC/Chrm1-KO (KPCM) mice (n=13). The median overall survival in KPCM mice (n=13) was significantly decreased compared to KPC mice (n=18) ($p<0.001$) (FIG. 11S). Furthermore, immunohistochemical staining showed significantly increased expression of CD44, p-EGFR, p-PI3K, and p-ERK1/2 in KPCM compared to KPC ($p<0.05$, respectively) (FIGS. 16I-Q). Thus, these data suggest that an absence of parasympathetic signaling CHRM1 leads to enhanced EGFR/MAPK and PI3K/AKT signaling, an expanded cancer stem cell compartment, and accelerated PDAC progression.

Parasympathetic Signaling Influences Survival in a Model of Hepatic Metastasis.

Figures 12A, 12B, 12C, 12D, 12E, 12F:
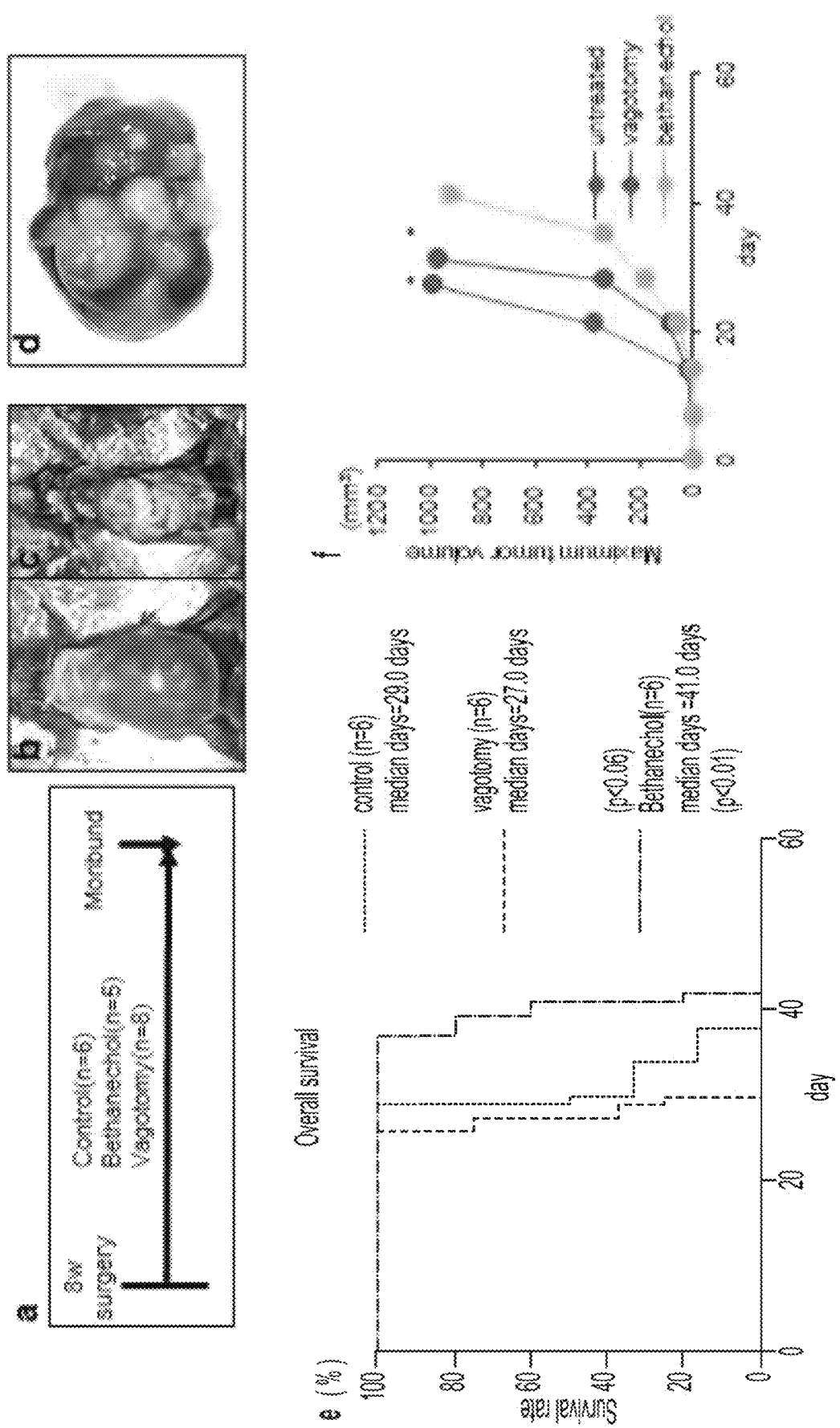
FIGS. 12A-T show that parasympathetic signaling influences survival in a model of hepatic metastasis.
FIGS. 12B-D, Representative macroscopic images of at the time of necropsy.
FIG. 12E, Kaplan-Meier curve comparing overall survival after splenic injection of GFP-labelled Panc02 cells in control mice (red), mice treated with selective hepatic vagotomy (blue) (p<0.05) or mice treated with bethanechol (green) (p<0.01).
FIG. 12F, Tumor number at necropsy in mice that received selective hepatic vagotomy (blue) (p<0.05) and bethanechol (green) (p<0.05), compared with untreated control (red).
Figure 12G:
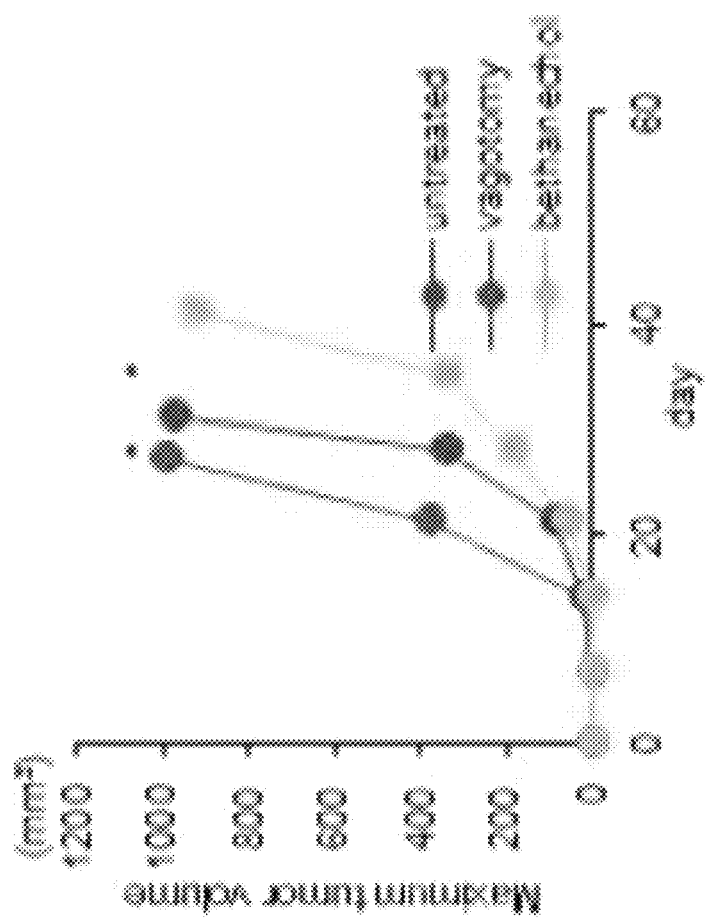
FIG. 12G, Maximum tumor volume in vagotomized (blue) (p<0.05) and bethanechol (green) (p<0.05) compared with untreated control (red).
Figures 12H, 12I, 12J, 12K:
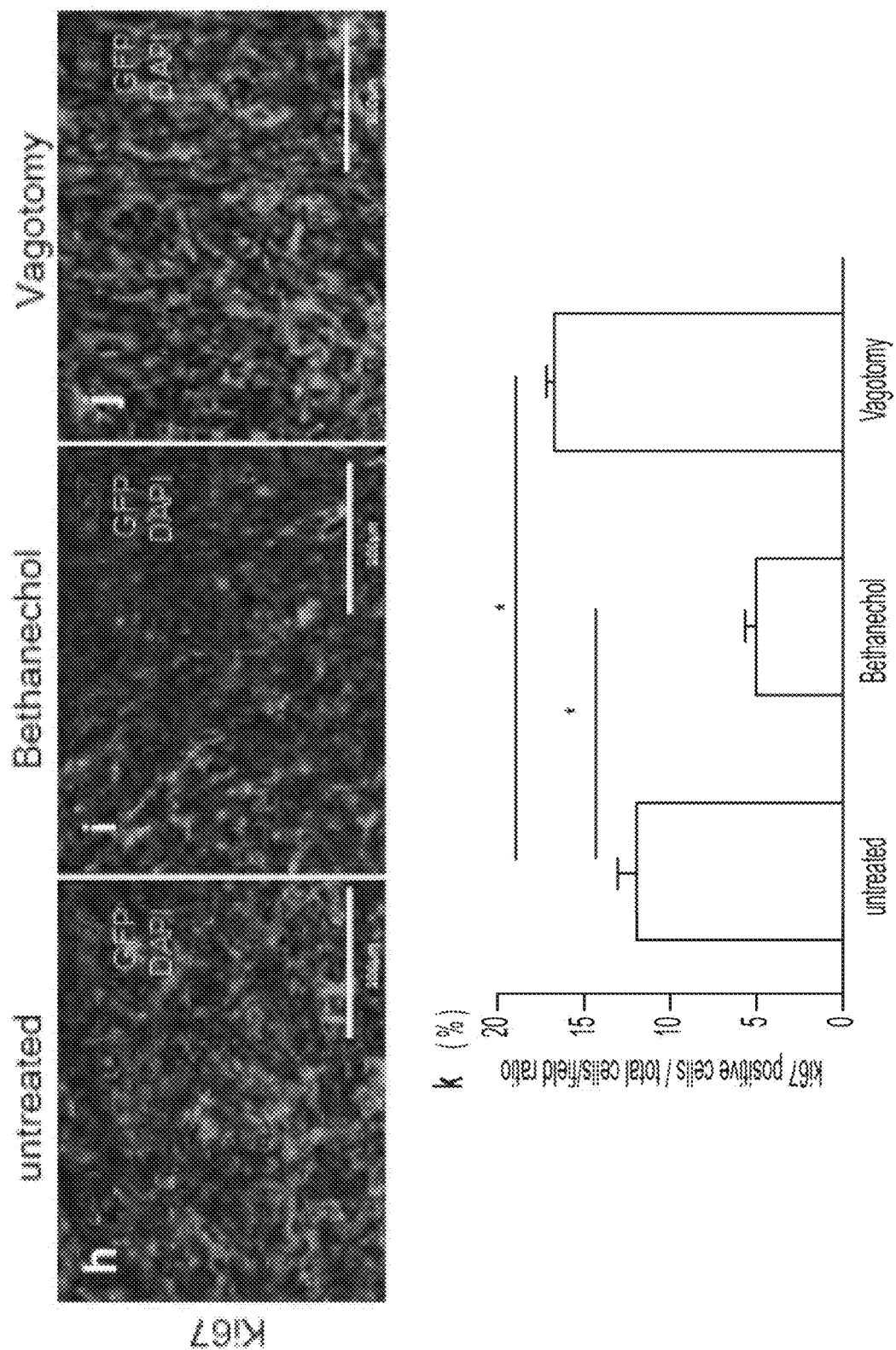
FIGS. 12H-J, Representative images of immunofluorescence staining for Ki67 in liver metastases from (FIG. 12H) untreated control, (FIG. 12I) bethanechol treated and (FIG. 12J) vagotomized mice.
FIG. 12K, Quantitative analysis of Ki67 positive cells in untreated control, bethanechol treated, and vagotomized mice (p<0.05, respectively).
Figures 12L, 12M, 12N, 12O:
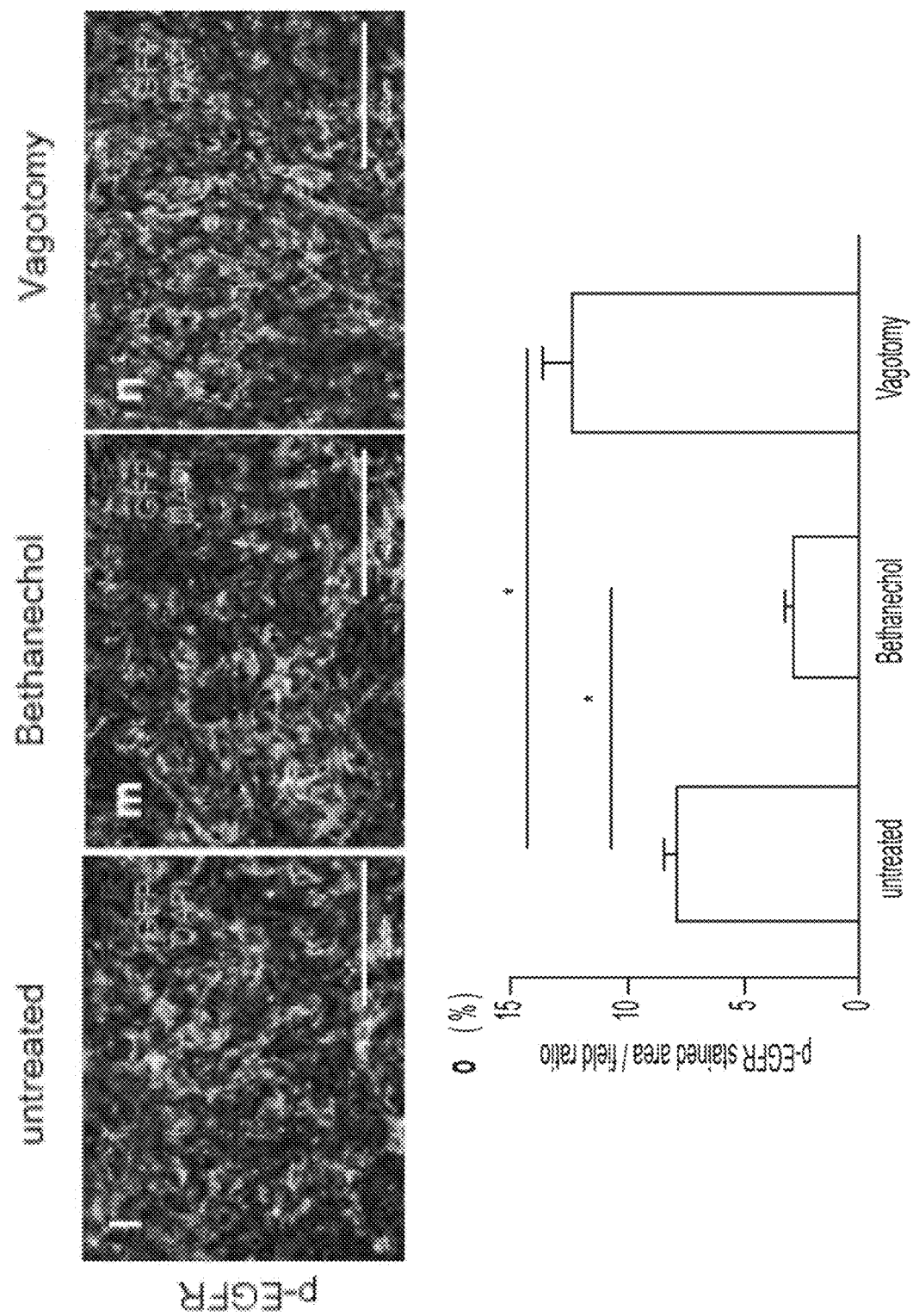
FIGS. 12L-N, Representative images of immunofluorescence staining for p-EGFR stain in liver metastatic lesions from (FIG. 12L) untreated control, (FIG. 12M) bethanechol treated, and (FIG. 12N) selectively vagotomized mice.
FIG. 12O, Quantitative analysis of p-EGFR stained area in liver metastases from untreated control, bethanechol treated, and vagotomized mice (p<0.05, respectively).
Figures 12P, 12Q, 12R, 12S:
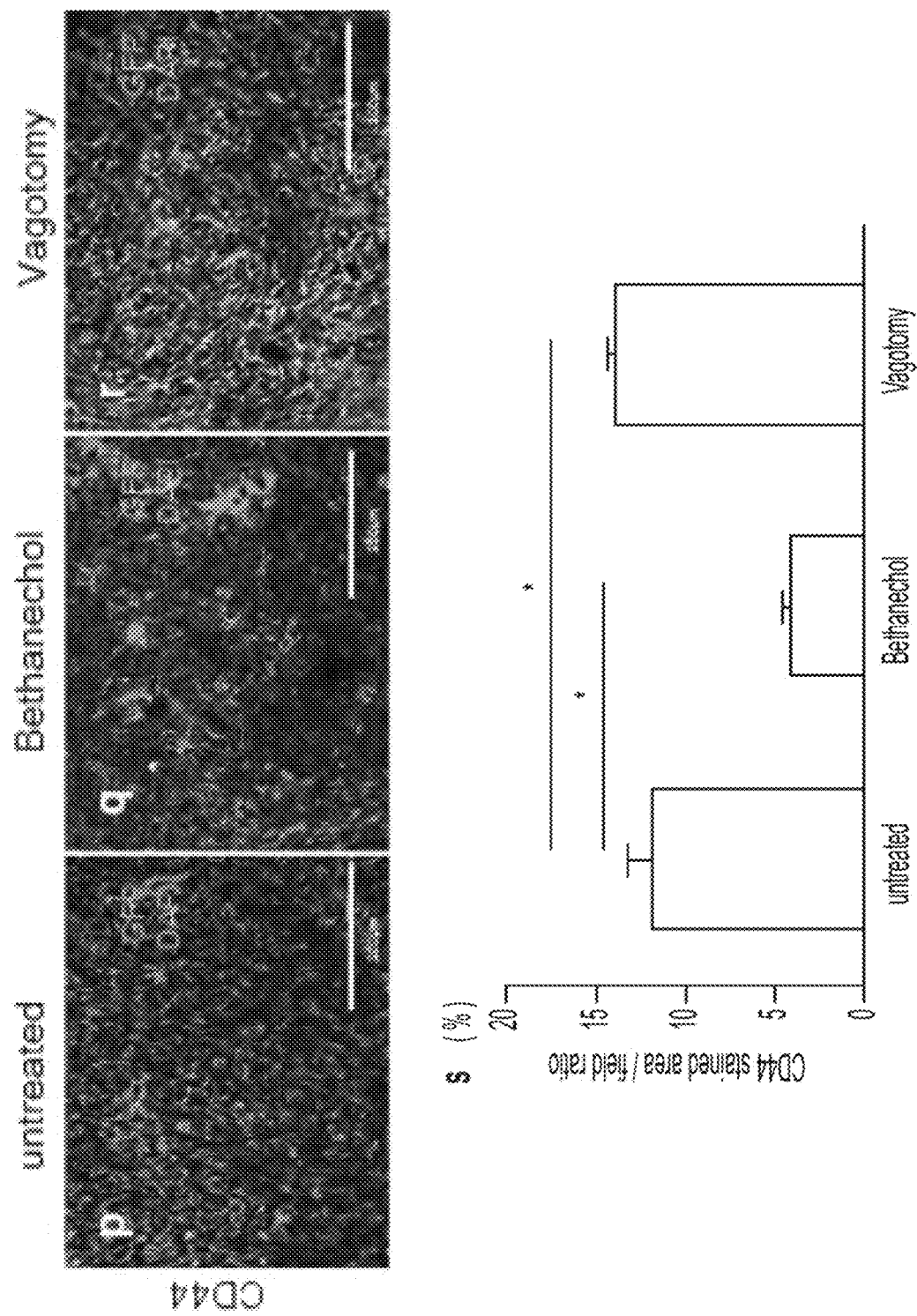
FIGS. 12P-Q, Representative pictures of immunofluorescence staining for CD44 in liver metastatic lesions from (FIG. 12P) untreated control, (FIG. 12Q) bethanechol treated, and (FIG. 12R) vagotomized mice.
FIG. 12S, Quantitative analysis of CD44 stained areas from metastatic lesions in untreated control, bethanechol, and vagotomized mice (p<0.05, respectively).
Figures 17A, 17B, 17C, 17D, 17E:
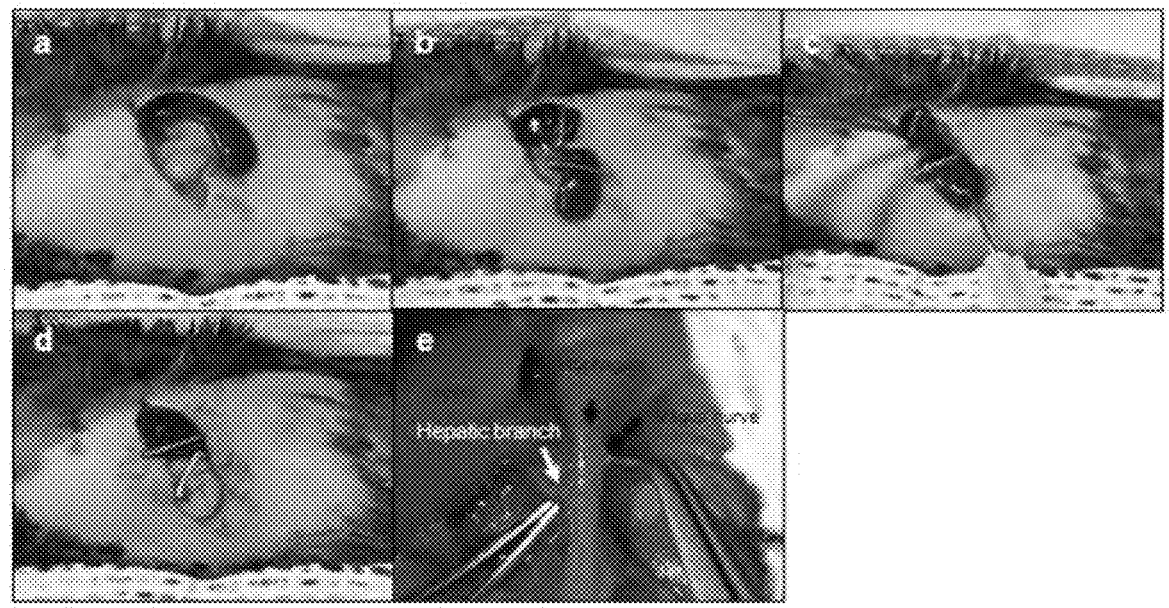
FIGS. 17A-H show surgical procedures and macroscopic findings in the hepatic metastatic model.
Figures 17F, 17G:
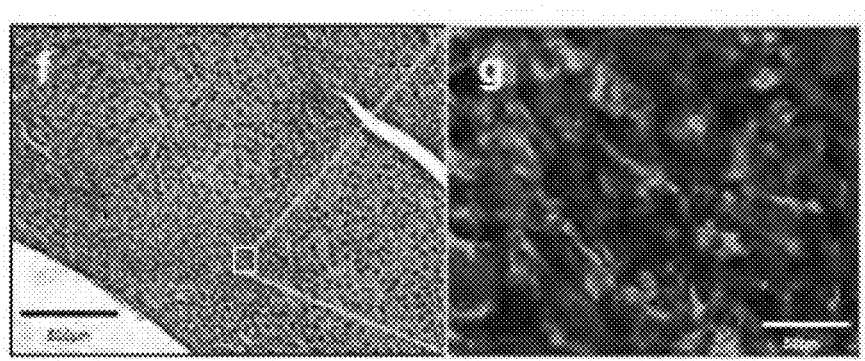
Figure 17H:
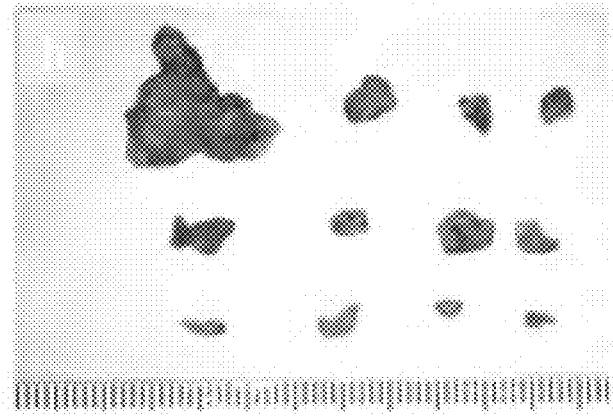

The studies in KC and KPC mice suggest that signaling through CHRM1 inhibits growth of primary pancreatic tumors through downregulation of growth factor pathways. However, given that many PDAC patients with metastatic disease (Stage IV) eventually die with liver metastases, the effect of parasympathetic signaling on the growth of hepatic lesions was examined utilizing a well-established syngeneic model of metastatic PDAC[32]. The protocol and surgical procedures are shown in FIG. 12A and FIGS. 17A-E. At 30 days after injection of PDAC cells (Panc02) into the spleen, cancer cells appear as large pale nodules replacing macroscopically normal liver tissue (FIGS. 12B-D). To increase the detection of small metastases, Panc02 cells were stably transfected with a GFP-expressing construct, which was readily detected following splenic injection (FIGS. 17F, G). Wild type C57BL/6 mice received splenic injections of $2 \times 10^6$ GFP-labeled Panc02 cells and were then divided into 3 groups: untreated controls (n=6), bethanechol treated (n=5), and mice which have undergone a selective parasympathetic liver denervation by transection of the hepatic branch of the vagus (n=8). Mice treated with bethanechol showed significantly longer survival ($p<0.01$), whereas the group pretreated with selective hepatic vagotomy showed significantly shorter survival ($p<0.05$) (FIG. 12E). As shown by quantification of tumor number and maximum tumor volume (FIGS. 12F, G), tumor growth was expanded by selective vagotomy ($p<0.05$), while tumor growth was inhibited by bethanechol ($p<0.05$). A gross image shows the representative sizes of liver metastatic nodule in untreated mice (FIG. 17H). Moreover, to confirm that the parasympathetic pathway directly regulated tumor cells at the liver metastatic site, expression of Ki67 (FIGS. 12H-K), p-EGFR (FIGS. 12L-O) and CD44 (FIGS. 12P-S) were analyzed immunohistochemically. As expected, quantitative scoring indicated that their expression was significantly decreased in the bethanechol group ($p<0.05$), and significantly increased in the selective vagotomy group ($p<0.05$). Therefore, these data suggest that parasympathetic signaling suppresses the growth of not only the primary tumor, but also modulates growth of hepatic metastases.

Discussion

Figure 12T:
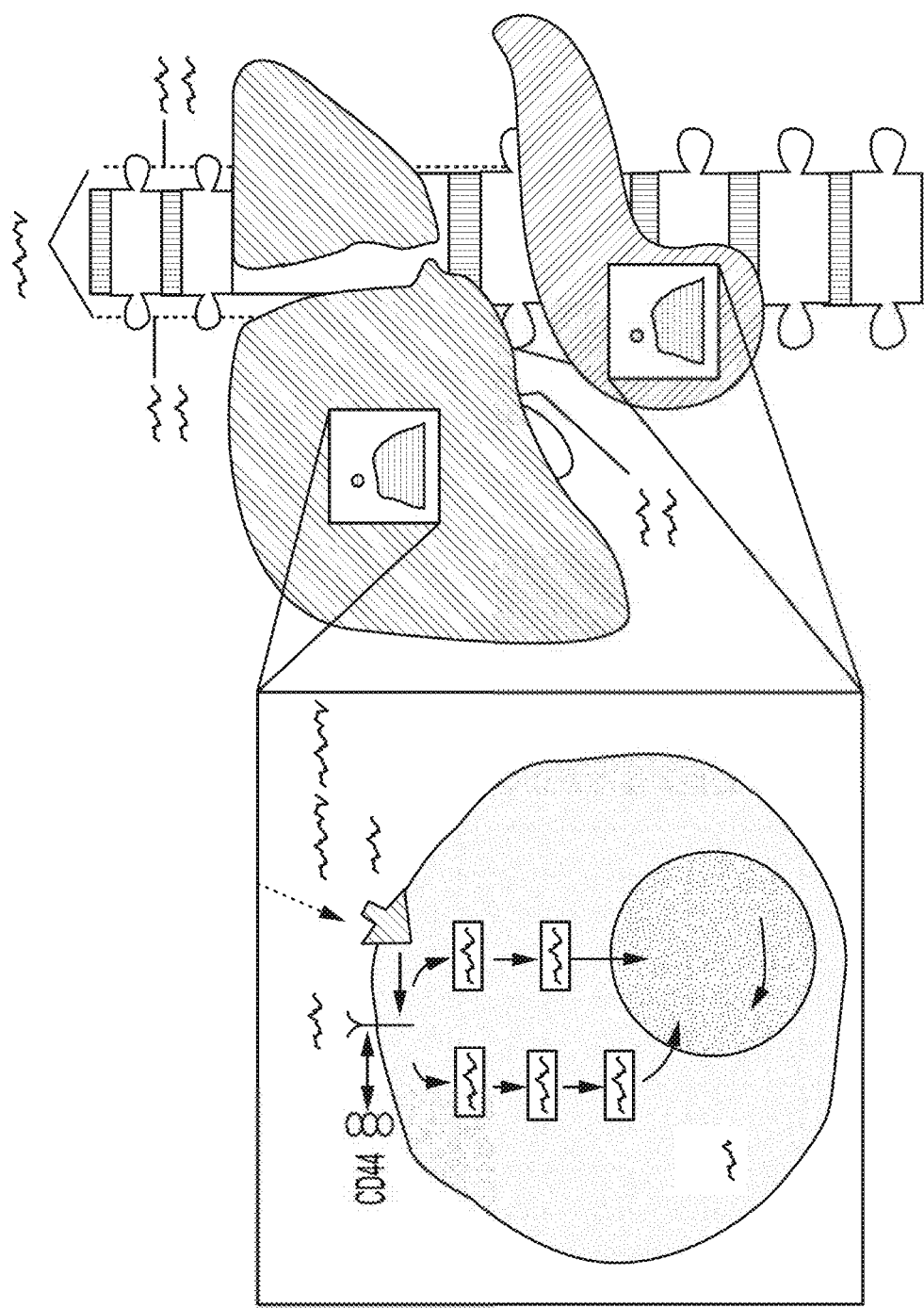

Accumulating evidence indicates that tumor growth is subject to neural regulation, particularly by the sympathetic and parasympathetic nervous systems. Here, it is shown that parasympathetic stimulation, primarily acting via CHRM1 expressed on tumor cells, suppresses PDAC growth. Thus, parasympathetic denervation through subdiaphragmatic vagotomy led to accelerated PanIN progression in KC mice, with the appearance of PDAC at 20 weeks of age (12 weeks post-vagotomy). Importantly, treatment with the broad muscarinic agonist bethanechol reduced PDAC and rescued the expected KC phenotype (e.g. early PanINs) in vagotomized KC mice, and significantly extended the survival of KPC mice with established PDAC. In vivo, bethanechol treatment reduced the expression of CD44, a potential cancer stem cell marker, in the pancreas. In vitro studies confirmed that muscarinic agonists suppressed growth of Kras mutant pancreatic spheres, and in PDAC cell lines suppressed the $CD44^+CD24^+EpCAM^+$ cell fraction. In KC mice, CHRM1 was selectively upregulated in the pancreas following vagal denervation. Through administration of specific agonists and antagonists, CHRM1 was identified as being primarily responsible for the suppressive effect of cholinergic stimulation. Analysis of downstream signaling pathways indicated that CHRM1 signaling was able to suppress a number of growth factor pathways, such as the EGFR/MAPK/PI3K/AKT pathway. Finally, it is shown here that the therapeutic benefits of bethanechol treatment extended beyond primary tumor models, and in fact was able to extend the survival of mice with hepatic metastases. Taken together, these data reveal that activation of muscarinic signaling via CHRM1 can directly suppress the growth of pancreatic tumor cells at both primary and metastatic tumor sites (FIG. 12T).

The nervous system in theory has the potential to influence the progression of cancer indirectly by modulating the immune system, tumor metabolism, angiogenesis, or tumor-stroma cross-talk, or through direct effects on tumor cells[11, 33, 34] In the latter case, autonomic neurotransmitters may stimulate cancer cell growth through the activation of numerous cancer-related signaling pathways[35]. In this regard, it has been recently shown that catecholamines promote ADRB2-dependent PDAC growth and secretion of neurotrophins (NT), which in turn promotes tumor innervation leading to increased intratumoral norepinephrine levels and accelerated tumor growth. In addition, blockade of ADRB2 or NT receptors improved gemcitabine's therapeutic effect[15]. In prostate cancer, both sympathetic and parasympathetic nerves are significantly involved in promoting all phases of murine cancer development[10, 11]. In gastric cancer, cholinergic signaling directly supported stem cell growth, and surgical or pharmacologic denervation of the mouse stomach strongly reduces tumor incidence and progression of gastric cancer[2, 13]. In particular, cholinergic signaling from the vagus nerve promotes gastric tumorigenesis directly via the M3 muscarinic receptor (CHRM3) through Wnt signaling.

The current study demonstrates that signaling from the vagus nerve can have an opposite and thereby inhibitory effect on tumorigenesis in the pancreas. Herein, the vagus nerve acts to suppress tumorigenesis in KC mice through downregulation of MAPK and PI3K pathways. Consistent with this finding, pancreatic cancer development was accelerated by vagotomy and inhibited by cholinergic muscarinic agonists. Previous studies in orthotopic and syngeneic PDAC models showed that vagotomy promoted tumor growth and shortened overall survival[23], and an indirect effect of parasympathetic signaling has been proposed[24]. Although vagal input plays an important role in immunomodulation[36, 37] and regulation of endothelial metabolism[11] within the tumor microenvironment, it is shown here that many of the parasympathetic effects are indeed direct, with suppressive effects on pancreatic epithelial growth mediated by muscarinic signaling. Nevertheless, an additional role of parasympathetic effects on tumor stroma are not precluded in this study.

Furthermore, CD44 expression correlates with tumor progression and metastatic phenotype in many cancers, including pancreatic cancer[27, 28] and EGFR contributes to the acquisition of cancer stem-like properties, including the enrichment of the CD44+ population of cancer cells in breast cancer[38]. CD44 also plays an important role in tumorigenesis and tumor progression by promoting cell proliferation and migration via several signaling pathways/networks, including p-AKT or p-ERK[39, 40]

Multiple lines of evidence indicated that the suppression of pancreatic tumorigenesis by muscarinic signaling was mediated by CHRM1. Only Chrm1 expression was upregulated in the pancreas following surgical denervation, and the growth of pancreas spheres and PDAC cell lines was suppressed by CHRM1 selective agonists (McN-34A) and stimulated by CHRM1 selective antagonist (pirenzepine). Finally, elimination of CHRM1 signaling by genetic knock-out resulted in the same accelerated PDAC phenotype as seen with surgical denervation.

Interestingly, it has been revealed revealed that CHRM1 was also expressed at high levels in the healthy prostate gland of mice, and that Chrm1-KO reduced prostate cancer progression in their orthotopic mouse model[10]. The results in PDAC appear to be the opposite of that reported in prostate cancer. CHRM1 is a G protein coupled receptor (GPCR), associated with both Gq- and arrestin-dependent pathways, and has been shown to enhance EGFR and ERK activation and stimulate cell proliferation[41]. Indeed, GPCRs have generally been considered to be pro-tumorigenic, over-expressed or activated to drive cancer progression. Nevertheless, it is also clear that some GPCRs can play tumor suppressive roles, including the melanocortin 1 receptor (MC1R)[42], GPRC5A[43], and the cannabinoid receptors CB1 and CB2[44]. CB2, for example, suppresses EGFR/ERK and AKT signaling in breast cancer cells, although the mechanisms have not been well defined[44]. Possible mechanisms could include modulation of receptor cross-talk through heterodimerization and altered β-arrestin interactions. It has been reported that CHRM1 can either stimulate or suppress ERK depending on whether β-arrestin-2 is stably or transiently bound to CHRM1[45]. Furthermore, it is known that GPCRs possess two different conformations, active and inactive, and they spontaneously alternate between the two in the absence of ligands[46], possibly explaining the increased sphere forming capacity of Chrm1-KO; $Kras^{+/LSL-G12D}$ sphere cultures compared to $Kras^{+/LSL-G12D}$ spheres. In any case, the findings that CHRM1 signaling has the potential to suppress numerous growth factor pathways broaden the view regarding the role of GPCRs in cancer.

In summary, it has been demonstrated herein that muscarinic signaling via CHRM1 can directly suppress pancreatic tumor development through downregulation of the MAPK and PI3K/AKT signaling pathway in cancer cells. Although the role of muscarinic signaling in modulating crosstalk between pancreatic tumor cells and the microenvironment needs to be further investigated, the findings reveal a surprising inhibitory role for parasympathetic signaling in cancer and point to cholinergic agonists as potentially useful adjunctive therapies in the treatment of pancreatic cancer in early phase and late phase.

REFERENCE

1. Hidalgo M. Pancreatic cancer. *N Engl J Med* 2010; 362:1605-1617.
2. Olive K P, Jacobetz M A, Davidson C J, Gopinathan A, McIntyre D, Honess D, Madhu B, Goldgraben M A. Inhibition of Hedgehog signaling enhances delivery of chemotherapy in a mouse model of pancreatic cancer. *Science.* 2009; 324:1457-1461.
3. Edwards B K, Brown M L, Wingo P A, Howe H L, Ward E, Ries L A, Schrag D, Jamison P M, Jemal A, Wu X C, Friedman C, Harlan L, Warren J, Anderson R N, Pickle L W. Annual report to the nation on the status of cancer, 1975-2002, featuring population-based-trends in cancer treatment. *J Natl Cancer Inst.* 2005; 97:1407-1427.
4. Arslan A A, Helzlsouer K J, Kooperberg C, Shu X O, Steplowski E, Bueno-de-Mesquita H B, Fuchs C S, Gross M D, Jacobs E J, Lacroix A Z, Petersen G M, Stolzenberg-Solomon R Z, Zheng W, Albanes D, Amundadottir L, Bamlet W R, Barricarte A, Bingham S A, Boeing H, Boutron-Ruault M C, Buring J E, Chanock S J, Clipp S, Gaziano J M, Giovannucci E L, Hankinson S E, Hartge P, Hoover R N, Hunter D J, Hutchinson A, Jacobs K B, Kraft P, Lynch S M, Manjer J, Manson J E, McTiernan A, McWilliams R R, Mendelsohn J B, Michaud D S, Palli D, Rohan T E, Slimani N, Thomas G, Tjonneland A, Tobias G S, Trichopoulos D, Virtamo J, Wolpin B M, Yu K, Zeleniuch-Jacquotte A, Patel A V; Pancreatic Cancer Cohort Consortium (PanScan). Anthropometric measures, body mass index, and pancreatic cancer: a pooled analysis from the Pancreatic Cancer Cohort Consortium (PanScan) *Arch Intern Med.* 2010; 170:791-802.
5. Siegel R L, Miller K D, Jemal A, 2018. Cancer statistics, 2018. CA: *A Cancer Journal for Clinicians* 2018: https://doi: 10.3322/caac.21442.
6. Demir I E, Friess H, Ceyhan G O Neural plasticity in pancreatitis and pancreatic cancer. *Nat Rev Gastroenterol Hepatol* 2015; 12, 649-659.
7. Sun X J, Jiang T H, Zhang X P, Mao A W. Role of the tumor microenvironment in pancreatic adenocarcinoma. *Front Biosci (Landmark Ed).* 2016; 21:31-41.
8. Ayala G E, Dai H, Powell M, Li R, Ding Y, Wheeler™, Shine D, Kadmon D, Thompson T, Miles B J, Ittmann M M, Rowley D., Cancer-related axonogenesis and neurogenesis in prostate cancer. *Clin Cancer Res.* 2008; 14, 7593-7603.
9. Albo D, Akay C L, Marshall C L, Wilks J A, Verstovsek G, Liu H, Agarwal N, Berger D H, Ayala G E. Neurogenesis in colorectal cancer is a marker of aggressive tumor behavior and poor outcomes. *Cancer.* 2011; 117: 4834-4845.
10. Magnon C, Hall S J, Lin J, Xue X, Gerber L, Freedland S J, Frenette P S. Autonomic nerve development contributes to prostate cancer progression. *Science.* 2013; 341: 1236361.
11. Zahalka A H, Arnal-Estapé A, Maryanovich M, Nakahara F, Cruz C D, Finley L W S, Frenette P S. Adrenergic nerves activate an angio-metabolic switch in prostate cancer. *Science.* 2017; 358:321-326.
12. Peterson S C, Eberl M, Vagnozzi A N, Belkadi A, Veniaminova N A, Verhaegen M E, Bichakjian C K, Ward N L, Dlugosz A A, Wong S Y. Basal Cell Carcinoma Preferentially Arises from Stem Cells within Hair Follicle and Mechanosensory Niches. *Cell Stem Cell.* 2015; 16:400-412.
13. Hayakawa Y, Sakitani K, Konishi M, Asfaha S, Niikura R, Tomita H, Renz B W, Tailor Y, Macchini M, Middelhoff M, Jiang Z, Tanaka T, Dubeykovskaya Z A, Kim W, Chen X, Urbanska A M, Nagar K, Westphalen C B, Quante M, Lin C S, Gershon M D, Hara A, Zhao C M, Chen D, Worthley D L, Koike K, Wang T C. Nerve Growth Factor Promotes Gastric Tumorigenesis through Aberrant Cholinergic Signaling. *Cancer Cell.* 2017; 31:21-34.
14. Zhao C M, Hayakawa Y, Kodama Y, Muthupalani S, Westphalen C B, Andersen G T, Flatberg A, Johannessen H, Friedman R A, Renz B W, Sandvik A K, Beisvag V, Tomita H, Hara A, Quante M, Li Z, Gershon M D, Kaneko K, Fox J G, Wang T C, Chen D. Denervation suppresses gastric tumorigenesis. *Sci Transl Med.* 2014; 20; 6:250ra115
15. Renz B W, Takahashi R, Tanaka T, Macchini M, Hayakawa Y, Dantes Z, Maurer H C, Chen X, Jiang Z, Westphalen C B, Ilmer M, Valenti G, Mohanta S K, Habenicht A J, Middelhoff M, Chu T, Nagar K, Tailor Y, Kleespies Al, Friedman R A, Reichert M, Worthley D L, Neumann J, Werner J, Iuga A C, Olive K P, Wang T C. β2 Adrenergic-Neurotrophin Feedforward Loop Promotes Pancreatic Cancer. *Cancer Cell.* 2017; https://doi.org/10.1016/j.ccell.2017.11.007
16. Hayakawa Y, Wang T C. Nerves switch on angiogenic metabolism. *Science.* 2017; 358:305-306.
17. Bonaz B. The cholinergic anti-inflammatory pathway and the gastrointestinal tract. *Gastroenterology.* 2007; 133:1370-1373.
18. Fernandez R, Nardocci G, Navarro C, Reyes E P, Acuna-Castillo C, Cortes P P. Neural reflex regulation of systemic inflammation: potential new targets for sepsis therapy. *Frontiers in physiology.* 2014; 5:489.
19. Chandra R, Liddle R A. Modulation of pancreatic exocrine and endocrine secretion. *Curr Opin Gastroenterol.* 2013; 29:517-522.
20. Holmgren S, Olsson C. Autonomic control of glands and secretion: A comparative view. *Autonomic Neuroscience.* 2011; 165:102-112.
21. Kiba T, Takana K, Numata K, Hoashino M, Misugi K, Inoue S., Ventromedial hypothalamic lesion-induced vagal hyperactivity stimulates rat pancreatic cell proliferation. *Gastroenterology.* 1996; 110:885-893.
22. Gidron Y, Perry H, Glennie M., Does the vagus nerve inform the brain about preclinical tumours and modulate them? *Lancet Oncol.* 2005; 6:245-248.
23. De Couck M, Mravec B, Gidron Y., You may need the vagus nerve to understand pathophysiology and to treat diseases. *Clin. Sci. (Lond.)* 2012; 122:323-328.
24. Partecke L I, Käding A, Trung D N, Diedrich S, Sendler M, Weiss F, Kahn J P, Mayerle J, Beyer K, von Bernstorff W, Heidecke C D, Keβler W. Subdiaphragmatic vagotomy promotes tumor growth and reduces survival via TNFα in a murine pancreatic cancer model. *Oncotarget.* 2017; 8:22501-22512.
25. Erin N, Akdas Barkan G, Harms J F, Clawson G A. Clawson, Vagotomy enhances experimental metastases of 4THMpc breast cancer cells and alters substance P level, *Regul. Pept.* 2008; 151:35-42.
26. Erin N, Duymuşs O, Oztürk S, Demir N., Activation of vagus nerve by semapimod alters substance P levels and decreases breast cancer metastasis, *Regul. Pept.* 2012; 10:101-108.
27. Du L, Wang H, He L, Zhang J, Ni B, Wang X, Jin H, Cahuzac N, Mehrpour M, Lu Y, Chen Q. CD44 is of functional importance for colorectal cancer stem cells. *Clin Cancer Res.* 2008; 14:6751-6760
28. Li C, Heidt D G, Dalerba P, Burant C F, Zhang L, Adsay V, Wicha M, Clarke M F, Simeone D M. Identification of pancreatic cancer stem cells. *Cancer Res.* 2007; 67:1030-1037
29. Hingorani S R, Wang L, Multani A S, Combs C, Deramaudt T B, Hruban R H, Rustgi A K, Chang S, Tuveson D A. Trp53R172H and KrasG12D cooperate to promote chromosomal instability and widely metastatic pancreatic ductal adenocarcinoma in mice. *Cancer Cell.* 2005; 7:469-483.
30. Franke T F. PI3K/Akt: getting it right matters. *Oncogene.* 2008; 27:6473-6488.
31. Keshet Y and Seger R. The MAP kinase signaling cascades: a system of hundreds of components regulates a diverse array of physiological functions. *Methods Mol Biol.* 2010; 661:3-38.
32. Soares K C, Foley K, Olino K, Leubner A, Mayo S C, Jain A, Jaffee E, Schulick R D, Yoshimura K, Edil B, Zheng L. A preclinical murine model of hepatic metastases. *J Vis Exp.* 2014; 91:51677. doi: 10.3791/51677.
33. Sloan E K, Priceman S J, Cox B F, Yu S, Pimentel M A, Tangkanangnukul V, Arevalo J M, Morizono K, Karanikolas B D, Wu L, Sood A K, Cole S W. The sympathetic nervous system induces a metastatic switch in primary breast cancer. *Cancer Res.* 2010; 70:7042-7052.
34. Shi M, Liu D, Yang Z, Guo N. Central and peripheral nervous systems: master controllers in cancer metastasis. *Cancer Metastasis Rev.* 2013; 32:603-621.

35. Jobling P, Pundavela J, Oliveira S M, Roselli S, Walker M M, Hondermarck H. Nerve-Cancer Cell Cross-talk: A Novel Promoter of Tumor Progression. *Cancer Res.* 2015; 75:1777-1781.
36. Borovikova L V, Ivanova S, Zhang M, Yang H, Botchkina G I, Watkins L R, Wang H, Abumrad N, Eaton J W, Tracey K J., Vagus nerve stimulation attenuates the systemic inflammatory response to endotoxin, *Nature.* 2000; 405:458-462.
37. de Jonge W J, van der Zanden E P, The F O, Bijlsma M F, van Westerloo D J, Bennink R J, Berthoud H R, Uematsu S, Akira S, van den Wijngaard R M, Boeckxstaens G E. Stimulation of the vagus nerve attenuates macrophage activation by activating the Jak2-STAT3 signaling pathway. *Nat Immunol.* 2005; 6:844-851. doi: 10.1038/ni1229.
38. Xu H, Wu K, Tian Y, Liu Q, Han N, Yuan X, Zhang L, Wu G S, Wu K. CD44 correlates with clinicopathological characteristics and is upregulated by EGFR in breast cancer. *Int J Oncol.* 2016; 49:1343-1350.
39. Hao J, Madigan M C, Khatri A, Power C A, Hung T T, Beretov J, Chang L, Xiao W, Cozzi P J, Graham P H, Kearsley J H, Li Y. In vitro and in vivo prostate cancer metastasis and chemoresistance can be modulated by expression of either CD44 or CD147. *PLoS One.* 2012; 7:e40716.
40. Xiaoping L, Xiaowei Z, Leizhen Z, Weijian G. Expression of CD44 in pancreatic cancer and its significance. *Int J Clin Exp Pathol.* 2015; 8:6724-6731
41. Blaukat A, Barac A, Cross M J, Offermanns S, Dikic I. G protein-coupled receptor-mediated mitogen-activated protein kinase activation through cooperation of Galpha (q) and Galpha(i) signals. *Mol Cell Biol.* 2000; 20:6837-6848.
42. Mitra D, Luo X, Morgan A, Wang J, Hoang M P, Lo J, Guerrero C R, Lennerz J K, Mihm M C, Wargo J A, Robinson K C, Devi S P, Vanover J C, D'Orazio J A, McMahon M, Bosenberg M W, Haigis K M, Haber D A, Wang Y, Fisher D E. An ultraviolet-radiation-independent pathway to melanoma carcinogenesis in the red hair/fair skin background. *Nature.* 2012; 491:449-453.
43. Zhong S, Yin H, Liao Y, Yao F, Li Q, Zhang J, Jiao H, Zhao Y, Xu D, Liu S, Song H, Gao Y, Liu J, Ma L, Pang Z, Yang R, Ding C, Sun B, Lin X, Ye X, Guo W, Han B, Zhou B P, Chin Y E, Deng J. Lung Tumor Suppressor GPRC5A Binds EGFR and Restrains Its Effector Signaling. *Cancer Res.* 2015; 75:1801-1814.
44. Elbaz M, Ahirwar D, Ravi J, Nasser M W, Ganju R K. Novel role of cannabinoid receptor 2 in inhibiting EGF/EGFR and IGF-I/IGF-IR pathways in breast cancer. *Oncotarget.* 2017; 8:29668-29678.
45. Jung S R, Kushmerick C, Seo J B, Koh D S, Hille B. Muscarinic receptor regulates extracellular signal regulated kinase by two modes of arrestin binding. *Proc Natl Acad Sci USA.* 2017; 114:E5579-E5588.
46. Nakashima A, Takeuchi H, Imai T, Saito H, Kiyonari H, Abe T, Chen M, Weinstein L S, Yu C R, Storm D R, Nishizumi H, Sakano H. Agonist-independent GPCR activity regulates anterior-posterior targeting of olfactory sensory neurons. *Cell.* 2013; 154:1314-1325.

Methods

Animals

LSL-Kras$^{+/LSL-G12D}$, LSL-Trp53$^{+/R172H}$, and Pdx1-Cre mice were bred by Dr. Kenneth P. Olive and co-workers. Chrm1KO mice (C57BL/6-Chrm1tm1 Stl/J, (M1RKO) mice[1] were purchased from the Jackson Laboratory. KC mice and KPC mice were crossed with M1RKO mice. In the vagotomy experiments, KC mice received pyloroplasty with or without vagotomy at 8 weeks, and some KC+VxPP mice were treated with bethanechol (400 g/ml in drinking water) immediately after surgery and then sacrificed at 20 weeks. KPC mice in treatment studies were palpated weekly for tumors in the pancreas. Once a tumor was suspected, KPC mice were screened by VEVO 2100—Ultrasound Imaging System (FUJIFILM VisualSonics) for pancreatic cancer. KPC mice were treated with gemcitabine, given by i.p. injection 100 mg/kg biweekly, with or without bethanechol, when a tumor size of 3-5 mm was detected using ultrasound. Mice were sacrificed when the mice were moribund. NOD/SCID mice were implanted with Panc1 cells subcutaneously and sacrificed at 30 days after implantation. For liver metastatic experiments, WT type C57/B6 mice received a splenic injection of labeled Panc02 cells, followed by hemi-splenectomy. The mice were then divided into three groups. One group was untreated, one group received selective vagotomy of the hepatic vagal branch, the third group was treated with bethanechol after surgery. Mice were then sacrificed when moribund. At necropsy, hepatic metastases that could clearly be identified as tumor nodules on gross inspection were separated. All animal studies and procedures were approved by the IACUC committee at Columbia University. All mice were bred under specific pathogen free conditions. Comparisons were made with age- and sex-matched control animals.

Animal Surgery

Vagotomy, Pyloroplasty, and Selective Hepatic Branch Vagotomy

All surgical procedures were performed under isoflurane (2-3%) inhalation anesthesia, with buprenorphine (0.1 mg/kg subcutaneously) given as postoperative analgesia. Vagotomy and pyloroplasty procedure were previously described[2]. Selective vagotomy of the hepatic branch was performed as previously reported[3]. Briefly, the hepatic branch of the vagal trunk was isolated and then transected by microcautery, thus severing the hepatic vagus. Anatomical nerve transaction was verified at necropsy by microscopic observation of the absence of vagal nerve fibers.

Liver Metastatic Procedure and Hemi-Splenectomy

The liver metastatic model was produced as previously described[4]. Briefly, a left subcostal incision was performed and the spleen exposed through the incision. The spleen was divided into upper and lower halves by placing two Horizon medium sized ligation clips in the center of the spleen. 150 µl of phosphate buffered saline was drawn up into a 27 G×⅝" syringe, and 100 µl of Panc02 (2×10$^6$) cells were also drawn up into the same syringe. Panc02 cells were injected slowly into the exposed lower-hemispleen. Lower hemisplenectomy was performed by ligating splenic vessels and then cutting distally.

Histology, Immunohistochemistry, Immunofluorescence and Microscopy

5 µm paraffin embedded or PFA-fixed frozen sections were prepared for immunohistochemistry and immunofluorescence, respectively. For immunofluorescence, slides were washed with 1% Triton X-100 in PBS, rinsed and blocked for 30 min with 2% bovine serum albumin (BSA—Sigma-Aldrich). Primary antibodies and fluorophore-conjugated secondary antibodies were diluted in 2% BSA and incubated over night at 4° C. The following primary antibodies were used; Chrm1 (1:200 Santa Cruz), Ki67 (1:500 Abcam), p-EGFR (1:200 Abcam), and CD44 (1:200 BIO-RAD). For immunohistochemical staining, slides were deparaffinized in xylene and endogenous peroxidase was blocked by incubation with 3% hydrogen peroxide in methanol for visualization using the peroxidase reaction. Alternatively, for visualization with the alkaline phosphatase reaction, slides were incubated with 20% acetic acid in methanol for 2 min. Antigen retrieval was performed by boiling the slides in citrate buffer (10 mM pH 6.0) in a water bath for 20 min. Slides were rinsed in PBS Tween 0.05% and blocked for 30 min. with 2% BSA. Primary antibodies and biotinylated secondary antibodies (Jackson Immunoresearch) were diluted in 2% BSA and incubated overnight at 4° C. The following primary antibodies were used; p-EGFR (1:200 Abcam), CD44 (1:200 BIO-RAD), and p-PI3K (1:100 Sigma-Aldrich). Subsequently, slides were incubated with alkaline phosphatase or peroxidase conjugated streptavidin (Dako) and either VectorRed substrate (Vector Laboratories) or 3,3'-diaminobenzidine (Sigma-Aldrich) as chromogens, respectively. Slides were counterstained with hematoxylin and mounted for viewing. Bright field and fluorescence images were acquired using an Eclipse TU2000-U microscope (Nikon) connected to a cooled color CCD camera (RTKE Diagnostic Instruments) using SPOT software (Spotimaging).

Quantification of Immunohistochemical Staining

CD44, p-EGFR, p-PI3K, p-ERK, and Ki67 positive cells were quantified in at least five high power fields from at least 3 mice per group. Total cells per field were counted via morphometric analysis using ImageJ and the ratio of positive cells to total cell number calculated.

Cell Lines and Cell Culture

Three human PDAC cell lines (MiaPaca2, BxPC3 and Panc1) and two murine PDAC cell lines (Panc02 and K8282) were used for experiments. All human pancreatic cancer cell lines and murine pancreatic cancer cell line (Panc02) were purchased from ATCC. Murine pancreatic cancer cell line (K8282) derived from KPC mice were provided. RPMI1640 (Sigma Aldrich Inc.) supplemented with 10% fetal bovine serum (FBS) and Penicillin/Streptomycin (Invitrogen Inc.) were used for cell culture. The cell medium was replaced with fresh medium every 48-72 hours. All cultures were maintained in a 5% CO2 air-humidified atmosphere at 37° C.

Quantitative RT-PCR (qRT-PCR)

Total RNA was extracted from whole stomach samples from each animal using TRIzol reagent (Invitrogen) or the RNAqueous-micro kit (Ambion) and subjected to first-strand complementary DNA synthesis using the Superscript III cDNA Amplification System (Invitrogen) following the manufacturer's instructions. qRT-PCR was performed using a three-step method, an ABI 7300 system and SYBR green (Roche). The results were expressed as the copy number of each gene relative to that of GAPDH.

RNA-Seq Experiments

Panc1 cells were treated with or without 1 mM Pilocarpine in RPMI1640 with 0.5% FBS and 1% antibiotics for 72 hours. Panc1 cells were lysed in RNA lysis buffer supplied in ARCTURUS PicoPure RNA isolation kit (Life Technologies)(n=4). Total RNA was isolated in accordance with the manufacturer's protocol. cDNA was amplified and libraries were constructed by using SMARTer Ultra Low Input RNA Kit (Clontech Laboratories) and Nextera XT DNA Library Preparation Kit (Illumina) according to the respective manufacturer's instructions. Sequencing was performed with Hiseq 2500 (Illumina) (30 M 100 bp single end reads per sample).

RNA-Seq Analysis

Sequenced reads were mapped to the NCBI annotated genes of the mm9 assembly of the mouse genome with BowTie2 and TopHat 2.0.4[5, 6]. Reads were counted with HTSeq. Expression datasets were deposited in the Gene Expression Omnibus (GEO)[7] (GSE102880 code: armlggayprundsh). Samples were normalized with the TMM algorithm. The statistical significance of differential expression was estimated with weighted Limma-Voom[8, 9] which runs under Bioconductor/R[10-12]. Significantly differentially expressed genes (Benjmamin-Hochberg fdr[13]≤0.05 and absolute value of log 2 fold change ≥0.6, were analyzed further. First, a screen in terms of Gene Ontology[14] categories for consistency with phenotype was performed. Genes were retained which either:

1. Upregulated and negatively regulate the cell cycle (GO:0045786).
2. Downregulated and positively regulate the cell cycle (GO:0045786).
3. Upregulated and positively regulate the apoptotic process (GO:0043065).
4. Downregulated and negatively regulate the apoptotic process (GO:0043066).

57 genes fulfilled these requirements, these genes were analyzed further in terms of KEGG pathways[15] with iPathwayGuide[16, 17]

Western Blot

To analyze EGFR, MAPK and PI3K-AKT pathways in human and murine pancreatic cancer cell lines, cells were grown in 12-well culture plates to ~70% confluency. The medium was then changed to 0.5% FBS medium, the respective drugs were added, and they were incubated for an additional 72 hours in a CO2 incubator (~5% CO2). After removing the medium, cells were washed twice with PBS, and protein extraction was performed on ice using RIPA buffer with protease inhibitor (Complete, Roche) cocktail and a phosphatase inhibitor (phosSTOP, Roche). Protein samples were subsequently separated by 10% Bis-Tris Gel NuPAGE® electrophoresis using MES SDS Running Buffer (Invitrogen, CA, USA). After transfer to nitrocellulose, membranes were blocked with 5% BSA, and samples were probed with the following primary antibodies: p-EGFR (Cell Signaling), EGFR (Cell Signaling), p-BRAF (Cell Signaling), BRAF (Cell Signaling), p-ERK1/2 (phosphorylated p44/42 MAPK) (Thr202/Tyr204) (Cell Signaling), ERK1/2 (p44/42 MAPK) (Thr202/Tyr204) (Cell Signaling), p-PI3K (Cell Signaling), PI3K (Cell Signaling), p-AKT (Cell Signaling), AKT (Cell Signaling), and β-actin (Cell Signaling) followed by horseradish peroxidase-coupled secondary antibody. Immunoreactive bands were visualized using 5-bromo-4-chloro-3-indolyl phosphate/nitro blue tetrazolium and bands were quantified with ImageJ.

MTT Assay and Soft Agar Assay

Cell proliferation in each cell line was assessed with a 3-(4,5-dimethylthiazol-2yl)-2,5-diphenyltetrazolium bromide (MTT) assay kit (Sigma) in accordance with the manufacturer's instructions. $3 \times 10^3$ cells were grown in 96-well plate to ~70% confluency, the media was changed to 0.5% FBS medium, the respective drugs were added, and they were incubated for an additional 72 hours in a CO2 incubator (~5% CO2). Treated cells were rinsed twice with PBS, incubated in 10 ul MTT (5 mg/ml PBS) solution for 4 hours at 37° C., and 100 uL DMSO was then added to each well. The absorbance of each well was measured at 570 nm using a Tilter-Tech 96-well multiscanner (Becton Dickinson, Heidelberg, Germany). The relative number of viable cells compared with the number of cells without drug treatment was expressed as percent cell viability using the following formula: cell viability (%)=$A_{570}$ of treated cells/$A_{570}$ of untreated cells.

Soft agar assay was employed to identify the ability of the A549-shTGIF cells and A549-shcon cells to grow as anchorage-independent colonies. Briefly, 2 ml of 0.6% of low-melting point agarose in RPMI-1640 medium containing 10% of FBS was poured into a 6-well plate and allowed to solidify at room temperature. After solidification, 500 cells were suspended in 1 ml of 0.35% low-melting point agarose in the same medium and then plated on top of the base layer (three wells per group). The cells were cultured for 18 days. Colonies with at least 50 cells were counted using a microscope at 100 times magnification, and the number of colonies in soft agar (five fields per well) was quantified.

Flow Cytometry

Panc1 and BxPC3 cells were grown in 6-well plate to ~70% confluency, the media was changed to 0.5% FBS medium, the respective drugs were added, and they were incubated for an additional 72 hrs in a typical CO2 incubator (~5% CO2). Subsequently, cells were kept on ice in blocking solution (PBS pH 7.2 containing 3% bovine serum albumin, 2 mM EDTA) for 20 minutes. Cells were then stained with a PE-conjugated antibody against CD24, a FITC-conjugated antibody against CD44, and an APC-conjugated antibody against CD326 (1:100 in blocking solution) on ice for 30 minutes. The cells were then washed, reconstituted in sorting buffer (PBS pH 7.2 containing 0.5% bovine serum albumin, 2 mM EDTA)+DAPI and analyzed using a BD FACSAria II.

Generation of Panc02 Cells Stably Expressing GFP Protein

Panc02 cells stably expressing GFP proteins (Panc02-GFP) was generated as follows. Parental Panc02 cells was transduced with $5 \times 10^6$ IFU Lentivirus particles containing GFP vectors under the control of suCMV promoter (GenTarget Inc.). Transduced cells were incubated with puromycin (2 μg/mL) for 1 week to select GFP-positive cells.

Strong GFP-expressing cells were pooled and further sorted by FACS and cultured in the complete medium containing puromycin. Stable Panc02-GFP cells were maintained by puromycin at 0.5 ug/mL prior to intra-splenic injection.

Sphere Cultures 3D cultures were performed as described previously[18]. Organoids were cultured for 5 days before analysis. Adenoviral delivered Cre (Ad-Cre) was added to the cultures and medium was changed after 12 hours. Pilocarpine, scopolamine, McN-34A and pirenzepine containing medium was changed every day. Sphere size and number were analyzed using ImageJ software.

Morphometric Analysis of Murine PanINs

KC+PP, KC+VxPP, KC+VxPP+bethanechol, KC, and KCM mice were analyzed 20 weeks after treatment. For each mouse, 2 level sections were analyzed and five fields (100×) were randomly selected per level section. Morphometric analysis was done using ImageJ. For this purpose, PanINs in each field were encircled by hand and the respective area calculated by the imaging software. Nodular clusters of coalescing small ducts expanded by solid neoplastic epithelial proliferation were seen. These microcarcinomas showed foci of microinvasion and were also seen adjacent to larger poorly differentiated carcinomas. The number of microcarcinomas was assessed on full-face sections of the entire mouse pancreas.

Statistical Analysis

The means of two groups were compared using Student's t-test or Mann-Whitney u-test. Survival was compared using log rank testing. P values <0.05 were considered to indicate statistical significance. All statistical analyses were performed using Prism 7 for Mac OS X (GraphPad Software, Inc.).

Antibodies

| Name | Company | Dilution |
| --- | --- | --- |
| anti-M1R | SantaCruz | 1:200 |
| anti-CD44 | Bio-Rad | 1:200 |
| anti-p-EGFR | abcam | 1:200 |
| anti-p-PI3K | Sigma-Aldrich | 1:100 |
| anti-p-ERK1/2 | Cell Signaling | 1:200 |
| anti-Ki67 | abcam | 1:500 |

List of qRT-PCR primers (mouse) used in this study.

| Gene | Forward (5'->3') | Reverse (5'->3') |
| --- | --- | --- |
| Chrm1 | CAGAAGTGGTGATCAAGATGCCT | GAGCTTTTGGGAGGCTGCTTAT |
| Chrm2 | TGGAGCACAACAAGATCCAGAAT | CCCCTGAACGCAGTTTTCA |
| Chrm3 | CCAGTTGGTGTGTTCTTCCTT | AGGAAGAGCTGATGTTGGGA |
| Chrm4 | GTGACTGCCATCGAGATCGTAC | CAAACTTTCGGGCCACATTG |
| Chrm5 | GGCCCAGAGAGAACGGAAC | TTCCCGTTGTTGAGGTGCTT |
| Gapdh | TCATTGTCATACCAGGAAATGAG | AGAAACCTGCCAAGTATGATGAC |

List of qRT-PCR primers (human) used in this study.

| Gene | Forward (5'->3') | Reverse (5'->3') |
| --- | --- | --- |
| CHRM1 | TTCCTCAGGGGAAAGTCATC | GTGTTTGGGTCCCTGGAGA |
| CHRM2 | TGCGTTCTCTAATCAGTAGCCA | CTTCAAGCCTCCACCACCTC |
| CHRM3 | GGCCTGTGCCGATCTGATTAT | CGGCCTCGTGATGGAAAAG |
| CHRM4 | AGATTGTGACGAAGCAGACAGGCA | TTTAAAGGTGGCGTTGCACAGAGC |
| CHRM5 | GACCAACAATGGCTGTCACAAGGT | TCTGTTGCAGAGGGCATAGCAGAT |
| GAPDH | CCCCATGGTGTCTGAGCG | CGACAGTCAGCCGCATCTT |

REFERENCES FOR METHODS OF EXAMPLE 4

1. D. J. Gerber, T. D. Sotnikova, R. R. Gainetdinov, S. Y. Huang, M. G. Caron, S. TonegawaHyperactivity, elevated dopaminergic transmission, and response to amphetamine in M1 muscarinic acetylcholine receptor-deficient mice. Proc. Natl. Acad. Sci. USA, 2001; 98:15312-15317
2. Zhao C M, Hayakawa Y, Kodama Y, Muthupalani S, Westphalen C B, Andersen G T, Flatberg A, Johannessen H, Friedman R A, Renz B W, Sandvik A K, Beisvag V, Tomita H, Hara A, Quante M, Li Z, Gershon M D, Kaneko K, Fox J G, Wang T C, Chen D. Denervation suppresses gastric tumorigenesis. Sci Transl Med. 2014; 20; 6:250ra115
3. Titchenell P M, Quinn W J1, Lu M, Chu Q, Lu W, Li C, Chen H, Monks B R, Chen J, Rabinowitz J D, Birnbaum M J. Direct Hepatocyte Insulin Signaling Is Required for Lipogenesis but Is Dispensable for the Suppression of Glucose Production. Cell Metab. 2016; 23:1154-1166.

4. Soares K C, Foley K, Olino K, Leubner A, Mayo S C, Jain A, Jaffee E, Schulick R D, Yoshimura K, Edil B, Zheng L. A preclinical murine model of hepatic metastases. J Vis Exp. 2014; 91:51677. doi: 10.3791/51677.

5. Langmead, B. and S. L. Salzberg, Fast gapped-read alignment with Bowtie 2. Nat Methods, 2012; 9:357-359

6. Kim D, Pertea G, Trapnell C, Pimentel H, Kelley R, Salzberg S L. TopHat2: accurate alignment of transcriptomes in the presence of insertions, deletions and gene fusions. Genome Biol. 2013; 14:R36.

7. Barrett T, Wilhite S E, Ledoux P, Evangelista C, Kim I F, Tomashevsky M, Marshall K A, Phillippy K H, Sherman P M, Holko M, Yefanov A, Lee H, Zhang N, Robertson C L, Serova N, Davis S, Soboleva A. NCBI GEO: archive for functional genomics data sets—update. Nucleic Acids Res. 2013; 41 (Database issue):D991-995.

8. Law C W, Chen Y, Shi W, Smyth G K. voom: Precision weights unlock linear model analysis tools for RNA-seq read counts. Genome Biol. 2014; 15:R29.

9. Liu R, Holik A Z, Su S, Jansz N, Chen K, Leong H S, Blewitt M E, Asselin-Labat M L, Smyth G K, Ritchie M E. Why weight? Modelling sample and observational level variability improves power in RNA-seq analyses. Nucleic Acids Res. 2015; 43:e97.

10. Gentleman RC1, Carey V J, Bates D M, Bolstad B, Dettling M, Dudoit S, Ellis B, Gautier L, Ge Y, Gentry J, Hornik K, Hothorn T, Huber W, Iacus S, Irizarry R, Leisch F, Li C, Maechler M, Rossini A J, Sawitzki G, Smith C, Smyth G, Tierney L, Yang J Y, Zhang J. Bioconductor: open software development for computational biology and bioinformatics. Genome Biol. 2004; 5:R80.

11. Ihaka, R. and R. Gentleman, R: A language for data analysis and graphics. Journal of Computational and Graphical Statistics, 1996; 5:299-314.

12. Team, R. C. R: A Language and Environment for Statistical Computing}. 2017, R Foundation for Statistical Computing: Vienna, Austria.

13. Benjamini, Y. and Y. Hochberg. Controlling the false discovery rate; A practical and powerful approach to multiple testing. J. Roy. Stat. Soc. Ser. B. 1995; 57:289-300.

14. Kanehisa M, Goto S, Kawashima S, Okuno Y, Hattori M. The KEGG resource for deciphering the genome. Nucleic Acids Res. 2004; 32 (Database issue):D277-280.

15. Draghici S, Khatri P, Tarca A L, Amin K, Done A, Voichita C, Georgescu C, Romero R. A systems biology approach for pathway level analysis. Genome Res. 2007; 17:1537-45.

16. Tarca A L, Draghici S, Khatri P, Hassan S S, Mittal P, Kim J S, Kim C J, Kusanovic J P, Romero R. A novel signaling pathway impact analysis. Bioinformatics. 2009; 25:75-82.

17. Tarca A L, Draghici S, Khatri P, Hassan S S, Mittal P, Kim J S, Kim C J, Kusanovic J P, Romero R. A novel signaling pathway impact analysis. Bioinformatics. 2009; 25:75-82.

18. Wescott M P, Rovira M, Reichert M, von Burstin J, Means A, Leach S D, Rustgi, A K.

Pancreatic ductal morphogenesis and the Pdx1 homeodomain transcription factor. Mol Biol Cell. 2009; 20:4838-4844.

Example 5—Bethanechol Treatment Results in a Reduction in Serum TNFα, Ki67, CD44, pERK and pEGFR Levels in Patients Significance Pancreatic ductal adenocarcinoma (PDA) is one of the most lethal malignant diseases, with an overall survival (OS) rate of 9%[1-3]. The resistance of PDA to treatment has been attributed in part to the tumor microenvironment and the complex desmoplastic stroma, which comprises numerous cells including nerves[4,5]. Although the least well-studied, recent evidence has suggested a role for nerves in the development of cancer. All solid tumors, apart from CNS tumors, are innervated by axonal fibers arising from the peripheral nervous system (PNS). Most of the past focus on nerves in cancer has been on the mechanisms of pain and the role of perineural invasion, with the narrow view of nerves as a passive conduit for cancer cell dissemination. However, nerve dependence has long been described in limb regeneration[6]. Thus, it is not surprising that nerves play important roles in cancer progression.

In most solid tumors, there is a marked increase in neural density and nerve size during cancer growth[7,8]. Experimental model systems have shown a direct contribution of nerves to the development of prostate cancer[9,10], basal cell carcinoma[11], breast cancer[12], and from our group, of gastric cancer[13,14]. In prostate cancer, sympathetic and parasympathetic nerves both promote tumor growth. Notably, pharmacologic blockade or genetic disruption (of the muscarinic 1 receptor, MIR) of parasympathetic signaling in prostate cancer models reduced invasion and metastasis and improved survival[9]. Similarly, we also found that blocking parasympathetic signaling in stomach cancer inhibited growth of stomach cancer, such that vagotomy inhibited tumorigenesis in 3 separate animal models of gastric cancer. Surgical denervation or chemical denervation by local injection of botulinum toxin reduced tumor incidence and progression, which was mediated by the muscarinic 3 receptor (M3R) and involved the Wnt/YAP pathways[14,15]. In gastric cancer, we showed increased crosstalk between tumor cells and nerves, as tumors induce active axonogenesis through upregulation of neurotrophins such as NGF[7,15,16]. However, we recently reported for the first time that parasympathetic signaling can profoundly suppress pancreatic cancer growth[17], and this inhibitory effect of muscarinic signaling in some solid tumors has now been confirmed in models of breast cancer[12].

Further, the effect of nerves on tumor growth may be direct or indirect. Nerves modulate growth directly through interactions with cancer cells or indirectly through interaction with stromal cells. In early development and during regeneration, nerves promote the growth of stromal cells derived from the mesenchymal blastema[6]. While we showed in stomach cancer a direct role for M3R signaling on gastric cancer epithelial cells, it has been shown that nerves strongly regulate the stroma, and demonstrate in prostate cancer models that knockout of the beta2-adrenergic receptor (Adrb2) in endothelial cells inhibited angiogenesis and tumor cell proliferation, through a switch in angiogenic metabolism[10,15]. Nerves also regulate immune and inflammatory responses, with adrenergic and cholinergic receptors expressed on lymphocytes and macrophages[12,18,19]. We have confirmed the findings that there is a suppressive effect of the vagus nerve on splenic macrophages and TNFα levels[20,21]. Thus, adrenergic and cholinergic signaling can modulate tumor growth through effects on both cancer cells and stroma.

In both prostate and gastric cancer models, rigorous studies have shown that nerves, particularly the vagus nerve, promote rather than inhibit tumor growth. Until recently, the role of cholinergic signaling in pancreatic cancer has not been studied.

Like many solid organs, the pancreas is innervated by sympathetic and parasympathetic nerves and sensory afferents. Pancreatic cancer cells stimulate nerve growth, such that PDA is characterized by high neural density and marked neural hypertrophy. We have shown that sympathetic nerves stimulate growth of PDA cells through the β2-adrenergic receptor (Adrb2)[16] The vagus nerve comprises both sensory (80% in mouse) and preganglionic fibers[22], and similar to its role in the luminal GI tract, has been shown to stimulate proliferation of the exocrine pancreas, such that vagal stimulation leads to pancreatic acinar hypertrophy, while vagotomy leads to decreased pancreatic acinar growth[23]. On the other hand, studies in the past have also suggested that vagus nerve signaling may actually slow tumor progression[24], with higher rates of PDA in patients post-vagotomy for gastric ulcer disease[25]. In orthotopic and syngeneic PDA mouse models, vagotomy promotes tumor growth and shortens overall survival, which was initially attributed in part, but without experimental support, to indirect effects on expansion of tumor-associated macrophages and elevated TNFα levels[27]. Transection of vagus nerve branches is unavoidable in pancreatic surgery. Furthermore, recent studies have shown an important role for sensory nerves in promoting the growth and progression of pancreatic cancer through VIP/NK1-R signaling[27,28]. However, until very recently, the role of cholinergic signaling in PDAC was not defined, nor was the pathway exploited for treatment. As detailed below, we recently investigated in PDA models the direct contribution of the vagus nerve, cholinergic signaling and muscarinic receptors to PDA progression.

Innovation

In one embodiment, the subject matter described herein relates to bethanechol, a drug approved by the FDA for the treatment of urinary retention, in the treatment of pancreatic cancer.

Novel Paradigms

The subject matter described herein relates to the role of cholinergic nerves, acting through the muscarinic M1 receptor, as an inhibitory pathway in pancreatic cancer. Agonists for muscarinic receptors, including both M1R and M3R, have been shown in other tumor models (e.g. prostate and gastric) to promote cancer growth, but the evidence is now clear that M1R signaling is inhibitory for pancreatic cancer in mouse models and human PDA cells. In one embodiment, cholinergic signaling downregulates both growth and cancer stem cell pathways in PDA.

Novel Therapeutic Intervention:

The use of bethanechol in a first-in-human pilot study will be described, and a Phase IIA clinical trial will be initiated soon.

Novel Murine Models and Methods:

Conditional knockout of the M1R in the pancreatic epithelium in both the KC and KPC backgrounds will be carried out. The mechanism of action (MoA) for bethanechol/acetylcholine will be explored for the first time through the use of new bioinformatics algorithms, including MARINa, DEMAND and VIPER.

Approach

Overview:

Muscarinic agonists have remarkable efficacy in suppressing PDA growth. We have focused primarily on bethanechol, given the absence of any nicotinic activity, its clinical availability and extensive safety experience in patients. The goal of the studies is to understand the mechanism of action (MoA) and move the drug into the clinic. In Aim 1, the possibility will be explored that bethanechol may have additional indirect effects, such as on the stroma. In Aim 2, neurotrophins and bioinformatics methods are used to understand better the MoA, and why M1R activation leads to growth suppression in PDA. In Aim 3, bethanechol will be used in Phase IIA neoadjuvant clinical trial in borderline resectable patients.

Scientific Rigor and Reproducibility:

A rigorous experimental plan has been designed that includes appropriate controls, randomization, blinding, technical replicates, the use of sufficient sample size and proper statistical methods. Core B (Biostatistics and Bioinformatics Core) will be used for routine statistical analysis Many studies utilize mouse models, including KC and KPC and metastatic models. These genetic mouse models have now been well studied allowing detailed understanding of therapeutic responses. To minimize bias and potential confounders due to biological variability, mice with the same genotype will be pseudo-randomized into experimental groups. To minimize stress, mice will be group-housed with littermates. Additional endpoints will include histopathological scoring, which will be done in our Core C (Biospecimen, Pathology and Models Core) on de-identified slides.

Specific Aim 1:

Whether muscarinic agonists only act directly on epithelial cells, or whether they modulate the stroma will be studied.

Rationale and Overview:

Consistent with previous observations[24-26,29,30], the vagus nerve restrains the growth and progression of pancreatic cancer. Further, cholinergic signaling directly suppresses the growth of pancreatic cancer cells and Kras mutated pancreatic spheroids (e.g. from KC mice)[17]. Recent studies on prostate cancer and other tumors suggest that both sympathetic and parasympathetic signaling can modulate cancer growth in part through actions on stromal cells, including both endothelial cells and immune cells[9,10,15,20]. Thus, in this Aim the effects of cholinergic signaling in suppressing cancer growth through actions on non-epithelial cells will be investigated. Without being bound by theory, while cholinergic agonists exert important suppressive effects directly on the epithelium, there are also significant actions on the stroma. Whole body knockout and Pdx1-directed conditional knockouts of the M1 receptor (M1R) will be used to determine if changes in muscarinic signaling impact PDA progression through effects on the stroma.

Figures 18A, 18B:
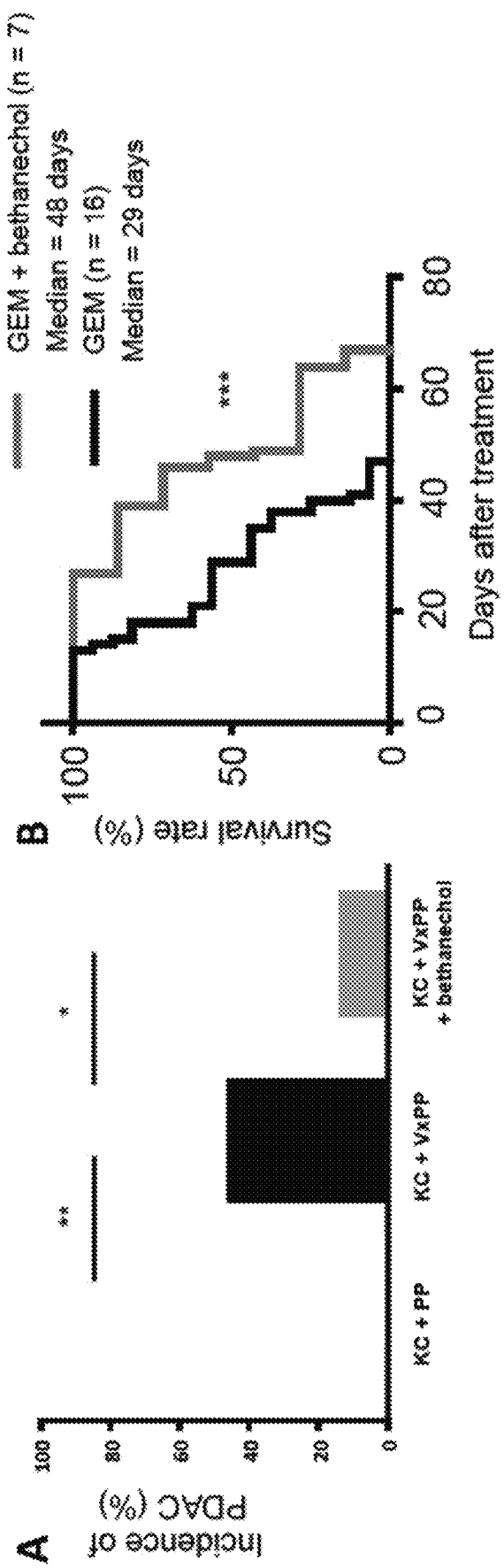
FIGS. 18A-B show that cholinergic signaling inhibits PDA in mice.

To investigate the role of cholinergic signaling in PDA, we examined the effect of parasympathetic denervation by surgical vagotomy. First, KC (Pdx1-Cre; LSL-Kras-G12D) mice at 8 weeks of age underwent subdiaphragmatic vagotomy (Vx) with pyloroplasty (PP), and were followed out to 20 weeks. Control KC mice underwent only pyloroplasty (PP). The PanIN area in KC+VxPP was significantly larger than in KC+PP mice (p<0.01)[17]. Importantly, full-blown pancreatic cancer (PDA) was detected in more than 40% of KC+VxPP mice, while no PDA was observed in KC+PP mice (p<0.05) (FIG. 18A). Interestingly, vagotomy significantly increased the expression of CD44 and of the M1 cholinergic receptor muscarinic (M1R, encoded by the Chrm1 gene), with no changes in other muscarinic receptors (Chrm2-5). Next, we examined the effect of treatment with a broad muscarinic agonist (bethanechol, 400 jpg/ml in the drinking water) in KC mice following vagotomy. Bethanechol, started at 8 weeks after surgery, led to a significant decrease in PDA incidence (FIG. 18A, p<0.05), and also reduced PanIN area. It also reduced CD44 and M1R expression. Finally, to investigate the role of muscarinic agonism in established PDA, we utilized KPC mice. KPC mice with 3-5 mm tumors by U/S were randomized to gemcitabine+bethanechol versus gemcitabine (GEM) alone. Overall survival increased with GEM+bethanechol (48d versus 29d) (p=0.002) (FIG. 18B).

Cholinergic signaling suppresses PDA growth through the muscarinic 1 receptor (M1R). While all five muscarinic receptors are expressed in PDA cells and mouse pancreas, we found that only the M1R was upregulated following vagotomy, suggesting loss of negative feedback control.

Figures 19A, 19B, 19C:
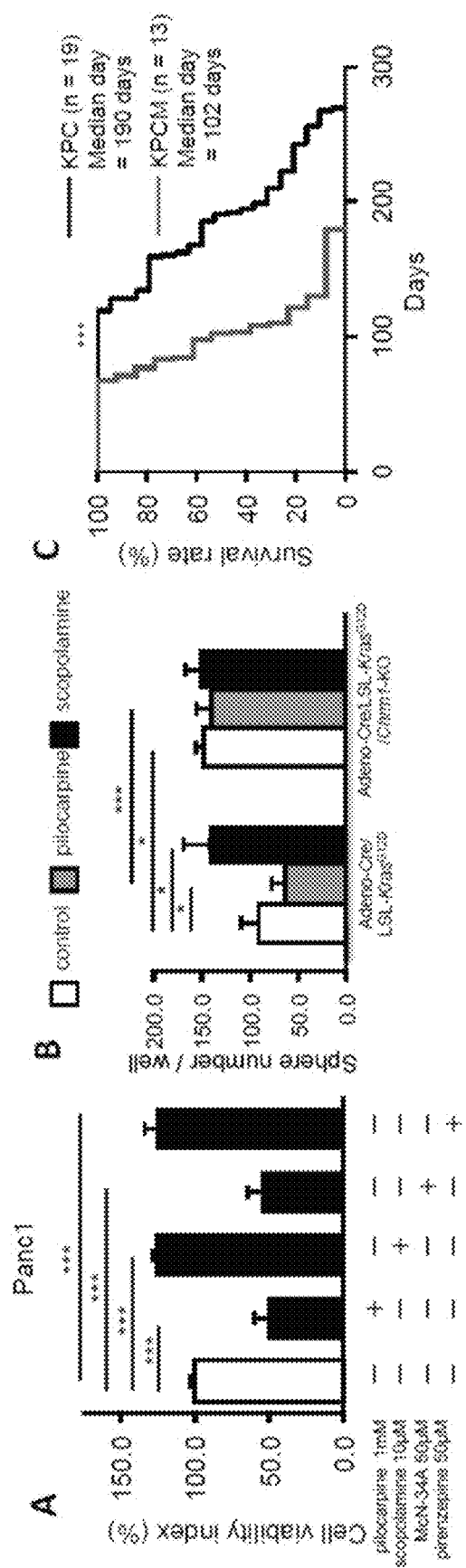
FIGS. 19A-C show that cholinergic signaling suppresses PDA through M1R.

We confirmed a role for M1R in directly regulating proliferation of human pancreatic cancer cells using the MTT assay. We have confirmed that all pancreatic cancer cell lines express the M1R, with highest levels in Panc1 cells. Growth of human Panc1 cells was stimulated by nonspecific (scopolamine) and M1R specific (pirenzepine) muscarinic antagonists, and suppressed by nonspecific (pilocarpine), and specific (McN-34A) muscarinic agonists (FIG. 19A).

Furthermore, we generated Kras mutant pancreas spheres by Adenovirus-Cre infection of LSL-Kras-G12D pancreas spheres, with or without knockout of the M1R. When grown in 3D matrigel, the number of Kras mutant spheres was increased by scopolamine and reduced by pilocarpine, but with knockout of the M1R, the effects were abrogated and the overall number was increased (FIG. 19B). Finally, when KPC mice were crossed to M1R knockout mice, the median survival of the KPCM mice was significantly decreased compared to KPC mice (FIG. 19C, p<0.001). However, in this latter study, M1R knockout could in theory accelerate cancer through deficiency of M1R in either the epithelium or stroma. Furthermore, we also found evidence for an immune modulating effect by cholinergic signaling. Vagotomy in KC mice resulted in increased systemic and splenic levels of TNFα, and increased CD11b+ and F4/80+ pancreatic myeloid cells, compared to control KC mice, which were all suppressed by treatment of the vagotomized KC mice with bethanechol[17]. Thus, our initial study does suggest beneficial effects by bethanechol on both the stroma and the epithelium in Kras mutant mice.

Experimental Methods

A. Analyze Changes in Stromal Cells after Muscarinic Agonism in Mouse Models of Pancreatic Cancer.

Treatment with bethanechol reduces PanIN progression in vagotomized KC mice and in KPC mice treated also with gemcitabine (FIGS. 19A-C). Parasympathetic nerve fibers are known to deliver cholinergic signals that act via muscarinic receptors expressed in the tumor microenvironment (TME), which could thus impact tumor progression[9]. In order to assess the effects of bethanechol on the TME, we will use Core C to complete immunohistochemical studies of KC+VxPP versus KC+VxPP+bethanechol, and KPC+ bethanechol+GEM versus KPC+GEM mice. The tumor microenvironment will be assessed by immunofluorescent analyses of cholinergic nerves (peripherin+ChAT+), sympathetic nerves (peripherin+TH+) and vessels (CD31+) in the various groups, and quantified using image analysis. The number of nerves and vessels will be adjusted for by PanIN stage. In addition, we will also examine other stromal cell populations, including pericytes (NG2+) and fibroblasts (FAP+ or αSMA+). In addition, we will examine the effect of cholinergic signaling on immune response in the vagotomized KC mice. Previous studies by our group have shown loss of the vagal inflammatory reflex can accelerate tumorigenesis through expansion of myeloid-derived suppressor cells leading to reduced activity of CD8+ T cells[20]. Thus, we will analyze changes in myeloid cells (Cd11b+Ly6C+monocytes, F4/80+ macrophages and Cd11b+Ly6G+granulocytic), B cells, and CD4+ and CD8+ T cells in the spleen and circulation and pancreas in KC+PP, KC+VxPP, and KC+VxPP+bethanechol at 20 weeks (12 weeks of treatment). In addition, we will also carry out immunofluorescent staining of pancreatic tissue for PD-1 and PD-L1 expression as described[12], given recent findings that parasympathetic signaling reduces expression of these in breast cancer models. Using the VECTRA platform (see Core C), will also carry out multiplex immunofluorescence studies on pancreata from KPC mice treated with bethanechol to determine if there are qualitatively similar changes these animals.

B. Examine Contribution of Stromal M1R to Growth of PDA Cells, Using Syngeneic Orthotopic and Metastatic Transplant Models.

Figures 20A, 20B, 20C, 20D, 20E:
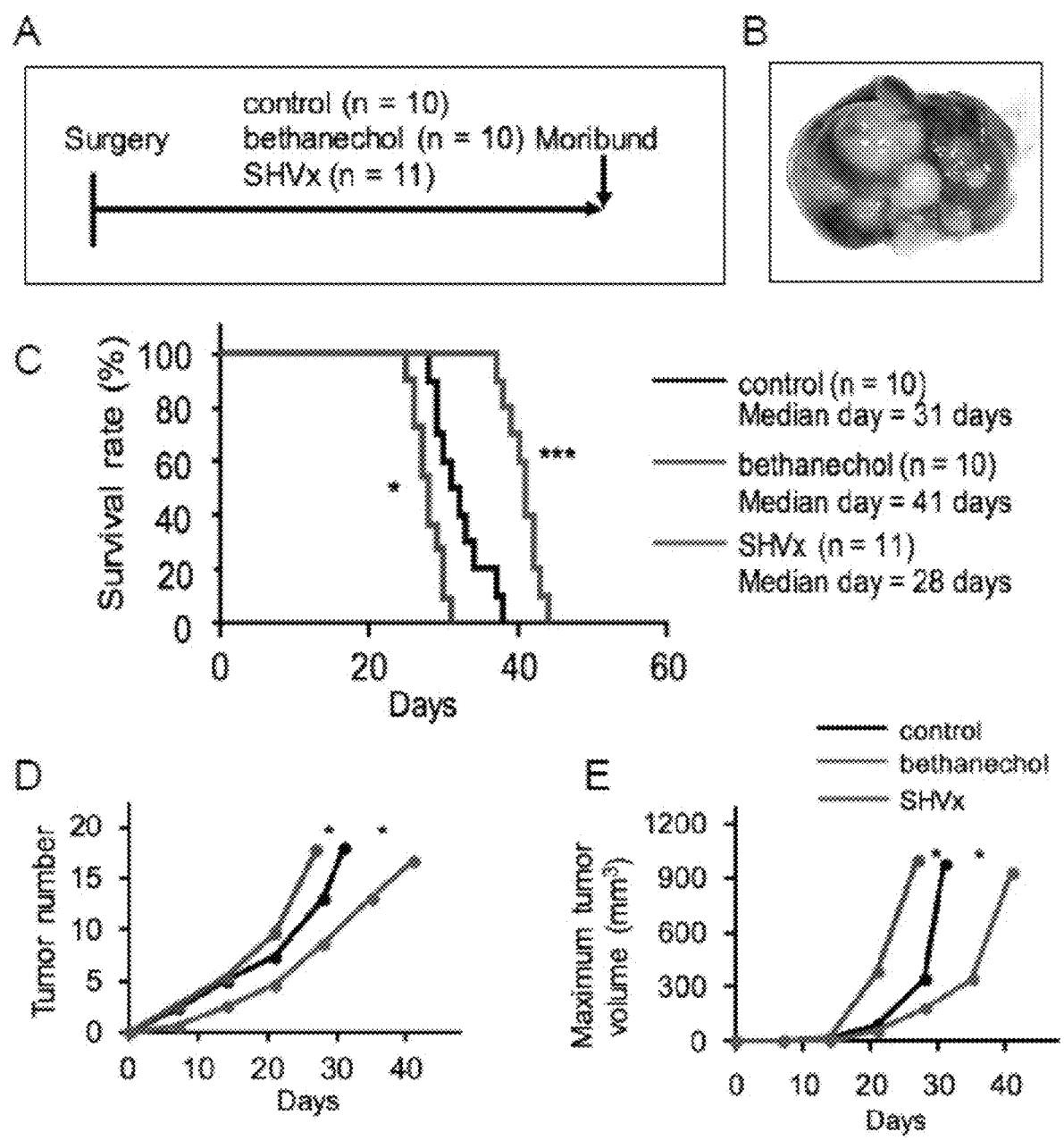
FIGS. 20A-E show that Cholinergic signaling prolongs survival in a liver metastatic model.

To explore whether bethanechol effects were mediated in part by stromal Chrm1 expression, we will transplant Panc02 cells into WT versus M1R−/− mice (all in a C57BL/6 background), with or without bethanechol treatment. We will use both orthotopic mouse PDA models, involving suspension in Matrigel and injection into the pancreatic tail[17,31], and our well-established metastatic model[17]. In our syngeneic orthotopic and metastatic models, we will inject Panc02 cells into WT B6 mice or M1R−/− mice (20 per group), and treat half (50%) with bethanechol. The main endpoint will be survival based on earlier studies. Panc02 cells were injected into the spleen of 8 week old WT mice followed by splenectomy[32], and then treated with selective liver denervation (cutting the hepatic branch of the vagal nerve) or bethanechol in the drinking water[17]. Vagotomy resulted in faster tumor growth and decreased survival (p<0.05), while bethanechol suppressed tumor growth and significantly prolonged survival (p<0.01) (FIG. 20A-C), with suppression of Ki67, pEGFR and CD44[17]. Furthermore, bethanechol inhibited the number of tumors formed (FIG. 20D) and tumor volume (FIG. 20E). Together these studies indicate that bethanechol can be effective in advanced, metastatic disease in M1R-expressing host animals. We will therefore carry out similar studies in M1R−/− mice, with endpoints as described above. In addition, we will compare stromal cells by staining (CD31, peripherin, FAP, αSMA, immune profiling) in PDA infiltrated livers in the M1R−/− background to WT mice. This will allow us to test the role of stromal M1R in a metastatic model.

C. Conditional Deletion of the M1R in Pancreatic Epithelium in KC and KPC Mice.

While we showed the deletion of M1R accelerates pancreatic tumorigenesis in KPC mice (FIGS. 20A-E), this result could in theory be due to effects on stromal cells as well as pancreatic epithelium. In some respects, a predominant tumor suppressive role for stromal M1R seems a little less likely given our findings of suppressive effects of M1R signaling on PDA cells and previous findings by Frenette et al indicating the opposite effects on prostate cancer stroma[9]. Nevertheless, we would predict that stromal M1R is likely important, and thus in order to assess the relative importance of pancreatic epithelial M1R expression, we propose to cross floxed M1RF/F mice to the KPC background, generating conditional knockout of M1R only in the Pdx1 lineage. A cohort of KPCM floxed mice (n=20) with loss of M1R in pancreatic epithelium will be generated and compared to regular KPC mice (n=20). Mice will be autopsied, and tumors stained for our M1R-dependent markers (Ki67, pEGFR, CD44) and the stroma analyzed as above. We would predict some acceleration of disease, but perhaps less than that seen in our previous whole body M1R−/− crosses (see FIG. 19C) given the absence here of stromal M1R expression.

D. Statistical Considerations and Alternative Approaches.

Described herein is the exploration of the association between stromal Chrm1 function and bethanechol. Note that the mice are commonly euthanized due to sickness during the experimental period. The primary interest is to compare the length of survival with and without bethanechol in each model. We assume that the mean survival time of the mice is 29 days in the control group based on extensive previous studies. With 10 mice in each group, we have 83% power to detect the mean survival of 41 days in the experimental group assuming the standard deviation of 10 days (corresponding to the effect size of 1.2) based on one-sided t-test at the significance level of 0.05. The nonparametric Wilcoxon rank-sum test will also be considered. In the scenario with censoring observations, we will compare the overall survival between treatment groups using the Kaplan-Meier method and the log-rank test. We will also study the association between the deletion of M1R and pancreatic tumorigenesis in KPC mice. In this experiment, we will primarily compare the length of survival time between two groups of 20 KPCM (floxed) mice and regular KPC mice. With 20 mice per group and assuming a mean survival time of 102 days in the KPCM mice (based on the preliminary study), we will have 86% power to detect an effect size of 0.88, when compared to the regular KPC mice which have a mean survival time of 190 days with the standard deviation of 100 days, using one-sided two-sample t-test at the significance level of 0.05. We would predict the studies will confirm significant effects in the epithelium, but also potentially reveal additional modifying effects by M1R signaling in the stroma. Alternative approaches may include deletion of the M1R in mouse and human PDA cells and PDX models using CRISPR-Cas9 methods, followed by analysis of growth in vivo.

Specific Aim 2:

Mechanisms by which M1 muscarinic receptor signaling suppresses stem cells and leads to an inhibition of PDA growth Rationale:

Muscarinic agonists clearly suppress PDA growth in vivo and in vitro, with direct effects on cancer stemness. The inhibitory effects of M1R signaling were in some ways surprising, given that GPCR signaling more often stimulates growth. We plan to investigate the mechanism of action (MoA) responsible for growth inhibition, primarily through studies of the GPCR signaling, validation of downstream candidate genes (e.g. BDNF, NGF) and RNAseq analysis+ bioinformatics.

Figures 21A, 21B, 21C, 21D:
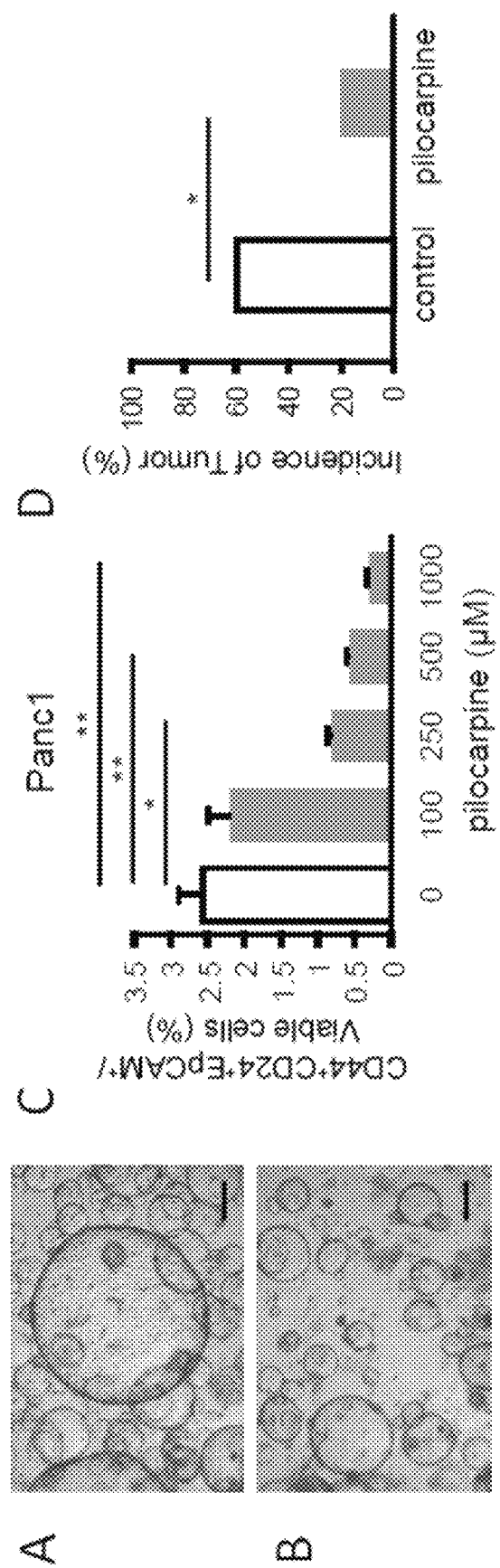
FIGS. 21A-D show muscarinic agonists inhibit pancreatic cancer stemness. Representative image of organoids generated from resected human PDA specimen (FIG. 21A) without treatment and (FIG. 21B) treated with 100DM pilocarpine.

Preliminary Data:

To better understand the effect of growth inhibition by muscarinic agonists in human pancreatic epithelial cells, we generated primary human PDA organoids. Treatment with the broad muscarinic agonist, pilocarpine, reduced the number of viable organoids in a dose-dependent manner (FIGS. 21A-B). Treatment of human pancreatic cancer cells (Panc1) with pilocarpine reduced the size of the CD44+CD24+ EpCAM+putative cancer stem cell population in a dose dependent manner (FIG. 21C) and inhibited tumor initiation in NOD/SCID mice (FIG. 21D). To better understand growth inhibition by muscarinic agonists, we analyzed changes in signaling molecules in animal models and PDA cell lines. KC mice treated with surgical denervation (vagotomy) showed increased ERK phosphorylation, which was suppressed with bethanechol treatment. Similar changes in phosphoproteins were observed in human (Panc-1) and murine (K8282) PDA cell lines treated with broad muscarinic agonists (pilocarpine) or antagonists (scopolamine), or M1R specific agonists (McN-34A) or antagonists (pirenzepine)[7]. Surprising, a number of signaling molecules were suppressed by both nonspecific and M1R-specific muscarinic agonists, including EGFR, B-RAF, ERK1/2, PI3K, and AKT kinase. These kinases all show reduced phosphorylation by muscarinic agonists, which was abrogated by treatment with muscarinic antagonists. Finally, we analyzed Panc-1 cells following pilocarpine treatment (1 mM, 72 hrs) using RNAseq, and noted that many of the genes suppressed by pilocarpine included EGFR and PI3K[17].

Methods:

A. Define the Optimal Kinetics and Signaling Pathways Mediating Growth Suppression by M1R.

Having shown strong effects by broad muscarinic agonists and M1R specific agonists on suppression of stem cells and signaling, we will now generate detailed dose response and time course curves. The primary endpoints in dose response and kinetic studies will be suppression of the CD44+CD24+ EpCAM+ population in Panc1 cells. Preliminary studies suggest that pilocarpine suppresses CD44+CD24+EpCAM+ cancer stem cells by >50% at doses of 100-500 ηµM. We will examine a more detailed range of doses and time points for suppression by pilocarpine and McN-34A to calculate IC20, IC50 and IC80 bases on dose response curves. Beyond the defined phosphorylation changes noted previously[17], we will also utilize a membrane-based multiplex antibody array (ProteomeProfiler™) to simultaneously detect relative levels of phosphorylation of 39 mouse kinase phosphorylation sites in our Panc1 studies. In addition, given the unexpected suppression of EGFR/ERK/PI3K signaling by muscarinic agonists, we will examine the effect of pilocarpine and bethanechol on Ca2+ flux in pancreatic cancer cell lines using biosensor plate readers. Preliminary studies suggest that pilocarpine suppresses growth of Kras pancreas spheres, but stimulates growth of WT spheres, and is unable to stimulate Ca2+ flux in Kras mutant Panc1 cells. Thus, we will address the possible differences in Kras mutant PDA cells in the role of G proteins and β-arrestin pathways by comparing signaling in a panel of Kras mutant PDA cell lines (Panc1, MiaPaCa-2, CAPAN1, ASPC-1, Patu8988S, and KP4) and Kras WT PDA lines (BxPc-3, HS766T, HS700T) in addition to other well studied cell lines engineered to harbor activating Kras mutations (e.g. HEK cells)[33]. M1R is typically Gq linked[34], and we will test the effect of Gαs, Gαi, and Gαq inhibitors (NF449, NFO23, UBO-QIC)[35] on ERK/PI3K inhibition in the Kras mutant versus Kras WT cells. Activated GPCRs also associate with β-arrestins ((βARRs), we will test their role by using siRNA to knock down (βARR1/2 mRNA as described[36]. Using tagged constructs, we will use bioluminescence resonance energy transfer (BRET) and super-resolution microscopy to study the association of M1R and βARRs[36]. Finally, we will use inhibitors of clathrin and dynamin to determine the role of endosomal signaling in mediating inhibitory effects of M1R signaling[35]. Thus, these studies will address broadly the role of M1R signaling in endosomes in modifying growth factor responses in PDA cells. We will also analyze M1R signaling in organoids from WT and Mutant Kras$^{G12D}$ pancreatic spheres, which will address the issue of whether mutant Kras contributes to the inhibitory effect of M1R signaling. We will study human PDX samples, and test the effects of muscarinic agonists in a panel of human primary organoids available in our Biospecimen, Pathology and Models Core (Core C). Human normal and cancerous (primary or metastatic) organoids can be established from patients and grown indefinitely in culture in vitro, and the organoid panels can be used as a validation platform for our findings. The 3-D organoid culture system, developed by Boj S F et al[38] and Chio I I et al[39], to model human PDA progression, will allow further confirmation of the inhibitory role of muscarinic agonists on growth of both cancerous and preneoplastic/normal pancreatic tissue.

B. Define the Potential Mechanism of Action (MoA).

1. Determine the Role of Suppression of Neurotrophin Signaling.

In addition to changes to GPCR signaling pathways in PDA, we are interested in candidate downstream targets of muscarinic agonists that account for the observed cancer stem cell suppression and inhibition of tumor initiation. In our preliminary analysis of genes regulated by pilocarpine[17], one of the most downregulated genes in Panc1 cells was the TRK-B receptor (NTRK2). Further, its ligands BDNF and NGF were moderately decreased. Thus, muscarinic agonists may act in part through suppression of neurotrophin signaling. We will pursue the effects of pilocarpine stimulation on human PDA cells, and primary organoids, on BDNF, TRK-B and other members of the family. We will examine the potential effects of pilocarpine on nerve-cancer cell interactions as previously described[16], and also determine if muscarinic agonists can inhibit in vitro, the proliferative responses to BDNF stimulation, and whether TRK inhibition results in similar effects on PDA behavior as muscarinic agonists.

2. Generate an Optimal RNAseq Data Set from Panc1 Cells.

To investigate downstream targets of muscarinic agonists using an unbiased approach, we will generate an RNAseq gene expression profile that can be used to infer the MoA. We will use human Panc1 cells, given the robust responses to pilocarpine (FIG. 21C)[17] and the availability of a detailed regulatory model for human pancreatic cancer (Core B). In this RNAseq study, we will sort the CD44+CD24+EpCAM+ population from Panc1 cells treated with 2 different doses of pilocarpine and 3 different time points for each dose, all done in triplicate as prescribed in the DeMAND protocol[40], where subsampling analysis demonstrated that this number of samples (2 doses×3 times points×3 replicates=18 samples) is well above the minimum required for detecting MoA proteins (see Core B for details). The doses that will be chosen will ideally be IC20 at 24 hrs, and $\frac{1}{10}^{th}$ of that, in order to analyze transcriptional events without eliciting apoptotic responses. The time points will be 1/2M, M, and 3/2M, following by experimental determination of the maximum (M) response. Following treatment, cells will be harvested, RNA prepared and cDNAs generated by random priming for sequencing. We will perform preliminary pathway analysis on those genes with the greatest difference in expression, and will prioritize pathways with known roles in the maintenance of stemness. In addition, we will perform network analysis as described below to identify downstream mechanistic targets.

3. Bioinformatics Approach for MoA.

We will analyze RNASeq database in Panc1 cells in response to muscarinic agonists to prioritize proteins representing their mechanism of action (MoA) for experimental validation. To approach this in an unbiased fashion, we will use experimentally validated regulatory network based methodologies for the de novo, genome-wide elucidation of compound-specific MoA proteins, using a pancreatic cancer regulatory model generated using the ARACNe algorithm[41].

To find the downstream mechanistic targets, they will interrogate this network with RNASeq-based gene expression profiles (GEP) in Panc1 cells treated or not with pilocarpine using two algorithms that provide complementary insight into drug MoA, including VIPER[41], which identifies specific changes in regulatory protein activity, and DEMAND[40], which identifies changes in protein interactions resulting from small molecule perturbations (see Core B). We will analyze RNAseq data using VIPER to identify proteins whose activity mediates the effect of muscarinic agonists, and then analyze the same data using DEMAND to identify proteins whose network connectivity changes significantly as a result of a pharmacological perturbation. Although DEMAND can accurately predict MoA proteins, it cannot predict changes following perturbation, but VIPER specifically compensates for this limitation[40]

4. Confirmatory Studies.

For our analysis and confirmation, we will prioritize pathways involved in the maintenance of stemness. We will select the three most differentially expressed genes for further analysis. Potential candidates (e.g. Master Regulators) will be investigated in followup experiments in other model systems, such as in Kras WT human pancreatic cancer cells (BxPC-3, HS766T, HS700T), WT and Mutant Kras murine pancreas spheres, and in limited studies in human PDX organoid samples. Promising downstream candidates will be tested functionally in 3D organoid cultures through in vitro shRNA knockdown studies or tet-dependent overexpression systems. Finally, we can potentially test some of the candidates that can be measured by IHC as in vivo biomarkers and predictors of response.

D. Bioinformatics Considerations and Alternative Approaches.

Described herein is the investigation of the mechanisms by which M1 muscarinic receptor (M1R) signaling leads to an inhibition of PDA growth. In Aim 2B we will use the DEMAND algorithm to identify the possible MoA for M1R inhibitory effects. The IC20 concentration of pilocarpine on the Panc-1 (mutant Kras) cell line will be determined at a number of time points through titration curves, with the size of the CD44+, CD24+, EpCAM+cell population as the primary endpoint. In each case, samples will be treated with pilocarpine at two concentrations (IC20 at 24 hours; and $\frac{1}{10}^{th}$ of that) and with DMSO. Gene expression profiles (RNA-seq, single-end 100 bp reads, 30M reads per sample) will be acquired at three time points in triplicate, as prescribed by the DeMAND protocol. The top MoA candidates identified by DEMAND will be validated experimentally, as described above. The proteins implicated in the pilocarpine MoA will be assessed separately in our panel of Kras mutant (Panc1, MiaPaCa-2, CAPAN1, ASPC-1, Patu8988S, and KP4) and Kras WT (BxPc-3, HS766T, HS700T) PDA cell lines. While the focus here is on human pancreatic cancer cell lines (e.g. Panc1), given that the mouse pancreatic cancer regulatory model is nearly complete, we could interrogate this system as well. Connecting targets directly to the Chrm1 receptor can be challenging, but achievable given our experience with GPCR's. Alternative approaches include RNAi or CRISPR-Cas9 screens.

Specific Aim 3:

Safety and efficacy of muscarinic agonism for patients against PDA, combination with chemotherapy, and effects on changes in tissue markers or outcome.

Rationale:

We plan to test the utility of bethanechol, an oral muscarinic parasympathetic agonist with proven ability to stimulate cholinergic signaling. It has a defined side effect profile, related to increasing cholinergic activity, that permits exclusion of patients in whom there could be toxicity. To this end, we have initiated a window of opportunity, pilot feasibility trial in surgical candidates (N=15). In this trial, patients with resectable PDA are treated with bethanechol for at least 1 week prior to surgery, to assess tolerability and impact on selected biomarkers. We received an IND exemption for bethanechol for this study, and have enrolled 5 patients. After demonstrating safety, we propose to conduct a prospective Phase IIA clinical trial of bethanechol in combination with "GA", gemcitabine plus nab-paclitaxel (Abraxane®) as neoadjuvant chemotherapy in patients (N=33) with borderline resectable PDA. The trial will determine safety, assess kinetics and effects on biomarkers in surgical samples, and provide efficacy data to support a randomized trial.

Background for Phase IIA Study:

Bethanechol Dosing and Experience in Cancer Patients.

Bethanechol is approved by the U.S. FDA for the treatment of nonobstructive urinary retention. It has a rapid onset of action, typically in one hour, and a 6 hr duration of action; side effects relate to stimulation of the parasympathetic nervous system, and there are no reported interactions with either gemcitabine or nab-paclitaxel. For urinary retention, bethanechol is dosed at 10 to 50 mg three—four times daily. It has been evaluated in oncology in the treatment of xerostomia at doses up to 50 mg three times daily without grade 3 toxicity or need for discontinuation[46]; in other studies, single doses up to 200 mg have been given with only mild cholinergic toxicity[47]. We utilized 100 mg twice daily in the pilot study, reasoning that we could achieve greater cholinergic effect with any single dose.

Figures 22A, 22B, 22C, 22D:
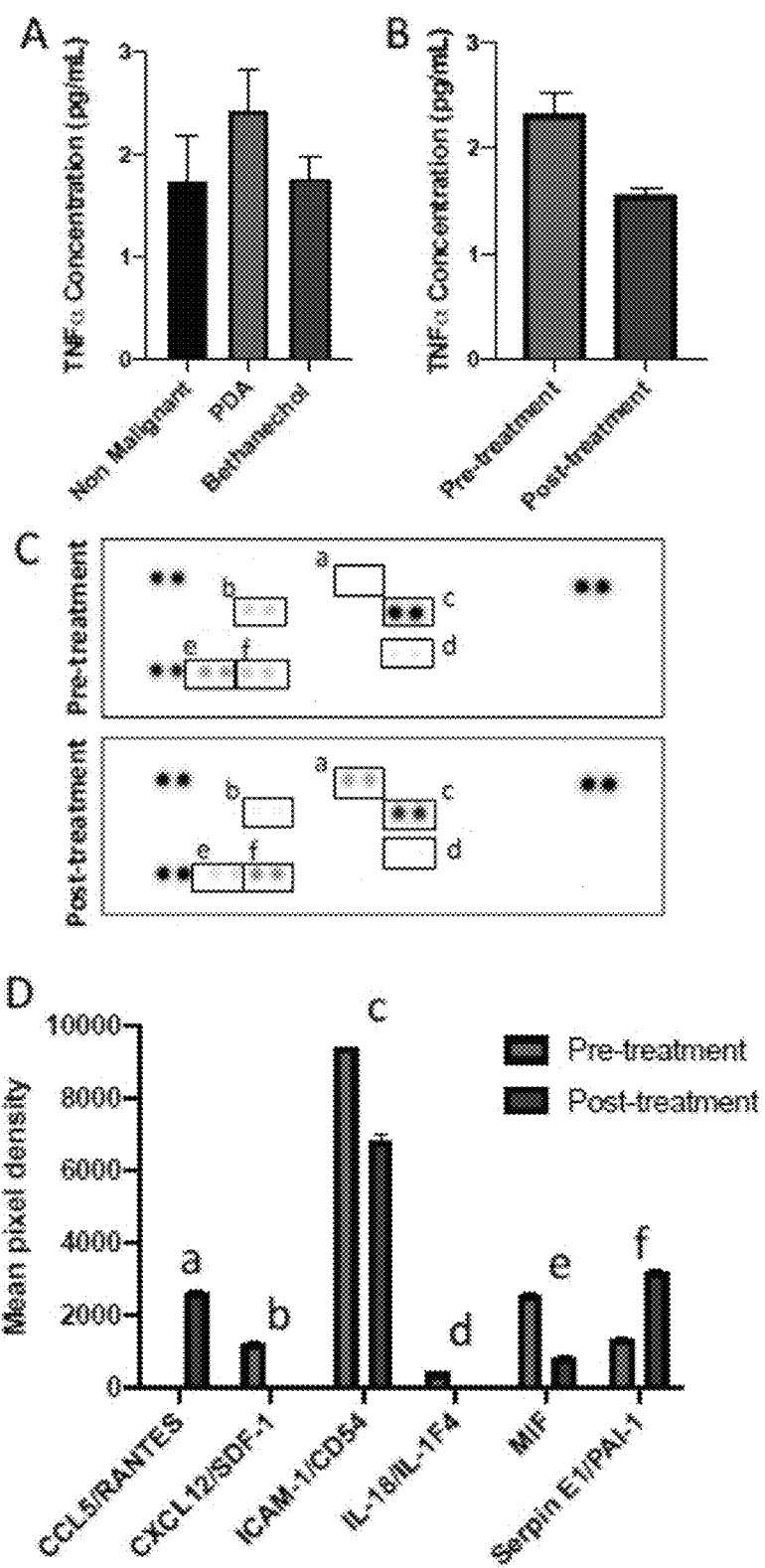
FIGS. 22A-D shows preliminary cytokine analysis from bethanechol pilot study.
Figure 23:
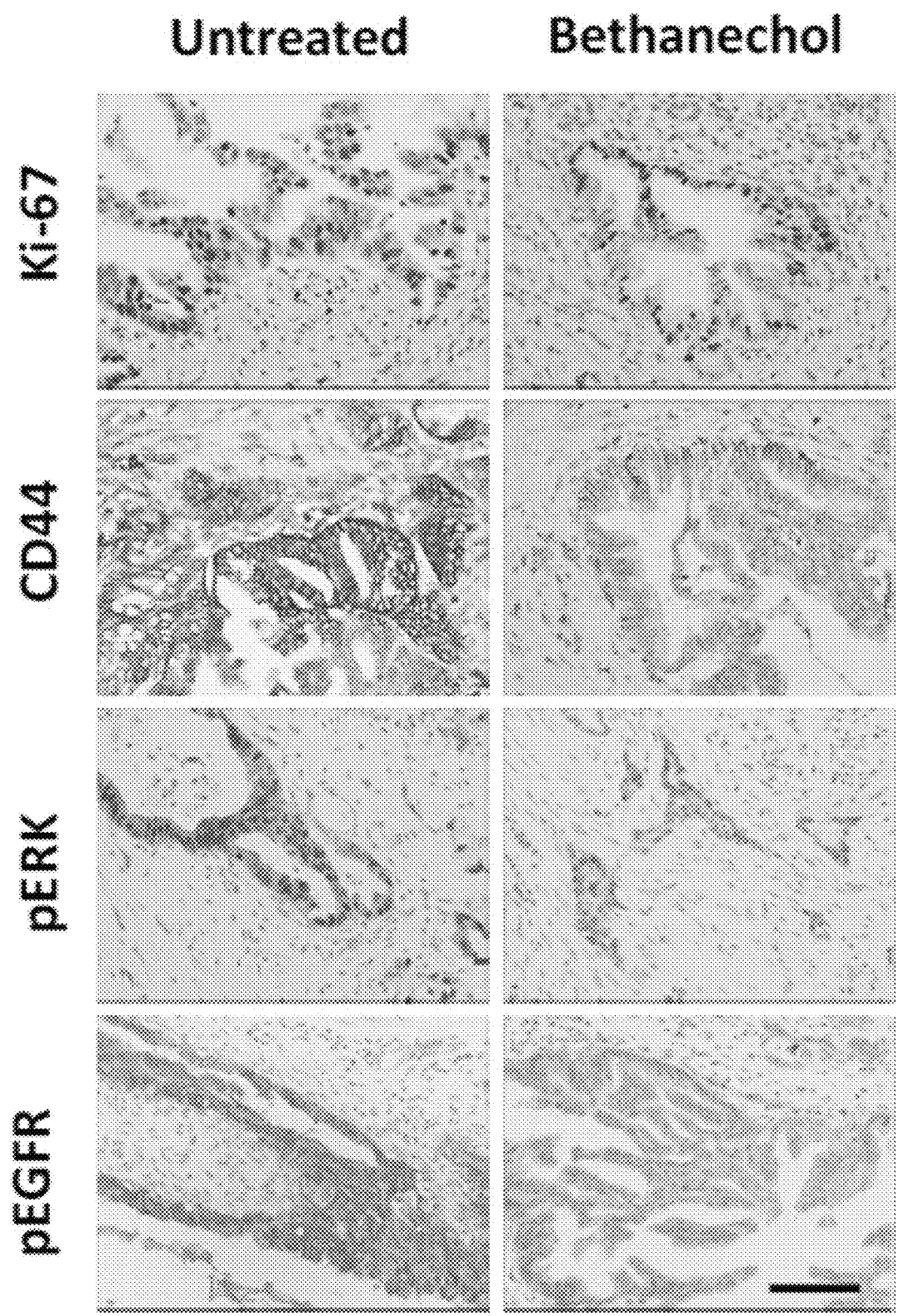
FIG. 23 shows representative immunohistochemistry for potential biomarkers of bethanechol treatment. Tissue sections were obtained from formalin fixed paraffin embedded PDA tissue collected at the time of resection in the bethanechol pilot study (Bethanechol) and compared with historical, treatment naïve PDA tissue from our biobank (Untreated). Tissue was stained for Ki-67, CD44, pERK and pEGFR. Scale bar represents 100 μM.

Pilot Study:

Our ongoing pilot feasibility study assesses the impact of 1 week of a fixed dose of bethanechol on pharmacodynamics endpoints in resected pancreatic cancer specimens. Trial subjects are patients with fully resectable pancreatic cancer who present to the CUIMC Pancreas Center for resection of PDA, who have not been treated, and who will have obtained adequate baseline tumor sampling to allow comparisons of pre- and post-treatment specimens. Subjects receive 100 mg of bethanechol by mouth twice daily for 1 week, discontinuing bethanechol 24 hours prior to scheduled surgery. All subjects will be assessed for toxicity while receiving bethanechol, and for 30 days thereafter. The primary endpoint in the pilot study is a change in cell proliferation (Ki-67 index). Plasma TNFα levels and other cytokines will be examined as a potential non-invasive biomarkers of drug efficacy based on findings from our preclinical model[17] and preliminary analysis from this pilot study (FIGS. 22A-D). These pilot data suggest a trend towards lower TNFα levels in PDA patients after bethanechol treatment (FIGS. 22A, 22B), and also point to possible reductions in other cytokine levels such as ICAM-1 and MIF (FIG. 22D). In addition, immunohistochemical (IHC) staining of PDA tissue from bethanechol-treated patients suggests that the drug might lead to a decrease in Ki-67, CD44, pERK and p-EGFR compared to untreated patients (FIG. 23), similar to our findings in KPC mice. These data do demonstrate the feasibility of our approach. We will compare gene expression profiles and regulatory networks between treated samples with matched controls in our dataset of >200 PDA, RNAseq analysis will be performed. Short-duration treatment in this patient population should be tolerable and will not interfere with plans for surgery or increase surgical complications.

Methods for Phase IIA Study:

A. Rationale for Selection of Neoadjuvant Therapy Setting.

Although surgical resection remains the only curative intervention for PDA, fewer than 25% of patients with a diagnosis of PDA are able to undergo a resection. Given the undisputed value of surgery and the progress made in the chemotherapy of PDA, pre-operative or neoadjuvant therapy is increasingly administered to patients with PDA to improve respectability and treat micrometastatic disease. The neoadjuvant setting offers the greatest opportunity for a meaningful impact (to increase resection and cure rates), and a unique opportunity to examine and compare histologic and biologic markers of response in the tumor. The neoadjuvant setting also offers the opportunity to treat at a time when neural innervation is intact; both indirect and direct effects can thus be exploited.

B. Gemcitabine/Abraxane Platform for Neoadjuvant Therapy.

FOLFIRINOX[45,48] is often selected as the neoadjuvant regimen in "fit patients", because of better overall survival (OS) rates in the metastatic setting. However, published data and our own internal data suggest gemcitabine+Abraxane is more comparable than the pivotal studies in the metastatic setting imply[49,50]. Irinotecan also has cholinergic activity that could lead to increased toxicity in combination with bethanechol. We have chosen gemcitabine plus nab-paclitaxel, due to its simplicity, tolerability, and weekly administration schedule that also allows frequent CA19-9 determinations. Parenthetically, the cholinergic activity of irinotecan could contribute to the efficacy of FOLFIRINOX and we consider that adding bethanechol to gemcitabine/nab-paclitaxel may mirror that contribution.

C. Patient Selection and Enrollment.

Subjects (33 patients) will be recruited from the CUIMC Pancreas Center. Study eligibility will be assessed by their primary surgeons, and will require a determination of "borderline resectable" (BR) pancreatic cancer, following definitions in the NCCN guidelines, as used in the CUIMC Pancreas Center[51-53]. Briefly, the study will include patients with (1) venous involvement amenable to reconstruction; (2) tumor <180° of the celiac and superior mesenteric arteries; or (3) hepatic artery amenable to reconstruction. We will obtain slides from available FFPE biopsy specimens, or where necessary obtain a new or confirmatory biopsy. Subjects will receive bethanechol in combination with gemcitabine/nab-paclitaxel prior to the planned surgery as outlined below. At the time of surgical resection, we will obtain both fresh frozen and FFPE tumor specimens for analysis. Plasma samples will also be collected prior to beginning and after completing treatment with bethanechol for inflammatory cytokine analysis. Patients will not be eligible if they have the potential for parasympathetic toxicity, including: recent urinary bladder surgery; recent gastrointestinal resection; peptic ulcer disease; Parkinson's disease; bronchial asthma; active coronary artery disease; bradycardia with HR<55 beats/min; systolic BP<90 mmHg; or vasomotor instability.

D. Gemcitabine/Abraxane Schedule for Phase IIA Study.

Chemotherapy will be administered on a day 1, 8 and 15 schedule with gemcitabine at a dose of 1000 mg/m$^2$ and Abraxane at 125 mg/m$^2$. We will plan to give 4-6 cycles of gemcitabine/Abraxane, enrolling 33 patients with borderline resectable pancreatic cancer. A small fraction of patients do not tolerate gemcitabine/Abraxane, and present with fever, edema, or early onset neuropathy. To avoid any confusion from the effects of the bethanechol, and to provide baseline tumor measurements and serum CA19-9 levels for pre-bethanechol kinetics, we will begin by administering gemcitabine/Abraxane alone in the first 2 cycles. Beginning with cycle 3, we will administer oral bethanechol at a dose of 100 mg twice daily for the remaining cycles. Biomarker assays that proved successful in the pilot study will be assessed in biopsy cores obtained at diagnosis, and in the surgical resection specimen.

Benchmarks for Phase IIA Study:

Assessing the efficacy of neoadjuvant therapy based on the literature is difficult in part due to varying definitions of respectability. Several novel efficacy endpoints will be assessed, including: (1) biomarkers selected based on results in the feasibility study; (2) tumor and CA19-9 kinetics in patients whose tumors express the marker; and (3) R0 resection rates.

A. Biomarkers from Pilot Study.

As noted, in the ongoing pilot feasibility study we will assess biopsy and resection specimens for biomarkers based on our mouse studies—Ki-67, CD44, CD68, S100, TUNEL, pERK, pEGFR, plasma TNFα and others. These all appear to be reliably measurable, based on preliminary studies in core needle biopsy specimens (see Core C). In particular, our preliminary analysis of Ki67 staining has shown a high degree of reproducibility, indicating potential utility as a biomarker, as suggested by our preclinical studies. Unless a better marker is identified in data emerging from the ongoing study, the primary endpoint in the Phase IIA neoadjuvant study will be a change in cell proliferation between pre- and post-bethanechol as measured by the Ki-67 index. In mice, bethanechol reduces Ki-67 staining in Panc02 liver metastases by 50%.

B. Tumor Growth (g) and Regression (d) Rates.

Figures 24A, 24B:
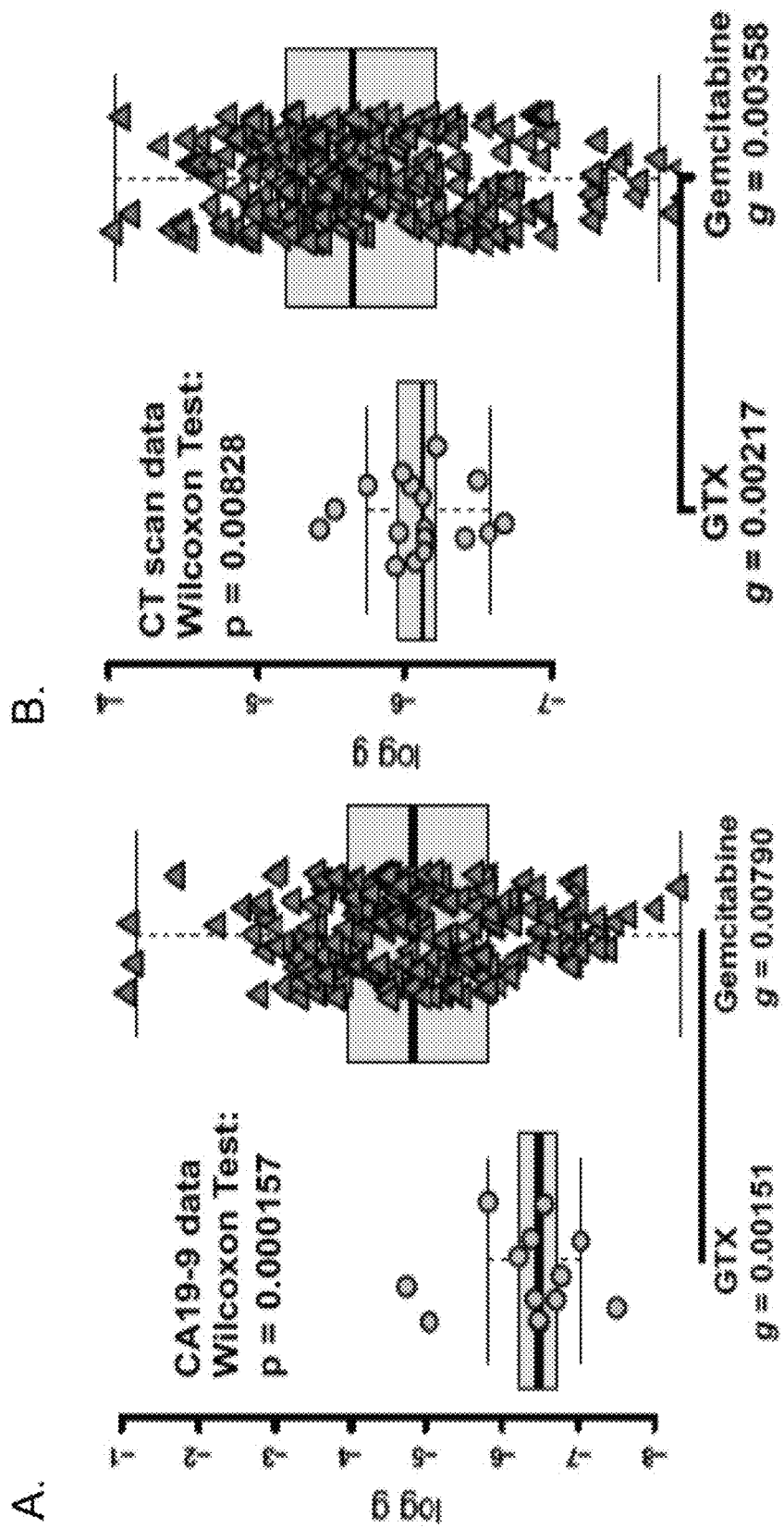
FIGS. 24A-B show scatterplots for estimated growth rates from data obtained during neoadjuvant administration of GTX (green dots), vs. data obtained from gemcitabine control arms of two clinical trials deposited to Project Data Sphere. Data were obtained from only while patients were on study.

We will also evaluate rates of tumor growth (g) and regression (d) using tumor measurements and CA19-9 values. We will assess the results in two ways—first by comparison to the data in the CUIMC Pancreas Center GTX neoadjuvant study reported by Sherman et al. using gemcitabine (G), paclitaxel (T) and capecitabine (X)[54]. Values of g estimated from CA19-9 and CT scans in this study are compared to publicly available gemcitabine data (FIGS. 24A-B). Second, using the CA19-9 data, we will compare the rates of tumor growth (g) and regression (d) during the first 2 cycles of GA, to the rates in the subsequent 2-4 cycles of GA plus bethanechol in individual patients and in the entire study population. We will estimate g and d using a series of kinetic equations validated in more than 10,000 patients, where clinical data including tumor measurements and serum markers are used to estimate g and d rate constants[55]. Previous studies have shown that g and d values statistically indistinguishable from those estimated with larger, more robust data sets, can be ascertained with as few as 3 to 4 serum marker levels, and that g values correlate highly with both progression-free survival (PFS) and OS. By obtaining blood samples weekly, we will have a minimum of eight CA19-9 values pre- and post-bethanechol; patients serve as their own controls to determine whether g or d change following bethanechol.

C. R0 Resection Rates.

We plan to benchmark data from the Phase IIA neoadjuvant trial against CUIMC Pancreas Center historical data, given there is currently only minimal published data for gemcitabine/nab-paclitaxel activity in the neoadjuvant setting. In a previously reported CUIMC Pancreas Center cohort receiving a gemcitabine-based regimen (GTX) a 62% R0 resection rate was noted for all patients enrolled[54]. We consider this a valuable reference dataset because of the continuity of surgical staff, and the likelihood that GTX and gemcitabine/nab-paclitaxel are comparably effective regimens. Generally, studies reporting on the efficacy of neoadjuvant therapy have noted R0 rates ranging from 44% to 73%, depending on the mix of patients with BR disease[56-58]. One single institution study in BR PDA reported an R0 rate of 67% with neoadjuvant gemcitabine/nab-paclitaxel[59], while another reported an R0 rate of 65% with FOLFIRINOX (taking as denominator all patients enrolled)[6].

D. Statistical Considerations for Clinical Trial Endpoints.

We plan to enroll 33 patients on the Phase IIA study and assess three endpoints as outlined below. Meeting these endpoints will support a randomized study of bethanechol with gemcitabine/nab-paclitaxel in the neoadjuvant setting. 1) Ki-67 index: In-house data and previous studies on paraffin sections from resected PDA specimens suggest at baseline a median 28% of nuclei are stained by Ki-67[61]. We intend to target an absolute change in Ki-67 of 12% to 16% in the post-treatment specimens. With 33 patients, we will have 99% power to detect an effect size of 0.8, equivalent to the change in Ki-67 of 12% with a standard deviation of 0.15 based on two-sided paired-t test at a significance level of 0.05. 2) Tumor kinetics: Estimating g and d values pre- and post-bethanechol in 33 patients we will have 75% power to detect a 40% change in g or d (equivalent to the effect size of 0.41 based on preliminary study) with the addition of bethanechol based on one-sided paired-t test at the significance level of 0.05. 3) R0 resection rates: In comparison to the reference level of 40% (R0), defined as at most 12 of 30 patients with R0 resection, based on the literature, the sample size of 33 patients gives 76% power to detect a successful R0 rate of 60% using one-sided one-proportion test at the significance level of 0.05 based on normal approximation. Finally, Simon's minimax two-stage design will be used for futility monitoring. The null hypothesis is that the true R0 resection rate is 0.2. and the alternative hypothesis is that the true R0 resection rate is 0.4. If there are 4 or fewer R0 resections among 18 patients accrued in stage I, the study will be stopped early. Otherwise, an additional 15 patients will be accrued in stage II, for a sample size of 33. If there are 11 or more R0 resections among these 33 patients, we reject the null hypothesis and claim that the treatment is promising. The design controls the type I error rate at 0.05 and yields the power of 0.8.

REFERENCES FOR EXAMPLE 5

1. Hidalgo M. Pancreatic cancer. *New England Journal of Medicine.* 2010; 362:1605-1617.
2. Siegel R L, Miller K D and Jemal A. Cancer statistics, 2018. *CA Cancer J Clin.* 2018; 68:7-30.
3. Olive K P, Jacobetz M A, Davidson C J, Gopinathan A, McIntyre D, Honess D, Madhu B, Goldgraben M A, Caldwell M E, Allard D, Frese K K, Denicola G, Feig C, Combs C, Winter S P, Ireland-Zecchini H, Reichelt S, Howat W J, Chang A, Dhara M, Wang L, Ruckert F, Grutzmann R, Pilarsky C, Izeradjene K, Hingorani S R, Huang P, Davies S E, Plunkett W, Egorin M, Hruban R H, Whitebread N, McGovern K, Adams J, Iacobuzio-Donahue C, Griffiths J and Tuveson D A. Inhibition of Hedgehog signaling enhances delivery of chemotherapy in a mouse model of pancreatic cancer. *Science.* 2009; 324:1457-61.
4. Demir I E, Friess H and Ceyhan G O. Neural plasticity in pancreatitis and pancreatic cancer. *Nat Rev Gastroenterol Hepatol.* 2015; 12:649-659.
5. Sun X J, Jiang T H, Zhang X P and A W M. Role of the tumor microenvironment in pancreatic adenocarcinoma. *Front Biosci (Landmark Ed).* 2016; 21:31-41.

6. Boilly B, Faulkner S, Jobling P and Hondermarck H. Nerve Dependence: From Regeneration to Cancer. *Cancer cell.* 2017; 31:342-354.
7. Ayala G E D H, Powell M, Li R, Ding Y, Wheeler™, Shine D, Kadmon D, Thompson T, Miles B J, Ittmann M M, Rowley D. Cancer-related axonogenesis and neurogenesis in prostate cancer. *Clin Cancer Res.* 2008; 14:7593-603.
8. Albo D, Akay C L, Marshall C L, Wilks J A, Verstovsek G, Liu H, Agarwal N, Berger D H and G E A. Neurogenesis in colorectal cancer is a marker of aggressive tumor behavior and poor outcomes. *Cancer* 2011; 117: 4834-4845.
9. Magnon C, Hall S J, Lin J, Xue X, Gerber L, Freedland S J and Frenette P S. Autonomic nerve development contributes to prostate cancer progression. *Science.* 2013; 341:1236361.
10. Zahalka A H, Amal-Estapé A, Maryanovich M, Nakahara F, Cruz C D, Finley L W S and Frenette P S. Adrenergic nerves activate an angio-metabolic switch in prostate cancer. Science. 2017:In press.
11. Peterson S C, Eberl M, Vagnozzi A N, Belkadi A, Veniaminova N A, Verhaegen M E, Bichakjian C K, Ward N L, Dlugosz A A and Wong S Y. Basal cell carcinoma preferentially arises from stem cells within hair follicle and mechanosensory niches. *Cell stem cell.* 2015; 16:400-12.
12. Kamiya A, Hayama Y, Kato S, Shimomura A, Shimomura T, Irie K, Kaneko R, Yanagawa Y, Kobayashi K and Ochiya T. Genetic manipulation of autonomic nerve fiber innervation and activity and its effect on breast cancer progression. *Nature neuroscience.* 2019; 22:1289-1305.
13. Hayakawa Y, Sakitani K, Konishi M, Asfaha S, Tomita H, Renz B W, Macchini M, Jiang Z, Tanaka T, Dubeykovskaya Z A, Kim W, Chen X, Urbanska A M, Middelhoff M, Tailor Y, Nagar K, Westphalen C B, Quante M, Lin C S, Gershon M D, Hara A, Zhao C M, Chen D, Kolke K, Worthley D L and Wang T C. Nerve growth factor promotes gastric tumorigenesis through aberrant cholinergic signaling. *Cancer cell.* 2017; 31:21-34.
14. Zhao C M, Hayakawa Y, Kodama Y, Muthupalani S, Westphalen C B, Andersen G T, Flatberg A, Johannessen H, Friedman R A, Renz B W, Sandvik A K, Beisvag V, Tomita H, Hara A, Quante M, Li Z, Gershon M D, Kaneko K, Fox J G, Wang T C and Chen D. Denervation suppresses gastric tumorigenesis. *Science translational medicine.* 2014; 6:250ra115.
15. Hayakawa Y and Wang T C. Nerves switch on angiogenic metabolism. *Science.* 2017; 358:305-306.
16. Renz B W, Takahashi R, Tanaka T, Macchini M, Hayakawa Y, Dantes Z, Maurer H C, Chen X, Jiang Z, Westphalen C B, Ilmer M, Valenti G, Mohanta S K, Tailor Y, Casadei R, Di Marco M, Kleespies A, Friedman R A, Remotti H, Reichert M, Worthley D L, Neumann J, Werner J, Iuga A C, Olive K P and Wang T C. β2 adrenergic-neurotrophin feed-forward loop promotes pancreatic cancer. *Cancer cell.* 2018; 34:863-867.
17. Renz B W, Tanaka T, Sunagawa M, Takahashi R, Jiang Z, Macchini M, Dantes Z, Valenti G, White R A, Middelhoff M A, Ilmer M, Oberstein P E, Angele M K, Deng H, Hayakawa Y, Westphalen C B, Werner J, Remotti H, Reichert M, Tailor Y H, Nagar K, Friedman R A, Iuga A C, Olive K P and Wang T C. Cholinergic Signaling via Muscarinic Receptors Directly and Indirectly Suppresses Pancreatic Tumorigenesis and Cancer Stemness. *Cancer Discov.* 2018; 8:1458-1473.
18. Fujii T, Mashimo M, Moriwaki Y, Misawa H, Ono S, Horiguchi K and K. K. Expression and Function of the Cholinergic System in Immune Cells. *Front Immunol.* 2017; 8:1085.
19. Padro C and Sanders V. Neuroendocrine regulation of inflammation. *Semin Immunol.* 2014; 26:357-68.
20. Dubeykovskaya Z, Si Y, Chen X, Worthley D L, Renz B W, Urbanska A M, Hayakawa Y, Xu T, Westphalen C B, Dubeykovskiy A, Chen D, Friedman R A, Asfaha S, Nagar K, Tailor Y, Muthupalani S, Fox J G, Kitajewski J and Wang T C. Neural innervation stimulates splenic TFF2 to arrest myeloid cell expansion and cancer. *Nature communications.* 2016; 7:10517.
21. Pavolv V A, Wang H, Czura C J, Friedman S G and Tracey K J. The cholinergic anti-inflammatory pathway: a missing link in neuroimmunomodulation. *Mol Med.* 2003; 9:125-134.
22. Berthoud H R and Neuhuber W L. Functional and chemical anatomy of the afferent vagal system. *Auton Neurosci.* 2000; 85:1-17.
23. Kiba T., Tanaka K., Numata K., Hoshino M., Misugi K. and S. I. Ventromedial hypothalamic lesion-induced vagal hyperactivity stimulates rat pancreatic cell proliferation. *Gastroenterology.* 1996; 110:885-93.
24. Gidron Y, Perry H and Glennie M. Does the vagus nerve inform the brain about preclinical tumours and modulate them? *Lancet Oncol.* 2005; 6:245-248.
25. De Couck M, Mravec B. and Y. G. You may need the vagus nerve to understand pathophysiology and to treat diseases. *Clin Sci (Lond).* 2012; 122:323-8.
26. Partecke LI K A, Trung D N, Diedrich S, Sendler M, Weiss F, Kühn J P, Mayerle J, Beyer K, von Bernstorff W, Heidecke C D, Keβler W. Subdiaphragmatic vagotomy promotes tumor growth and reduces survival via TNFα in a murine pancreatic cancer model. *Oncotarget.* 2017; 8:22501-22512.
27. Saloman J L, Albers K M, Li D, Hartman D J, Crawford H C, Muha E A, Rhim A D and Davis B M. Ablation of sensory neurons in a genetic model of pancreatic ductal adenocarcinoma slows initiation and progression of cancer. *Proc Natl Acad Sci USA.* 2016; 113:3078-83.
28. Sinha S, Fu Y Y, Grimont A, Ketcham M, Lafaro K, Saglimbeni J A, Askan G, Bailey J M, Melchor J P, Zhong Y, Joo M G, Grbovic-Huezo O, Yang I H, Basturk O, Baker L, Park Y, Kurtz R C, Tuveson D, Leach S D and P J. P. PanIN Neuroendocrine Cells Promote Tumorigenesis via Neuronal Cross-talk. *Cancer Res.* 2017; 77:1868-1879.
29. Erin N., Akdas Barkan G., Harms J. F. and G. A. C. Vagotomy enhances experimental metastases of 4THMpc breast cancer cells and alters substance P level. *Regul Pept.* 2008; 151:35-42.
30. Erin N., Duymuşs O., Oztuřk S. and N. D. Activation of vagus nerve by semapimod alters substance P levels and decreases breast cancer metastasis. *Regul Pept.* 2012; 179:101-8.
31. Morena J A, Sanchez A, Hoffman R M, Nur S and Lambros M P. Fluorescent orthotopic mouse model of pancreatic cancer. *J Vis Exp.* 2016; 115: doi: 10.3791/54337.
32. Soares K C, Foley K, Olino K, Leubner A, Mayo S C, Jain A, Jaffee E, Schulick R D, Yoshimura K, Edil B and Zheng L. A preclinical murine model of hepatic metastases. *J Vis Exp.* 2014; 91:51677. doi:10.3791/51677.
33. Abdul-Ridha A, Lane J R, Mistry S N, López L, Sexton P M, Scammells P J, Christopoulos A and M. C. Mechanistic insights into allosteric structure-function relationships at the M1 muscarinic acetylcholine receptor. *J Biol Chem.* 2014; 289:33701-11.
34. Jin G, Westphalen C B, Hayakawa Y, Worthley D L, Asfaha S, Yang X, Chen X, Si Y, Wang H, Tailor Y, Friedman R A and Wang T C. Progastrin stimulates colonic cell proliferation via CCK2R- and β-arrestin-dependent suppression of BMP2. *Gastroenterology.* 2013; 145:820-830.
35. Yarwood R E, Imlach W L, Lieu T M, Veldhuis N A, Jensen D D, Herenbrink C K, Aurelio L, Cai Z, Christie M J, poole D P, Porter C J H, McLean P, Hicks G A, Geppetti P, Halls M L, Canals M and Bunnett N W. Endosomal signaling of the receptor for calcitonin gene-related peptide mediates pain transmission. *Proc Natl Acad Sci USA* 2017; 114:12309-12314.
36. Jensen D D, Lieu T, Halls M L, Veldhuis N A, Imlach W L, Mai Q N, Poole D P, Quach T, Aurelio L, Conner J, Herenbrink C K, Barlow N, Simpson J S, Scanlon M J, Graham B, McCluskey A, Robinson P J, Escriou V, Nassini R, Materazzi S, Geppetti P, Hicks G A, Christie M J, Porter C J H, Canals M and N W B. Neurokinin 1 receptor signaling in endosomes mediates sustained nociception and is a viable therapeutic target for prolonged pain relief. *Science translational medicine.* 2017; 9:eaal3447. doi: 10.
37. Loukopoulos P, Kanetaka K, Takamura M, Shibata T, Sakamoto M and Hirohashi S. Orthotopic transplantation models of pancreatic adenocarcinoma derived from cell lines and primary tumors and displaying varying metastatic activity. *Pancreas.* 2004; 29:193-203.
38. Boj S F, Hwang C I, Baker L A, Chio, I I, Engle D D, Corbo V, Jager M, Ponz-Sarvise M, Tiriac H, Spector M S, Gracanin A, Oni T, Yu K H, van Boxtel R, Huch M, Rivera K D, Wilson J P, Feigin M E, Ohlund D, Handly-Santana A, Ardito-Abraham C M, Ludwig M, Elyada E, Alagesan B, Biffi G, Yordanov G N, Delcuze B, Creighton B, Wright K, Park Y, Morsink F H, Molenaar I Q, Borel Rinkes I H, Cuppen E, Hao Y, Jin Y, Nijman I J, Iacobuzio-Donahue C, Leach S D, Pappin D J, Hammell M, Klimstra D S, Basturk O, Hruban R H, Offerhaus G J, Vries R G, Clevers H and Tuveson D A. Organoid models of human and mouse ductal pancreatic cancer. *Cell.* 2015; 160:324-38.
39. Chio I I C, Jafarnejad S M, Ponz-Sarvise M, Park Y, Rivera K, Palm W, Wilson J, Sangar V, Hao Y, Ohlund D, Wright K, Filippini D, Lee E J, Da Silva B, Schoepfer C, Wilkinson J E, Buscaglia J M, DeNicola G M, Tiriac H, Hammell M, Crawford H C, Schmidt E E, Thompson C B, Pappin D J, Sonenberg N and Tuveson D A. NRF2 Promotes Tumor Maintenance by Modulating mRNA Translation in Pancreatic Cancer. *Cell.* 2016; 166:963-976.
40. Woo H H, Shimoni Y, Yang W S, Subramaniam P, Iyer A, Nicoletti P, Martinez M R, Lopez G, Mattioli M, Realubit R, Karan C, Stockwell B R, Bansai M and Califano A. Elucidating compound mechanism of action by network perturbation analysis. *Cell.* 2015; 162:441-451.
41. Alvarez M J, Shen Y, Giorgi F M, Lachmann A, Ding B B, Ye B H and Califano A. Functional characterization of somatic mutations in cancer using network-based inference of protein activity. *Nat Genet.* 2016; 48:838-47.
42. Renz B W, Takahashi R, Tanaka T, Macchini M, Hayakawa Y, Dantes Z, Maurer H C, Chen X, Jiang Z, Westphalen C B, Ilmer M, Valenti G, Mohanta S K, Tailor Y, Casadei R, Di Marco M, Kleespies A, Friedman R A, Remotti H, Reichert M, Worthley D L, Neumann J, Werner J, Iuga A C, Olive K P and Wang T C. β2 adrenergic-neurotrophin feed-forward loop promotes pancreatic cancer. *Cancer cell.* 2018; 33:75-90.
43. Chou T. Drug combination studies and their synergy quantification using the Chou-Talalay method. *Cancer Res.* 2010; 70:440-6.
44. Zhang N, Fu J N and Chou T C. Synergistic combination of microtubule targeting anticancer fludelone with cytoprotective panaxytriol derived from *Panax ginseng* against MX-1 cells in vitro: experimental design and data analysis using the combination index method. *Am J Cancer Res.* 2015; 6:97-104.
45. Conroy T, Hammel P, Hebbar M, Ben Abdelghani M, Wei A C, Raoul J L, Choné L, Francois E, Artru P, Biagi J J, Lecomte T, Assenat E, Faroux R, Ychou M, Volet J, Sauvanet A, Breysacher G, Di Fiore F, Cripps C, Kavan P, Texereau P, Bouhier-Leporrier K, Khemissa-Akouz F, Legoux J L, Juzyna B, Gourgou S, O'Callaghan C J, Jouffroy-Zeller C, Rat P, Malka D, Castan F, J B; B and Group. CCTGatU-GP. FOLFIRINOX or Gemcitabine as Adjuvant Therapy for Pancreatic Cancer. *N Engl J Med.* 2018; 379:2395-2406.
46. Jaguar G C, Lima E N, Kowalski L P, Pellizzon A C, Carvalho A L, Boccaletti K W and Alves F A. Double blind randomized prospective trial of bethanechol in the prevention of radiation-induced salivary gland dysfunction in head and neck cancer patients. *Radiotherapy and oncology: journal of the European Society for Therapeutic Radiology and Oncology.* 2015; 115:253-6.
47. Chowdhury S, Wang S, Dunai J, Kilpatrick R, Oestricker L Z, Wallendorf M J, Patterson B W, Reeds D N and Wice B M. Hormonal Responses to Cholinergic Input Are Different in Humans with and without Type 2 Diabetes Mellitus. *PloS one.* 2016; 11:e0156852.
48. Conroy T, Desseigne F, Ychou M, Bouché O, Guimbaud R, Bécouarn Y, Adenis A, Raoul J L, Gourgou-Bourgade S, de la Fouchardière C, Bennouna J, Bachet J B, Khemissa-Akouz F, Péré-Vergé D, Delbaldo C, Assenat E, Chauffert B, Michel P, Montoto-Grillot C and M; D. FOLFIRINOX versus gemcitabine for metastatic pancreatic cancer. *N Engl J Med.* 2011; 364:1817-25.
49. Muranaka T, Kuwatani M, Komatsu Y, Sawada K, Nakatsumi H, Kawamoto Y, Yuki S, Kubota Y, Kubo K, Kawahata S, Kawakubo K, Kawakami H and N. S. Comparison of efficacy and toxicity of FOLFIRINOX and gemcitabine with nab-paclitaxel in unresectable pancreatic cancer. *J Gastrointest Oncol.* 2017; 8:566-571.
50. Wang Y, Camateros P and Cheung W Y. A Real-World Comparison of FOLFIRINOX, Gemcitabine Plus nab-Paclitaxel, and Gemcitabine in Advanced Pancreatic Cancers. *J Gastrointest Cancer.* 2017;November 16. doi: 10.1007/s12029-017-0028-5. [Epub ahead of print].
51. Katz M H, Marsh R, Herman J M, Shi Q, Collison E, Venook A P, Kindler H L, Alberts S R, Philip P, Lowy A M, Pisters P W, Posner M C, Berlin J D and S A. A. Borderline resectable pancreatic cancer: need for standardization and methods for optimal clinical trial design. *Ann Surg Oncol.* 2013; 20:2197-203.
52. Lutz M P, Zalcberg J R, Ducreux M, Aust D, Bruno M J, Büchler M W, Delpero J R, Gloor B, Glynne-Jones R, Hartwig W, Huguet F, Laurent-Puig P, Lordick F, Maisonneuve P, Mayerle J, Martignoni M, Neoptolemos J, Rhim A D, Schmied B M, Seufferlein T, Werner J, van Laethem J L and F. O. 3rd St. Gallen EORTC Gastrointestinal Cancer Conference: Consensus recommendations on controversial issues in the primary treatment of pancreatic cancer. *Eur J Cancer.* 2017; 79:41-49.

53. Tempero M A, Malafa M P, Al-Hawary M, Asbun H B A, Behrman S W, Benson A B 3rd, Binder E, Cardin D B, Cha C, Chiorean E G, Chung V, Czito B, Dillhoff M, Dotan E, Ferrone C R, Hardacre J, Hawkins W G, Herman J, Ko A H, Komanduri S, Koong A, LoConte N, Lowy A M, Moravek C, Nakakura E K, O'Reilly E M, Obando J, Reddy S, Scaife C, Thayer S, Weekes C D, Wolff R A, Wolpin B M, Burns J and S. D. Pancreatic Adenocarcinoma, Version 2.2017, NCCN Clinical Practice Guidelines in Oncology. *J Natl Compr Canc Netw.* 2017; 15:1028-1061.

54. Sherman W H, Chu K, Chabot J, Allendorf J, Schrope B A, Hecht E, Jin B, Leung D, Remotti H, Addeo G, Postolov I, Tsai W and R L F. Neoadjuvant gemcitabine, docetaxel, and capecitabine followed by gemcitabine and capecitabine/radiation therapy and surgery in locally advanced, unresectable pancreatic adenocarcinoma. *Cancer.* 2015; 121:673-80.

55. Stein W D F W, Dahut W, Stein A D, Hoshen M B, Price D, Bates S E, Fojo T. Tumor growth rates derived from data for patients in a clinical trial correlate strongly with patient survival: a novel strategy for evaluation of clinical trial data. *Oncologist.* 2008; 13:1046-54.

56. Blazer M, Wu C, Goldberg R M, Phillips G, Schmidt C, Muscarella P, Wuthrick E, Williams T M, Reardon J, Ellison E C, Bloomston M and T. B-S. Neoadjuvant modified (m) FOLFIRINOX for locally advanced unresectable (LAPC) and borderline resectable (BRPC) adenocarcinoma of the pancreas. *Ann Surg Oncol.* 2015; 22:1153-9.

57. Hosein P J, Macintyre J, Kawamura C, Maldonado J C, Ernani V, Loaiza-Bonilla A, Narayanan G, Ribeiro A, Portelance L, Merchan J R, Levi J U and C M. R-L. *A retrospective study of neoadjuvant FOLFIRINOX in unresectable or borderline-resectable locally advanced pancreatic adenocarcinoma.* 2012; BMC Cancer.

58. Addeo P, Rosso E, Fuchshuber P, Oussoultzoglou E, De Blasi V, Simone G, Belletier C, Dufour P and P. B. Resection of Borderline Resectable and Locally Advanced Pancreatic Adenocarcinomas after Neoadjuvant Chemotherapy. *Oncology.* 2015; 89:37-46.

59. Ielpo B, Caruso R, Duran H, Diaz E, Fabra I, Malavé L, Ferri V, Alvarez R, Cubillo A, Plaza C, Lazzaro S, Kalivaci D, Quijano Y and E. V. A comparative study of neoadjuvant treatment with gemcitabine plus nab-paclitaxel versus surgery first for pancreatic adenocarcinoma. *Surg Oncol.* 2017; 26:402-410.

60. Murphy J E, Wo J Y, Ryan D P and al e. Total Neoadjuvant Therapy With FOLFIRINOX Followed by Individualized Chemoradiotherapy for Borderline Resectable Pancreatic Adenocarcinoma A Phase 2 Clinical Trial. *JAMA Oncol.* 2018; Published online May 3, 2018. doi: 10.1001/jamaoncol.2018.0329.

61. Stanton K J, Sidner R A, Miller G A, Cummings O W, Schmidt C M, Howard T J and E A. W. Analysis of Ki-67 antigen expression, DNA proliferative fraction, and survival in resected cancer of the pancreas. *Am J Surg.* 2003; 186:486-92.

62. Koo J, MacEwan M R, Kang S K, Won S M, Stephen M, Gamble P, Xie Z, Yan Y, Chen Y Y, Shin J, Birenbaum N, Chung S, Kim S B, Khalifeh J, Harburg D V, Bean K, Paskett M, Kim J, Zohny Z S, Lee S M, Zhang R, Luo K, Ji B, Banks A, Lee H M, Huang Y, Ray W Z and J A. R. Wireless bioresorbable electronic system enables sustained nonpharmacological neuroregenerative therapy. *Nat Med.* 2018; 24:1830-1836.

What is claimed:

1. A method for treating pancreatic cancer in a subject in need thereof, the method comprising administering a therapeutically effective amount of cholinergic agonist to the subject in need thereof, wherein the cholinergic agonist is a M3 receptor agonist or a cholinergic muscarinic receptor 1 (CHRM1) agonist.

2. The method of claim 1, wherein the cholinergic agonist is a M3 receptor agonist.

3. The method of claim 1, wherein the cholinergic agonist is a cholinergic muscarinic receptor 1 (CHRM1) agonist.

4. The method of claim 3, wherein the cholinergic muscarinic receptor 1 (CHRM1) agonist is McN-34A.

5. The method of claim 1, further comprising administering a cytotoxic therapy.

6. The method of claim 5, wherein the cytotoxic therapy is gemcitabine, nab-paclitaxel, or a combination thereof.

7. The method of claim 3, further comprising administering a cytotoxic therapy.

8. The method of claim 7, wherein the cytotoxic therapy is gemcitabine, nab-paclitaxel, or a combination thereof.

9. The method of claim 1, further comprising performing a resection surgery, a Whipple surgery, or a distal pancreatectomy.

10. The method of claim 9, wherein the cholinergic agonist is administered before, during, or after the resection surgery, the Whipple surgery, or the distal pancreatectomy is performed.

11. The method of claim 1, wherein the cholinergic agonist is administered before, during, or after a resection surgery, a Whipple surgery, or a distal pancreatectomy.

12. The method of claim 3, further comprising performing a resection surgery, a Whipple surgery, or a distal pancreatectomy.

13. The method of claim 12, further comprising administering a cytotoxic therapy.

14. The method of claim 13, wherein the cytotoxic therapy is gemcitabine, nab-paclitaxel, or a combination thereof.

15. The method of claim 1, wherein the pancreatic cancer is pancreatic adenocarcinoma (PDAC).

16. The method of claim 15, wherein the PDAC is Grade 1 or Grade 2A PDAC.

17. The method of claim 11, wherein the subject is administered 200 mg of bethanechol per day for at least 14 days prior to the resection surgery, Whipple surgery, or distal pancreatectomy.

18. The method of claim 11, wherein the subject is administered 30 mg of pilocarpine per day prior to the resection surgery, Whipple surgery, or distal pancreatectomy.

19. The method of claim 4, wherein the subject is administered 50 mg of McN-34A per day.

20. The method of claim 4, wherein the subject is administered 100 mg of McN-34A per day.

21. The method of claim 4, wherein the subject is administered 200 mg of McN-34A per day.

22. The method of claim 11, wherein the subject is administered 200 mg of McN-34A per day prior to the resection surgery, Whipple surgery, or distal pancreatectomy.

23. The method of claim 1, wherein the subject has metastatic pancreatic cancer.

24. The method of claim 6, wherein the cytotoxic therapy is gemcitabine and nab-paclitaxel.

25. The method of claim 8, wherein the cytotoxic therapy is gemcitabine and nab-paclitaxel.

26. The method of claim 14, wherein the cytotoxic therapy is gemcitabine and nab-paclitaxel.

27. The method of claim 9, further comprising administering a cytotoxic therapy.

28. The method of claim 27, wherein the cytotoxic therapy is gemcitabine, nab-paclitaxel, or a combination thereof.

29. The method of claim 28, wherein the cytotoxic therapy is gemcitabine and nab-paclitaxel.

* * * * *

UNITED STATES PATENT AND TRADEMARK OFFICE
CERTIFICATE OF CORRECTION

| | | |
|---|---|---|
| PATENT NO. | : 11,344,534 B2 | Page 1 of 1 |
| APPLICATION NO. | : 16/725668 | |
| DATED | : May 31, 2022 | |
| INVENTOR(S) | : Timothy C. Wang et al. | |

It is certified that error appears in the above-identified patent and that said Letters Patent is hereby corrected as shown below:

In the Specification

At Column 1, Line number 15 should read:
GOVERNMENT SUPPORT
This invention was made with government support under Grant No. DK097016 and DK103155 awarded by the National Institutes of Health. The Government has certain rights in the invention.

Signed and Sealed this
Ninth Day of August, 2022

Katherine Kelly Vidal
*Director of the United States Patent and Trademark Office*